(12) United States Patent
Sebhat et al.

(10) Patent No.: US 11,407,768 B2
(45) Date of Patent: Aug. 9, 2022

(54) AMPK ACTIVATORS

(71) Applicant: Kallyope, Inc., New York, NY (US)

(72) Inventors: Iyassu Sebhat, Jersey City, NJ (US); Shuwen He, Fanwood, NJ (US)

(73) Assignee: KALLYOPE, INC., New York, NY (US)

( * ) Notice: Subject to any disclaimer, the term of this patent is extended or adjusted under 35 U.S.C. 154(b) by 0 days.

(21) Appl. No.: 17/358,385

(22) Filed: Jun. 25, 2021

(65) Prior Publication Data
US 2022/0002317 A1 Jan. 6, 2022

Related U.S. Application Data

(60) Provisional application No. 63/044,565, filed on Jun. 26, 2020.

(51) Int. Cl.
| | | |
|---|---|---|
| *C07D 519/00* | (2006.01) | |
| *C07D 493/04* | (2006.01) | |
| *A61P 3/10* | (2006.01) | |
| *A61P 1/00* | (2006.01) | |
| *C07F 9/6561* | (2006.01) | |

(52) U.S. Cl.
CPC .............. *C07D 519/00* (2013.01); *A61P 1/00* (2018.01); *A61P 3/10* (2018.01); *C07D 493/04* (2013.01); *C07F 9/6561* (2013.01)

(58) Field of Classification Search
CPC ... C07D 519/00; C07D 493/04; C07F 9/6561; A61P 1/00; A61P 3/10
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 7,750,048 B2 | 7/2010 | Kuo et al. |
| 8,796,258 B2 | 8/2014 | Anand et al. |
| 9,567,330 B2 | 2/2017 | Kojima et al. |
| 9,884,876 B2 | 2/2018 | Iadonato et al. |
| 10,093,670 B2 | 10/2018 | Kojima et al. |
| 2007/0275984 A1 | 11/2007 | Imogai et al. |
| 2012/0053180 A1 | 3/2012 | Kang et al. |
| 2013/0184240 A1 | 7/2013 | Tonogaki et al. |
| 2014/0194420 A1 | 7/2014 | Kojima et al. |
| 2015/0284411 A1 | 10/2015 | Apgar et al. |

FOREIGN PATENT DOCUMENTS

| | | |
|---|---|---|
| EP | 2733141 B1 | 1/2019 |
| WO | WO-0240019 A1 | 5/2002 |
| WO | WO-02066511 A2 | 8/2002 |
| WO | WO-03104816 A1 | 12/2003 |
| WO | WO-2005051890 A1 | 6/2005 |
| WO | WO-2005067368 A2 | 7/2005 |
| WO | WO-2005095338 A1 | 10/2005 |
| WO | WO-2006011615 A1 | 2/2006 |
| WO | WO-2006071095 A1 | 7/2006 |
| WO | WO-2006083612 A1 | 8/2006 |
| WO | WO-2006083781 A1 | 8/2006 |
| WO | WO-2006117565 A2 | 11/2006 |
| WO | WO-2006128803 A1 | 12/2006 |
| WO | WO-2007002461 A1 | 1/2007 |
| WO | WO-2007003962 A2 | 1/2007 |
| WO | WO-2007067828 A2 | 6/2007 |
| WO | WO-2007088857 A1 | 8/2007 |
| WO | WO-2007120689 A2 | 10/2007 |
| WO | WO-2007120702 A2 | 10/2007 |
| WO | WO-2007123225 A1 | 11/2007 |
| WO | WO-2007136572 A2 | 11/2007 |
| WO | WO-2008006432 A1 | 1/2008 |
| WO | WO-2008016278 A1 | 2/2008 |
| WO | WO-2008025798 A1 | 3/2008 |
| WO | WO-2008028117 A1 | 3/2008 |
| WO | WO-2008054674 A2 | 5/2008 |
| WO | WO-2008054675 A2 | 5/2008 |
| WO | WO-2008056155 A1 | 5/2008 |
| WO | WO-2008063768 A2 | 5/2008 |
| WO | WO-2008067219 A2 | 6/2008 |
| WO | WO-2008067222 A1 | 6/2008 |
| WO | WO-2008070692 A2 | 6/2008 |
| WO | WO-2008083124 A1 | 7/2008 |
| WO | WO-2008083238 A2 | 7/2008 |
| WO | WO-2008091540 A2 | 7/2008 |
| WO | WO-2008097428 A2 | 8/2008 |

(Continued)

OTHER PUBLICATIONS

Samsam, M., "Pathophysiology of autism spectrum disorders: revisiting gastrointestinal involvement and immune imbalance." World journal of gastroenterology: WJG 20.29 (2014): 9942.*
Van De Sande, M. "Autism and nutrition: the role of the gut-brain axis." Nutrition research reviews 27.2 (2014): 199-214.*
Eissa, N.,"Current enlightenment about etiology and pharmacological treatment of autism spectrum disorder." Frontiers in neuroscience 12 (2018): 304.*
Feng et al. Discovery of MK-8722: A systemic, direct pan-activator of AMP-activated protein kinase. ACS Med Chem Letters 9(1):39-44 (2018).
PCT/US2021/032933 International Search Report and Written Opinion dated Sep. 13, 2021.

(Continued)

*Primary Examiner* — John M Mauro
(74) *Attorney, Agent, or Firm* — Wilson Sonsini Goodrich & Rosati

(57) ABSTRACT

This disclosure is directed, at least in part, to AMPK activators useful for the treatment of conditions or disorders associated with AMPK. In some embodiments, the condition or disorder is associated with the gut-brain axis. In some embodiments, condition or disorder is associated with systemic infection and inflammation from having a leaky gut barrier. In some embodiments, the AMPK activators are gut-restricted compounds. In some embodiments, the AMPK activators are agonists, super agonists, full agonists, or partial agonists.

21 Claims, No Drawings

(56) References Cited

FOREIGN PATENT DOCUMENTS

| | | |
|---|---|---|
| WO | WO-2008097976 A1 | 8/2008 |
| WO | WO-2008109702 A1 | 9/2008 |
| WO | WO-2008136642 A1 | 11/2008 |
| WO | WO-2008137435 A1 | 11/2008 |
| WO | WO-2008137436 A1 | 11/2008 |
| WO | WO-2009012275 A1 | 1/2009 |
| WO | WO-2009026241 A1 | 2/2009 |
| WO | WO-2009039942 A1 | 4/2009 |
| WO | WO-2009039943 A1 | 4/2009 |
| WO | WO-2009050309 A1 | 4/2009 |
| WO | WO-2009054390 A1 | 4/2009 |
| WO | WO-2009054423 A1 | 4/2009 |
| WO | WO-2009054468 A1 | 4/2009 |
| WO | WO-2009054479 A1 | 4/2009 |
| WO | WO-2009058237 A1 | 5/2009 |
| WO | WO-2009076631 A1 | 6/2009 |
| WO | WO-2009105715 A1 | 8/2009 |
| WO | WO-2009105717 A1 | 8/2009 |
| WO | WO-2009105722 A1 | 8/2009 |
| WO | WO-2009106561 A1 | 9/2009 |
| WO | WO-2009106565 A1 | 9/2009 |
| WO | WO-2009117421 A2 | 9/2009 |
| WO | WO-2009123992 A1 | 10/2009 |
| WO | WO-2009124636 A1 | 10/2009 |
| WO | WO-2009126535 A1 | 10/2009 |
| WO | WO-2009132136 A1 | 10/2009 |
| WO | WO-2009135580 A1 | 11/2009 |
| WO | WO-2009141238 A1 | 11/2009 |
| WO | WO-2009143049 A1 | 11/2009 |
| WO | WO-2009152909 A1 | 12/2009 |
| WO | WO-2010006191 A1 | 1/2010 |
| WO | WO-2010008739 A2 | 1/2010 |
| WO | WO-2010008851 A1 | 1/2010 |
| WO | WO-2010009183 A1 | 1/2010 |
| WO | WO-2010013849 A1 | 2/2010 |
| WO | WO-2010014739 A2 | 2/2010 |
| WO | WO-2010014836 A2 | 2/2010 |
| WO | WO-2010016846 A1 | 2/2010 |
| WO | WO-2010036613 A1 | 4/2010 |
| WO | WO-2010042145 A1 | 4/2010 |
| WO | WO-2010047982 A1 | 4/2010 |
| WO | WO-2010048149 A2 | 4/2010 |
| WO | WO-2010051176 A1 | 5/2010 |
| WO | WO-2010051206 A1 | 5/2010 |
| WO | WO-2010056717 A1 | 5/2010 |
| WO | WO-2010059853 A1 | 5/2010 |
| WO | WO-2010059859 A1 | 5/2010 |
| WO | WO-2010066901 A2 | 6/2010 |
| WO | WO-2010085522 A1 | 7/2010 |
| WO | WO-2010085525 A1 | 7/2010 |
| WO | WO-2010085528 A1 | 7/2010 |
| WO | WO-2010091176 A1 | 8/2010 |
| WO | WO-2010093845 A1 | 8/2010 |
| WO | WO-2010123016 A1 | 10/2010 |
| WO | WO-2010123017 A1 | 10/2010 |
| WO | WO-2010128414 A1 | 11/2010 |
| WO | WO-2010143733 A1 | 12/2010 |
| WO | WO-2011008663 A1 | 1/2011 |
| WO | WO-2011025006 A1 | 3/2011 |
| WO | WO-2011029855 A1 | 3/2011 |
| WO | WO-2011030139 A1 | 3/2011 |
| WO | WO-2011032320 A1 | 3/2011 |
| WO | WO-2011033099 A1 | 3/2011 |
| WO | WO-2011041154 A1 | 4/2011 |
| WO | WO-2011044001 A1 | 4/2011 |
| WO | WO-2011046851 A1 | 4/2011 |
| WO | WO-2011050174 A1 | 4/2011 |
| WO | WO-2011052756 A1 | 5/2011 |
| WO | WO-2011061679 A1 | 5/2011 |
| WO | WO-2011066183 A1 | 6/2011 |
| WO | WO-2011069298 A1 | 6/2011 |
| WO | WO-2011071565 A1 | 6/2011 |
| WO | WO-2011078371 A1 | 6/2011 |
| WO | WO-2011080277 A1 | 7/2011 |
| WO | WO-2011106273 A1 | 9/2011 |
| WO | WO-2011113947 A1 | 9/2011 |
| WO | WO-2011127106 A1 | 10/2011 |
| WO | WO-2011128251 A1 | 10/2011 |
| WO | WO-2011138307 A1 | 11/2011 |
| WO | WO-2011138427 A2 | 11/2011 |
| WO | WO-2011140160 A1 | 11/2011 |
| WO | WO-2011140161 A1 | 11/2011 |
| WO | WO-2011146324 A1 | 11/2011 |
| WO | WO-2011146335 A1 | 11/2011 |
| WO | WO-2011147951 A1 | 12/2011 |
| WO | WO-2011150067 A1 | 12/2011 |
| WO | WO-2011153435 A1 | 12/2011 |
| WO | WO-2011161030 A1 | 12/2011 |
| WO | WO-2011163090 A1 | 12/2011 |
| WO | WO-2012001020 A1 | 1/2012 |
| WO | WO-2012004269 A1 | 1/2012 |
| WO | WO-2012004270 A1 | 1/2012 |
| WO | WO-2012010413 A1 | 1/2012 |
| WO | WO-2012011125 A1 | 1/2012 |
| WO | WO-2012016217 A1 | 2/2012 |
| WO | WO-2012024183 A1 | 2/2012 |
| WO | WO-2012025811 A1 | 3/2012 |
| WO | WO-2012028602 A1 | 3/2012 |
| WO | WO-2012033149 A1 | 3/2012 |
| WO | WO-2012037393 A1 | 3/2012 |
| WO | WO-2012046249 A1 | 4/2012 |
| WO | WO-2012046792 A1 | 4/2012 |
| WO | WO-2012046869 A1 | 4/2012 |
| WO | WO-2012072691 A1 | 6/2012 |
| WO | WO-2012077655 A1 | 6/2012 |
| WO | WO-2012080476 A1 | 6/2012 |
| WO | WO-2012082947 A1 | 6/2012 |
| WO | WO-2012098217 A1 | 7/2012 |
| WO | WO-2012101068 A1 | 8/2012 |
| WO | WO-2012103806 A1 | 8/2012 |
| WO | WO-2012111849 A1 | 8/2012 |
| WO | WO-2012116145 A1 | 8/2012 |
| WO | WO-2012117996 A1 | 9/2012 |
| WO | WO-2012119978 A1 | 9/2012 |
| WO | WO-2012119979 A1 | 9/2012 |
| WO | WO-2012138919 A2 | 10/2012 |
| WO | WO-2012145361 A1 | 10/2012 |
| WO | WO-2012145603 A1 | 10/2012 |
| WO | WO-2012145604 A1 | 10/2012 |
| WO | WO-2012147518 A1 | 11/2012 |
| WO | WO-2012149236 A1 | 11/2012 |
| WO | WO-2012170702 A1 | 12/2012 |
| WO | WO-2013011932 A1 | 1/2013 |
| WO | WO-2013025424 A1 | 2/2013 |
| WO | WO-2013040093 A2 | 3/2013 |
| WO | WO-2013054338 A1 | 4/2013 |
| WO | WO-2013055910 A1 | 4/2013 |
| WO | WO-2013057743 A1 | 4/2013 |
| WO | WO-2013066869 A1 | 5/2013 |
| WO | WO-2013074388 A1 | 5/2013 |
| WO | WO-2013096771 A1 | 6/2013 |
| WO | WO-2013104257 A1 | 7/2013 |
| WO | WO-2013122028 A1 | 8/2013 |
| WO | WO-2013122029 A1 | 8/2013 |
| WO | WO-2013122821 A1 | 8/2013 |
| WO | WO-2013128378 A1 | 9/2013 |
| WO | WO-2013144097 A1 | 10/2013 |
| WO | WO-2013153479 A2 | 10/2013 |
| WO | WO-2013154163 A1 | 10/2013 |
| WO | WO-2013164292 A1 | 11/2013 |
| WO | WO-2013164484 A1 | 11/2013 |
| WO | WO-2013167514 A1 | 11/2013 |
| WO | WO-2013173198 A1 | 11/2013 |
| WO | WO-2013178575 A1 | 12/2013 |
| WO | WO-2014001554 A1 | 1/2014 |
| WO | WO-2014019186 A1 | 2/2014 |
| WO | WO-2014031441 A1 | 2/2014 |
| WO | WO-2014031445 A1 | 2/2014 |
| WO | WO-2014031465 A1 | 2/2014 |
| WO | WO-2014031468 A1 * 2/2014 ......... A61K 31/4245 |
| WO | WO-2014031515 A1 | 2/2014 |
| WO | WO-2014031517 A1 | 2/2014 |
| WO | WO-2014052619 A1 | 4/2014 |

(56) References Cited

FOREIGN PATENT DOCUMENTS

| | | |
|---|---|---|
| WO | WO-2014056938 A1 | 4/2014 |
| WO | WO-2014066819 A1 | 5/2014 |
| WO | WO-2014069426 A1 | 5/2014 |
| WO | WO-2014073904 A1 | 5/2014 |
| WO | WO-2014074668 A1 | 5/2014 |
| WO | WO-2014082918 A1 | 6/2014 |
| WO | WO-2014085474 A1 | 6/2014 |
| WO | WO-2014086712 A1 | 6/2014 |
| WO | WO-2014096440 A2 | 6/2014 |
| WO | WO-2014100021 A1 | 6/2014 |
| WO | WO-2014100025 A1 | 6/2014 |
| WO | WO-2014122067 A1 | 8/2014 |
| WO | WO-2014128549 A1 | 8/2014 |
| WO | WO-2014130608 A1 | 8/2014 |
| WO | WO-2014133008 A1 | 9/2014 |
| WO | WO-2014140704 A1 | 9/2014 |
| WO | WO-2014146604 A1 | 9/2014 |
| WO | WO-2014169817 A1 | 10/2014 |
| WO | WO-2014170842 A2 | 10/2014 |
| WO | WO-2014175330 A1 | 10/2014 |
| WO | WO-2014187343 A1 | 11/2014 |
| WO | WO-2014200349 A1 | 12/2014 |
| WO | WO-2014202528 A1 | 12/2014 |
| WO | WO-2014202580 A1 | 12/2014 |
| WO | WO-2015000412 A1 | 1/2015 |
| WO | WO-2015007669 A1 | 1/2015 |
| WO | WO-2015010655 A1 | 1/2015 |
| WO | WO-2015017710 A1 | 2/2015 |
| WO | WO-2015020184 A1 | 2/2015 |
| WO | WO-2015024448 A1 | 2/2015 |
| WO | WO-2015024526 A1 | 2/2015 |
| WO | WO-2015028960 A1 | 3/2015 |
| WO | WO-2015032328 A1 | 3/2015 |
| WO | WO-2015044073 A1 | 4/2015 |
| WO | WO-2015051496 A1 | 4/2015 |
| WO | WO-2015052910 A1 | 4/2015 |
| WO | WO-2015062486 A1 | 5/2015 |
| WO | WO-2015063011 A1 | 5/2015 |
| WO | WO-2015073342 A1 | 5/2015 |
| WO | WO-2015078802 A1 | 6/2015 |
| WO | WO-2015080446 A1 | 6/2015 |
| WO | WO-2015084692 A1 | 6/2015 |
| WO | WO-2015088868 A1 | 6/2015 |
| WO | WO-2015089809 A1 | 6/2015 |
| WO | WO-2015091937 A1 | 6/2015 |
| WO | WO-2015097713 A1 | 7/2015 |
| WO | WO-2015105779 A1 | 7/2015 |
| WO | WO-2015105786 A1 | 7/2015 |
| WO | WO-2015119899 A1 | 8/2015 |
| WO | WO-2015150563 A1 | 10/2015 |
| WO | WO-2015150564 A1 | 10/2015 |
| WO | WO-2015150565 A1 | 10/2015 |
| WO | WO-2015160772 A1 | 10/2015 |
| WO | WO-2015176267 A1 | 11/2015 |
| WO | WO-2015181275 A1 | 12/2015 |
| WO | WO-2015183794 A1 | 12/2015 |
| WO | WO-2015198199 A1 | 12/2015 |
| WO | WO-2016000771 A1 | 1/2016 |
| WO | WO-2016001224 A1 | 1/2016 |
| WO | WO-2016019587 A1 | 2/2016 |
| WO | WO-2016022446 A1 | 2/2016 |
| WO | WO-2016022448 A1 | 2/2016 |
| WO | WO-2016022742 A1 | 2/2016 |
| WO | WO-2016023789 A1 | 2/2016 |
| WO | WO-2016031842 A1 | 3/2016 |
| WO | WO-2016032120 A1 | 3/2016 |
| WO | WO-2016054208 A1 | 4/2016 |
| WO | WO-2016057731 A1 | 4/2016 |
| WO | WO-2016066818 A1 | 5/2016 |
| WO | WO-2016068099 A1 | 5/2016 |
| WO | WO-2016068453 A1 | 5/2016 |
| WO | WO-2016073767 A1 | 5/2016 |
| WO | WO-2016086115 A1 | 6/2016 |
| WO | WO-2016092413 A1 | 6/2016 |
| WO | WO-2016113299 A1 | 7/2016 |
| WO | WO-2016113300 A1 | 7/2016 |
| WO | WO-2016130809 A1 | 8/2016 |
| WO | WO-2016161003 A1 | 10/2016 |
| WO | WO-2016205032 A1 | 12/2016 |
| WO | WO-2016205475 A2 | 12/2016 |
| WO | WO-2017002786 A1 | 1/2017 |
| WO | WO-2017025368 A1 | 2/2017 |
| WO | WO-2017027309 A1 | 2/2017 |
| WO | WO-2017027310 A1 | 2/2017 |
| WO | WO-2017027312 A1 | 2/2017 |
| WO | WO-2017027396 A1 | 2/2017 |
| WO | WO-2017042121 A1 | 3/2017 |
| WO | WO-2017053826 A1 | 3/2017 |
| WO | WO-2017079062 A1 | 5/2017 |
| WO | WO-2017106112 A1 | 6/2017 |
| WO | WO-2017106818 A1 | 6/2017 |
| WO | WO-2017146186 A1 | 8/2017 |
| WO | WO-2017147137 A1 | 8/2017 |
| WO | WO-2017147159 A1 | 8/2017 |
| WO | WO-2017147174 A1 | 8/2017 |
| WO | WO-2017147742 A1 | 9/2017 |
| WO | WO-2017172505 A1 | 10/2017 |
| WO | WO-2017175066 A1 | 10/2017 |
| WO | WO-2017175068 A1 | 10/2017 |
| WO | WO-2017180571 A1 | 10/2017 |
| WO | WO-2017180577 A1 | 10/2017 |
| WO | WO-2017188288 A1 | 11/2017 |
| WO | WO-2017200068 A1 | 11/2017 |
| WO | WO-2017222713 A1 | 12/2017 |
| WO | WO-2018005794 A2 | 1/2018 |
| WO | WO-2018005801 A2 | 1/2018 |
| WO | WO-2018009778 A1 | 1/2018 |
| WO | WO-2018026890 A1 | 2/2018 |
| WO | WO-2018035128 A1 | 2/2018 |
| WO | WO-2018064441 A1 | 4/2018 |
| WO | WO-2018071493 A1 | 4/2018 |
| WO | WO-2018077699 A1 | 5/2018 |
| WO | WO-2018081047 A1 | 5/2018 |
| WO | WO-2018095877 A1 | 5/2018 |
| WO | WO-2018103868 A1 | 6/2018 |
| WO | WO-2018104558 A1 | 6/2018 |
| WO | WO-2018104559 A1 | 6/2018 |
| WO | WO-2018104560 A1 | 6/2018 |
| WO | WO-2018104561 A1 | 6/2018 |
| WO | WO-2018106518 A1 | 6/2018 |
| WO | WO-2018111012 A1 | 6/2018 |
| WO | WO-2018118670 A1 | 6/2018 |
| WO | WO-2018138026 A1 | 8/2018 |
| WO | WO-2018138027 A1 | 8/2018 |
| WO | WO-2018138028 A1 | 8/2018 |
| WO | WO-2018138029 A1 | 8/2018 |
| WO | WO-2018138030 A1 | 8/2018 |
| WO | WO-2018142363 A1 | 8/2018 |
| WO | WO-2018146008 A1 | 8/2018 |
| WO | WO-2018153849 A1 | 8/2018 |
| WO | WO-2018161077 A1 | 9/2018 |
| WO | WO-2018172727 A1 | 9/2018 |
| WO | WO-2018181847 A1 | 10/2018 |
| WO | WO-2018182050 A1 | 10/2018 |
| WO | WO-2018189679 A1 | 10/2018 |
| WO | WO-2018189683 A1 | 10/2018 |
| WO | WO-2018219204 A1 | 12/2018 |
| WO | WO-2018222701 A1 | 12/2018 |
| WO | WO-2018226724 A1 | 12/2018 |
| WO | WO-2018229252 A1 | 12/2018 |
| WO | WO-2018237350 A1 | 12/2018 |
| WO | WO-2019040399 A1 | 2/2019 |
| WO | WO-2019086559 A1 | 5/2019 |
| WO | WO-2019090209 A1 | 5/2019 |
| WO | WO-2019099315 A1 | 5/2019 |
| WO | WO-2019134984 A1 | 7/2019 |
| WO | WO-2020229375 A1 | 11/2020 |
| WO | WO-2021236617 A1 | 11/2021 |

OTHER PUBLICATIONS

Berge et al. Pharmaceutical Salts. Journal of Pharmaceutical Sciences 66(1):1-19 (Jan. 1977).

(56) References Cited

OTHER PUBLICATIONS

Bundgard, H. Design of Prodrugs. 1985; pp. 7-9, 21-24 (Elsevier, Amsterdam).

Burwinkel et al. Fatal congenital heart glycogenosis caused by a recurrent activating R531Q mutation in the gamma 2-subunit of AMP-activated protein kinase (PRKAG2), not by phosphorylase kinase deficiency. Am J Hum Genet 76(6):1034-1049 (2005).

Di Fusco et al. Metformin inhibits inflammatory signals in the gut by controlling AMPK and p38 MAP kinase activation. Clinical Science 132(11):1155-1168 (2018).

Evans. Synthesis of radiolabeled compounds. J Radioanal Chem 64(1-2):9-32 (1981).

Kabalka et al. The Synthesis of Radiolabeled Compounds via Organometallic Intermediates. Tetrahedron 45(21):6601-6621 (1989).

Myers et al. Systemic pan-AMPK activator MK-8722 improves glucose homeostasis but induces cardiac hypertrophy. Science 357(6350):507-511 (2017).

Sun et al. AMP-activated protein kinase: a therapeutic target in intestinal diseases. Open Biology 7(8):170104 (2017).

Sun et al. AMPK improves gut epithelial differentiation and barrier function via regulating Cdx2 expression. Cell Death Differ 24(5):819-831 (2017).

Xue et al. Metformin Improves Ileal Epithelial Barrier Function in Interleukin-10 Deficient Mice. PLoS One 11(12):1-18 (2016).

Co-pending U.S. Appl. No. 17/502,474, inventors Sebhat; Iyassu et al., filed Oct. 15, 2021.

PCT/US2021/038975 International Search Report and Written Opinion dated Oct. 15, 2021.

Anonymous. Positive Results in Phase 2b Study of Metformin Delayed Release in Type 2 Diabetes. Available at https://endocrinenews.endocrine.org/positive-results-phase-2b-study-metformin-delayed-release-type-2-diabetes/ Endocrine News (2 pgs) (Nov. 2016).

Giordanetto et al. Direct AMP-activated protein kinase activators: a review of evidence from the patent literature. Expert Opin Ther Pat 22(12):1467-77 (2012).

Henry et al. Improved glycemic control with minimal systemic metformin exposure: Effects of Metformin Delayed-Release (Metformin DR) targeting the lower bowel over 16 weeks in a randomized trial in subjects with type 2 diabetes. PLoS One 13(9):e0203946 (2018).

Lan et al. Hit-to-Lead Optimization and Discovery of 5-((5-([1,1'-Biphenyl]-4-yl)-6-chloro-1H-benzo[d]imidazol-2-yl)oxy)-2-methylbenzoic Acid (MK-3903): A Novel Class of Benzimidazole-Based Activators of AMP-Activated Protein Kinase. J Med Chem 60(21):9040-9052 (2017).

Olivier et al. Deletion of intestinal epithelial AMP-activated protein kinase alters distal colon permeability but not glucose homeostasis. Mol Metab 47:101183 (2021).

\* cited by examiner

AMPK ACTIVATORS

CROSS-REFERENCE TO RELATED APPLICATIONS

This application claims the benefit of US Provisional Application No. 63/044,565 filed on Jun. 26, 2020, which is incorporated herein by reference in its entirety.

BACKGROUND OF THE INVENTION

Adenosine 5'-monophosphate-activated protein kinase (AMPK) is a serine/threonine kinase and is evolutionarily conserved from yeast to mammals. AMPK acts as an energy sensor and is activated by upstream enzymes when the cellular ratio of adenosine 5'—monophosphate (AMP) to adenosine triphosphate (ATP) is elevated due to nutrient deprivation. Activated AMPK phosphorylates downstream substrates to promote catabolism and impede anabolism, leading to ATP production and energy restoration. AMPK activity can be altered due to numerous physiological factors, such as hormones, cytokines and dietary nutrients, as well as pathological conditions such as obesity, chronic inflammation and type 2 diabetes. AMPK activation can lead to lower hepatic glucose production and plasma glucose levels. Thus, AMPK is an attractive target to treat various metabolic diseases.

Additionally, AMPK has beneficial effects for gut health, such as enhancing intestinal absorption, improving barrier function, suppressing colorectal carcinogenesis, and reducing intestinal inflammation and metabolic-related disease, and is important for the maintenance of intestinal homeostasis. For example, AMPK activation enhances paracellular junctions, nutrient transporters, autophagy and apoptosis, and suppresses inflammation and carcinogenesis in the intestine. Accordingly, AMPK is associated with the maintenance of tight junctions in colonic epithelium and controls the progression of colitis.

In various mouse models of colitis, treatment with a direct AMPK activator has been shown to be efficacious at restoring gut barrier function (see, for example, WO 2018/189683; Sun, X., et al. (2017), Cell Death and Differentiation, 24(5), 819-831; Xue, Y., et al. (2016), PLoS ONE, 11(12), 1-18; and Sun, X., et al. (2017), Open Biology, 7(8). This effect has also been recapitulated with metformin, which is an indirect AMPK activator having additional biological activities (see, for example, WO 2018/161077; and Di Fusco, D., et al. (2018), Clinical Science, 132(11). However, there are safety concerns with sustained direct AMPK activation, particularly in the heart. Chronic treatment with systemic, direct activators can lead to cardiac hypertrophy (concomitant with increased cardiac glycogen) in rodents and non-human primates (See, Myers, R. W., et al. (2017), Science, 357(6350), 507-511). Additionally, human genetic polymorphisms in AMPK are associated with cardiac glycogen deposition, cardiac hypertrophy and Wolff-Parkinson-White syndrome, a condition characterized by electrocardiogram (ECG) abnormalities (see, Burwinkel, B., et al. (2005), Am Journal of Human Genetics, 76(6), 1034-1049). Due to this risk of cardiac hypertrophy, treatment with known AMPK activators, which are systemic in nature, is unsuitable to address the problem of treating IBD, colitis, and other diseases with a leaky gut barrier with a direct AMPK activator.

Direct AMPK activation in the intestine without systemic engagement has never been demonstrated or proposed until the instant disclosure. All reported direct AMPK activators which have been optimized and entered clinical studies (for example, PF-06409577 from Pfizer) or extensive preclinical evaluation (for example, MK-3903 and MK-8722 from Merck) are systemic AMPK activators and have been developed for systemic engagement, as is reflected in the routes of administration and biological assays present in patent applications and published manuscripts relating to direct AMPK activators. A delayed-release formulation has been investigated to deliver higher concentrations of the indirect AMPK activator metformin to the colon for treatment of IBD. However, metformin does not optimally activate AMPK, metformin has other activities, and this approach requires specific formulation development. Thus it is not an optimal solution to the problem.

Disclosed herein is the discovery and development of the first gut-restricted, direct AMPK activators that do not require sophisticated formulations to reach the target tissue and avoid systemic circulation.

BRIEF SUMMARY OF THE INVENTION

Disclosed herein, in some embodiments, are adenosine 5'-monophosphate-activated protein kinase (5' AMP-activated protein kinase, AMPK) activators useful for the treatment of conditions or disorders associated with AMPK. In some embodiments, the condition or disorder is associated with the gut-brain axis. In some embodiments, the condition or disorder is associated with systemic infection and inflammation from having a leaky gut barrier. In some embodiments, the AMPK activators are gut-restricted or selectively modulate AMPK located in the gut. In some embodiments, the condition is selected from the group consisting of: central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, checkpoint inhibitor-induced colitis, psoriasis and celiac disease; necrotizing enterocolitis; gastrointestinal injury resulting from toxic insults such as radiation or chemotherapy; diseases/disorders of gastrointestinal barrier dysfunction including environmental enteric dysfunction; spontaneous bacterial peritonitis; allergy including food allergy, celiac sprue, and childhood allergy; graft vs. host disease; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

Disclosed herein, in some embodiments, is a compound of Formula (I):

Formula (I)

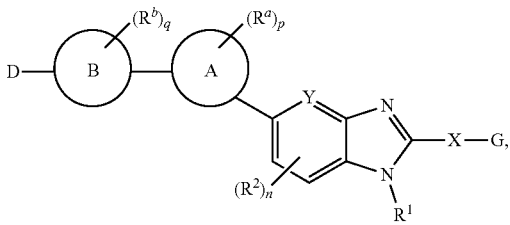

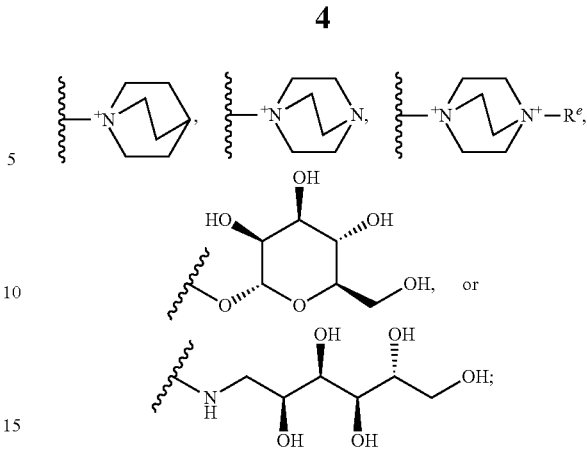

or a pharmaceutically acceptable salt, solvate, stereoisomer, or prodrug thereof, wherein: X is —O—, —S—, —NR$^3$—, —C(O)—, —C(O)O—, —C(O)NR$^3$—, —NR$^3$C(O)—, —SO$_2$—, or —SO$_2$NR$^3$—;

wherein ** indicates the attachment point to G;

Y is N, CH, or CR$^2$;

G is C$_1$-C$_5$ alkyl, —(CH$_2$)$_j$-(C$_3$-C$_{10}$ cycloalkyl), —(CH$_2$)$_j$-(C$_{4-10}$ Cycloalkenyl), —(CH$_2$)$_j$-(aryl), —(CH$_2$)$_j$-(heteroaryl), —(CH$_2$)$_j$-(3- to 10-membered heterocycloalkyl), or —(CH$_2$)$_j$-(5- to 10-membered heterocycloalkenyl), which is substituted with 1, 2, 3, or 4 substituents selected from —(CH$_2$)$_h$—C(O)OR$^7$, —(CH$_2$)$_h$—P(O)(R$^7$)OR$^7$, —(CH$_2$)$_h$—P(O)(OR$^7$)$_2$, —(CH$_2$)$_h$—S(O)$_2$OR$^7$, —and —(CH$_2$)$_n$OH; and is further optionally substituted with 1, 2, 3, or 4 substituents selected from C$_1$-C$_6$ alkyl, C$_3$-C$_6$ cycloalkyl, C$_1$-C$_6$ hydroxyalkyl, C$_1$-C$_6$ fluoroalkyl, —O—(C$_1$-C$_6$ alkyl), =O and =S;

is aryl, heteroaryl, or absent; wherein if

is —C≡C— or absent, then p is 0;

is aryl, heteroaryl, cycloalkyl, heterocycloalkyl, C$_{5-10}$ Cycloalkenyl, or 5- to 10-membered heterocycloalkenyl;

D is K, -Z-NR$^5$R$^6$, or R$^c$;

Z is —(CH$_2$)$_r$—, —(CH(CH$_3$)—, *—(CH$_2$)$_r$-C(=O)—, or *—(CH$_2$)r—S(=O)$_2$—, where * represents attachment to

;

K is —SO$_2$OH, —S(O)OH, —P(O)(OH)(R$^d$), —P(O)(OH)(OR$^d$), —CH$_2$P(O)(OH)(OR$^d$), —B(OR$^d$)(OH), —NHC(O)H, —N(R$^d$)C(O)NHSO$_2$(R$^d$), —C(O)NHSO$_2$(R$^d$), —SO$_2$NHC(O)(R$^d$), —NHC(O)NH(R$^d$), —N(R$^d$)C(=N(R$^d$)N(R$^d$)$_2$, —N(R$^d$)C(=NH)NHC(=NH)NH$_2$, each R$^a$ and R$^b$ is independently halogen, —CN, —OH, —OR$^{13}$, —NR$^{14}$R$^{14}$, —C(O)R$^{13}$, —C(O)OR$^{13}$, —C(O)OR$^{14}$, —OC(O)R$^{13}$, —C(O)NR$^{14}$R$^{14}$, —NR$^{14}$C(O)R$^{14}$, —NR$^{14}$C(O)NR$^{14}$R$^{14}$, —OC(O)NR$^{14}$R$^{14}$, —NR$^{14}$C(O)OR$^{14}$, —OC(O)OR$^{14}$, C$_1$-C$_6$ alkyl, C$_2$-C$_6$ alkenyl, C$_2$-C$_6$ alkynyl, C$_3$-C$_6$ cycloalkyl, 4- to 6-membered heterocycloalkyl, phenyl, or monocyclic heteroaryl, wherein the alkyl, alkenyl, akynyl, cycloalkyl, heterocycloalkyl, phenyl, or heteroaryl are unsubstituted or substituted by 1, 2, or 3 halogen or —OH groups;

R$^c$ is C$_{1-10}$ alkyl, C$_{2-10}$ alkenyl, C$_{2-10}$ alkynyl, C$_{3-10}$ cycloalkyl, c$_{1-10}$ alkoxyl, or —[(C(R$^d$)$_2$)$_s$-V]$_t$—R$^9$; wherein each V is independently —C(R$^d$)$_2$O—, —C(R$^d$)$_2$NR$^d$—, —C(R$^d$)$_2$N$^+$(R$^d$)$_2$—, —N(R$^d$)—C(O)—N(R$^d$)—, —C(O)N(R$^d$)—, —C(R$^d$)$_2$SO$_2$—, or —C(R$^d$)$_2$S(O)—; and wherein each alkyl, alkenyl, alkynyl, cycloalkyl, and alkoxyl is substituted by 1-6 groups selected from —N(R$^e$)$_3$$^+$, K, and -Z-NR$^5$R$^6$; or wherein each alkyl, alkenyl, alkynyl, cycloalkyl, and alkoxyl is substituted by 2-6 groups selected from —CO$_2$H, —OH, and —N(R$^d$)$_2$;

each R$^d$ is independently hydrogen, C$_{1-6}$ alkyl or C$_{3-6}$ cycloalkyl; wherein the alkyl and cycloalkyl are unsubstituted or substituted by 1-3 halogen or —OH groups;

each R$^e$ is independently C$_{1-6}$ alkyl or C$_{3-6}$ cycloalkyl; wherein the alkyl and cycloalkyl are unsubstituted or substituted by 1-3 halogen or —OH groups;

R$^1$ is hydrogen or C$_1$-C$_{b\ 4}$ alkyl;

each R$^2$ is independently halogen, —CN, C$_1$-C$_4$ alkyl, C$_1$-C$_4$ fluoroalkyl, or C$_3$-C$_6$ cycloalkyl;

R$^3$ is hydrogen or C$_1$-C$_4$ alkyl;

R$^5$ is C$_6$-C$_{10}$ alkyl that is substituted by 5 to 9 —OH groups;

or R$^5$ is C$_{1-10}$ alkyl, C$_{2-10}$ alkenyl, C$_{2-10}$ alkynyl, C$_{3-10}$ Cycloalkyl, C$_{5-10}$ cycloalkenyl, 3- to 8-membered heterocycloalkyl, or 5- to 10-membered heterocycloalkenyl; wherein the alkyl, alkenyl, alkynyl, cycloalkyl, cycloalkenyl, heterocycloalkyl, or heterocycloalkenyl is substituted by 1-6 groups selected from —N(R$^e$)$_3$$^+$ and K; or wherein the alkyl, alkenyl, alkynyl, cycloalkyl, cycloalkenyl, heterocycloalkyl, or heterocycloalkenyl is substituted by 2-6 groups selected from —CO$_2$H, —OH, and —N(R$^d$)$_2$; and wherein the alkyl, alkenyl, alkynyl, cycloalkyl, cycloalkenyl, heterocycloalkyl, or heterocycloalkenyl is optionally further substituted by 1, 2, or 3 R$^f$ groups;

each R$^f$ is independently halogen, —CN, —OH, —OR$^{13}$, —NR$^{14}$R$^{14}$, —C(O)R$^{13}$, —C(O)OR$^{14}$, —OC(O)R$^{13}$, —C(O)NR$^{14}$R$^{14}$, —NR$^{14}$C(O)R$^{14}$, —NR$^{14}$C(O)NR$^{14}$R$^{14}$, —OC(O)NR$^{14}$R$^{14}$, —NR$^{14}$C(O)OR$^{14}$, —OC(O)OR$^{14}$, C$_1$-C$_6$ alkyl, C$_2$-C$_6$ alkenyl, C$_2$-C$_6$ alkynyl, C$_3$-C$_6$ cycloalkyl, 4- to 6-membered heterocycloalkyl, phenyl, or monocyclic heteroaryl, wherein the alkyl, alkenyl, akynyl, cycloalkyl, heterocycloalkyl, phenyl, or heteroaryl are unsubstituted or substituted by 1, 2, or 3 halogen or —OH groups;

or $R^5$ is —[$C(R^d)_2)_s$—V]$_t$—$R^9$; wherein each V is independently —$C(R^d)_2O$—, —$C*R^d)_2NR^d$—, —$C(R^d)_2$—, —$N(R^{d)-2}$- —$N(R^d)$—C(O)—$N(R^d)$—, —C(O)N($R^d$)—, $C(R^d)_2SO_2$—, or —$C(R^d)_2S(O)$-;

or $R^5$ is —($C_1$-$C_6$ alkylene)—aryl, or —($C_1$-$C_6$ alkylene)-heteroaryl; wherein the aryl or heteroaryl is substituted by 1-6 groups selected from —$CO_2H$, —OH, —$N(R^d)_2$, —$N(R^e)_3^+$, and K; and wherein the alkylene is unsubstituted or substituted by 1, 2, or 3 $R^f$ groups; $R^6$ is hydrogen, $C_{1-6}$ alkyl, or $C_{3-6}$ cycloalkyl; wherein the alkyl and cycloalkyl are unsubstituted or substituted by 1-3 groups independently selected from halogen, —CN, —OH, —$OR^{13}$, —$NR^{14}R^{14}$, —$C(O)R^{13}$, —$C(O)OR^{14}$, —$OC(O)R^{13}$, —$C(O)NR^{14}R^{14}$, —$NR^{14}C(O)R^{14}$—$NR^{14}C(O)NR^{14}R^{14}$, —$OC(O)NR^{14}R^{14}$, —$NR^{14}C(O)OR^{14}$, —$OC(O)OR^{14}$, or —$P(O)(OR^{14})_2$;

or $R^5$ and $R^6$ are taken together with the nitrogen to which they are attached to form a 3- to 6-membered N-heterocycloalkyl which is unsubstituted or substituted with 1-6 groups selected from —$CH_3$, —$CH_2OH$, —$CH_2NH_2$, —$CH_2CH_2OH$, —$CH_2OCH_2CH_2OH$, —$N(R^e)_3^+$, and K; or with 2-6 groups selected from —$CO_2H$, —OH, —$CH_2OH$, —$CH_2NH_2$, —$CH_2CH_2OH$, —$CH_2OCH_2CH_2OH$, and —$N(R^d)_2$;

each $R^7$ is independently hydrogen or $C_1$-$C_4$ alkyl;

$R^9$ is hydrogen, $C_{1-8}$ alkyl, $C_{2-8}$ alkenyl, $C_{2-8}$ alkynyl, $C_{3-8}$ cycloalkyl, $C_{5-8}$ cycloalkenyl, 3 - to 8-membered heterocycloalkyl, phenyl, naphthyl, monocyclic heteroaryl, or bicyclic heteroaryl, wherein the alkyl, alkenyl, alkynyl, cycloalkyl, cycloalkenyl, heterocycloalkyl phenyl, naphthyl, monocyclic heteroaryl, or bicyclic heteroaryl is unsubstituted or substituted by 1-6 groups selected from —OH, —$CO_2H$, —$N(R^e)_2$, —$N(R^e)_3^+$, and K;

each $R^-$is independently $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl; and each $R^{14}$ is independently hydrogen, $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl; or two $R^{14}$ on the same nitrogen atom are taken together with the nitrogen to which they are attached to form a 3- to 6-membered N-heterocycloalkyl;

each h is independently 0-4;

j is 0-4;

n is 0-2;

p is 0-3;

q is 0-3;

r is 0-3;

each s is independently 1-6; and each t is independently 1-6.

Any combination of the groups described above or below for the various variables is contemplated herein. Throughout the specification, groups and substituents thereof are chosen by one skilled in the field to provide stable moieties and compounds.

In some embodiments, Y is N or CH; $R^1$ is hydrogen or methyl; and each $R^2$ is independently —F, —Cl, —CN, methyl, ethyl, isopropyl, or —$CF_3$. In some embodiments, Y is N; $R^1$ is hydrogen; $R^2$ is —F, —Cl, or —CN; and n is 1.

In some embodiments,

is aryl or heteroaryl; and

is aryl, heteroaryl, cycloalkyl, heterocycloalkyl, $C_{5-10}$ Cycloalkenyl, or 5- to 10-membered heterocycloalkenyl. In some embodiments,

is phenyl or 5- or 6-membered monocyclic heteroaryl; and

is phenyl, 5- or 6-membered monocyclic heteroaryl, $C_3$-$C_6$ cycloalkyl, 3- to 8-membered heterocycloalkyl, or 5- to 10-membered heterocycloalkenyl.

In some embodiments, the compound of Formula (I), or a pharmaceutically acceptable salt, solvate, stereoisomer, or prodrug thereof, is a compound of Formula (II):

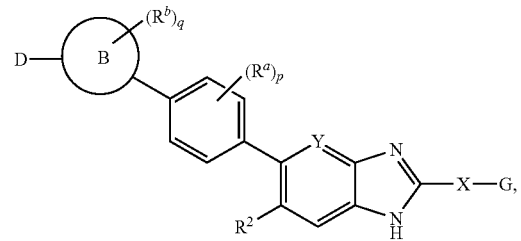

Formula (II)

or a pharmaceutically acceptable salt, solvate, stereoisomer, or prodrug thereof, wherein:

is phenyl, $C_3$-$C_6$ cycloalkyl, 3- to 8-membered heterocycloalkyl, or 5- to 10-membered bicyclic heterocycloalkenyl.

In some embodiments, the compound of Formula (I), or a pharmaceutically acceptable salt, solvate, stereoisomer, or prodrug thereof, is a compound of Formula (III):

Formula (III)

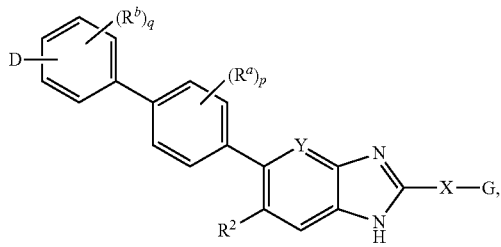

or a pharmaceutically acceptable salt, solvate, stereoisomer, or prodrug thereof In some embodiments, each $R^a$ and $R^b$ is independently halogen, —CN, —OH, —$OR^{13}$, —$NR^{14}R^{14}$, —C(O)$OR^{14}$, —C(O)$NR^{14}R^{14}$, $C_1$-$C_6$ alkyl, or $C_1$-$C_6$ fluoroalkyl; p is 0 or 1; and q is 0 or 1. In some embodiments, p is 0; and q is 0.

In some embodiments, the compound of Formula (I), or a pharmaceutically acceptable salt, solvate, stereoisomer, or prodrug thereof, is a compound of Formula (IV):

Formula (IV)

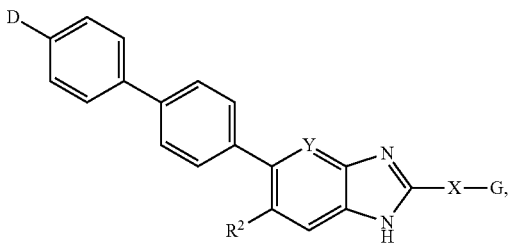

or a pharmaceutically acceptable salt, solvate, stereoisomer, or prodrug thereof.

In some embodiments, X is —O—, —S—, —$NR^3$—, —C(O)$NR^3$—, —$NR^3$C(O)—, or —$SO_2NR^3$—; wherein  indicates the attachment point to G; and $R^3$ is hydrogen or methyl. In some embodiments, X is —O— or —S—. In some embodiments, X is —O—.

In some embodiments, G is $C_1$-$C_5$ alkyl, $C_3$-$C_{10}$ Cycloalkyl, —$CH_2$—($C_3$—$C_{10}$ cycloalkyl), aryl, 3-to 10-membered heterocycloalkyl, or 5- to 10-membered heterocycloalkenyl, which is substituted with 1, 2, 3, or 4 substituents selected from —$(CH_2)_h$-C(O)$OR^7$, —$(CH_2)_h$—P(O)($R^7$)$OR^7$, —$(CH_2)_h$—P(O)($OR^7$)$_2$, —$(CH_2)_h$—S(O)$_2OR^7$, -and —$(CH_2)_h$OH; and is further optionally substituted with 1, 2, 3, or 4 substituents selected from $C_1$-$C_6$ alkyl, $C_3$-$C_6$ cycloalkyl, $C_1$-$C_6$ hydroxyalkyl, $C_1$-$C_6$ fluoroalkyl, and —O—($C_1$-$C_6$ alkyl); each $R^7$ is independently hydrogen, methyl, or ethyl; and h is 0-1. In some embodiments, G is $C_1$-$C_5$ alkyl, $C_3$-$C_{10}$ Cycloalkyl, —$CH_2$—($C_3$—$C_{10}$ cycloalkyl), aryl, 3- to 10-membered heterocycloalkyl, or 5- to 10-membered heterocycloalkenyl, which is substituted with 1, 2, 3, or 4 substituents selected from —C(O)OH, —$CH_2$C(O)OH, —P(O)(Me)OH, —P(O)(OH)$_2$, —S(O)$_2$OH, —OH, and —$CH_2$OH; and is further optionally substituted with 1, 2, 3, or 4 substituents selected from $C_1$-$C_6$ alkyl, $C_3$-$C_6$ cycloalkyl, $C_1$-$C_6$ hydroxyalkyl, $C_1$-$C_6$ fluoroalkyl, and —O-($C_1$-$C_6$ alkyl). In some embodiments, G is 3- to 10-membered heterocycloalkyl, which is substituted with 1, 2, 3, or 4 substituents selected from —C(O)OH, —$CH_2$C(O)OH, —P(O)(Me)OH, —P(O)(OH)$_2$, - S(O)$_2$OH, —OH, and —$CH_2$OH. In some embodiments, G is monocyclic 3- to 6-membered heterocycloalkyl containing 1 oxygen atom, which is substituted with 1 or 2 substituents selected from —C(O)OH, —$CH_2$C(O)OH, —P(O)(Me)OH, —P(O)(OH)$_2$, —S(O)$_2$OH, —OH, and —$CH_2$OH. In some embodiments, G is bicyclic 8- to 10-membered heterocycloalkyl containing 2 oxygen atoms, which is substituted with 1 or 2 substituents selected from —C(O)OH, —$CH_2$C(O)OH, —P(O)(Me)OH, —P(O)(OH)$_2$, —S(O)$_2$OH, —OH, and —$CH_2$OH. In some embodiments, G is $C_1$-$C_5$ alkyl, $C_3$-$C_6$ cycloalkyl, —$CH_2$-($C_3$-$C_6$ cycloalkyl), or phenyl, which is substituted with 1, 2, 3, or 4 substituents selected from —C(O)OH, —$CH_2$C(O)OH, —P(O)(Me)OH, —P(O)(OH)$_2$, —S(O)$_2$OH, —OH, and —$CH_2$OH; and is further optionally substituted with 1 or 2 substituents selected from $C_1$-$C_6$ alkyl, $C_3$-$C_6$ cycloalkyl, and $C_1$-$C_6$ hydroxyalkyl.

In some embodiments, —X—G is selected from:

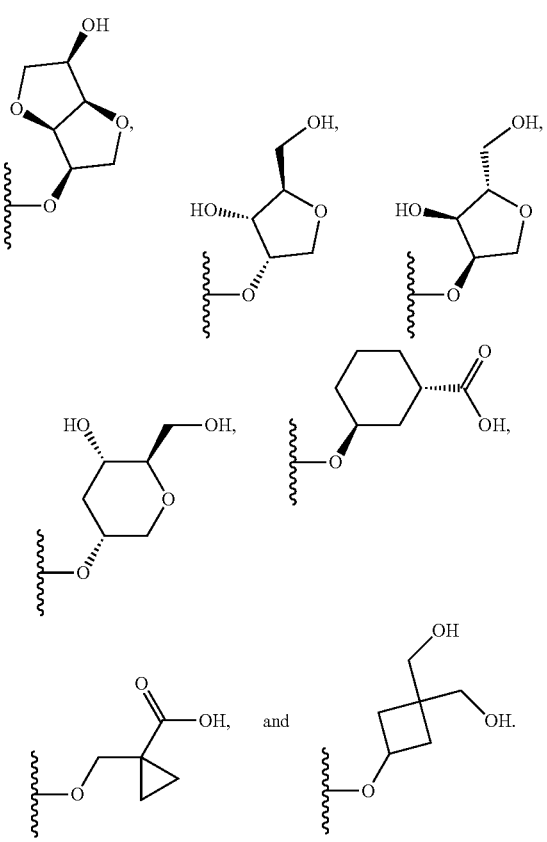

In some embodiments, D is K or -Z-$NR^5R^6$.

In some embodiments, D is K. In some embodiments, K is —$SO_2$OH, —P(O)(OH)($R^d$), —P(O)(OH)($OR^d$), —$CH_2$P(O)(OH)($OR^d$), —C(O)$NHSO_2$($R^d$), or —$SO_2$NHC(O)($R^d$); and each $R^d$ is independently hydrogen or $C_{1-6}$ alkyl. In some embodiments, K is —$SO_2$OH, —P(O)(OH)$_2$, —$CH_2$P(O)(OH)$_2$, —P(O)(OH)(Me), —P(O)(OH)(H), or —P(O)(OH)(OMe).

In some embodiments, D is -Z-$NR^5R^6$. In some embodiments, Z is —($CH_2$)—, —(CH($CH_3$))—, —C(=O)—, or —S(=O)$_2$—. In some embodiments, $R^5$ is $C_6$-$C_{10}$ alkyl that is substituted by 5 to 9 —OH groups; and $R^6$ is hydrogen or $C_{1-6}$ alkyl. In some embodiments, $R^5$ is $C_{1-10}$ alkyl which is substituted by 1-6 groups selected from —N($R^e$)$_3^+$ and K; or with 2-6 groups selected from —$CO_2$H, —OH, and —N $(R^d)_2$; and is optionally further substituted by 1, 2, or 3 $R^f$ groups; each $R^f$ is independently halogen, —CN, —OH, —OR$^{13}$, NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups; and R$^6$ is hydrogen or C$_{1-6}$ alkyl, which is unsubstituted or substituted by 1-3 groups independently selected from halogen, —CN, —OH, —OR$^{13}$, —NR$^{14}$R$^{14}$, C(O)OR$^{14}$, C(O)NR$^{14}$R$^{14}$, —NR$^{14}$C(O)R$^{14}$, —NR$^{14}$C(O)NR$^{14}$R$^{14}$, or —P(O)(OR$^{14}$)$_2$. In some embodiments, R$^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—; each R$^d$ is independently hydrogen or C$_{1-6}$ alkyl; R$^6$ is hydrogen or C$_{1-6}$ alkyl; and R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3^+$, and K. In some embodiments, R$^5$ is —(C$_1$-C$_6$ alkylene)—aryl, or —(C$_1$-C$_6$ alkylene)—heteroaryl; wherein the aryl or heteroaryl is substituted by 1-6 groups selected from —CO$_2$H, —OH, —N(R$^d$)$_2$, —N(R$^e$)$_3^+$, and K; and wherein the alkylene is unsubstituted or substituted by 1, 2, or 3 R$^f$ groups; and R$^6$ is hydrogen or C$_{1-6}$ alkyl. In some embodiments, R$^5$ and R$^6$ are taken together with the nitrogen to which they are attached to form a 3- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl. In some embodiments, K is —SO$_2$OH, —P(O)(OH)$_2$, —CH$_2$P(O)(OH)$_2$, —P(O)(OH)(Me), —P(O)(OH)(H), or —P(O)(OH)(OMe).

In some embodiments, D is

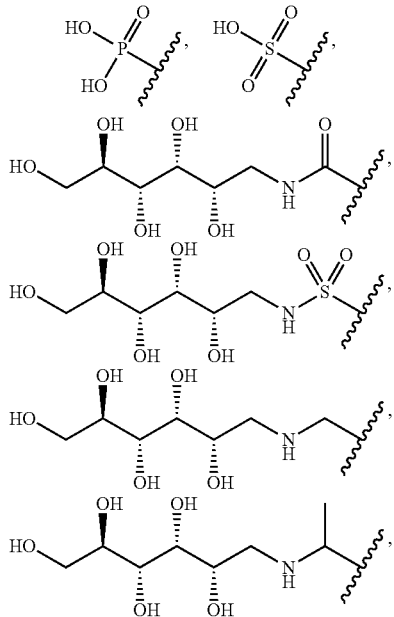

-continued

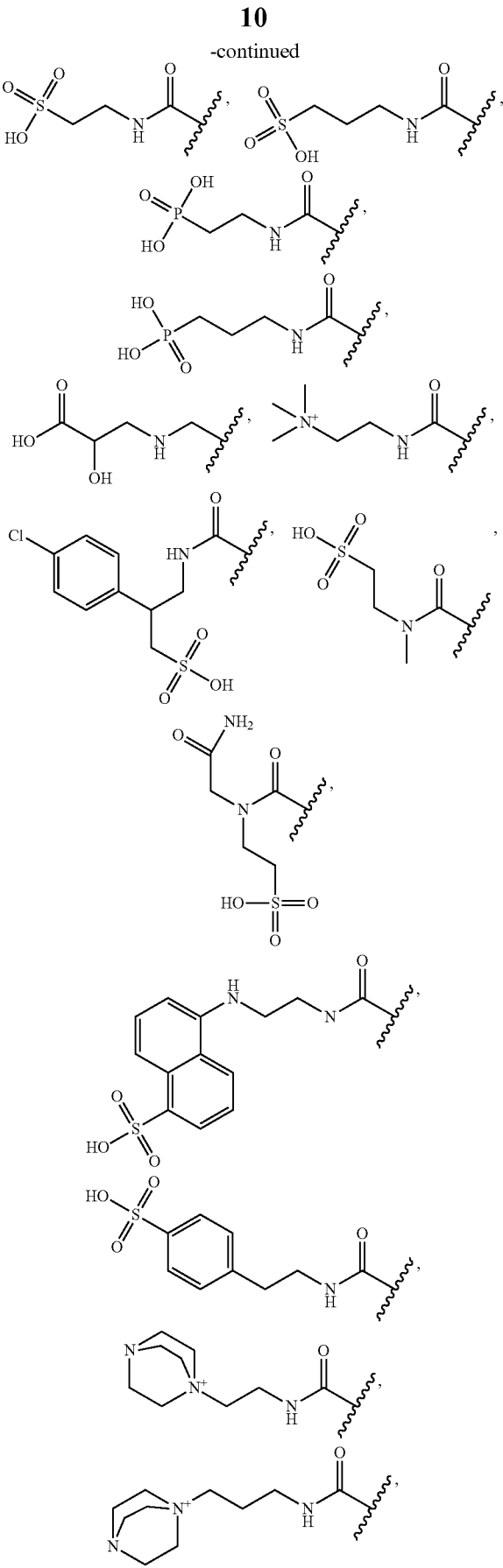

-continued

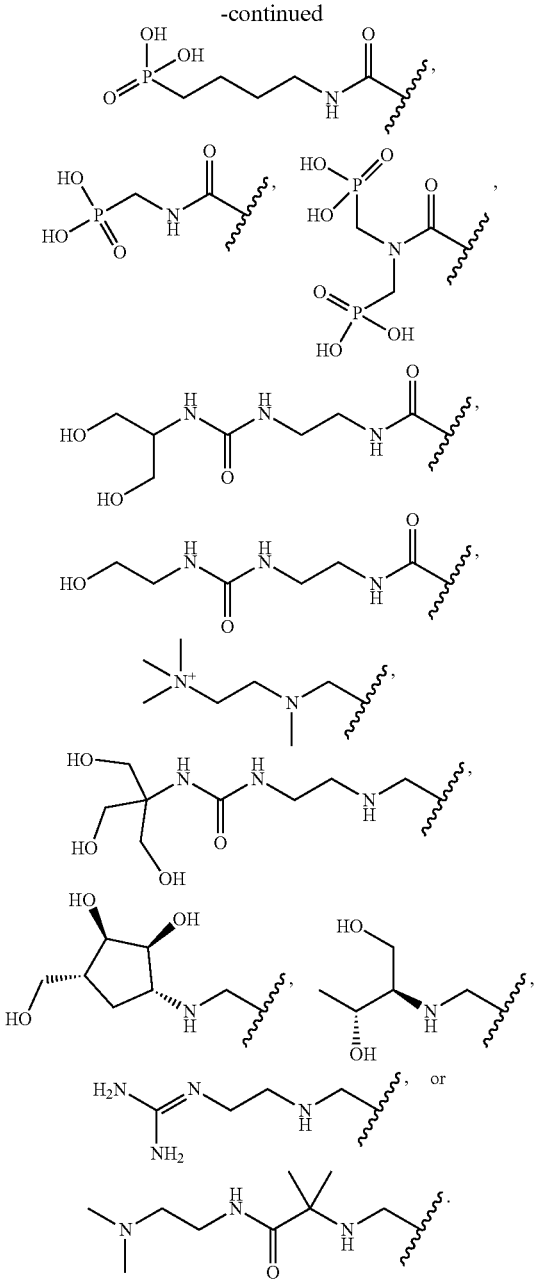

In some embodiments, the compound of Formula (I), or a pharmaceutically acceptable salt, solvate, stereoisomer, or prodrug thereof, is a compound of Formula (V):

Formula (V)

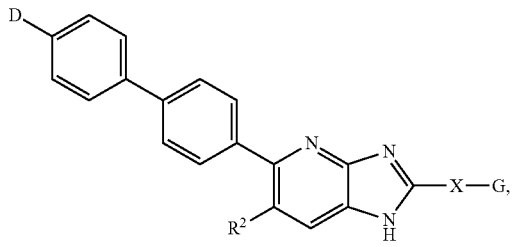

or a pharmaceutically acceptable salt, solvate, stereoisomer, or prodrug thereof, wherein:

$R^2$ is —F, —Cl, or —CN;

X is O or S;

G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

D is K or -Z-NR$^5$R$^6$.

In some embodiments, D is K; K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl.

In some embodiments, D is -Z-NR$^5$R$^6$; Z is —(CH$_2$)—, —(CH(CH$_3$))—, —C(=O)—, or —S(=O)$_2$-; and R$^5$ is C$_6$-C$_{10}$ alkyl that is substituted by 5 to 9 —OH groups; or R$^5$ is C$_{1-10}$ alkyl which is substituted by 1-6 groups selected from —N(R$^e$)$_3$$^+$ and K; or with 2-6 groups selected from —CO$_2$H, —OH, and —N(R$^d$)$_2$; and is optionally further substituted by 1, 2, or 3 R$^f$ groups; or R$^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—; each R$^d$ is independently hydrogen or C$_{1-6}$ alkyl; R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3$$^+$, and K; or R$^5$ is —(C$_1$-C$_6$ alkylene)—aryl, or —(C$_1$-C$_6$ alkylene)—heteroaryl; wherein the aryl or heteroaryl is substituted by 1-6 groups selected from —CO$_2$H, —OH, —N(R$^d$)$_2$, —N(R$^e$)$_3$$^+$, and K; and wherein the alkylene is unsubstituted or substituted by 1, 2, or 3 R$^f$ groups; R$^6$ is hydrogen or C$_{1-6}$ alkyl, which is unsubstituted or substituted by 1-3 groups independently selected from halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, or —P(O)(OR$^{14}$)$_2$; and or R$^5$ and R$^6$ are taken together with the nitrogen to which they are attached to form a 4- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3$$^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$; each R$^f$ is independently halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups. In some embodiments, R$^5$ is C$_6$-C$_{10}$ alkyl that is substituted by 5 to 9 —OH groups; and R$^6$ is hydrogen or C$_{1-6}$ alkyl.

In some embodiments, D is

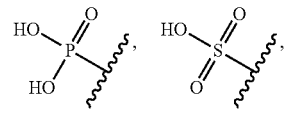

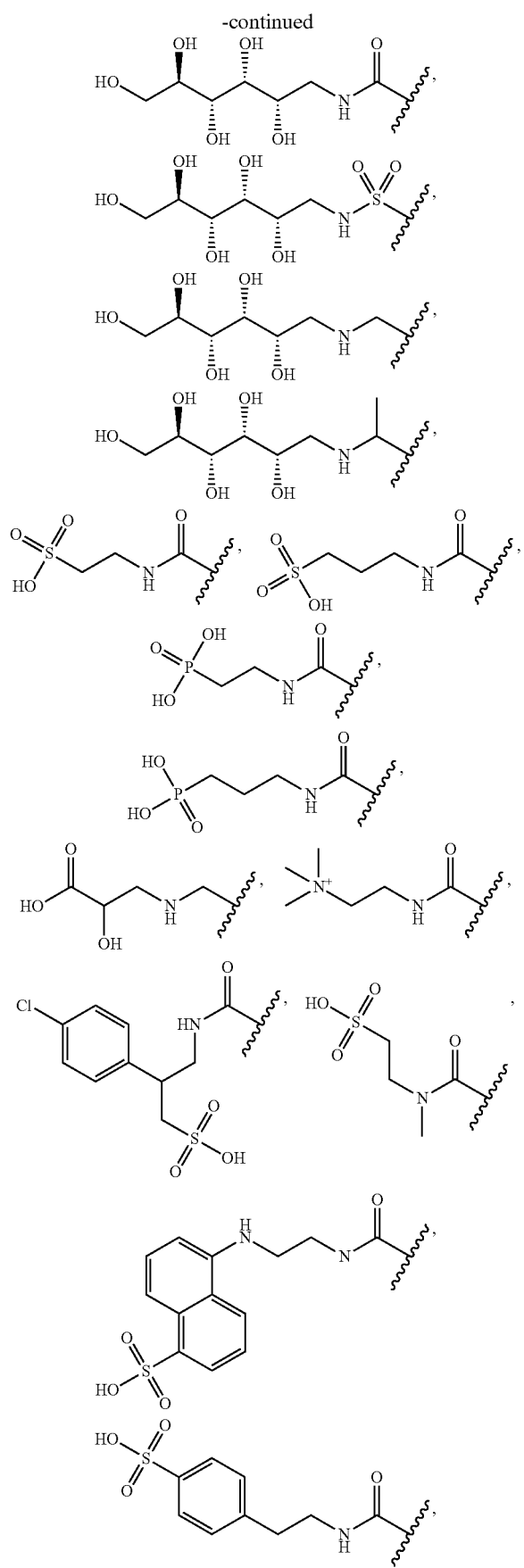
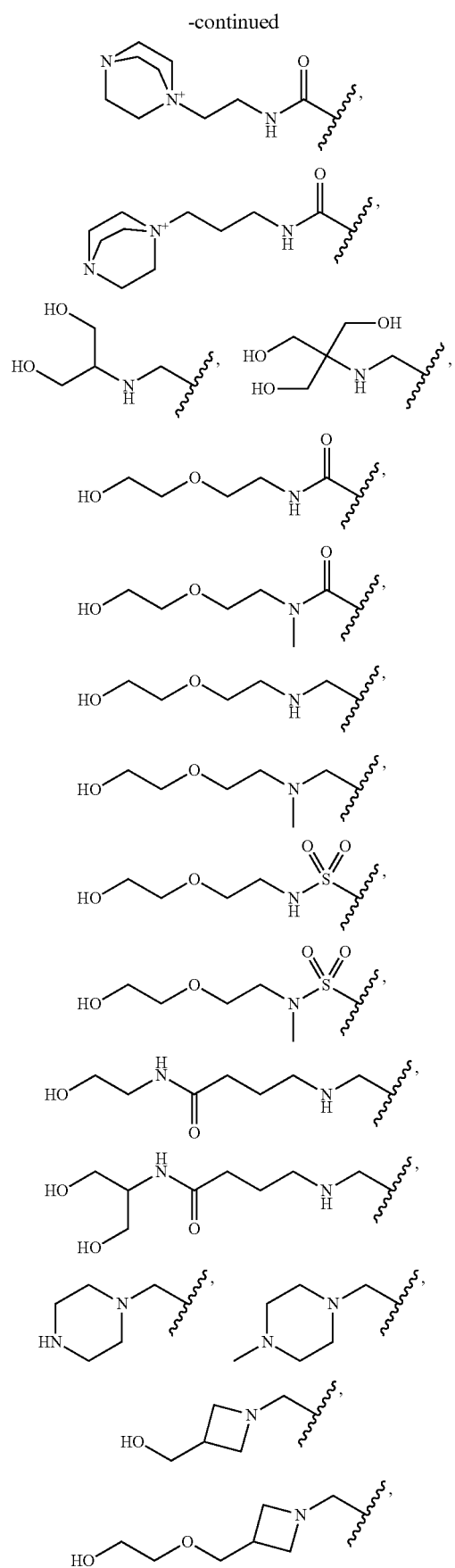

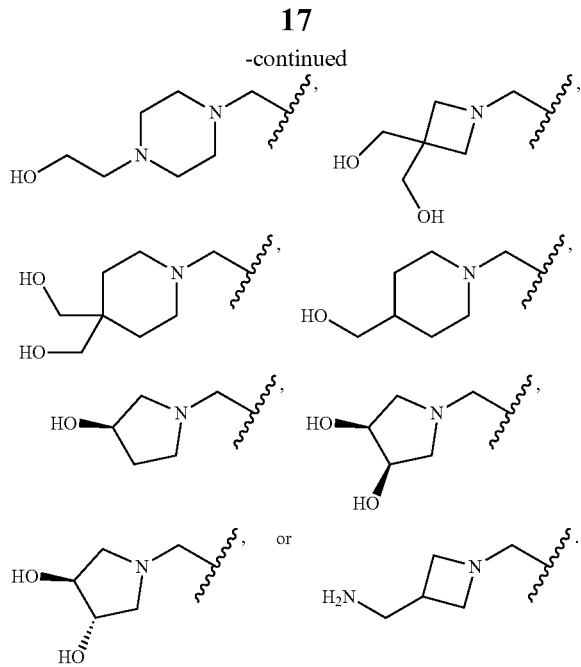

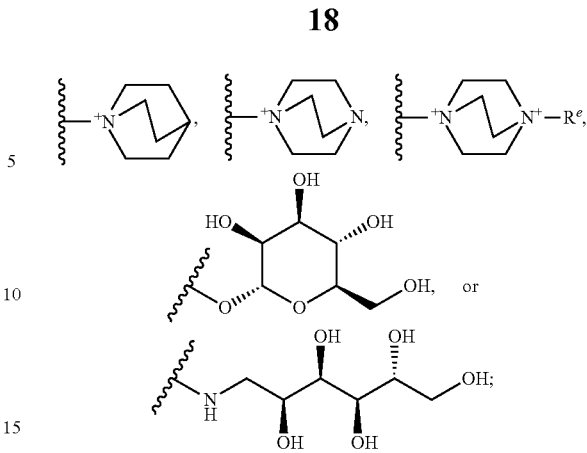

Also disclosed herein, in some embodiment is a compound of Formula (III):

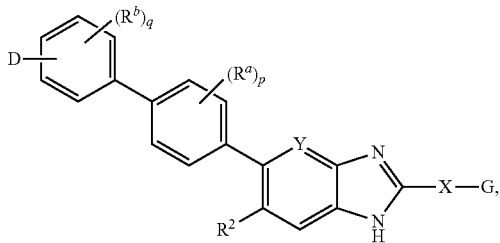

Formula (III)

or a pharmaceutically acceptable salt, solvate, stereoisomer, or prodrug thereof, wherein:

X is —O— or —S—;

Y is N or CH;

G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH; or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

D is K or -Z-NR$^5$R$^6$;

Z is —(CH$_2$)—, —(CH(CH$_3$))—, —C(=O)—, or —S(=O)$_2$-;

K is —SO$_2$OH, —S(O)OH, —P(O)(OH)(R$^d$), —P(O)(OH)(OR$^d$), —CH$_2$P(O)(OH)(OR$^d$), —B(OR$^d$)(OH), —NHC(O)H, —N(R$^d$)C(O)NHSO$_2$(R$^d$), —C(O)NHSO$_2$(R$^d$), —SO$_2$NHC(O)(R$^d$), —NHC(O)NH(R$^d$), —N(R$^d$)C(=N(R$^d$)N(R$^d$)$_2$, —N(R$^d$)C(=NH)NHC(=NH)NH$_2$,

R$^a$ and R$^b$ are each independently halogen, —CN, —OH, —OR$^{13}$, —NR$^{14}$R$^{14}$, —C(O)OR$^{14}$, —C(O)NR$^{14}$R$^{14}$, C$_1$-C$_6$ alkyl, or C$_1$-C$_6$ fluoroalkyl;

each R$^d$ is independently hydrogen or C$_{1-6}$ alkyl;

each R$^e$ is independently C$_{1-6}$ alkyl;

each R$^2$ is independently halogen, —CN, C$_1$-C$_4$ alkyl, C$_1$-C$_4$ fluoroalkyl, or C$_3$-C$_6$ cycloalkyl;

R$^5$ is C$_6$-C$_{10}$ alkyl that is substituted by 5 to 9 —OH groups;

or R$^5$ is C$_{1-10}$ alkyl which is substituted by 1-6 groups selected from —N(R$^e$)$_3$$^+$ and K; or with 2-6 groups selected from —CO$_2$H, —OH, and —N(R$^d$); and is optionally further substituted by 1, 2, or 3 R$^f$ groups;

each R$^f$ is independently halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups;

or R$^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—;

or R$^5$ is —(C$_1$-C$_6$ alkylene)—aryl, or —(C$_1$-C$_6$ alkylene)—heteroaryl; wherein the aryl or heteroaryl is substituted by 1-6 groups selected from —CO$_2$H, —OH, —N(R$^d$)$_2$, —N(R$^e$)$_3$$^+$, and K; and wherein the alkylene is unsubstituted or substituted by 1, 2, or 3 R$^f$ groups;

R$^6$ is hydrogen or C$_{1-6}$ alkyl;

or R$^5$ and R$^6$ are taken together with the nitrogen to which they are attached to form a 3- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3$$^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$;

R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3$$^+$, and K;

each R$^{13}$ is independently c$_1$-C$_6$ alkyl, C$_2$-C$_6$ alkenyl, C$_2$-C$_6$ alkynyl, 0-C$_6$ fluoroalkyl, C$_3$-C$_6$ cycloalkyl, 3- to 6-membered heterocycloalkyl, phenyl, or monocyclic heteroaryl; and each R$^{14}$ is independently hydrogen, C$_1$-C$_6$ alkyl, C$_2$-C$_6$ alkenyl, C$_2$-C$_6$ alkynyl, C$_1$-C$_6$ fluoroalkyl, C$_3$-C$_6$ cycloalkyl, 3- to 6-membered heterocycloalkyl, phenyl, or monocyclic heteroaryl;

or two $R^{14}$ on the same nitrogen atom are taken together with the nitrogen to which they are attached to form a 3- to 6-membered N-heterocycloalkyl;

p is 0 or 1;
q is 0 or 1;
each s is independently 1-6; and
each t is independently 1-6.

In some embodiments, $R^2$ is —F, —Cl, or —CN; $r^a$ is —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF2, or —CF$_3$; and $R^b$ is —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF$_2$, or —CF$_3$.

In some embodiments, the compound of Formula (III), or a pharmaceutically acceptable salt, solvate, stereoisomer, or prodrug thereof, is a compound of Formula (IV):

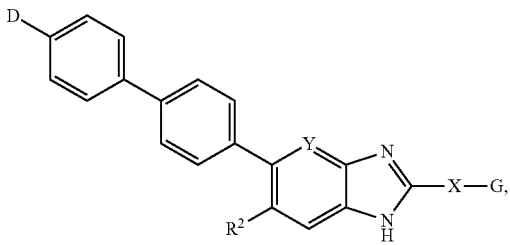

Formula (IV)

or a pharmaceutically acceptable salt, solvate, stereoisomer, or prodrug thereof.

In some embodiments, X is —O—.

In some embodiments, G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH.

In some embodiments, —X—G is selected from:

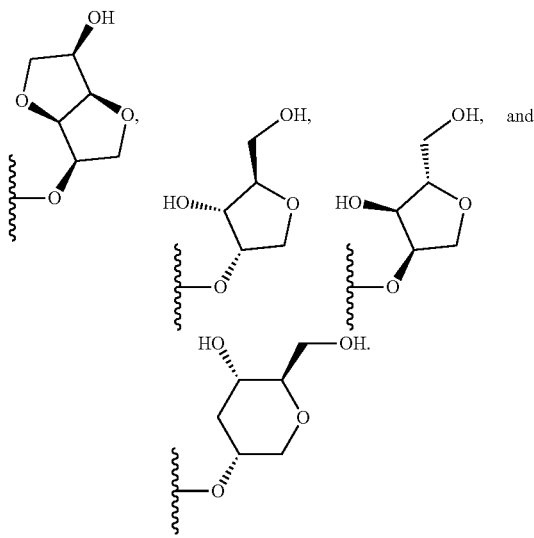

In some embodiments, Y is N. In some embodiments, Y is CH.

In some embodiments, D is K; and K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$).

In some embodiments, D is -Z-NR$^5$R$^6$. In some embodiments, Z is —(CH$_2$)—, —C(=O)—, or —S(=O)$_2$—. In some embodiments, $R^5$ is C$_6$-C$_{10}$ alkyl that is substituted by 5 to 9 —OH groups. In some embodiments, $R^5$ is C$_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 R$^f$ groups; and each R$^f$ is independently halogen, —CN, —OH, —OR$^{13}$, NR$^{14}$R$^{14}$, —C(O)OR$^{14}$, —C(O)NR$^{14}$R$^{14}$R$^{14}$, —NR$^{14}$C(O)R$^{14}$, —NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups. In some embodiments, $R^5$ is —[C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—; each R$^d$ is independently hydrogen or C$_{1-6}$ alkyl; $R^6$ is hydrogen or C$_{1-6}$ alkyl; and $R^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3^+$, and K. In some embodiments, $R^5$ and $R^6$ are taken together with the nitrogen to which they are attached to form a 3- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$. In some embodiments, $R^5$ and $R^6$ are taken together with the nitrogen to which they are attached to form a 4- to 6-membered N-heterocycloalkyl which is substituted with 2-4 groups selected from —OH and —CH$_2$OH. In some embodiments, $R^5$ is C$_6$-C$_{10}$ alkyl that is substituted by 5 to 9 —OH groups; or $R^5$ is C$_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 R$^f$ groups. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$). In some embodiments, K is —SO$_2$OH, —P(O)(OH)$_2$, —CH$_2$P(O)(OH)$_2$, —P(O)(OH)(Me), —P(O)(OH)(H), or —P(O)(OH)(OMe). In some embodiments, K is —SO$_2$OH or —P(O)(OH)$_2$.

In some embodiments, D is

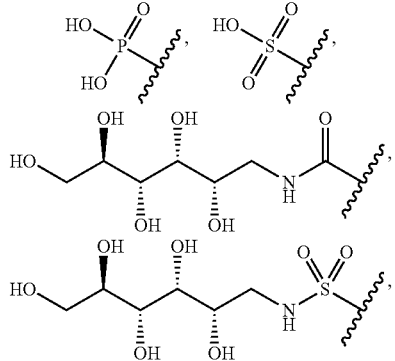

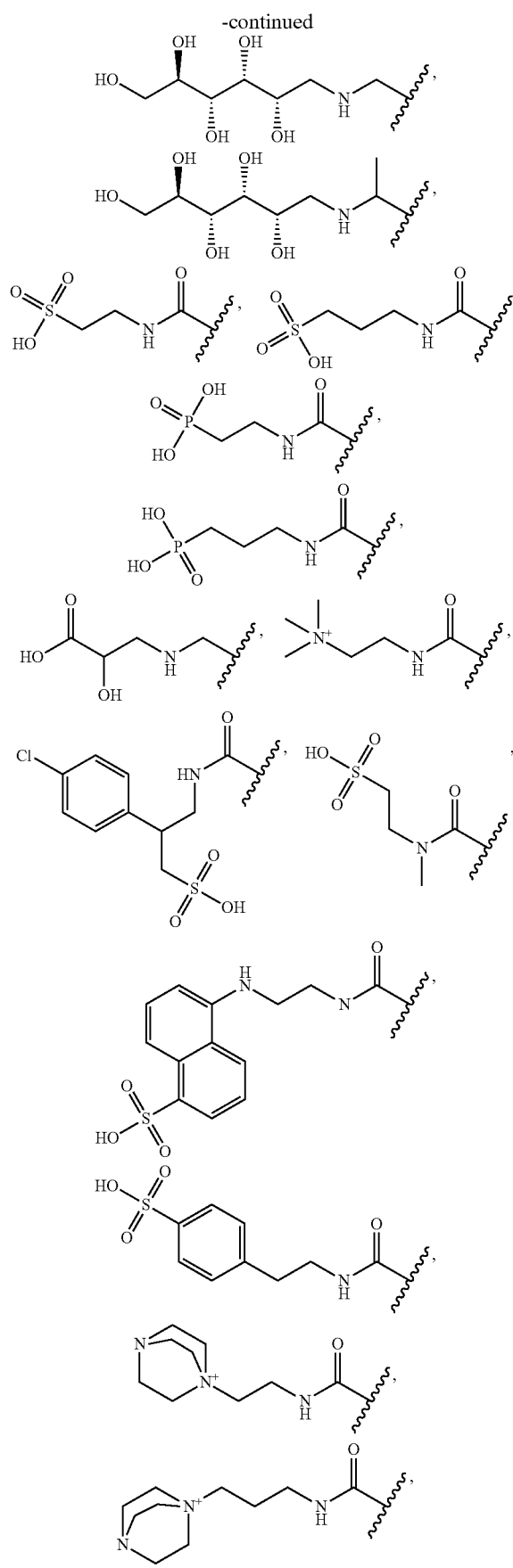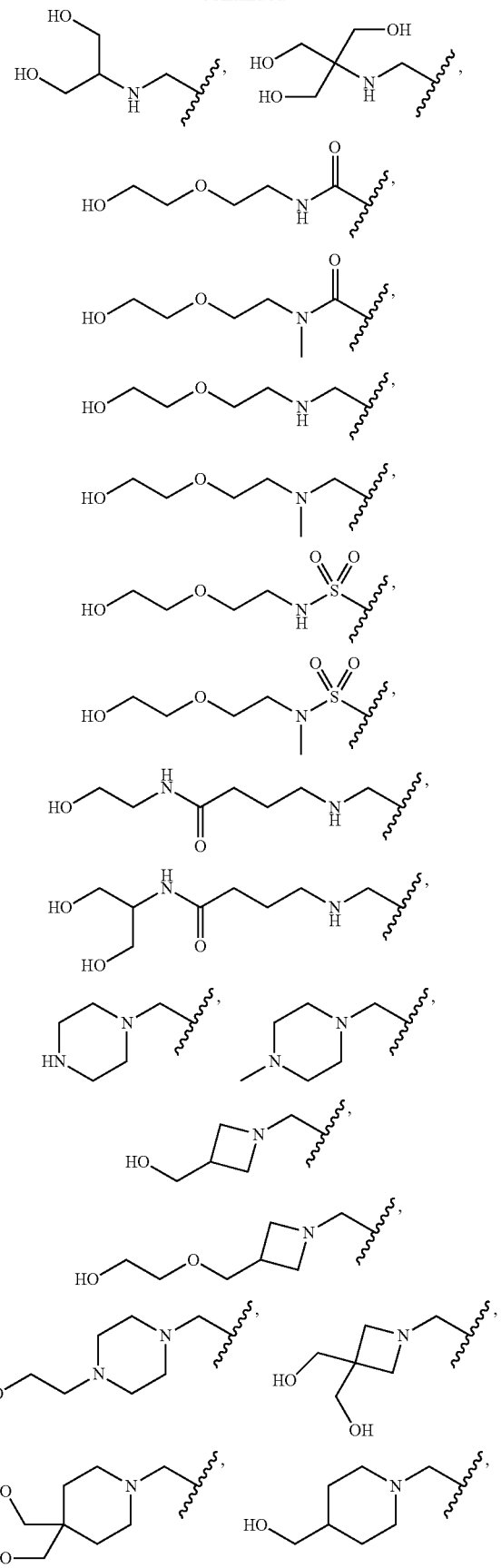

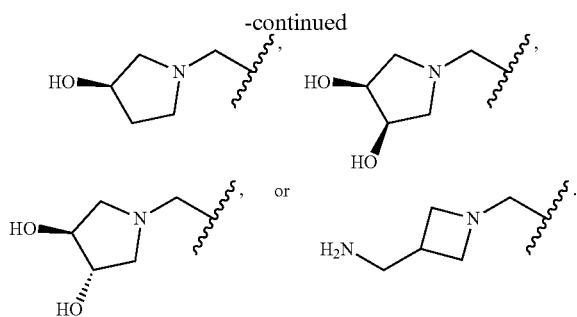

Disclosed herein, in some embodiments, are pharmaceutical compositions comprising a compound disclosed herein, or a pharmaceutically acceptable salt, solvate, stereoisomer, or prodrug thereof, and at least one pharmaceutically acceptable excipient.

Disclosed herein, in some embodiments, are methods of treating an adenosine 5'-monophosphate-activated protein kinase (AMPK) associated condition or disorder in a subject in need thereof, the method comprising administering to the subject a therapeutically effective amount of a compound disclosed herein, or a pharmaceutically acceptable salt, solvate, stereoisomer, or prodrug thereof. In some embodiments, the condition or disorder involves the gut-brain axis. In some embodiments, the condition or disorder is a nutritional disorder. In some embodiments, the condition or disorder is short bowel syndrome, intestinal failure, or intestinal insufficiency. In some embodiments, the condition or disorder is associated with systemic infection and inflammation from having a leaky gut barrier. In some embodiments, the condition or disorder is metabolic syndrome, obesity, type 2 diabetes, coronary artery disease, fatty liver, nonalcoholic steatohepatitis (NASH), cirrhosis, hepatic encephalopathy, fibrotic disorders including scleroderma, inflammatory bowel disease including Crohn's disease, ulcerative colitis, and checkpoint inhibitor-induced colitis, psoriasis, celiac disease, necrotizing enterocolitis, gastrointestinal injury resulting from toxic insults such as radiation or chemotherapy, environmental enteric dysfunction, allergy including food allergy, celiac sprue, and childhood allergy, graft vs. host disease, irritable bowel syndrome, spontaneous bacterial peritonitis, ischemic colitis, sclerosing cholangitis, Alzheimer's disease, Parkinson's disease, cancer including colorectal cancer, depression, autism, or a combination thereof.

Also disclosed herein, in some embodiments, are methods of treating gastrointestinal injury resulting from toxic insult, the method comprising administering to the subject a therapeutically effective amount of a compound disclosed herein, or a pharmaceutically acceptable salt, solvate, stereoisomer, or prodrug thereof. In some embodiments, the toxic insult is from radiation, chemotherapy, or a combination thereof. In some embodiments, the toxic insult is radiation-induced. In some embodiments, the toxic insult is chemotherapy-induced.

Also disclosed herein, in some embodiments, is the use of a compound disclosed herein, or a pharmaceutically acceptable salt, solvate, stereoisomer, or prodrug thereof, as a medicine.

Also disclosed herein, in some embodiments, is the use of a compound disclosed herein, or a pharmaceutically acceptable salt, solvate, stereoisomer, or prodrug thereof, for the treatment of an adenosine 5'-monophosphate-activated protein kinase (AMPK) associated condition or disorder in a subject in need thereof. In some embodiments, the condition or disorder involves the gut-brain axis. In some embodiments, the condition or disorder is a nutritional disorder. In some embodiments, the condition or disorder is short bowel syndrome, intestinal failure, or intestinal insufficiency. In some embodiments, the condition or disorder is associated with systemic infection and inflammation from having a leaky gut barrier. In some embodiments, the condition or disorder is metabolic syndrome, obesity, type 2 diabetes, coronary artery disease, fatty liver, nonalcoholic steatohepatitis (NASH), cirrhosis, hepatic encephalopathy, fibrotic disorders including scleroderma, inflammatory bowel disease including Crohn's disease, ulcerative colitis, and checkpoint inhibitor-induced colitis, psoriasis, celiac disease, necrotizing enterocolitis, gastrointestinal injury resulting from toxic insults such as radiation or chemotherapy, environmental enteric dysfunction, allergy including food allergy, celiac sprue, and childhood allergy, graft vs. host disease, irritable bowel syndrome, spontaneous bacterial peritonitis, ischemic colitis, sclerosing cholangitis, Alzheimer's disease, Parkinson's disease, cancer including colorectal cancer, depression, autism, or a combination thereof.

Also disclosed herein, in some embodiments, is the use of a compound disclosed herein, or a pharmaceutically acceptable salt, solvate, stereoisomer, or prodrug thereof, for the treatment of gastrointestinal injury resulting from toxic insult in a subject in need thereof. In some embodiments, the toxic insult is from radiation, chemotherapy, or a combination thereof. In some embodiments, the toxic insult is radiation-induced. In some embodiments, the toxic insult is chemotherapy-induced.

Also disclosed herein, in some embodiments, is the use of a compound disclosed herein, or a pharmaceutically acceptable salt, solvate, stereoisomer, or prodrug thereof, for the preparation of a medicament for the treatment of the diseases disclosed herein.

DETAILED DESCRIPTION OF THE INVENTION

This disclosure is directed, at least in part, to AMPK activators useful for the treatment of conditions or disorders involving the gut-brain axis. In some embodiments, the AMPK activators are gut-restricted compounds. In some embodiments, the AMPK activators are agonists, super agonists, full agonists, or partial agonists.

Compounds disclosed herein directly activate AMPK in the intestine without systemic engagement. The preferred compounds are more potent, efficacious at lower doses, and have decreased systemic exposure compared to other previously-known AMPK activators.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulas, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "comprising" (and related terms such as "comprise" or "comprises" or "having" or "including") is not intended to exclude that in other embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below:

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec- butyl, and t-butyl.

"Alkyl" refers to an optionally substituted straight-chain, or optionally substituted branched- chain saturated hydrocarbon monoradical having from one to about ten carbon atoms, or more preferably, from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3- methyl-1-butyl, 2-methyl-3-butyl, 2,2-dimethyl-1-propyl, 2-methyl-1-pentyl, 3-methyl-1-pentyl, 4- methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^a$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an $sp^2$-hybridized carbon or an $sp^3$-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=$CH_2$), n-propenyl (—CH=$CHCH_3$, —$CH_2$CH=$CH_2$), isopropenyl (—C($CH_3$)=$CH_2$), butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. Unless stated otherwise specifically in the specification, an alkenyl group is optionally substituted as described below by one or more of the following substituents: halo, cyano, nitro, oxo, thioxo, imino, oximo, trimethylsilanyl, —$OR^a$, —$SR^a$, —$OC(O)$—$R^f$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^a$, —$N(R^a)S(O)_tR^f$ (where t is 1 or 2), —$S(O)_tOR^a$ where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms, wherein an sp-hybridized carbon or an $sp^2$-hybridized carbon of the alkynyl residue is attached to the rest of the molecule by a single bond. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^a$, —$N(R^a)S(O)_tR^f$ (where t is 1 or 2), —$S(O)_tO(R^a)$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. Unless stated otherwise specifically in the specification, an alkylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$O(R$^a$) (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. Unless stated otherwise specifically in the specification, an alkenylene group is optionally substituted as described below by one or more of the following substituents: halo, cyano, nitro, oxo, thioxo, imino, oximo, trimethylsilanyl, —OR$^a$, —SR$^a$, —OC(O)—R$^f$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. Unless stated otherwise specifically in the specification, an alkynylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$O(R$^a$) (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkoxy" or "alkoxyl" refers to a radical bonded through an oxygen atom of the formula —O-alkyl, where alkyl is an alkyl chain as defined above.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from 6 to 18 carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. In some embodiments, the aryl is a $C_6$-$C_{10}$ aryl. In some embodiments, the aryl is a phenyl. Unless stated otherwise specifically in the specification, the term "aryl" or the prefix "ar-" (such as in "aralkyl") is meant to include aryl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—SR$^a$, R$^b$—OC(O)—R$^a$, —R$^b$—OC(O)—OR$^f$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$-C(O)N(R$^a$)$_2$, —R$^b$—O—R$^c$—C(O)N(R$^a$)$_2$, —R$^b$—N(R$^a$)C(O)OR$^f$, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, R$^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

An "arylene" refers to a divalent radical derived from an "aryl" group as described above linking the rest of the molecule to a radical group. The arylene is attached to the rest of the molecule through a single bond and to the radical group through a single bond. In some embodiments, the arylene is a phenylene. Unless stated otherwise specifically in the specification, an arylene group is optionally substituted as described above for an aryl group.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[1.1.1]pentyl, bicyclo[3.3.0]octyl, bicyclo[4.3.0]nonyl, cis-decalyl, trans-decalyl, bicyclo[2.1.1]hexyl, bicyclo[2.2.1]heptyl, bicyclo[2.2.2]octyl, bicyclo[3.2.2]nonyl, bicyclo[3.3.2]decyl, 7,7-dimethyl-bicyclo[2.2.1]heptyl, and the like. Unless otherwise stated specifically in the specification, the term "cycloalkyl" is meant to include cycloalkyl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, $-R^b-OR^a$, $-R^b-SR^a$, $-R^b-OC(O)-R^a$, $-R^b,-OC(O)-OR^f$, $-R^b-OC(O)-N(R^a)_2$, $-R^b-N(R^a)_2$, $-R^b-N^+(R^a)_3$, $-R^b-C(O)R^a$, $-R^b-C(O)OR^a$, $R^b-C(O)N(R^a)_2$, $-R^b-O-R^c-C(O)N(R^a)_2$, $-R^b-N(R^a)C(O)OR^f$, $-R^b-N(R^a)C(O)R^a$, $-R^bN(R^a)S(O)_tR^f$ (where t is 1 or 2), $-R^b-S(O)_tOR^a$ (where t is 1 or 2), $-R^b-S(O)_tR^f$ (where t is 1 or 2) and $-R^b-S(O))_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "cycloalkylene" refers to a divalent radical derived from a "cycloalkyl" group as described above linking the rest of the molecule to a radical group. The cycloalkylene is attached to the rest of the molecule through a single bond and to the radical group through a single bond. Unless stated otherwise specifically in the specification, a cycloalkylene group is optionally substituted as described above for a cycloalkyl group.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like.

"Haloalkoxy" or "haloalkoxyl" refers to an alkoxyl radical, as defined above, that is substituted by one or more halo radicals, as defined above.

"Fluoroalkoxy" or "fluoroalkoxyl" refers to an alkoxy radical, as defined above, that is substituted by one or more fluoro radicals, as defined above, for example, trifluoromethoxy, difluoromethoxy, fluoromethoxy, and the like.

"Hydroxyalkyl" refers to an alkyl radical, as defined above, that is substituted by one or more hydroxyl radicals, as defined above, e.g., hydroxymethyl, 1-hydroxyethyl, 2-hydroxyethyl, 2-hydroxypropyl, 3-hydroxypropyl, 1,2-dihydroxyethyl, 2,3-dihydroxypropyl, 2,3,4,5,6-pentahydroxyhexyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 8-membered heterocycloalkyl. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. More preferably, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, $-R^b$-$OR^3$, $-R^b-SR^a$, $-R^b-OC(O)-R^a$, $-R^b-OC(O)-OR^f$, $-R^b-OC(O)-N(R^a)_2$, $-R^b-N(R^a)_2$, $-R^b-N^+(R^a)_3$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^f$, $-R^b-N(R^a)C(O)R^a$, $-R^b-N(R^a)S(O)_tR^f$ (where t is 1 or 2), $-R^b-S(O)_tOR^a$ (where t is 1 or 2), $-R^b$-$S(O)_tR^f$ (where t is 1 or 2) and $-R^b-S(O))_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals.

"C-heterocycloalkyl" refers to a heterocycloalkyl radical as defined above and where the point of attachment of the heterocycloalkyl radical to the rest of the molecule is through a carbon atom in the heterocycloalkyl radical. A C-heterocycloalkyl radical is optionally substituted as described above for heterocycloalkyl radicals.

A "heterocycloalkylene" refers to a divalent radical derived from a "heterocycloalkyl" group as described above linking the rest of the molecule to a radical group. The heterocycloalkylene is attached to the rest of the molecule through a single bond and to the radical group through a single bond. Unless stated otherwise specifically in the specification, a heterocycloalkylene group is optionally substituted as described above for a heterocycloalkyl group.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. In some embodiments, the heteroaryl is a 5- to 10-membered heteroaryl. In some embodiments, the heteroaryl is a monocyclic heteroaryl, or a monocyclic 5- or 6-membered heteroaryl. In some embodiments, the heteroaryl is a 6,5-fused bicyclic heteroaryl. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b SR^a$, *—$R^b$—OC(O)—$R^a$, —$R^b$—OC(O)—$OR^f$, —$R^b$—OC(O)—N($R^a$)$_2$, —$R^b$—N($R^a$)$_2$, —$R^b$—N$^+$($R^a$)$_3$, —$R^b$-C(O)$R^a$, —$R^b$-C(O)$OR^a$, —$R^b$—C(O)N($R^a$)$_2$, —$R^b$—O—$R^c$-C(O)N($R^a$)$_2$, —$R^b$—N($R^a$)C(O)$OR^f$, —$R^b$—N($R^a$)C(O)$R^a$, —$R^b$—N($R^a$)S(O)$_t R^f$ (where t is 1 or 2), —$R^b$—S(O)$_t OR^a$ (where t is 1 or 2), —$R^b$—S(O)$_t R^f$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "heteroarylene" refers to a divalent radical derived from a "heteroaryl" group as described above linking the rest of the molecule to a radical group. The heteroarylene is attached to the rest of the molecule through a single bond and to the radical group through a single bond. Unless stated otherwise specifically in the specification, a heteroarylene group is optionally substituted as described above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be unsubstituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF2, —CH$_2$CF$_3$, —CF$_2$CH$_3$, —CFHCHF2, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

The term "modulate" or "modulating" or "modulation" refers to an increase or decrease in the amount, quality, or effect of a particular activity, function or molecule. By way of illustration and not limitation, activators, agonists, partial agonists, inverse agonists, antagonists, inhibitors, and allosteric modulators of an enzyme are modulators of the enzyme.

The term "agonism" as used herein refers to the activation of a receptor or enzyme by a modulator, or agonist, to produce a biological response.

The term "agonist" or "activator" as used herein refers to a modulator that binds to a receptor or target enzyme and activates the receptor or enzyme to produce a biological response. By way of example, "AMPK activator" can be used to refer to a compound that exhibits an EC$_{50}$ with respect to AMPK activity of no more than about 100 μM, as measured in the pAMPK1 kinase activation assay. In some embodiments, the term "agonist" includes super agonists, full agonists or partial agonists.

The term "super agonist" as used herein refers to a modulator that is capable of producing a maximal response greater than the endogenous agonist for the target receptor or enzyme, and thus has an efficacy of more than 100%.

The term "full agonist" refers to a modulator that binds to and activates a receptor or target enzyme with the maximum response that an endogenous agonist can elicit at the receptor or enzyme.

The term "partial agonist" refers to a modulator that binds to and activates a receptor or target enzyme, but has partial efficacy, that is, less than the maximal response, at the receptor or enzyme relative to a full agonist.

The term "positive allosteric modulator" refers to a modulator that binds to a site distinct from the orthosteric binding site and enhances or amplifies the effect of an agonist.

The term "antagonism" or "inhibition" as used herein refers to the inactivation of a receptor or target enzyme by a modulator, or antagonist. Antagonism of a receptor, for example, is when a molecule binds to the receptor or target enzyme and does not allow activity to occur.

The term "antagonist" or "neutral antagonist" or "inhibitor" as used herein refers to a modulator that binds to a receptor or target enzyme and blocks a biological response. An antagonist has no activity in the absence of an agonist or inverse agonist but can block the activity of either, causing no change in the biological response.

The term "inverse agonist" refers to a modulator that binds to the same receptor or target enzyme as an agonist but induces a pharmacological response opposite to that agonist, i.e., a decrease in biological response.

The term "negative allosteric modulator" refers to a modulator that binds to a site distinct from the orthosteric binding site and reduces or dampens the effect of an agonist.

As used herein, "EC$_{50}$" is intended to refer to the concentration of a substance (e.g., a compound or a drug) that is required for 50% activation or enhancement of a biological process. In some instances, EC$_{50}$ refers to the concentration of agonist that provokes a response halfway between the baseline and maximum response in an in vitro assay. In some embodiments as used herein, EC$_{50}$ refers to the concentration of an activator (e.g., an AMPK activator) that is required for 50% activation of AMPK.

As used herein, "IC$_{50}$" is intended to refer to the concentration of a substance (e.g., a compound or a drug) that is required for 50% inhibition of a biological process. For example, $IC_{50}$ refers to the half maximal (50%) inhibitory concentration (IC) of a substance as determined in a suitable assay. In some instances, an $IC_{50}$ is determined in an in vitro assay system. In some embodiments as used herein, $IC_{50}$ refers to the concentration of a modulator (e.g., an antagonist or inhibitor) that is required for 50% inhibition of a receptor or a target enzyme.

The terms "subject," "individual," and "patient" are used interchangeably. These terms encompass mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The term "gut-restricted" as used herein refers to a compound, e.g., an AMPK activator, that is predominantly active in the gastrointestinal system. In some embodiments, the biological activity of the gut-restricted compound, e.g., a gut-restricted AMPK activator, is restricted to the gastrointestinal system. In some embodiments, gastrointestinal concentration of a gut-restricted modulator, e.g., a gut-restricted AMPK activator, is higher than the $IC_{50}$ value or the $EC_{50}$ value of the gut-restricted modulator against its receptor or target enzyme, e.g., AMPK, while the plasma levels of said gut-restricted modulator, e.g., gut-restricted AMPK activator, are lower than the ICso value or the $EC_{50}$ value of the gut-restricted modulator against its receptor or target enzyme, e.g., AMPK. In some embodiments, the gut-restricted compound, e.g., a gut-restricted AMPK activator, is non-systemic. In some embodiments, the gut-restricted compound, e.g., a gut-restricted AMPK activator, is a non-absorbed compound. In other embodiments, the gut-restricted compound, e.g., a gut-restricted AMPK activator, is absorbed, but is rapidly metabolized to metabolites that are significantly less active than the modulator itself toward the target receptor or enzyme, i.e., a "soft drug." In other embodiments, the gut-restricted compound, e.g., a gut-restricted AMPK activator, is minimally absorbed and rapidly metabolized to metabolites that are significantly less active than the modulator itself toward the target receptor or enzyme. In some embodiments, the gut-restricted AMPK activator has high efflux. In other embodiments, the gut-restricted AMPK activator is a substrate for one or more intestinal efflux transporters such as P-gp ($MDR^1$), BCRP, or MRP2.

In some embodiments, the gut-restricted modulator, e.g., a gut-restricted AMPK activator, is non-systemic but is instead localized to the gastrointestinal system. For example, the modulator, e.g., a gut-restricted AMPK activator, may be present in high levels in the gut, but low levels in serum. In some embodiments, the systemic exposure of a gut-restricted modulator, e.g., a gut-restricted AMPK activator, is, for example, less than 100, less than 50, less than 20, less than 10, or less than 5 nM, bound or unbound, in blood serum. In some embodiments, the intestinal exposure of a gut-restricted modulator, e.g., a gut-restricted AMPK activator, is, for example, greater than 1000, 5000, 10000, 50000, 100000, or 500000 nM. In some embodiments, a modulator, e.g., a gut-restricted AMPK activator, is gut-restricted due to poor absorption of the modulator itself, or because of absorption of the modulator which is rapidly metabolized in serum resulting in low systemic circulation, or due to both poor absorption and rapid metabolism in the serum. In some embodiments, a modulator, e.g., a gut-restricted AMPK activator, is covalently bonded to a kinetophore, optionally through a linker, which changes the pharmacokinetic profile of the modulator.

In other embodiments, the gut-restricted modulator is a soft drug. The term "soft drug" as used herein refers to a modulator that is biologically active but is rapidly metabolized to metabolites that are significantly less active than the modulator itself toward the target receptor. In some embodiments, the gut-restricted modulator is a soft drug that is rapidly metabolized in the blood to significantly less active metabolites. In some embodiments, the gut-restricted modulator is a soft drug that is rapidly metabolized in the liver to significantly less active metabolites. In some embodiments, the gut-restricted modulator is a soft drug that is rapidly metabolized in the blood and the liver to significantly less active metabolites. In some embodiments, the gut-restricted modulator is a soft drug that has low systemic exposure. In some embodiments, the biological activity of the metabolite (s) is/are 10-fold, 20-fold, 50-fold, 100-fold, 500-fold, or 1000-fold lower than the biological activity of the soft drug gut-restricted modulator.

The term "kinetophore" as used herein refers to a structural unit tethered to a small molecule modulator, e.g., an AMPK activator, optionally through a linker, which makes the whole molecule larger and increases the polar surface area while maintaining biological activity of the small molecule modulator. The kinetophore influences the pharmacokinetic properties, for example solubility, absorption, distribution, rate of elimination, and the like, of the small molecule modulator, e.g., an AMPK activator, and has minimal changes to the binding to or association with a receptor or target enzyme. The defining feature of a kinetophore is not its interaction with the target, for example an enzyme, but rather its effect on specific physiochemical characteristics of the modulator to which it is attached, e.g., an AMPK activator. In some instances, kinetophores are used to restrict a modulator, e.g., an AMPK activator, to the gut.

The term "linked" as used herein refers to a covalent linkage between a modulator, e.g., an AMPK activator, and a kinetophore. The linkage can be through a covalent bond, or through a "linker." As used herein, "linker" refers to one or more bifunctional molecules which can be used to covalently bonded to the modulator, e.g., an AMPK activator, and kinetophore. In some embodiments, the linker is attached to any part of the modulator, e.g., an AMPK activator, so long as the point of attachment does not interfere with the binding of the modulator to its receptor or target enzyme. In some embodiments, the linker is non-cleavable. In some embodiments, the linker is cleavable. In some embodiments, the linker is cleavable in the gut. In some embodiments, cleaving the linker releases the biologically active modulator, e.g., an AMPK activator, in the gut.

The term "gastrointestinal system" (GI system) or "gastrointestinal tract" (GI tract) as used herein, refers to the organs and systems involved in the process of digestion. The gastrointestinal tract includes the esophagus, stomach, small intestine, which includes the duodenum, jejunum, and ileum, and large intestine, which includes the cecum, colon, and rectum. In some embodiments herein, the GI system refers to the "gut," meaning the stomach, small intestines, and large intestines or to the small and large intestines, including, for example, the duodenum, jejunum, and/or colon.

Gut-Brain Axis

The gut-brain axis refers to the bidirectional biochemical signaling that connects the gastrointestinal tract (GI tract)

with the central nervous system (CNS) through the peripheral nervous system (PNS) and endocrine, immune, and metabolic pathways.

In some instances, the gut-brain axis comprises the GI tract; the PNS including the dorsal root ganglia (DRG) and the sympathetic and parasympathetic arms of the autonomic nervous system including the enteric nervous system and the vagus nerve; the CNS; and the neuroendocrine and neuroimmune systems including the hypothalamic-pituitary-adrenal axis (HPA axis). The gut-brain axis is important for maintaining homeostasis of the body and is regulated and modulates physiology through the central and peripheral nervous systems and endocrine, immune, and metabolic pathways.

The gut-brain axis modulates several important aspects of physiology and behavior. Modulation by the gut-brain axis occurs via hormonal and neural circuits. Key components of these hormonal and neural circuits of the gut-brain axis include highly specialized, secretory intestinal cells that release hormones (enteroendocrine cells or EECs), the autonomic nervous system (including the vagus nerve and enteric nervous system), and the central nervous system. These systems work together in a highly coordinated fashion to modulate physiology and behavior.

Defects in the gut-brain axis are linked to a number of diseases, including those of high unmet need. Diseases and conditions affected by the gut-brain axis, include central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, checkpoint inhibitor-induced colitis, psoriasis, celiac disease, and enteritis, including chemotherapy-induced enteritis or radiation-induced enteritis; necrotizing enterocolitis; gastrointestinal injury resulting from toxic insults such as radiation or chemotherapy; diseases/disorders of gastrointestinal barrier dysfunction including environmental enteric dysfunction, spontaneous bacterial peritonitis; allergy including food allergy, celiac sprue, and childhood allergy; graft vs. host disease; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

Adenosine 5'-Monophosphate-Activated Protein Kinase (AMPK) in the Gut-Brain Axis Adenosine 5'-monophosphate-activated protein kinase (AMPK) is a serine/threonine kinase and is evolutionarily conserved from yeast to mammals. In some instances, AMPK is a heterotrimeric protein complex that is formed by one α (α1 or α2), one β(β1 or β2), and one γ(γ1, γ2, or γ3) subunit. Due to the presence of isoforms of its components, there are 12 versions of AMPK (AMPK1, AMPK2, etc., through AMPK12). In some instances, AMPK acts as an energy sensor and is activated by upstream enzymes when the cellular ratio of adenosine 5'—monophosphate (AMP) to adenosine triphosphate (ATP) is elevated due to nutrient deprivation. In some instances, activated AMPK phosphorylates downstream substrates to promote catabolism and impede anabolism, leading to ATP production and energy restoration. In some instances, AMPK activity can be altered due to numerous physiological factors, such as hormones, cytokines and dietary nutrients, as well as pathological conditions such as obesity, chronic inflammation and type 2 diabetes. In some instances, AMPK activation leads to lower hepatic glucose production and plasma glucose levels. Thus, in some instances, AMPK activation can act as a therapeutic agent to treat various metabolic diseases.

In some instances, AMPK has beneficial effects for gut health, such as enhancing intestinal absorption, improving barrier function, suppressing colorectal carcinogenesis, and reducing intestinal inflammation and metabolic-related disease, and is important for the maintenance of intestinal homeostasis. In some instances, AMPK is essential for proper intestinal health. In some instances, AMPK activation enhances paracellular junctions, nutrient transporters, autophagy and apoptosis, and suppresses inflammation and carcinogenesis in the intestine.

In some embodiments, this disclosure provides AMPK activators that can be broadly used for multiple conditions and disorders associated with AMPK. In some embodiments, the condition or disorder is associated with the gut-brain axis. In some embodiments, the condition or disorder is a central nervous system (CNS) disorder including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, checkpoint inhibitor-induced colitis, psoriasis, celiac disease, and enteritis, including chemotherapy-induced enteritis or radiation-induced enteritis; necrotizing enterocolitis; gastrointestinal injury resulting from toxic insults such as radiation or chemotherapy; diseases/disorders of gastrointestinal barrier dysfunction including environmental enteric dysfunction, spontaneous bacterial peritonitis; allergy including food allergy, celiac sprue, and childhood allergy; graft vs. host disease; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis. In some embodiments, the condition or disorder is a metabolic disorder. In some embodiments, the condition or disorder is type 2 diabetes, hyperglycemia, metabolic syndrome, obesity, hypercholesterolemia, nonalcoholic steatohepatitis, or hypertension. In some embodiments, the condition or disorder is a nutritional disorder. In some embodiments, the condition or disorder is short bowel syndrome, intestinal failure, or intestinal insufficiency. In some embodiments, the condition or disorder is inflammatory bowel disease including ulcerative colitis, Crohn's disease and checkpoint inhibitor-induced colitis. In some embodiments, the condition or disorder is celiac disease, enteritis including chemotherapy-induced enteritis or radiation-induced enteritis, necrotizing enterocolitis; or gastrointestinal injury resulting from toxic insults such as radiation or chemotherapy. In some embodiments, the condition or disorder is diseases/disorders of gastrointestinal barrier dysfunction including environmental enteric dysfunction, spontaneous bacterial peritonitis; allergy including food allergy, celiac sprue, and childhood allergy; graft vs. host disease; functional gastrointestinal disorders such as irritable bowel syndrome, functional dyspepsia, functional abdominal bloating/distension, functional diarrhea, functional constipation, opioid-induced constipation; gastroparesis; or nausea and vomiting. In some embodiments, the condition or disorder is associated with systemic infection and inflammation from having a leaky gut barrier. In some embodiments, the condition or disorder is metabolic syndrome, obesity, type 2 diabetes, coronary artery disease, fatty liver, nonalcoholic steatohepatitis (NASH), cirrhosis, hepatic encephalopathy, fibrotic disorders including scleroderma, inflammatory bowel disease including Crohn's disease and ulcerative colitis, allergy including food allergy, celiac sprue, and childhood allergy, graft vs. host disease, irritable bowel syndrome, spontaneous bacterial peritonitis, ischemic colitis, sclerosing cholangitis, Alzheimer's disease, Parkinson's disease, cancer including colorectal cancer, depression, autism, or a combination thereof.

Adenosine 5'-Monophosphate-Activated Protein Kinase (AMPK) and the Gut Barrier

In some instances, the gut mucosa maintains immune homeostasis under physiological circumstances by serving as a barrier that restricts access of microbes, diverse microbial products, food antigens and toxins in the lumen of the gut to rest of the body. In some instances, the gut barrier is comprised of a single layer of epithelial cells, bound by cell-cell junctions, and a layer of mucin that covers the epithelium. In some instances, loosening of the junctions induced either by exogenous or endogenous stressors, compromises the gut barrier and allows microbes and antigens to leak through and encounter the host immune system, thereby generating inflammation and systemic endotoxemia. In some instances, an impaired gut barrier (e.g. a leaky gut) is a major contributor to the initiation and/or progression of various chronic diseases including, but not limited to, metabolic endotoxemia, type 2 diabetes, fatty liver disease, obesity, atherosclerosis, inflammatory bowel diseases, and cancers. In some instances, activation of AMPK, which is associated with the maintenance of tight junction in colonic epithelium, controls the progression of colitis. In some instances, expression and assembly of tight junctions is dependent on AMPK activity.

In some embodiments, the present disclosure provides methods effective to strengthen/protect the gut barrier and reduce and/or prevent the progression of chronic diseases. The gut barrier is a critical frontier that separates microbes and antigens in the lumen of the gut from the rest of the body; a compromised "leaky" gut barrier is frequently associated with systemic infection and inflammation, which is a key contributor to many chronic allergic, infectious, metabolic and autoimmune diseases such as obesity, diabetes, inflammatory bowel diseases, food allergy, and metabolic endotoxemia.

In some embodiments, this disclosure provides AMPK activators that can be broadly used for multiple conditions and disorders associated with AMPK. In some embodiments, the condition or disorder is associated with systemic infection and inflammation from having a leaky gut barrier. In some embodiments, a leaky gut barrier can fuel the progression of multiple chronic diseases, including but not limited to: metabolic syndrome, obesity, type 2 diabetes, coronary artery disease, fatty liver, nonalcoholic steatohepatitis (NASH), cirrhosis, hepatic encephalopathy, fibrotic disorders including scleroderma, inflammatory bowel disease including Crohn's disease, ulcerative colitis, checkpoint inhibitor-induced colitis, allergy including food allergy, celiac sprue, and childhood allergy, graft vs. host disease, irritable bowel syndrome, spontaneous bacterial peritonitis, ischemic colitis, sclerosing cholangitis, Alzheimer's disease, Parkinson's disease, cancer including colorectal cancer, depression, autism, or a combination thereof.

In some instances, injury to the intestinal mucosa is frequently a dose-limiting complication of radiotherapy and chemotherapy. Approaches to limit the damage to the intestine during radiation and chemotherapy have been largely ineffective. In some embodiments described herein, AMPK activators are useful for the treatment of gastrointestinal injury. In some embodiments, AMPK activators are useful for the treatment of gastrointestinal injury resulting from toxic insult. In some embodiments, the toxic insult is from radiation, chemotherapy, or a combination thereof. In some embodiments, the toxic insult is radiation-induced. In some embodiments, the toxic insult is chemotherapy-induced.

Gut-Restricted Modulators

In some instances, there are concerns associated with systemic AMPK activation, for example, AMPK activation in the heart. For example, in some instances, activating mutations in the AMPK γ2-subunit lead to PRKAG2 cardiomyopathy. In other instances, systemic AMPK activation results in cardiac hypertrophy and increased cardiac glycogen. In some instances, given the potential association of adverse effects with systemic AMPK activation, tissue selective AMPK activation is an attractive approach for developing AMPK activators to treat disease.

In some embodiments, the AMPK activator is gut-restricted. In some embodiments, the AMPK activator is designed to be substantially non-permeable or substantially non-bioavailable in the blood stream. In some embodiments, the AMPK activator is designed to activate AMPK activity in the gut and is substantially non-systemic. In some embodiments, the AMPK activator has low systemic exposure.

In some embodiments, a gut-restricted AMPK activator has low oral bioavailability. In some embodiments, a gut-restricted AMPK activator has <40% oral bioavailability, <30% oral bioavailability, <20% oral bioavailability, <10% oral bioavailability, <8% oral bioavailability, <5% oral bioavailability, <3% oral bioavailability, or <2% oral bioavailability.

In some embodiments, the unbound plasma levels of a gut-restricted AMPK activator are lower than the $EC_{50}$ value of the AMPK activator against AMPK. In some embodiments, the unbound plasma levels of a gut-restricted AMPK activator are significantly lower than the $EC_{50}$ value of the gut-restricted AMPK activator against AMPK. In some embodiments, the unbound plasma levels of the AMPK activator are 2-fold, 10-fold, 20-fold, 30-fold, 40-fold, 50-fold, or 100-fold lower than the $EC_{50}$ value of the gut-restricted AMPK activator against AMPK.

In some embodiments, a gut-restricted AMPK activator has low systemic exposure. In some embodiments, the systemic exposure of a gut-restricted AMPK activator is, for example, less than 500, less than 200, less than 100, less than 50, less than 20, less than 10, or less than 5 nM, bound or unbound, in blood serum. In some embodiments, the systemic exposure of a gut-restricted AMPK activator is, for example, less than 500, less than 200, less than 100, less than 50, less than 20, less than 10, or less than 5 ng/mL, bound or unbound, in blood serum.

In some embodiments, a gut-restricted AMPK activator has high intestinal exposure. In some embodiments, the intestinal exposure of a gut-restricted AMPK activator is, for example, greater than 1, 5, 10, 50, 100, 250 or 500 µM.

In some embodiments, a gut-restricted AMPK activator has high exposure in the colon.

In some embodiments, the colon exposure of a gut-restricted AMPK activator is, for example, greater than 1, 5, 10, 50, 100, 250 or 500 µM. In some embodiments, the colon exposure of a gut-restricted AMPK activator is, for example, greater than 100 µM.

In some embodiments, a gut-restricted AMPK activator has low permeability. In some embodiments, a gut-restricted AMPK activator has low intestinal permeability. In some embodiments, the permeability of a gut-restricted AMPK activator is, for example, less than $5.0 \times 10^{-6}$ cm/s, less than $2.0 \times 10^{-6}$ cm/s, less than $1.5 \times 10^{-6}$ cm/s, less than $1.0 \times 10^{-6}$ cm/s, less than $0.75 \times 10^{-6}$ cm/s, less than $0.50 \times 10^{-6}$ cm/s, less than $0.25 \times 10^{-6}$ cm/s, less than $0.10 \times 10^{-6}$ cm/s, or less than $0.05 \times 10^{-6}$ cm/s.

In some embodiments, a gut-restricted AMPK activator has low absorption. In some embodiments, the absorption of a gut-restricted AMPK activator is less than 40%, less than 30%, less than 20%, less than 10%, less than 5%, or less than 1%.

In some embodiments, a gut-restricted AMPK activator has high plasma clearance. In some embodiments, a gut-restricted AMPK activator is undetectable in plasma in less than 8 hours, less than 6 hours, less than 4 hours, less than 3 hours, less than 120 min, less than 90 min, less than 60 min, less than 45 min, less than 30 min, or less than 15 min.

In some embodiments, a gut-restricted AMPK activator is rapidly metabolized upon administration. In some embodiments, a gut-restricted AMPK activator has a short half-life. In some embodiments, the half-life of a gut-restricted AMPK activator is less than less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted AMPK activator have rapid clearance. In some embodiments, the metabolites of a gut-restricted AMPK activator are undetectable in less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted AMPK activator have low bioactivity. In some embodiments, the $EC_{50}$ value of the metabolites of a gut-restricted AMPK activator is 10-fold, 20-fold, 30-fold, 40-fold, 50-fold, 100-fold, 500-fold, or 1000-fold higher than the $EC_{50}$ value of the gut-restricted AMPK activator against AMPK. In some embodiments, the metabolites of a gut-restricted AMPK activator have rapid clearance and low bioactivity.

In some embodiments, the gut-restricted AMPK activator has high efflux. In some embodiments, the gut-restricted AMPK activator is a substrate for one or more intestinal efflux transporters such as P-gp (MDR1), BCRP, or MRP2. In some embodiments, the efflux of the gut-restricted AMPK activator as measured by the B-A/A-B ratio in a cell line such as Caco-2 or MDCK with or without over-expression of one or more efflux transporters is, for example, greater than 2, greater than 5, greater than 10, greater than 25, or greater than 50.

In some embodiments of the methods described herein, the AMPK activator is gut-restricted. In some embodiments, the AMPK activator is a gut-restricted AMPK agonist. In some embodiments, the AMPK activator is a gut-restricted AMPK super agonist. In some embodiments, the AMPK activator is a gut-restricted AMPK full agonist. In some embodiments, the AMPK activator is a gut-restricted AMPK partial agonist. In some embodiments, the AMPK activator is covalently bonded to a kinetophore. In some embodiments, the AMPK activator is covalently bonded to a kinetophore through a linker.

Compounds

Disclosed herein, in some embodiments, is a compound of Formula (I):

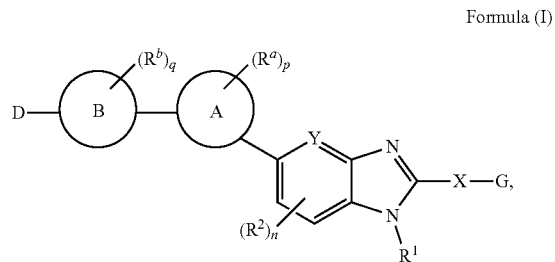

Formula (I)

or a pharmaceutically acceptable salt, solvate, stereoisomer, or prodrug thereof, wherein:

X is —O—, —S—, —NR$^3$—, —C(O)—, —C(O)O—, —C(O)NR$^3$—, —NR$^3$C(O)—, —SO$_2$—, or —SO$_2$NR$^3$—; wherein ** indicates the attachment point to G;

Y is N, CH, or CR$^2$;

G is C$_1$-C$_5$ alkyl, —(CH$_2$)$_j$-(C$_3$-C$_{10}$ cycloalkyl), —(CH$_2$)$_j$-(C$_4$-lo cycloalkenyl), —(CH$_2$)$_j$-(aryl), —(CH$_2$)$_j$-(heteroaryl), —(CH$_2$)$_j$-(3- to 10-membered heterocycloalkyl), or —(CH$_2$)$_j$-(5- to 10-membered heterocycloalkenyl), which is substituted with 1, 2, 3, or 4 substituents selected from —(CH$_2$)$_h$-C(O)OR$^7$, —(CH$_2$)$_h$—P(O)(R$^7$)OR$^7$, —(CH$_2$)$_h$—P(O)(OR$^7$)$_2$, —(CH$_2$)$_h$—S(O)$_2$OR$^7$, -and —(CH$_2$)$_h$OH; and is further optionally substituted with 1, 2, 3, or 4 substituents selected from C$_1$-C$_6$ alkyl, C$_3$-C$_6$ cycloalkyl, C$_1$-C$_6$ hydroxyalkyl, C$_1$-C$_6$ fluoroalkyl, —O—(C$_1$-C$_6$ alkyl), =O and =S;

is aryl, heteroaryl, —C≡C—, or absent; wherein if

is —C≡C—or absent, then p is 0;

is aryl, heteroaryl, cycloalkyl, heterocycloalkyl, $C_{5-10}$ cycloalkenyl, or 5- to 10-membered heterocycloalkenyl;

D is K, -Z-$NR^5R^6$, or $R^c$;

Z is —$(CH_2)_r$—, —$(CH(CH_3))$—, *—$(CH_2)_r$-C(=O)—, or *—$(CH_2)_r$—S(=O)$_2$—, where * represents attachment to

;

K is —$SO_2OH$, —$S(O)OH$, —$P(O)(OH)(R^d)$, —$P(O)(OH)(OR^d)$, —$CH_2P(O)(OH)(OR^d)$, —$B(OR^d)(OH)$, —$NHC(O)H$, —$N(R^d)C(O)NHSO_2(R^d)$, —$C(O)NHSO_2(R^d)$, —$SO_2NHC(O)(R^d)$, —$NHC(O)NH(R^d)$, —$N(R^d)C(=N(R^d)N(R^d)_2$, —$N(R^d)C(=NH)NHC(=NH)NH_2$,

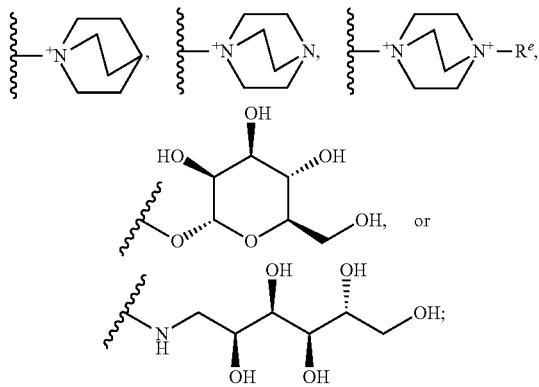

each $R^a$ and $R^b$ is independently halogen, —CN, —OH, —$OR^{13}$, —$NR^{14}R^{14}$, —$C(O)R^{13}$, —$C(O)OR^{14}$, —$OC(O)R^{13}$, —$C(O)NR^{14}R^{14}$, —$NR^{14}C(O)R^{14}$, —$NR^{14}C(O)NR^{14}R^{14}$, —$OC(O)NR^{14}R^{14}$, —$NR^{14}C(O)OR^{14}$, —$OC(O)OR^{14}$, $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, phenyl, or monocyclic heteroaryl, wherein the alkyl, alkenyl, alkynyl, cycloalkyl, heterocycloalkyl, phenyl, or heteroaryl are unsubstituted or substituted by 1, 2, or 3 halogen or —OH groups;

$R^c$ is $C_{1-10}$ alkyl, $C_{2-10}$ alkenyl, $C_{2-10}$ alkynyl, $C_{3-10}$ cycloalkyl, $C_{1-10}$ alkoxyl, or —$[(C(R^d)_2)_s$—V$]_t$—$R^9$; wherein each V is independently —$C(R^d)_2O$—, —$C(R^d)_2NR^d$—, —$C(R^d)_2N^+(R^d)_2$—, —$N(R^d)$—$C(O)$—$N(R^d)$—, —$C(O)N(R^d)$—, —$C(R^d)_2SO_2$—, or —$C(R^d)_2S(O)$—; and wherein each alkyl, alkenyl, alkynyl, cycloalkyl, and alkoxyl is substituted by 1-6 groups selected from —$N(R^e)_3^+$, K, and -Z-$NR^5R^6$; or wherein each alkyl, alkenyl, alkynyl, cycloalkyl, and alkoxyl is substituted by 2-6 groups selected from —$CO_2H$, —OH, and —$N(R^d)_2$;

each $R^d$ is independently hydrogen, $C_{1-6}$ alkyl or $C_{3-6}$ cycloalkyl; wherein the alkyl and cycloalkyl are unsubstituted or substituted by 1-3 halogen or —OH groups;

each $R^e$ is independently $C_{1-5}$ alkyl or $C_{3-6}$ cycloalkyl; wherein the alkyl and cycloalkyl are unsubstituted or substituted by 1-3 halogen or —OH groups;

$R^t$ is hydrogen or $C_1$-$C_4$ alkyl;

each $R^2$ is independently halogen, —CN, $C_1$-$C_4$ alkyl, $C_1$-$C_4$ fluoroalkyl, or $C_3$-$C_6$ cycloalkyl;

$R^3$ is hydrogen or $C_1$-$C_4$ alkyl;

$R^5$ is $C_6$-$C_{10}$ alkyl that is substituted by 5 to 9 —OH groups;

or $R^5$ is $C_{1-10}$ alkyl, $C_{2-10}$ alkenyl, $C_{2-10}$ alkynyl, $C_3$-10 cycloalkyl, $C_{5-10}$ cycloalkenyl, 3- to 8-membered heterocycloalkyl, or 5- to 10-membered heterocycloalkenyl; wherein the alkyl, alkenyl, alkynyl, cycloalkyl, cycloalkenyl, heterocycloalkyl, or heterocycloalkenyl is substituted by 1-6 groups selected from —$N(R^e)_3^+$ and K; or wherein the alkyl, alkenyl, alkynyl, cycloalkyl, cycloalkenyl, heterocycloalkyl, or heterocycloalkenyl is substituted by 2-6 groups selected from —$CO_2H$, —OH, and —$N(R^d)_2$; and wherein the alkyl, alkenyl, alkynyl, cycloalkyl, cycloalkenyl, heterocycloalkyl, or heterocycloalkenyl is optionally further substituted by 1, 2, or 3 $R^f$ groups;

each $R^f$ is independently halogen, —CN, —OH, —$OR^{13}$, —$NR^{14}R^{14}$, —$C(O)R^{13}$, —$C(O)OR^{14}$, —$OC(O)R^{13}$, —$C(O)NR^{14}R^{14}$, —$NR^{14}C(O)R^{14}$, —$NR^{14}C(O)NR^{14}R^{14}$, —$OC(O)NR^{14}R^{14}$, —$NR^{14}C(O)OR^{14}$, —$OC(O)OR^{14}$, $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, phenyl, or monocyclic heteroaryl, wherein the alkyl, alkenyl, alkynyl, cycloalkyl, heterocycloalkyl, phenyl, or heteroaryl are unsubstituted or substituted by 1, 2, or 3 halogen or —OH groups;

or $R^5$ is —$[(C(R^d)_2)_s$—V$]_t$—$R^9$; wherein each V is independently —$C(R^d)_2O$—, —$C(R^d)_2NR^d$—, —$C(R^d)_2N^+(R^d)_2$—, —$N(R^d)$—$C(O)$—$N(R^d)$—, —$C(O)N(R^d)$—, —$C(R^d)_2SO_2$—, or —$C(R^d)_2S(O)$—;

or $R^5$ is —$(C_1$-$C_6$ alkylene)—aryl, or —$(C_1$-$C_6$ alkylene)—heteroaryl; wherein the aryl or heteroaryl is substituted by 1-6 groups selected from —$CO_2H$, —OH, —$N(R^d)_2$, —$N(R^e)_3^+$, and K; and wherein the alkylene is unsubstituted or substituted by 1, 2, or 3 $E^f$ $^{groups}$;

$R^6$ is hydrogen, $C_{1-6}$ alkyl, or $C_{3-6}$ cycloalkyl; wherein the alkyl and cycloalkyl are unsubstituted or substituted by 1-3 groups independently selected from halogen, —CN, —OH, —$OR^{13}$, —$NR^{14}R^{14}$, —$C(O)R^{13}$, —$C(O)OR^{14}$, —$OC(O)R^{13}$, —$C(O)NR^{14}R^{14}$, $NR^{14}C(O)R^{14}$, —$NR^{14}C(O)NR^{14}R^{14}$, —$OC(O)NR^{14}R^{14}$, $NR^{14}C(O)OR^{14}$, —$OC(O)OR^{14}$, or —$P(O)(OR^{14})_2$;

or $R^5$ and $R^6$ are taken together with the nitrogen to which they are attached to form a 3- to 6-membered N-heterocycloalkyl which is unsubstituted or substituted with 1-6 groups selected from —$CH_3$, —$CH_2OH$, —$CH_2NH_2$, —$CH_2CH_2OH$, —$CH_2OCH_2CH_2OH$, —$N(R^e)_3^+$ and K; or with 2-6 groups selected from —$CO_2H$, —OH, —$CH_2OH$, —$CH_2NH_2$, —$CH_2CH_2OH$, —$CH_2OCH_2CH_2OH$, and —$N(R^d)_2$;

each $R^7$ is independently hydrogen or $C_1$-$C_4$ alkyl;

$R^9$ is hydrogen, $C_{1-8}$ alkyl, $C_{2-8}$ alkenyl, $C_{2-8}$ alkynyl, $C_{3-8}$ cycloalkyl, $C_{5-8}$ cycloalkenyl, 3- to 8-membered heterocycloalkyl, phenyl, naphthyl, monocyclic heteroaryl, or bicyclic heteroaryl, wherein the alkyl, alkenyl, alkynyl, cycloalkyl, cycloalkenyl, heterocycloalkyl phenyl, naphthyl, monocyclic heteroaryl, or bicyclic heteroaryl is unsubstituted or substituted by 1-6 groups selected from —OH, —$CO_2H$, —$N(R^e)_2$, —$N(R^e)_3^+$, and K;

each $R^{13}$ is independently $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl; and each $R^{14}$ is independently hydrogen, $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl;

or two $R^{14}$ on the same nitrogen atom are taken together with the nitrogen to which they are attached to form a 3- to 6-membered N-heterocycloalkyl;

each h is independently 0-4;
j is 0-4;
n is 0-2;
p is 0-3;
q is 0-3;
r is 0-3;
each s is independently 1-6; and
each t is independently 1-6.

For any and all of the embodiments, substituents are selected from among a subset of the listed alternatives. For example, in some embodiments, Y is N, CH, or $CR^2$. In some embodiments, Y is N or CH. In some embodiments, Y is N. In some embodiments, Y is CH. In some embodiments, Y is $CR^2$.

In some embodiments, n is 0-1. In some embodiments, n is 1-2. In some embodiments, n is 0. In some embodiments, n is 1. In some embodiments, n is 2.

In some embodiments, $R^1$ is methyl, ethyl, n-propyl, i-propyl, n-butyl, i-butyl, sec-butyl, or tert-butyl. In some embodiments, $R^1$ is methyl, ethyl, or i-propyl. In some embodiments, $R^1$ is hydrogen or methyl. In some embodiments, $R^1$ is hydrogen. In some embodiments, $R^1$ is methyl.

In some embodiments, each $R^2$ is independently halogen, —CN, $C_1$-$C_4$ alkyl, or $C_1$-$C_4$ fluoroalkyl. In some embodiments, each $R^2$ is independently —F, —Cl, —CN, methyl, ethyl, n-propyl, i-propyl, n-butyl, i-butyl, sec-butyl, tert-butyl, —$CH_2F$, —CHF2, or —$CF_3$. In some embodiments, each $R^2$ is independently —F, —Cl, —CN, methyl, ethyl, isopropyl, or —$CF_3$. In some embodiments, each $R^2$ is independently —F, —Cl, or —CN. In some embodiments, each $R^2$ is independently —Cl.

In some embodiments, Y is N or CH; $R^{14}$ is hydrogen or methyl; and each $R^2$ is independently —F, —Cl, —CN, methyl, ethyl, isopropyl, or —$CF_3$. In some embodiments, Y is N; $R^1$ is hydrogen; $R^2$ is —F, —Cl, or —CN; and n is 1. In some embodiments, Y is N or CH; $R^{14}$ is hydrogen; $R^2$ is —Cl; and n is 1. In some embodiments, Y is N; $R^{14}$ is hydrogen; $R^2$ is —Cl; and n is 1. In some embodiments, Y is CH; $R^{14}$ is hydrogen; $R^2$ is —Cl; and n is 1.

In some embodiments, (A)

is aryl, heteroaryl, —C≡C—, or absent. In some embodiments, (A)

is —C≡C- and p is 0. In some embodiments, (A)

is absent and p is 0.
In some embodiments, (A)

is aryl or heteroaryl. In some embodiments, (A)

is aryl. In some embodiments, (A)

is heteroaryl. In some embodiments, (A)

is phenyl or 5- or 6-membered monocyclic heteroaryl. In some embodiments, (A)

is phenyl or 6-membered monocyclic heteroaryl. In some embodiments, (A)

is phenyl, pyridinyl, pyrimidinyl, pyrazinyl, pyridazinyl, triazinyl, furanyl, thienyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments, (A)

is phenyl, pyridinyl, pyrimidinyl, pyrazinyl, or pyridazinyl. In some embodiments, (A)

is phenyl or pyridinyl. In some embodiments, (A)

is phenyl.
In some embodiments, (B)

is aryl, heteroaryl, cycloalkyl, heterocycloalkyl, $C_{5-10}$ cycloalkenyl, or 5- to 10-membered heterocycloalkenyl. In some embodiments, (B)

is aryl, heteroaryl, $C_3$-$C_6$ cycloalkyl, 3- to 8-membered heterocycloalkyl, or 5- to 10-membered bicyclic heterocycloalkenyl. In some embodiments, (B)

is phenyl, 5- or 6-membered monocyclic heteroaryl, $C_3$-$C_6$ cycloalkyl, 3- to 8-membered heterocycloalkyl, or 5- to 10-membered heterocycloalkenyl. In some embodiments, (B)

is phenyl, $C_3$-$C_6$ cycloalkyl, or 3- to 8-membered heterocycloalkyl.

In some embodiments, (B)

is aryl or heteroaryl. In some embodiments, (B)

is phenyl, 5- or 6-membered monocyclic heteroaryl, or 8- to 10-membered bicyclic heteroaryl. In some embodiments, (B)

is phenyl or 5- or 6-membered monocyclic heteroaryl. In some embodiments, (B)

is phenyl or 6-membered monocyclic heteroaryl. In some embodiments, (B)

is phenyl, pyridinyl, pyrimidinyl, pyrazinyl, pyridazinyl, triazinyl, furanyl, thienyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments, (B)

is phenyl, pyridinyl, pyrimidinyl, pyrazinyl, or pyridazinyl. In some embodiments, (B)

is phenyl or pyridinyl. In some embodiments, (B)

is phenyl.

In some embodiments, (B)

is cycloalkyl, heterocycloalkyl, $C_{5-10}$ cycloalkenyl, or 5- to 10-membered heterocycloalkenyl. In some embodiments, (B)

is $C_3$-$C_6$ cycloalkyl, 3- to 8-membered heterocycloalkyl, or 5- to 10-membered bicyclic heterocycloalkenyl. In some embodiments, (B)

is $C_3$-$C_6$ cycloalkyl or 3- to 8-membered heterocycloalkyl.

In some embodiments, (A)

is aryl or heteroaryl; and (B)

is aryl, heteroaryl, cycloalkyl, heterocycloalkyl, $C_{5-10}$ cycloalkenyl, or 5- to 10-membered heterocycloalkenyl. In some embodiments,

is phenyl or 5- or 6-membered monocyclic heteroaryl; and

is phenyl, 5- or 6-membered monocyclic heteroaryl, $C_3$-$C_6$ cycloalkyl, 3- to 8-membered heterocycloalkyl, or 5- to 10-membered heterocycloalkenyl. In some embodiments,

is phenyl and

is phenyl.

In some embodiments,

is —C≡C-; p is 0; and

and is phenyl or 5- or 6-membered monocyclic heteroaryl. In other embodiments,

is absent; p is 0; and

is phenyl, 5- or 6-membered monocyclic heteroaryl, or 8- to 10-membered bicyclic heteroaryl.

In some embodiments, the compound has the structure of Formula (II):

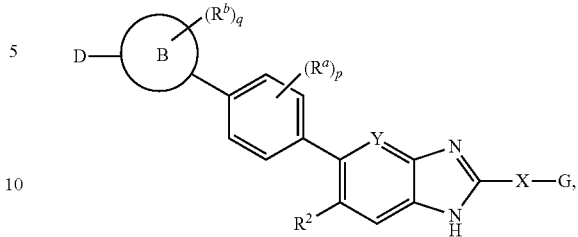

Formula (II)

or a pharmaceutically acceptable salt, solvate, stereoisomer, or prodrug thereof. In some embodiments of a compound of Formula (II),

is phenyl, $C_3$-$C_6$ cycloalkyl, 3- to 8-membered heterocycloalkyl, or 5- to 10-membered bicyclic heterocycloalkenyl. In some embodiments of a compound of Formula (II),

is phenyl, $C_3$-$C_6$ cycloalkyl, or 3- to 8-membered heterocycloalkyl. In some embodiments of a compound of Formula (II),

is phenyl.

In some embodiments, the compound has the structure of Formula (III):

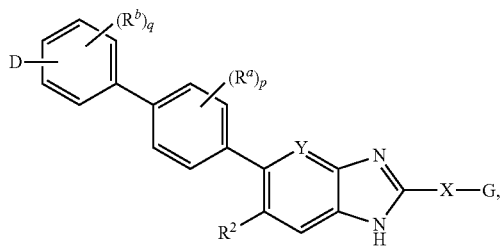

Formula (III)

or a pharmaceutically acceptable salt, solvate, stereoisomer, or prodrug thereof.

In some embodiments, each $R^3$ is independently halogen, —CN, —OH, —OR$^{13}$, —NR$^{14}$R$^{14}$, —C(O)OR$^{14}$, —C(O)NR$^{14}$R$^{14}$, 1 $C_1$-$C_6$ alkyl, or $C_1$-$C_6$ fluoroalkyl. In some embodiments, each $R^a$ is independently —F, —Cl, —CN, —OH, —O-($C_1$-$C_6$ alkyl), $C_1$-$C_6$ alkyl, or $C_1$-$C_6$ fluoroalkyl. In some embodiments, each $R^a$ is independently —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF2, or —CF$_3$. In some embodiments, each R$^a$ is independently —F, —Cl, —CN, —OH, —OCH$_3$, —OCF$_3$, methyl, or —CF$_3$.

In some embodiments, p is 0, 1, 2, or 3. In some embodiments, p is 0, 1, or 2. In some embodiments, p is 0 or 1. In some embodiments, p is 0. In some embodiments, p is 1, 2, or 3.

In some embodiments, each R$^b$ is independently halogen, —CN, —OH, —OR$^{13}$, —NR$^{14}$R$^{14}$, —C(O)OR$^{14}$, —C(O)NR$^{14}$R$^{14}$, C$_1$-C$_6$ alkyl, or C$_1$-C$_6$ fluoroalkyl. In some embodiments, each R$^b$ is independently —F, —Cl, —CN, —OH, —O-(C$_1$-C$_6$ alkyl), C$_1$-C$_6$ alkyl, or C$_1$-C$_6$ fluoroalkyl. In some embodiments, each R$^b$ is independently —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF$_2$, or —CF$_3$. In some embodiments, each R$^b$ is independently —F, —Cl, —CN, —OH, —OCH$_3$, —OCF$_3$, methyl, or —CF$_3$. In some embodiments, each R$^b$ is independently —OH.

In some embodiments, q is 0, 1, 2, or 3. In some embodiments, q is 0, 1, or 2. In some embodiments, q is 0 or 1. In some embodiments, q is 0. In some embodiments, q is 1, 2, or 3.

In some embodiments, each R$^a$ and R$^b$ is independently halogen, —CN, —OH, —OR$^{13}$, —NR$^{14}$R$^{14}$, C(O)OR$^{14}$, C(O)NR$^{14}$R$^{14}$, C$_1$-C$_6$ alkyl, or C$_1$-C$_6$ fluoroalkyl; p is 0 or 1; and q is 0 or 1. In some embodiments, each R$^a$ and R$^b$ is independently —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF$_2$, or —CF$_3$; p is 0 or 1; and q is 0 or 1. In some embodiments, each R$^a$ and R$^b$ is independently —F, —Cl, —CN, —OH, —OCH$_3$, —OCF$_3$, methyl, or —CF$_3$; p is 0 or 1; and q is 0 or 1. In some embodiments, p is 0; q is 1, and R$^b$ is —OH. In some embodiments, p is 0; and q is 0.

In some embodiments, the compound has the structure of Formula (IV):

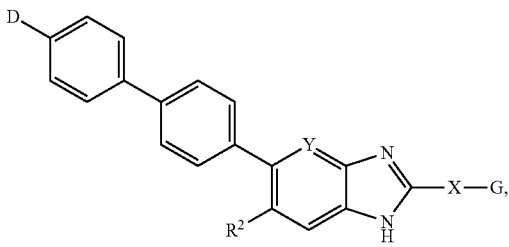

Formula (IV)

or a pharmaceutically acceptable salt, solvate, stereoisomer, or prodrug thereof.

In some embodiments,

Ⓐ is —C≡C-; p is 0; and

Ⓑ is phenyl or 5- or 6-membered monocyclic heteroaryl. In other embodiments,

Ⓐ is absent; p is 0; and

Ⓑ is phenyl, 5- or 6-membered monocyclic heteroaryl, or 8- to 10-membered bicyclic heteroaryl.

In some embodiments, X is —O—, —S—, —NR$^3$—, —C(O)NR$^3$—, —NR$^3$C(O)—, or —SO$_2$NR$^3$—; wherein  indicates the attachment point to G. In some embodiments, X is —O—, —S—, or —NR$^3$—. In some embodiments, X is —O— or —S—. In some embodiments, X is —O—. In some embodiments, X is —S—. In some embodiments, X is —NR$^3$—. In some embodiments, X is —C(O)NR$^3$—; wherein  indicates the attachment point to G. In some embodiments, X is —NR$^3$C(O)—; wherein  indicates the attachment point to G. In some embodiments, X is —SO$_2$NR$^3$—; wherein  indicates the attachment point to G.

In some embodiments, R$^3$ is hydrogen, methyl, ethyl, n-propyl, i-propyl, n-butyl, i-butyl, sec-butyl, or tert-butyl. In some embodiments, R$^3$ is hydrogen, methyl, ethyl, or i-propyl. In some embodiments, R$^3$ is hydrogen or methyl. In some embodiments, R$^3$ is hydrogen. In some embodiments, R$^3$ is methyl.

In some embodiments, X is —O—, —S—, —NR$^3$—, —C(O)NR$^3$—, —NR$^3$C(O)—, or —SO$_2$NR$^3$—; wherein  indicates the attachment point to G; and R$^3$ is hydrogen or methyl. In some embodiments, X is —O— or —S—. In some embodiments, X is —O—.

In some embodiments, G is C$_1$-C$_5$ alkyl, C$_3$-C$_{10}$ cycloalkyl, —CH$_2$-(C$_3$-C$_{10}$ cycloalkyl), aryl, 3- to 10-membered heterocycloalkyl, or 5- to 10-membered heterocycloalkenyl, which is substituted with 1, 2, 3, or 4 substituents selected from —(CH$_2$)$_h$—C(O)OR$^7$, —(CH$_2$)$_h$—P(O)(R$^7$)OR$^7$, —(CH$_2$)$_h$—P(O)(OR$^7$)$_2$, —(CH$_2$)$_h$—S(O)$_2$OR$^7$, —and —(CH$_2$)$_h$OH; and is further optionally substituted with 1, 2, 3, or 4 substituents selected from C$_1$-C$_6$ alkyl, C$_3$-C$_6$ cycloalkyl, C$_1$-C$_6$ hydroxyalkyl, C$_1$-C$_6$ fluoroalkyl, and —O-(C$_1$-C$_6$ alkyl); each R$^7$ is independently hydrogen, methyl, or ethyl; and his 0-1.

In some embodiments, G is C$_1$-C$_5$ alkyl, C$_3$-C$_{10}$ cycloalkyl, —CH$_2$-(C$_3$-C$_{10}$ cycloalkyl), aryl, 3- to 10-membered heterocycloalkyl, or 5- to 10-membered heterocycloalkenyl, which is substituted with 1, 2, 3, or 4 substituents selected from —C(O)OH, —CH$_2$C(O)OH, —P(O)(Me)OH, —P(O)(OH)$_2$, —S(O)$_2$OH, —OH, and —CH$_2$OH; and is further optionally substituted with 1, 2, 3, or 4 substituents selected from C$_1$-C$_6$ alkyl, C$_3$-C$_6$ cycloalkyl, C$_1$-C$_6$ hydroxyalkyl, C$_1$-C$_6$ fluoroalkyl, and —O-(C$_1$-C$_6$ alkyl).

In some embodiments, G is C$_1$-C$_5$ alkyl, C$_3$-C$_{10}$ cycloalkyl, —CH$_2$-(C$_3$-C$_{10}$ cycloalkyl), aryl, 3- to 10-membered heterocycloalkyl, or 5- to 10-membered heterocycloalkenyl, which is substituted with 1 or 2 substituents selected from —C(O)OH, —OH, and —CH$_2$OH; and is further optionally substituted with 1 or 2 substituents selected from $C_1$-$C_6$ alkyl, $C_1$-$C_6$ hydroxyalkyl, $C_1$-$C_6$ fluoroalkyl, and —O-($C_1$-$C_6$ alkyl).

In some embodiments, G is 3- to 10-membered heterocycloalkyl, which is substituted with 1, 2, 3, or 4 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is 3- to 10-membered heterocycloalkyl, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is 3- to 10-membered heterocycloalkyl, which is substituted with 1 or 2 substituents selected from —C(O)OH, —OH, and —CH$_2$OH. In some embodiments, G is 3- to 10-membered heterocycloalkyl, which is substituted with 1 or 2 substituents selected from —OH and —CH$_2$OH.

In some embodiments, G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH; or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH.

In some embodiments, G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is monocyclic 3- to 6-membered heterocycloalkyl containing 1 oxygen atom, which is substituted with 1 or 2 substituents selected from —C(O)OH, —OH, and —CH$_2$OH.

In some embodiments, G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is bicyclic 8- to 10-membered heterocycloalkyl containing 2 oxygen atoms, which is substituted with 1 or 2 substituents selected from —C(O)OH, —OH, and —CH$_2$OH. In some embodiments, G is bicyclic 8- to 10-membered heterocycloalkyl containing 2 oxygen atoms, which is substituted with 1 or 2 substituents selected from —OH and —CH$_2$OH. In some embodiments, G is bicyclic 8- to 10-membered heterocycloalkyl containing 2 oxygen atoms, which is substituted with 1 substituent selected from —OH and —CH$_2$OH. In some embodiments, G is bicyclic 8- to 10-membered heterocycloalkyl containing 2 oxygen atoms, which is substituted with 1 —OH substituent.

In some embodiments, G is $C_1$-$C_5$ alkyl, $C_3$-$C_6$ cycloalkyl, —CH$_2$—($C_3$-$C_6$ cycloalkyl), or phenyl, which is substituted with 1, 2, 3, or 4 substituents selected from —C(O)OH, —CH$_2$C(O)OH, —P(O)(Me)OH, —P(O)(OH)$_2$, —S(O)$_2$OH, —OH, and —CH$_2$OH; and is further optionally substituted with 1 or 2 substituents selected from $C_1$-$C_6$ alkyl, $C_3$-$C_6$ cycloalkyl, and $C_1$-$C_6$ hydroxyalkyl. In some embodiments, G is $C_1$-$C_5$ alkyl, $C_3$-$C_6$ cycloalkyl, —CH$_2$-($C_3$-$C_6$ cycloalkyl), or phenyl, which is substituted with 1 or 2 substituents selected from —C(O)OH, —OH, and —CH$_2$OH; and is further optionally substituted with 1 or 2 substituents selected from $C_1$-$C_6$ alkyl and $C_1$-$C_6$ hydroxyalkyl.

In some embodiments, -X-G is selected from:

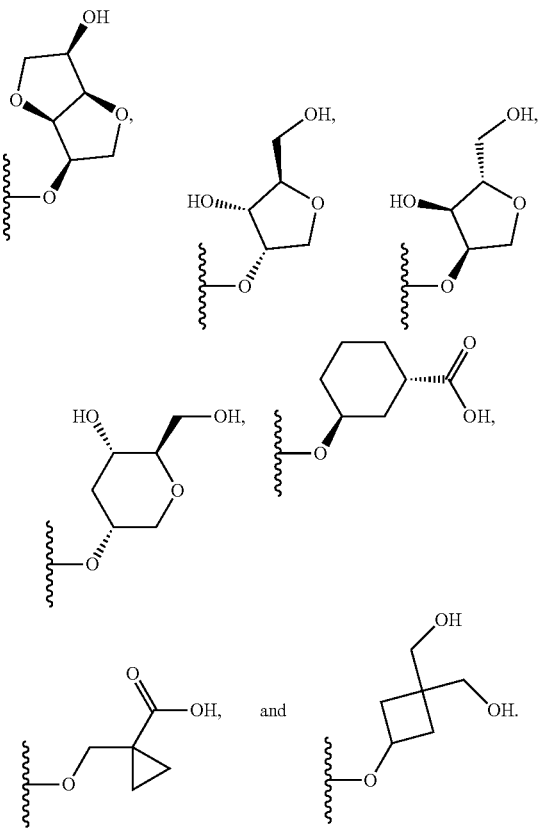

In some embodiments, -X-G is selected from:

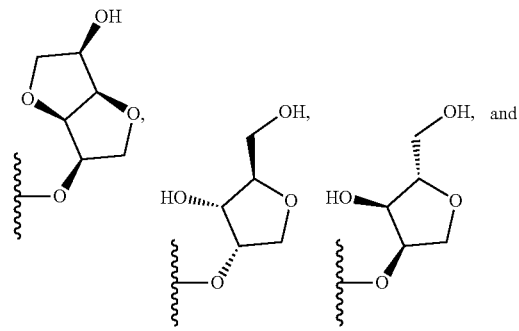

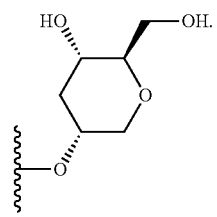

In some embodiments, -X-G is:

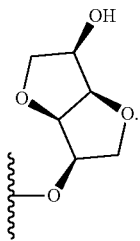 [SMILES: *O[C@@H]1CO[C@H]2[C@@H]1OC[C@H]2O]

In some embodiments, -X-G is:

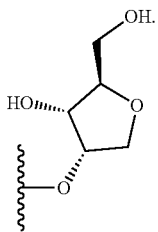

In some embodiments, -X-G is:

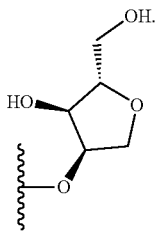

In some embodiments, -X-G is:

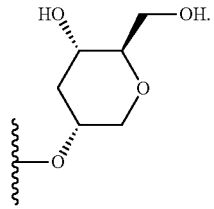

In some embodiments, D is $R^c$. In some embodiments, D is $R^c$; and $R^c$ is substituted by K. In some embodiments, D is $R^c$; and $R^c$ is substituted by -Z-$NR^5R^6$.

In some embodiments, D is $R^c$; and $R^c$ is $C_{1-10}$ alkyl, $C_{2-10}$ alkenyl, $C_{2-10}$ alkynyl, $C_{3-10}$ cycloalkyl, $C_{1-10}$ alkoxyl, or —[$C(R^d)_2)_s$-V$]_t$—$R^9$; wherein each V is independently —$C(R^d)_2O$—, —$C(R^d)_2NR^d$—, —$C(R^d)_2N^+(R^d)_2$—, —$N(R^d)$—$C(O)$—$N(R^d)$—, —$C(O)N(R^d)$—, —$C(R^d)_2SO_2$—, or —$C(R^d)_2S(O)$—; and wherein each alkyl, alkenyl, alkynyl, cycloalkyl, and alkoxyl is substituted by 1-6 groups selected from —$N(R^e)_3^+$, K, and -Z-$NR^5R^6$. In some embodiments, D is $R^c$; and $R^c$ is $C_{1-10}$ alkyl, $C_{2-10}$ alkenyl, $C_{2-10}$ alkynyl, or $C_{1-10}$ alkoxyl; wherein the alkyl, alkenyl, alkynyl, or alkoxyl is substituted by 1-6 groups selected from —$N(R^e)_3^+$, K, and -Z-$NR^5R^6$. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by 1-3 groups selected from —$N(R^e)_3^+$, K, and -Z-$NR^5R^6$. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by 1 group selected from —$N(R^e)_3^+$, K, and -Z-$NR^5R^6$. In some embodiments, each Re is independently $C_{1-6}$ alkyl. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by 1 group selected from —$N(R^e)_3^+$, K, and -Z-$NR^5R^6$; and each $R^e$ is independently $C_{1-6}$ alkyl. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by K. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by -Z-$NR^5R^6$.

In some embodiments, D is $R^c$; and $R^c$ is $C_{1-10}$ alkyl, $C_{2-10}$alkenyl, $C_{2-10}$ alkynyl, $C_{3-10}$ cycloalkyl, $C_{1-10}$ alkoxyl, or —[$(C(R^d)_2)_s$—V$]_t$—$R^9$; wherein each V is independently —$C(R^d)_2O$—, —$C(R^d)_2NR^d$—, —$C(R^d)_2N^+(R^d)_2$—, —$N(R^d)$—$C(O)$—$N(R^d)$—, —$C(O)N(R^d)$—, —$C(R^d)_2SO_2$—, or —$C(R^d)_2S(O)$—; and wherein each alkyl, alkenyl, alkynyl, cycloalkyl, and alkoxyl is substituted by 2-6 groups selected from —$CO_2H$, —OH, and —$N(R^d)_2$. In some embodiments, D is $R^c$; and $R^c$ is $C_{1-10}$ alkyl, $C_{2-10}$ alkenyl, $C_{2-10}$ alkynyl, or $C_{1-10}$ alkoxyl; wherein the alkyl, alkenyl, alkynyl, or alkoxyl is substituted by 2-6 groups selected from —$CO_2H$, —OH, and —$N(R^d)_2$. In some embodiments, D is $R^c$; and $R^c$ is $C_{1-10}$ alkyl, $C_{2-10}$ alkynyl, or $C_{1-10}$ alkoxyl; wherein the alkyl, alkynyl, or alkoxyl is substituted by 4-6 groups selected from —$CO_2H$, —OH, and —$N(R^d)_2$. In some embodiments, D is $R^c$; and $R^c$ is $C_{1-10}$ alkyl, $C_{2-10}$alkynyl, or $C_{1-10}$ alkoxyl; wherein the alkyl, alkynyl, or alkoxyl is substituted by 5 —OH groups.

In some embodiments, D is $R^c$; and $R^c$ is —[$(C(R^d)_2)_s$—V$]_t$—$R^9$; wherein each V is independently —$C(R^d)_2O$—, —$C(R^d)_2NR^d$—, —$C(R^d)_2N^+(R^d)_2$, —$N(R^d)$—$C(O)$—$N(R^d)$—, —$C(O)N(R^d)$—, —$C(R^d)_2SO_2$—, or —$C(R^d)_2S(O)$—; and wherein each alkyl, alkenyl, alkynyl, cycloalkyl, and alkoxyl is substituted by 1-6 groups selected from —$N(R^e)_3^+$, K, and -Z-$NR^5R^6$; or wherein each alkyl, alkenyl, alkynyl, cycloalkyl, and alkoxyl is substituted by 2-6 groups selected from —$CO_2H$, —OH, and —$N(R^d)_2$. In some embodiments, D is $R^c$; and $R^c$ is —[$(C(R^d)_2)_s$-V$]_t$—$R^9$; wherein each V is independently —$C(R^d)_2O$—, —$C(R^d)_2$ $NR^d$—, or —$C(R^d)_2N^+(R^d)_2$-; and wherein each alkyl, alkenyl, alkynyl, cycloalkyl, and alkoxyl is substituted by 1-6 groups selected from —$N(R^e)_3^+$, K, and -Z- $NR^5R^6$; or wherein each alkyl, alkenyl, alkynyl, cycloalkyl, and alkoxyl is substituted by 2-6 groups selected from —$CO_2H$, —OH, and —$N(R^d)_2$.

In some embodiments, D is K or -Z-$NR^5R^6$.

In some embodiments, D is K; or D is Re; wherein $R^c$ is substituted by K. In some embodiments, D is K. In some embodiments, K is —$SO_2OH$, —$P(O)(OH)(R^d)$, —$P(O)(OH)(OR^d)$, —$CH_2P(O)(OH)(OR^d)$, —$N(R^d)C(O)NHSO_2(R^d)$, —$C(O)NHSO_2(R^d)$, —$SO_2NHC(O)(R^d)$, —

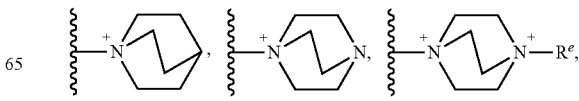

-continued

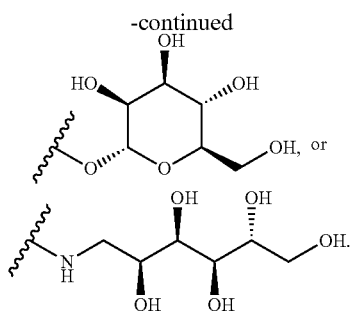

NHC(O)NH($R^d$), In some embodiments,

K is —$SO_2OH$, —P(O)(OH)($R^d$), —P(O)(OH)(O$R^d$), —$CH_2$P(O)(OH)(O$R^d$), —N($R^d$)C(O)NHSO$_2$($R^d$), —

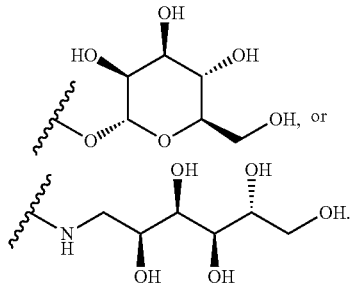

C(O)NHSO$_2$($R^d$), —SO$_2$NHC(O)($R^d$), —NHC(O)NH ($R^d$), In some embodiments, K is —SO$_2$OH, —P(O)(OH) ($R^d$), —P(O)(OH)(O$R^d$), —CH$_2$P(O)(OH)(O$R^d$), —C(O) NHSO$_2$($R^d$), or —SO$_2$NHC(O)($R^d$). In some embodiments, each $R^d$ is independently hydrogen or C$_{1-6}$ alkyl. In some embodiments, K is —SO$_2$OH, —P(O)(OH)($R^d$), —P(O) (OH)(O$R^d$), —CH$_2$P(O)(OH)(O$R^d$), —C(O)NHSO$_2$($R^d$), or —SO$_2$NHC(O)($R^d$); and each $R^d$ is independently hydrogen or C$_{1-6}$ alkyl. In some embodiments, K is —SO$_2$OH, —P(O) (OH)($R^d$), —P(O)(OH)(O$R^d$), —CH$_2$P(O)(OH)(O$R^d$), —C(O)NHSO$_2$($R^d$), or —SO$_2$NHC(O)($R^d$); and each $R^d$ is independently hydrogen or C$_{1-3}$ alkyl. In some embodiments, K is —SO$_2$OH, —P(O)(OH)($R^d$), —P(O)(OH) (O$R^d$), —CH$_2$P(O)(OH)(O$R^d$), —C(O)NHSO$_2$($R^d$), or —SO$_2$NHC(O)($R^d$); and each $R^d$ is independently hydrogen or methyl. In some embodiments, K is —SO$_2$OH, —P(O) (OH)$_2$, —CH$_2$P(O)(OH)$_2$, - P(O)(OH)(Me), —P(O)(OH) (H), or —P(O)(OH)(OMe). In some embodiments, K is —SO$_2$OH or - P(O)(OH)$_2$. In some embodiments, K is —SO$_2$OH. In some embodiments, K is —P(O)(OH)$_2$.

In some embodiments, D is —SO$_2$OH, —P(O)(OH)($R^d$), —P(O)(OH)(O$R^d$), —CH$_2$P(O)(OH)(O$R^d$), —C(O)NHSO$_2$ ($R^d$), or —SO$_2$NHC(O)($R^d$); and each $R^d$ is independently hydrogen or C$_{1-6}$ alkyl. In some embodiments, D is —SO$_2$OH, —P(O)(OH)$_2$, —CH$_2$P(O)(OH)$_2$, - P(O)(OH) (Me), —P(O)(OH)(H), or —P(O)(OH)(OMe). In some embodiments, D is —SO$_2$OH or - P(O)(OH)$_2$. In some embodiments, D is —SO$_2$OH. In some embodiments, D is —P(O)(OH)$_2$.

In some embodiments, D is -Z-NR$^5$R$^6$; or D is Re; wherein R$^c$ is substituted by -Z-NR$^5$R$^6$. In some embodiments, D is -Z-NR$^5$R$^6$.

In some embodiments, Z is —(CH$_2$)$_r$—, *—(CH$_2$)$_r$—C (=O)—, or *—(CH$_2$)$_r$—S(=O)$_2$—, where * represents attachment to

In some embodiments, r is 0, 1, 2, or 3. In some embodiments, r is 0 or 1. In some embodiments, r is 0. In some embodiments, r is 1. In some embodiments, Z is —(CH$_2$)—, —C(=O)—, *—(CH$_2$)—C(=O)—, —S(=O)$_2$—, or *—(CH$_2$)—S(=O)$_2$—. In some embodiments, Z is —(CH$_2$)—, —(CH(CH$_3$))—, —C(=O)—, or —S(=O)$_2$—. In some embodiments, Z is —(CH$_2$)—, —C(=O)—, or —S(=O)$_2$—. In some embodiments, Z is —(CH$_2$)—. In some embodiments, Z is —(CH(CH$_3$))—. In some embodiments, Z is —C(=O)—or —S(=O)$_2$—. In some embodiments, Z is —C(=O)—. In some embodiments, Z is —S(=O)$_2$—.

In some embodiments, R$^5$ is C$_6$-C$_{10}$ alkyl that is substituted by 5 to 9 —OH groups. In some embodiments, R$^5$ is C$_6$-C$_{10}$ alkyl that is substituted by 5 —OH groups.

In some embodiments, R$^5$ is C$_{1-10}$ alkyl, C$_{2-10}$ alkenyl, C$_{2-10}$ alkynyl, C$_{3-10}$ cycloalkyl, C$_{5-10}$ cycloalkenyl, 3- to 8-membered heterocycloalkyl, or 5- to 10-membered heterocycloalkenyl; wherein the alkyl, alkenyl, alkynyl, cycloalkyl, cycloalkenyl, heterocycloalkyl, or heterocycloalkenyl is substituted by 1-6 groups selected from —N(R$^e$)$_3^+$ and K; or wherein the alkyl, alkenyl, alkynyl, cycloalkyl, cycloalkenyl, heterocycloalkyl, or heterocycloalkenyl is substituted by 2-6 groups selected from —CO$_2$H, —OH, and —N(R$^d$)$_2$; and wherein the alkyl, alkenyl, alkynyl, cycloalkyl, cycloalkenyl, heterocycloalkyl, or heterocycloalkenyl is optionally further substituted by 1, 2, or 3 R$^f$ groups. In some embodiments, R$^5$ is C$_{1-10}$ alkyl, C$_{2-10}$ alkenyl, C$_{2-10}$ alkynyl, or C$_{3-10}$ cycloalkyl wherein the alkyl, alkenyl, alkynyl, or cycloalkyl is substituted by 1-6 groups selected from —N(R$^e$)$_3^+$ and K; and the alkyl, alkenyl, alkynyl, or cycloalkyl is optionally further substituted by 1, 2, or 3 R$^f$ groups. In some embodiments, R$^5$ is C$_{1-10}$ alkyl, C$_{2-10}$ alkenyl, or C$_{2-10}$ alkynyl; wherein the alkyl, alkenyl, or alkynyl is substituted by 1-6 groups selected from —N(R$^e$)$_3^+$ and K; and the alkyl, alkenyl, or alkynyl is optionally further substituted by 1, 2, or 3 R$^f$ groups. In some embodiments, R$^5$ is C$_{1-10}$ alkyl or C$_{2-10}$ alkynyl; wherein the alkyl or alkynyl is substituted by 1-3 groups selected from —N(R$^e$)$_3^+$ and K; and the alkyl or alkynyl is optionally further substituted by 1, 2, or 3 R$^f$ groups. In some embodiments, R$^5$ is C$_{1-10}$ alkyl or C$_{2-10}$ alkynyl; wherein the alkyl or alkynyl is substituted by 1 group selected from —N(R$^e$)$_3^+$ and K; and the alkyl or alkynyl is optionally further substituted by 1, 2, or 3 R$^f$ groups. In some embodiments, each R$^e$ is independently C$_{1-6}$ alkyl. In some embodiments, R$^5$ is C$_{1-10}$ alkyl or C$_{2-10}$ alkynyl; wherein the alkyl, or alkynyl is substituted by 1 group selected from —N(R$^e$)$_3^+$ and K; and the alkyl or alkynyl is optionally further substituted by 1, 2, or 3 R$^f$ groups; and each Re is independently C$_{1-6}$ alkyl. In some embodiments, R$^5$ is C$_{1-10}$ alkyl or C$_{2-10}$ alkynyl; wherein the alkyl or alkynyl is substituted by K; and the alkyl or alkynyl is optionally further substituted by 1, 2, or 3 R$^f$ groups. In some embodiments, R$^5$ is C$_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 R$^f$ groups.

In some embodiments, R$^5$ is —[(C(R$^d$)$_2$)$_s$—V]$_t$—R$^9$; wherein each V is independently - C(R$^d$)$_2$O—, —C(R$^d$)$_2$ NR$^d$—, —C(R$^d$)$_2$N$^+$(R$^d$)$_2$—, —N(R$^d$)—C(O)—N(R$^d$)—, —C(O)N(R$^d$)—, —C(R$^d$)$_2$SO$_2$—, or —C(R$^d$)$_2$S(O)—. In some embodiments, $R^5$ is $-[(C(R^d)_2)_s-V]_t-R^9$; wherein each V is independently - $C(R^d)_2O-$, $-C(R^d)_2NR^d-$, $-C(R^d)_2N^+(R^d)_2-$, $-N(R^d)-C(O)-N(R^d)-$, or $-C(O)N(R^d)-$. In some embodiments, $R^5$ is $-[(C(R^d)_2)_s-V]_t-R^9$; wherein each V is independently $-C(R^d)_2O-$, $-C(R^d)_2NR^d-$, $-C(R^d)_2N^+(R^d)_2-$, or $-N(R^d)-C(O)-N(R^d)-$. In some embodiments, $R^5$ is $-[(C(R^d)_2)_s-V]_t-R^9$; wherein each V is independently $-C(R^d)_2O-$, $-C(R^d)_2NR^d-$, or $-N(R^d)-C(O)-N(R^d)-$, or $-C(O)N(R^d)-$. In some embodiments, $R^5$ is $-[(C(R^d)_2)_s-V]_t-R^9$; wherein each V is independently $-C(R^d)_2O-$, $-C(R^d)_2NR^d-$, or $-N(R^d)-C(O)-N(R^d)-$. In some embodiments, $R^5$ is $-[(C(R^d)_2)_s-V]_t-R^9$; wherein each V is independently $-C(R^d)_2O-$. In some embodiments, each $R^d$ is independently hydrogen or $C_{1-6}$ alkyl. In some embodiments, $R^9$ is hydrogen, $C_{1-8}$ alkyl, phenyl, or naphthyl, wherein the alkyl, phenyl, or naphthyl is unsubstituted or substituted by 1-6 groups selected from $-OH$, $-CO_2H$, $-N(R^e)_2$, $-N(R^e)_3^+$, and K. In some embodiments, $R^9$ is hydrogen. In some embodiments, $R^9$ is $C_{1-8}$ alkyl, phenyl, or naphthyl, wherein the alkyl, phenyl, or naphthyl is unsubstituted or substituted by 1-3 groups selected from $-OH$, $-CO_2H$, $-N(R^e)_2$, $-N(R^e)_3^+$, and K. In some embodiments, $R^9$ is naphthyl, which is unsubstituted or substituted by 1 group selected from K.

In some embodiments, $R^5$ is $-(C_1-C_6$ alkylene)-aryl, or $-(C_1-C_6$ alkylene)-heteroaryl; wherein the aryl or heteroaryl is substituted by 1-6 groups selected from $-CO_2H$, $-OH$, $-N(R^d)_2$, $-N(R^e)_3^+$, and K; and wherein the alkylene is unsubstituted or substituted by 1, 2, or 3 $R^f$ groups. In some embodiments, $R^5$ is $-(C_1-C_4$ alkylene)-aryl, or $-(C_1-C_4$ alkylene)-heteroaryl; wherein the aryl or heteroaryl is substituted by 1-6 groups selected from $-CO_2H$, $-OH$, $-N(R^d)_2$, $-N(R^e)_3^+$, and K; and wherein the alkylene is unsubstituted or substituted by 1, 2, or 3 $R^f$ groups. In some embodiments, $R^5$ is $-(C_1-C_4$ alkylene)-aryl, or $-(C_1-C_4$ alkylene)-heteroaryl; wherein the aryl or heteroaryl is substituted by 1-6 groups selected from $-CO_2H$, $-OH$, $-N(R^d)_2$, $-N(R^e)_3^+$, and K; and wherein the alkylene is unsubstituted. In some embodiments, the aryl is selected from phenyl and naphthyl. In some embodiments, the heteroaryl is selected from monocyclic or bicyclic heteroaryl.

In some embodiments, $R^5$ and $R^6$ are taken together with the nitrogen to which they are attached to form a 3- to 6-membered N-heterocycloalkyl which is unsubstituted or substituted with 1-6 groups selected from $-CH_3$, $-CH_2OH$, $-CH_2NH_2$, $-CH_2CH_2OH$, $-CH_2OCH_2CH_2OH$, $-N(R^e)_3^+$ and K; or with 2-6 groups selected from $-CO_2H$, $-OH$, $-CH_2OH$, $-CH_2NH_2$, $-CH_2CH_2OH$, $-CH_2OCH_2CH_2OH$, and $-N(R^d)_2$. In some embodiments, $R^5$ and $R^6$ are taken together with the nitrogen to which they are attached to form a 3- to 6-membered N-heterocycloalkyl which is unsubstituted or substituted with 1-6 groups selected from $-N(R^e)_3^+$ and K; or with 2-6 groups selected from $-CO_2H$, $-OH$, $-CH_2OH$, and $-N(R^d)_2$. In some embodiments, $R^5$ and $R^6$ are taken together with the nitrogen to which they are attached to form a 3- to 6-membered N-heterocycloalkyl which is unsubstituted or substituted with 2-6 groups selected from $-CO_2H$, $-OH$, $-CH_2OH$, $-CH_2NH_2$, $-CH_2CH_2OH$, $-CH_2OCH_2CH_2OH$, and $-N(R^d)_2$. In some embodiments, $R^5$ and $R^6$ are taken together with the nitrogen to which they are attached to form a 3- to 6-membered N-heterocycloalkyl which is unsubstituted or substituted with 2-6 groups selected from $-CO_2H$, $-OH$, $-CH_2OH$, and $-N(R^d)_2$. In some embodiments, $R^5$ and $R^6$ are taken together with the nitrogen to which they are attached to form a 3- to 6-membered N-heterocycloalkyl which is unsubstituted or substituted with 2-4 groups selected from $-OH$ and $-CH_2OH$. In some embodiments, $R^5$ and $R^6$ are taken together with the nitrogen to which they are attached to form a 4- to 6-membered N-heterocycloalkyl which is unsubstituted or substituted with 2-4 groups selected from $-OH$ and $-CH_2OH$. In some embodiments, $R^5$ and $R^6$ are taken together with the nitrogen to which they are attached to form a 4- to 6-membered N-heterocycloalkyl which is substituted with 2-4 groups selected from $-OH$ and $-CH_2OH$.

In some embodiments, each $R^f$ is independently halogen, $-CN$, $-OH$, $-OR^{13}$, $-NR^{14}R^{14}$, $-C(O)OR^{14}$, $-C(O)NR^{14}R^{14}$, $-NR^{14}C(O)NR^{14}$, $-NR^{14}C(O)NR^{14}R^{14}$, $C_1-C_6$ alkyl, $C_3-C_6$ cycloalkyl, or phenyl, wherein the alkyl, cycloalkyl, or phenyl, is unsubstituted or substituted by 1, 2, or 3 halogen or $-OH$ groups. In some embodiments, each $R^f$ is independently halogen, $-CN$, $-OH$, $-OR^{13}$, $-NR^{14}R^{14}$, $-C(O)OR^{14}R^{14}$, $C_3-C_6$ cycloalkyl, or phenyl, wherein the cycloalkyl, or phenyl, is unsubstituted or substituted by 1, 2, or 3 halogen or $-OH$ groups. In some embodiments, each $R^f$ is $-OH$.

In some embodiments, $R^6$ is hydrogen or $C_{1-6}$ alkyl; wherein the alkyl is unsubstituted or substituted by 1-3 groups independently selected from halogen, $-CN$, $-OH$, $-OR^{13}$, $-NR^{14}R^{14}$, $-C(O)R^{13}$, $-C(O)OR^{14}$, $-OC(O)R^{13}$, $-C(O)NR^{14}R^{14}$, $-NR^{14}C(O)R^{14}$, $-NR^{14}C(O)NR^{14}R^{14}$, $-OC(O)NR^{14}R^{14}$, $-NR^{14}C(O)OR^{14}$, $-OC(O)OR^{14}$, or $-P(O)(OR^{14})_2$. In some embodiments, $R^6$ is hydrogen or $C_{1-6}$ alkyl; wherein the alkyl is unsubstituted or substituted by 1-3 groups independently selected from halogen, $-CN$, $-OH$, $-OR^{13}$, $-NR^{14}R^{14}$, $-C(O)NR^{14}R^{14}$, $-NR^{14}C(O)R^{14}$, $-NR^{14}C(O)NR^{14}R^{14}$, or $-P(O)(OR^{14})_2$. In some embodiments, $R^6$ is hydrogen or $C_{1-6}$ alkyl; wherein the alkyl is unsubstituted or substituted by 1-3 groups independently selected from halogen, $-OH$, or $-C(O)NR^{14}R^{14}$. In some embodiments, $R^6$ is hydrogen or $C_{1-6}$ alkyl; wherein the alkyl is unsubstituted or substituted by 1-3 halogen or $-OH$ groups. In some embodiments, $R^6$ is hydrogen or $C_{1-6}$ alkyl; wherein the alkyl is unsubstituted or substituted by 1-3 $-OH$ groups. In some embodiments, $R^6$ is hydrogen or $C_{1-6}$ alkyl. In some embodiments, $R^6$ is hydrogen. In some embodiments, $R^6$ is $C_{1-6}$ alkyl.

In some embodiments, $R^5$ is $C_6-C_{10}$ alkyl that is substituted by 5 to 9 $-OH$ group and $R^6$ is hydrogen or $C_{1-6}$ alkyl. In some embodiments, $R^5$ is $C_6-C_{10}$ alkyl that is substituted by 5 to 9 $-OH$ groups and $R^6$ is $C_{1-6}$ alkyl. In some embodiments, $R^5$ is $C_6-C_{10}$ alkyl that is substituted by 5 to 9 $-OH$ groups and $R^6$ is hydrogen. In some embodiments, $R^5$ is $C_6-C_{10}$ alkyl that is substituted by 5 $-OH$ groups and $R^6$ is hydrogen.

In some embodiments, $R^5$ is $C_{1-10}$ alkyl which is substituted by 1-6 groups selected from $-N(R^e)_3^+$ and K; or with 2-6 groups selected from $-CO_2H$, $-OH$, and $-N(R^d)_2$; and is optionally further substituted by 1, 2, or 3 $R^f$ groups; each $R^f$ is independently halogen, $-CN$, $-OH$, $-OR^{13}$, $-NR^{14}R^{14}$, $-C(O)OR^{14}$, $-C(O)NR^{14}R^{14}$, $-NR^{14}C(O)R^{14}$, $-NR^{14}C(O)NR^{14}R^{14}$, $C_1-C_6$ alkyl, $C_3-C_6$ cycloalkyl, or phenyl, wherein the alkyl, cycloalkyl, or phenyl, is unsubstituted or substituted by 1, 2, or 3 halogen or $-OH$ groups; and $R^6$ is hydrogen or $C_{1-6}$ alkyl, which is unsubstituted or substituted by 1-3 groups independently selected from halogen, $-CN$, $-OH$, $-OR^{13}$, $-NR^{14}R^{14}$, $-C(O)OR^{14}$, $-C(O)NR^{14}R^{14}$, $-NR^{14}C(O)R^{14}$, $-NR^{14}C(O)NR^{14}R^{14}$, or $-P(O)(OR^{14})_2$. In some embodiments, $R^5$ is $C_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 R$^f$ groups; each R$^f$ is independently halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups; and R$^6$ is hydrogen or C$_{1-6}$ alkyl.

In some embodiments, R$^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—; each R$^d$ is independently hydrogen or C$_{1-6}$ alkyl; R$^6$ is hydrogen or C$_{1-6}$ alkyl; and R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3^+$, and K. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl. In some embodiments, K is —SO$_2$OH, —P(O)(OH)$_2$, - CH$_2$P(O)(OH)$_2$, —P(O)(OH)(Me), —P(O)(OH)(H), or —P(O)(OH)(OMe). In some embodiments, K is —SO$_2$OH or —P(O)(OH)$_2$.

In some embodiments, R$^5$ is —(C$_1$-C$_6$ alkylene)-aryl, or —(C$_1$-C$_6$ alkylene)-heteroaryl; wherein the aryl or heteroaryl is substituted by 1-6 groups selected from —CO$_2$H, —OH, —N(R$^d$)$_2$, —N(R$^e$)$_3^+$, and K; and wherein the alkylene is unsubstituted or substituted by 1, 2, or 3 R$^f$ groups; and R$^6$ is hydrogen or C$_{1-6}$ alkyl. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl. In some embodiments, K is —SO$_2$OH, —P(O)(OH)$_2$, —CH$_2$P(O)(OH)$_2$, —P(O)(OH)(Me), —P(O)(OH)(H), or —P(O)(OH)(OMe). In some embodiments, K is —SO$_2$OH or —P(O)(OH)$_2$.

In some embodiments, R$^5$ and R$^6$ are taken together with the nitrogen to which they are attached to form a 3- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl. In some embodiments, K is —SO$_2$OH, —P(O)(OH)$_2$, —CH$_2$P(O)(OH)$_2$, —P(O)(OH)(Me), —P(O)(OH)(H), or —P(O)(OH)(OMe). In some embodiments, K is —SO$_2$OH or —P(O)(OH)$_2$.

In some embodiments, D is

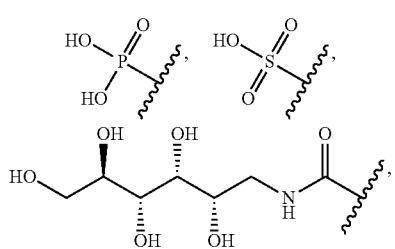

-continued

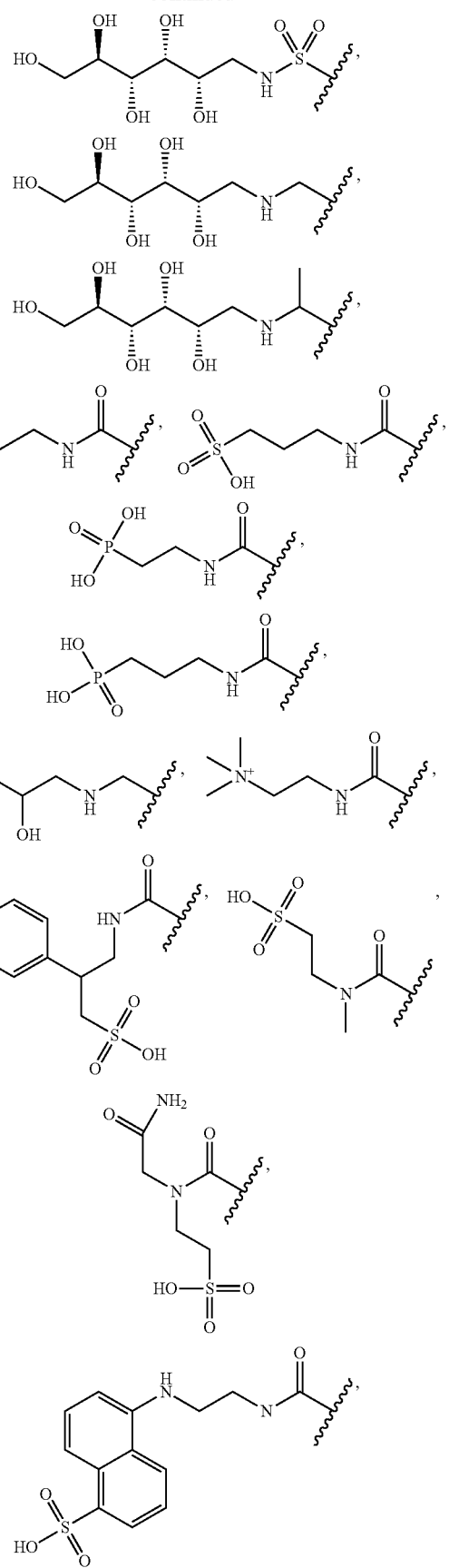

61
-continued
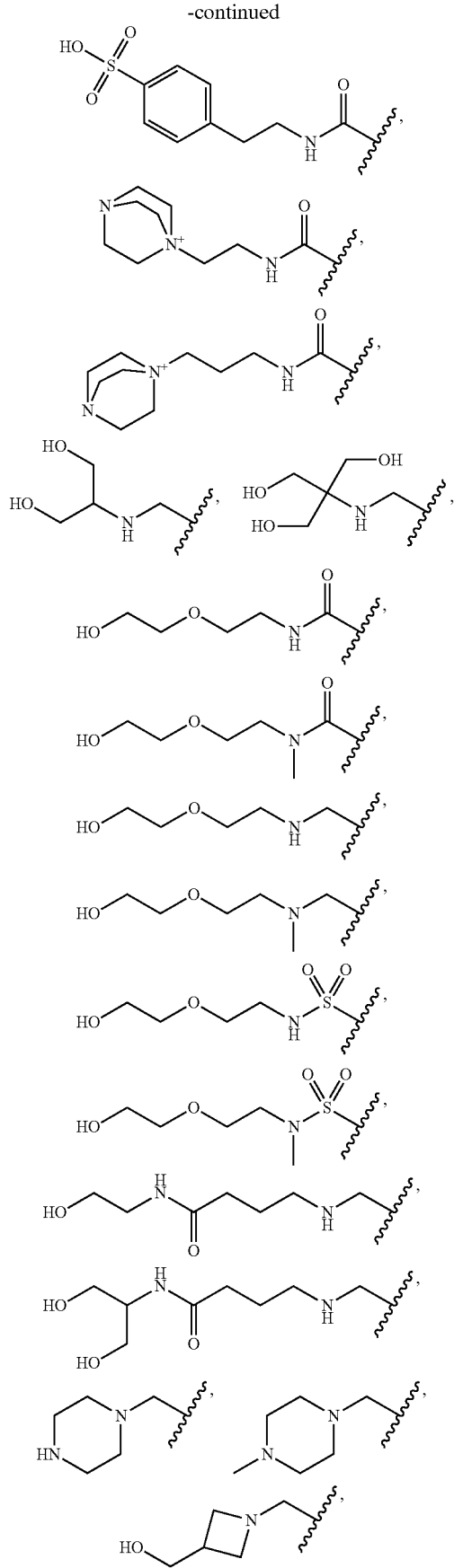
62
-continued
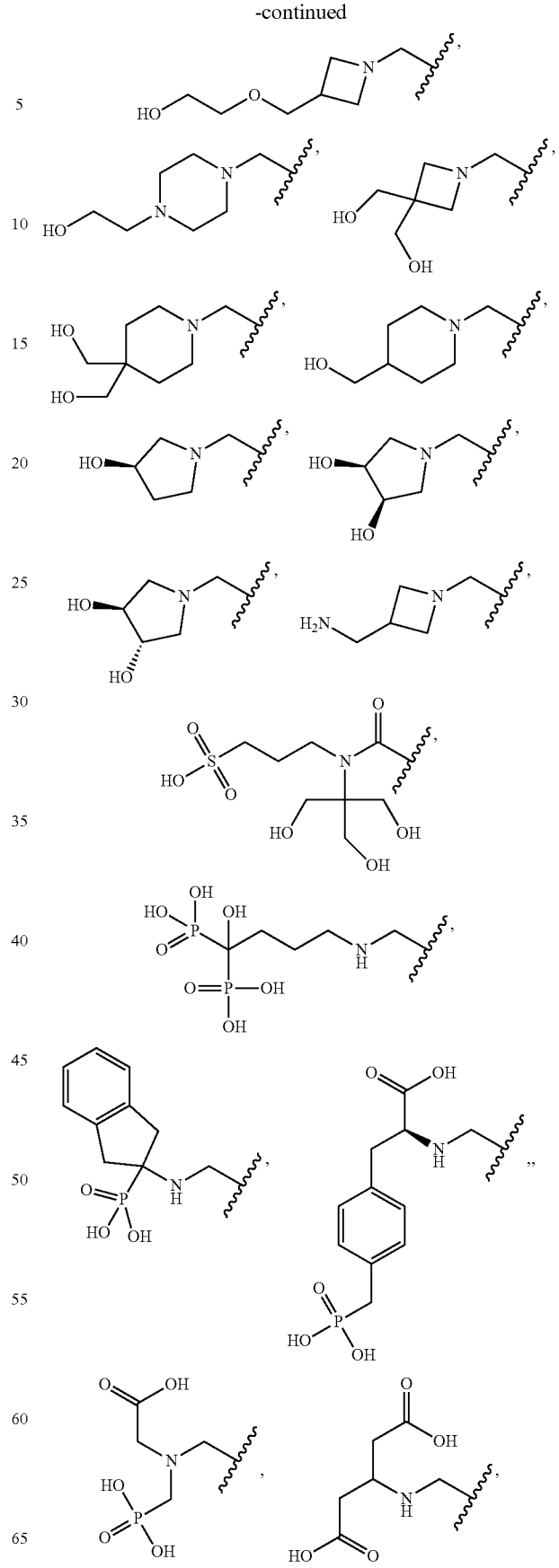

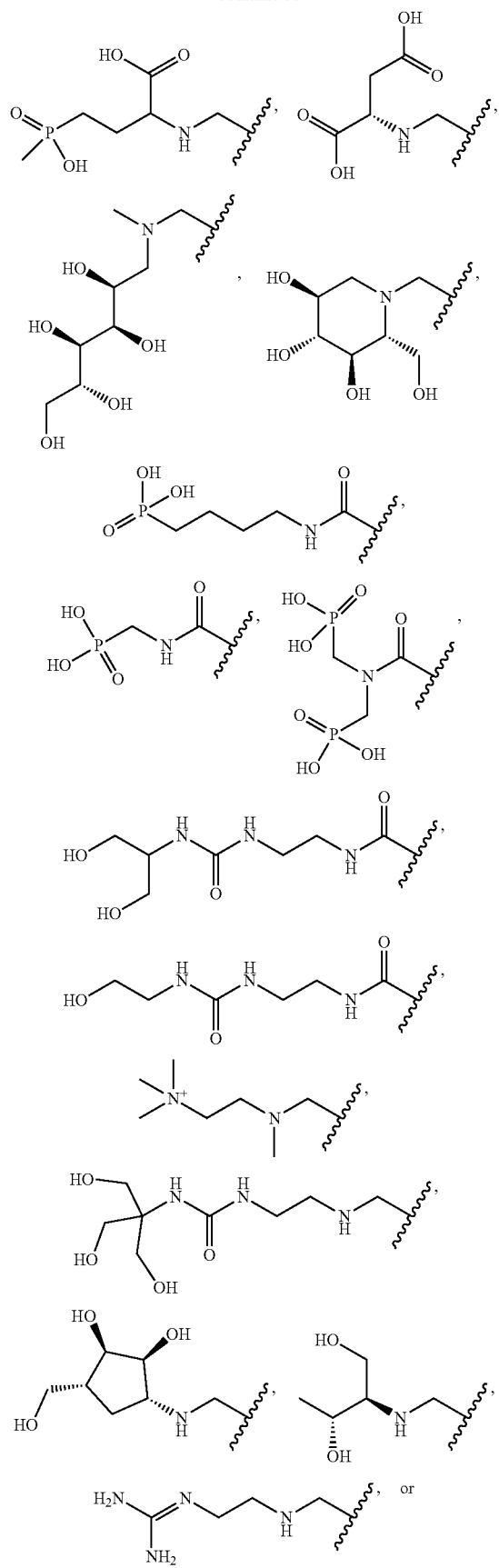
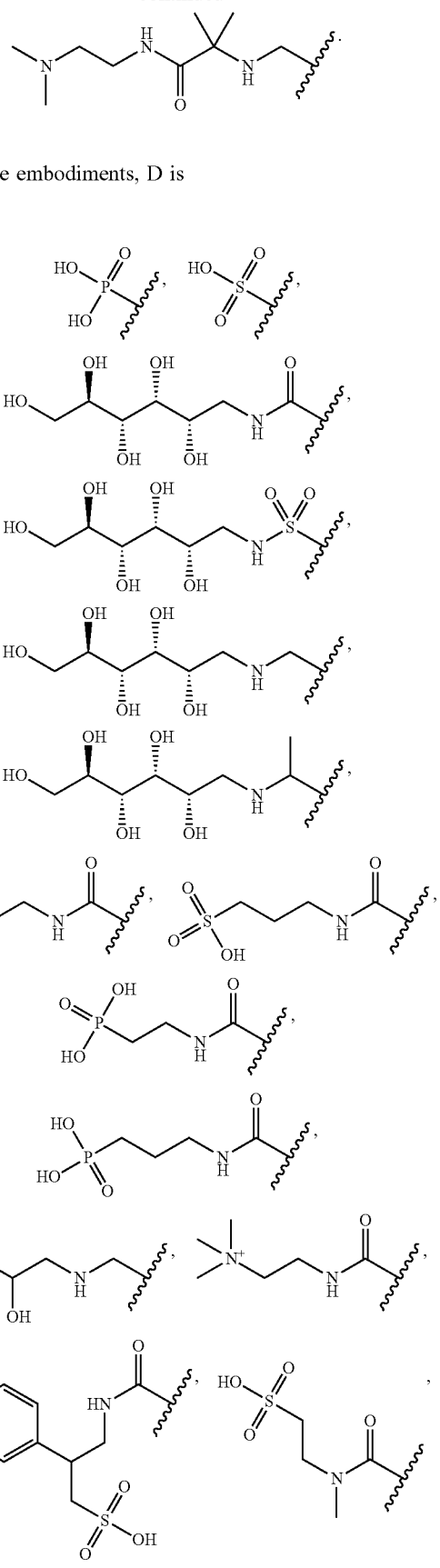
In some embodiments, D is

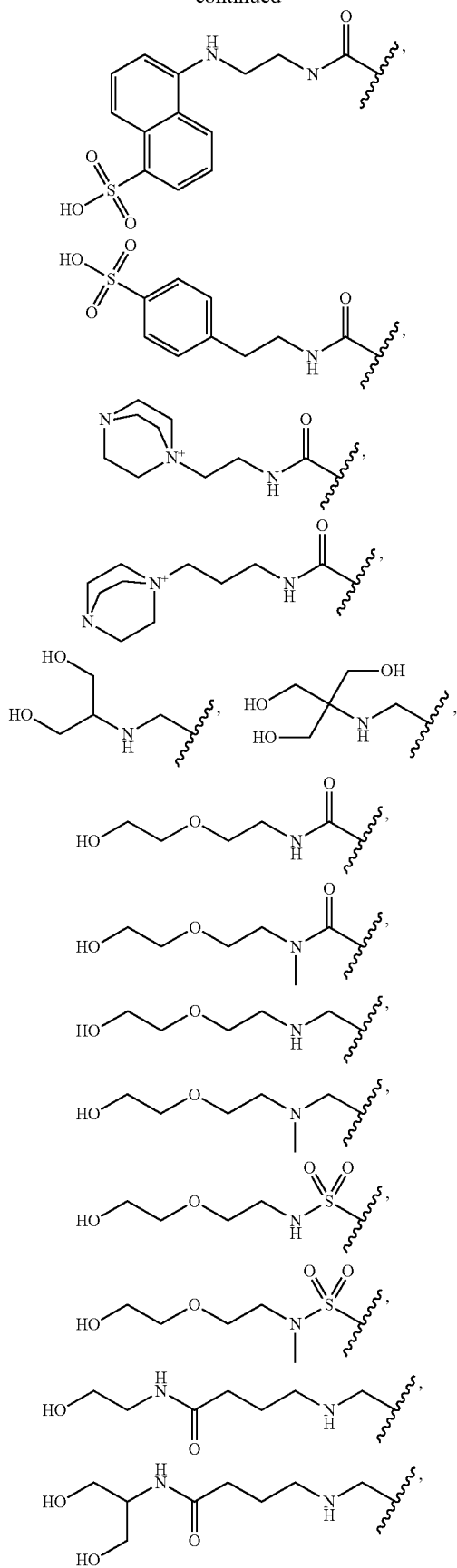
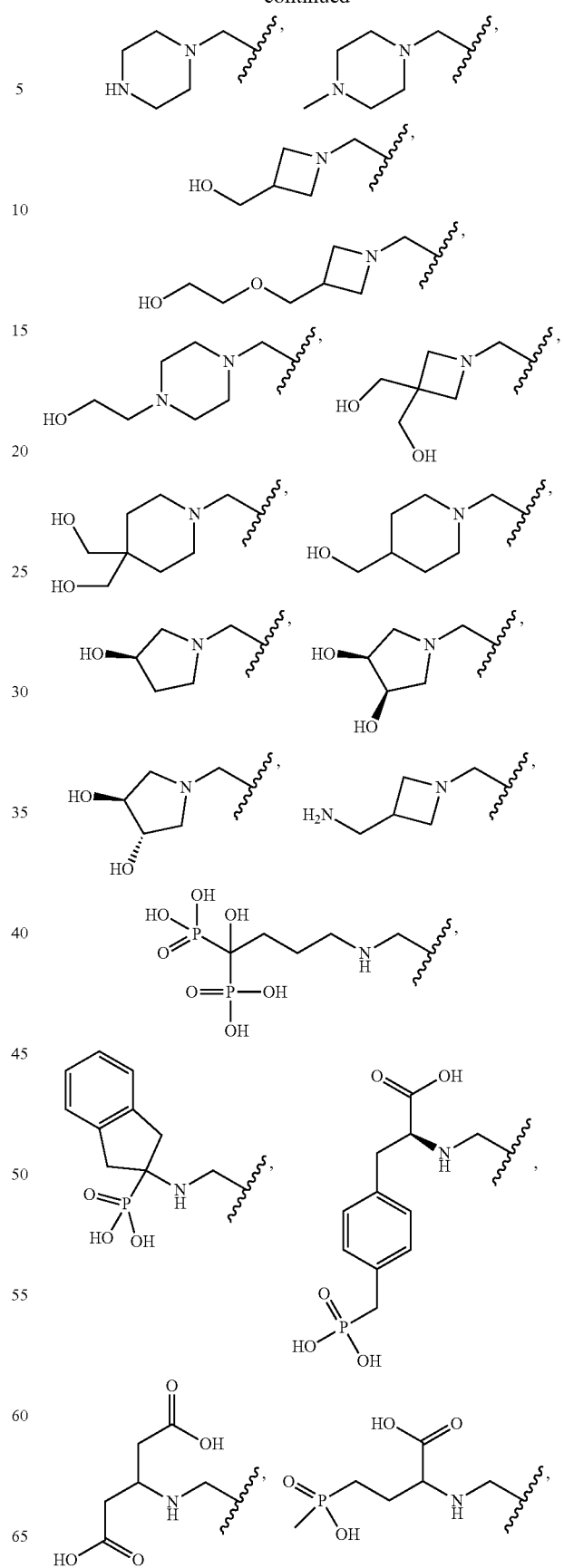

-continued
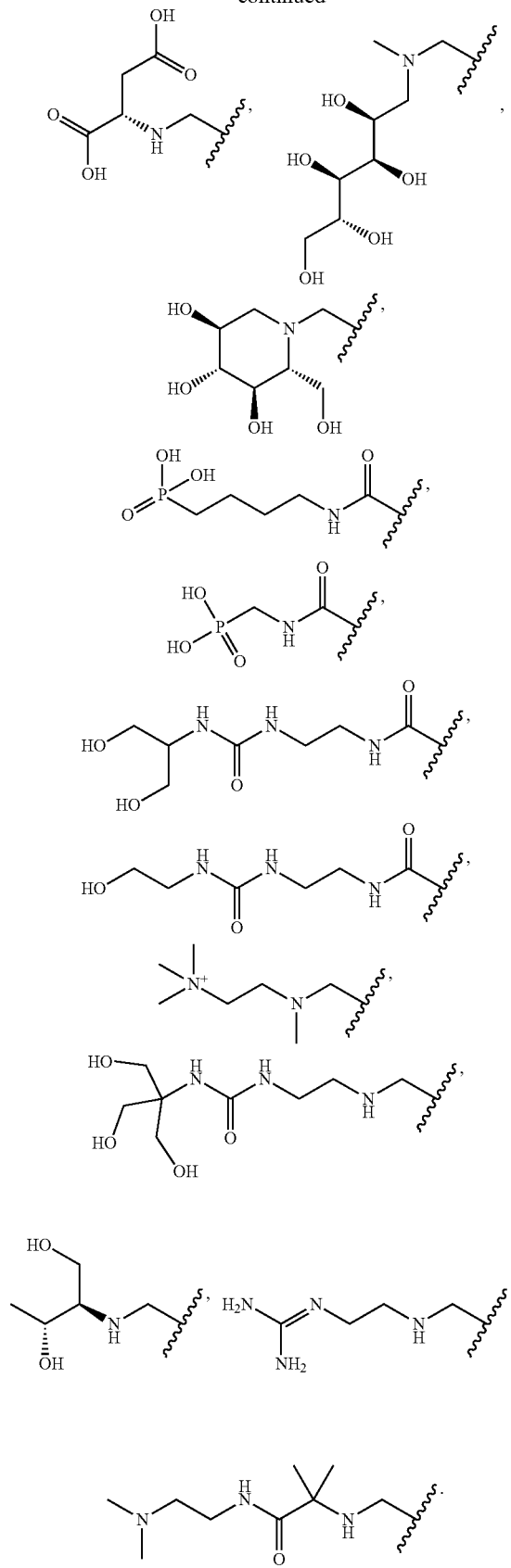
In some embodiments, D is
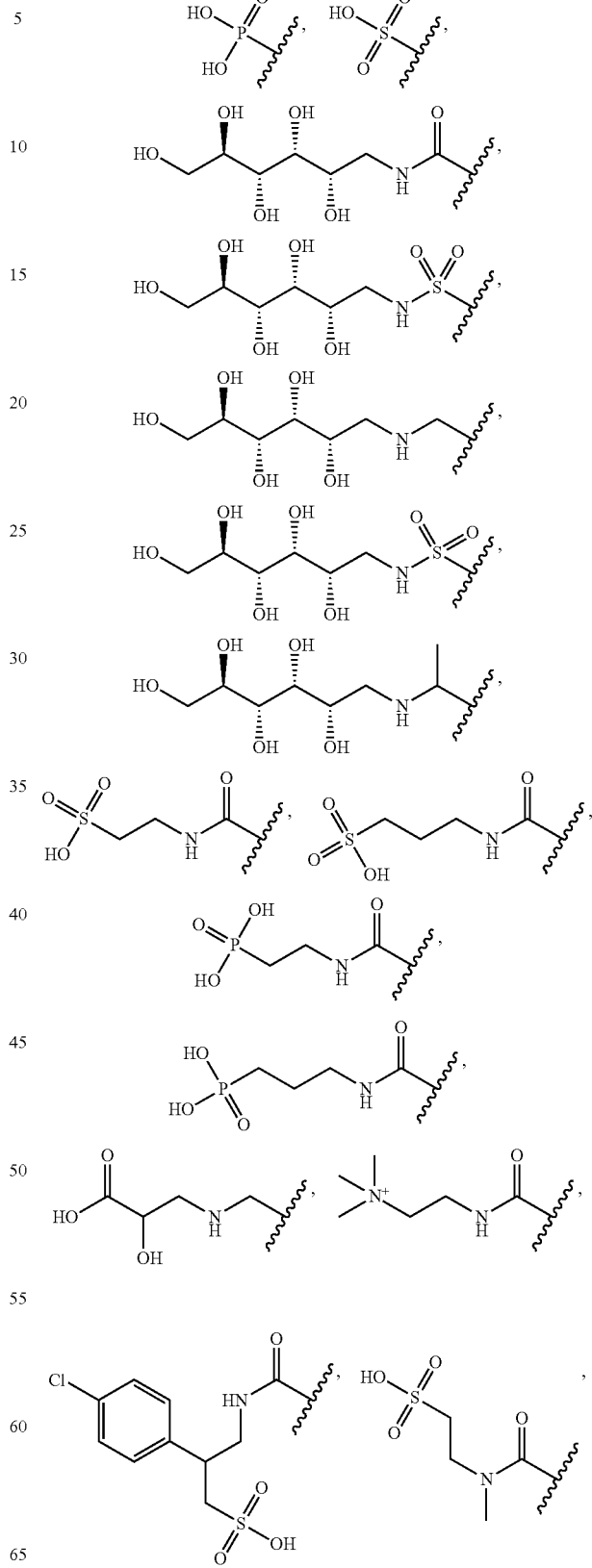

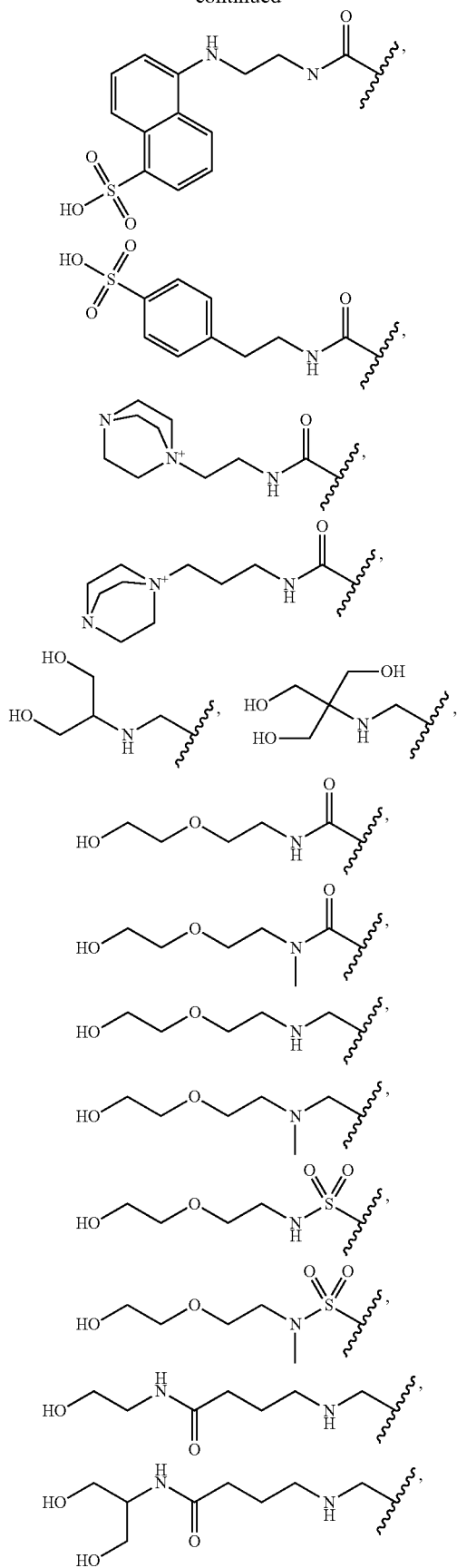
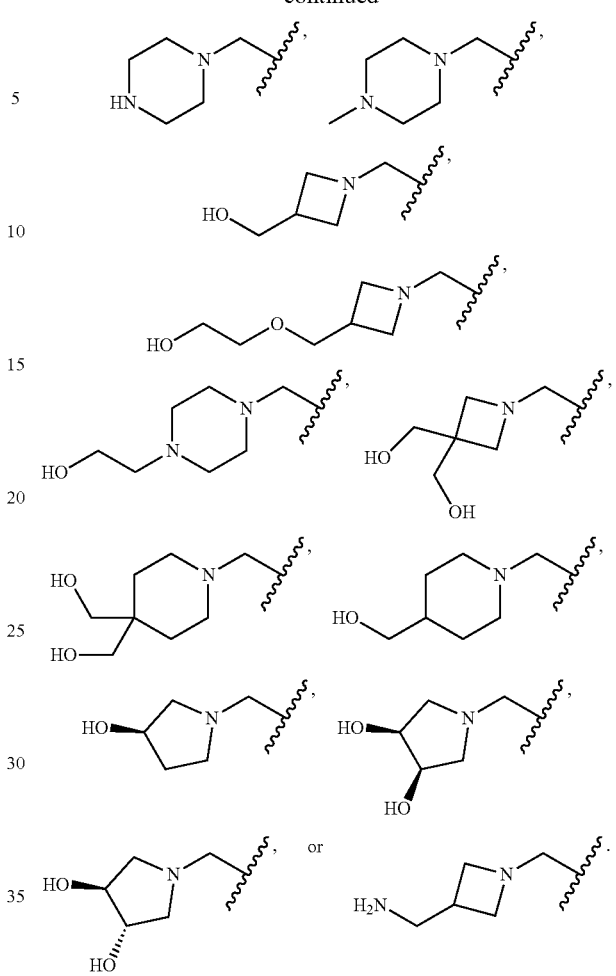
In some embodiments, D is
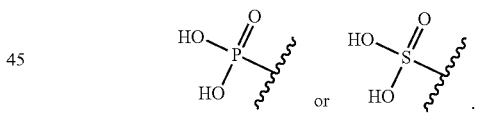
In some embodiments, D is
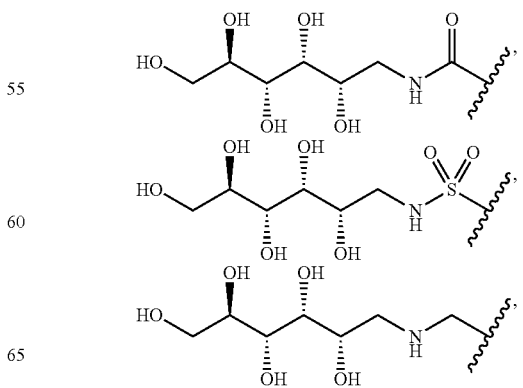

-continued
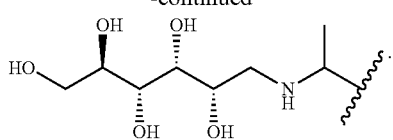
In some embodiments, D is
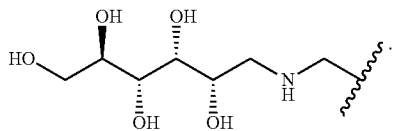 [SMILES: *CNC[C@H](O)[C@@H](O)[C@H](O)[C@H](O)CO]
In some embodiments, D is
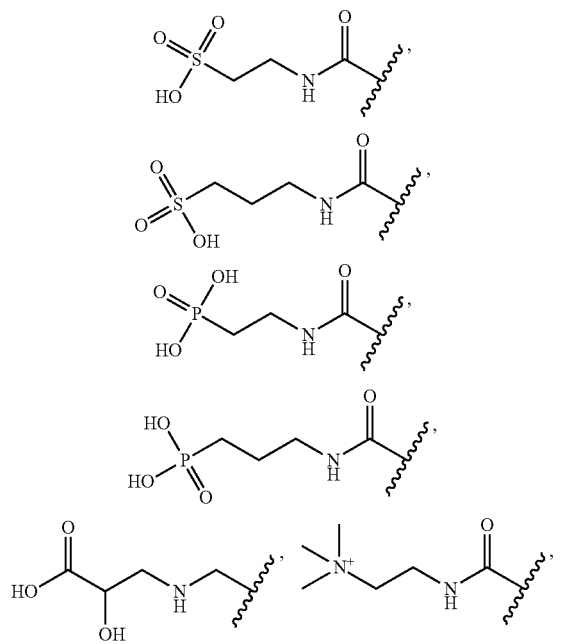
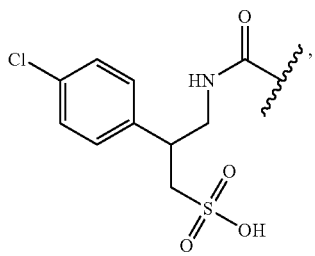
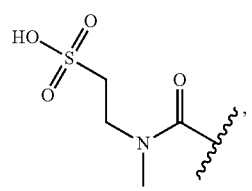
-continued
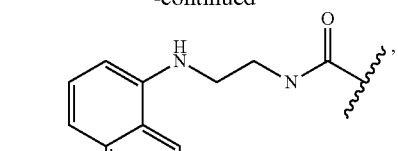
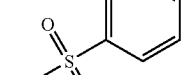
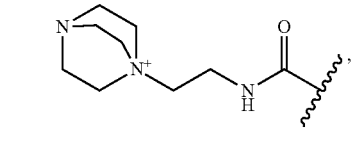
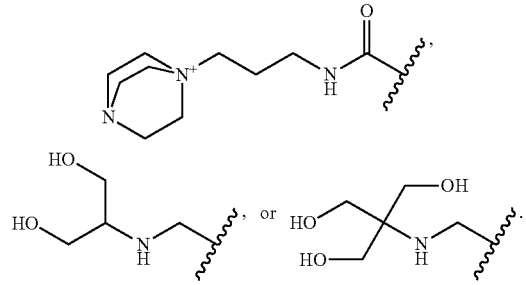
In some embodiments, D is
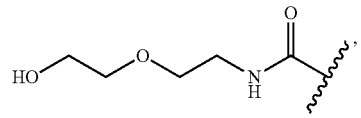
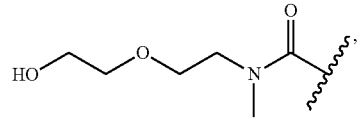
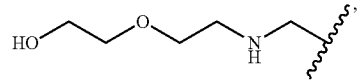
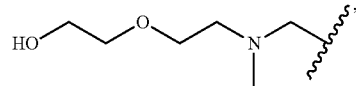
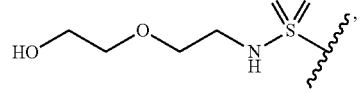
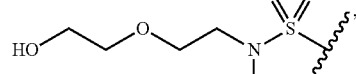
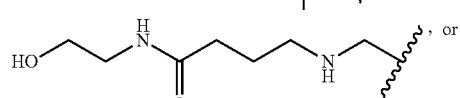
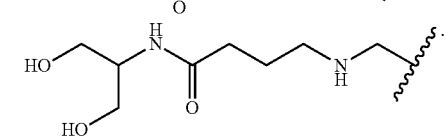

In some embodiments, D is

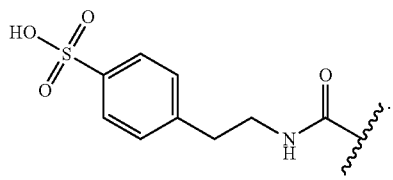 [SMILES: *C(=O)NCCc1ccc(S(=O)(=O)O)cc1]

In some embodiments, D is

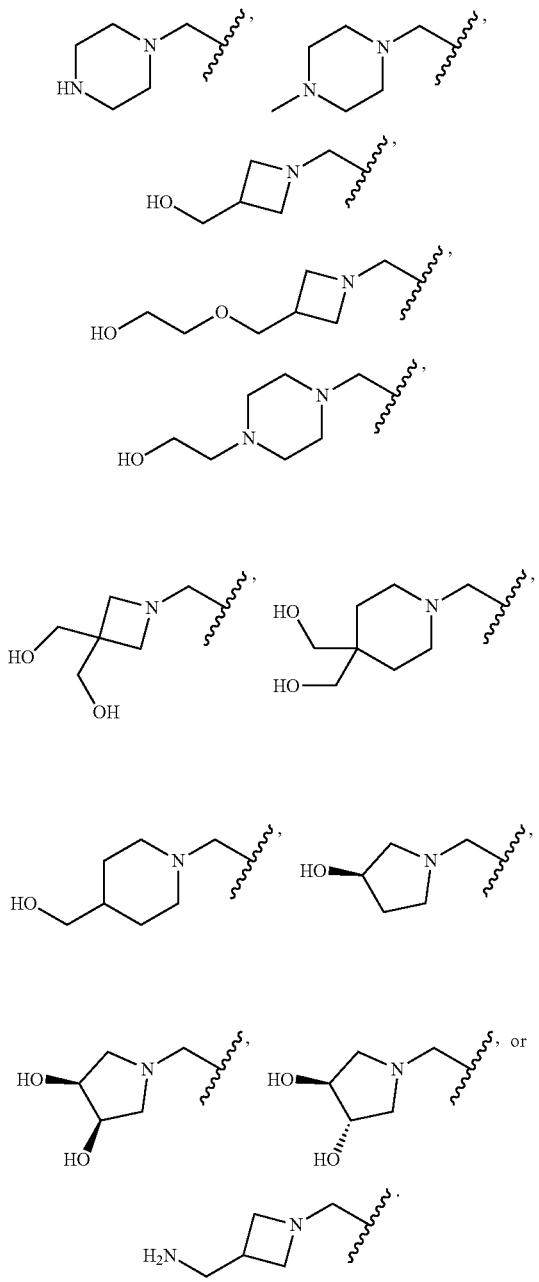

In some embodiments, the compound has the structure of Formula (V):

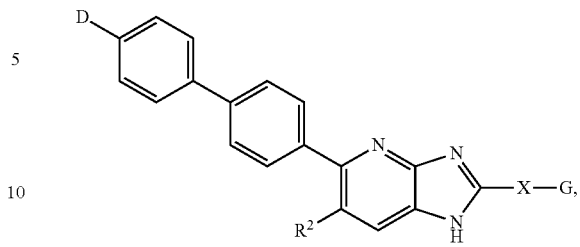

Formula (V)

or a pharmaceutically acceptable salt, solvate, stereoisomer, or prodrug thereof. In some embodiments of a compound of Formula (V), $R^2$ is —F, —Cl, or —CN; X is O or S; G is monocyclic 3-to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH; or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH; D is K or —Z—NR$^5$R$^6$. In some embodiments, G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH; D is K or —Z—NR$^5$R$^6$ In some embodiments of a compound of Formula (V), D is K; K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl.

In some embodiments of a compound of Formula (V), D is —Z—NR$^5$R$^6$; Z is —(CH$_2$)—, —(CH(CH$_3$))—, —C(=O)—, or —S(=O)$_2$-; and R$^5$ is C$_6$-C$_{10}$ alkyl that is substituted by 5 to 9 —OH groups; or R$^5$ is C$_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 R$^f$ groups; or R$^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—; each R$^d$ is independently hydrogen or C$_{1-6}$ alkyl; R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3^+$, and K; or R$^5$ is —(C$_1$-C$_6$ alkylene)—aryl, or —(C$_1$-C$_6$ alkylene)—heteroaryl; wherein the aryl or heteroaryl is substituted by 1-6 groups selected from —CO$_2$H, —OH, —N(R$^d$)$_2$, —N(R$^e$)$_3^+$, and K; and wherein the alkylene is unsubstituted or substituted by 1, 2, or 3 R$^f$ groups; R$^6$ is hydrogen or C$_{1-6}$ alkyl, which is unsubstituted or substituted by 1-3 groups independently selected from halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, or —P(O)(OR$^{14}$)$_2$; or R$^5$ and R$^6$ are taken together with the nitrogen to which they are attached to form a 4- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3$$^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$; and each R$^f$ is independently halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{14}$, —NR$^{14}$C(O)R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups. In some embodiments, D is —Z—NR$^5$R$^6$; Z is —(CH$_2$)—, —C(=O)—, or —S(=O)$_2$-; and R$^5$ is C$_6$-C$_{10}$ alkyl that is substituted by 5 to 9 —OH groups; or R$^5$ is C$_{1-10}$ alkyl which is substituted by 1-6 groups selected from —N(R$^e$)$_3$$^+$ and K; or with 2-6 groups selected from —CO$_2$H, —OH, and —N(R$^d$)$_2$; and is optionally further substituted by 1, 2, or 3 R$^f$ groups; or R$^5$ is —[(C(R$^d$)$_2$)$_s$—V]$_t$—R$^9$; wherein each V is independently —C(R$^d$)$_2$O—, —C(R$^d$)$_2$NR$^d$—, or —N(R$^d$)—C(O)—N(R$^d$)—; each R$^d$ is independently hydrogen or C$_{1-6}$ alkyl; R$^9$ is hydrogen, C$_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3$$^+$, and K; or R$^5$ is —(C$_1$-C$_6$ alkylene)—aryl, or —(C$_1$-C$_6$ alkylene)—heteroaryl; wherein the aryl or heteroaryl is substituted by 1-6 groups selected from —CO$_2$H, —OH, —N(R$^d$)$_2$, —N(R$^e$)$_3$$^+$, and K; and wherein the alkylene is unsubstituted or substituted by 1, 2, or 3 R$^f$ groups; R$^6$ is hydrogen or C$_{1-6}$ alkyl, which is unsubstituted or substituted by 1-3 groups independently selected from halogen, —CN, —OH, —OR$^-$, —NR$^{14}$R$^{14}$, —C(O)OR$^{14}$, —C(O)NR$^{14}$R$^{14}$, —NR$^{14}$C(O)R$^{14}$, —NR$^{14}$C(O)NR$^{14}$R$^{14}$, or —P(O)(OR$^{14}$)$_2$; and each R$^f$ is independently halogen, —CN, —OH, —OR$^{13}$, —NR$^{14}$R$^{14}$, C(O)OR$^{14}$, —C(O)NR$^{14}$R$^{14}$, —NR$^{14}$C(O)R$^{14}$, NR$^{14}$C(O)NR$^{14}$R$^{14}$, C$_1$-C$_6$ alkyl, C$_3$-C$_6$ cycloalkyl, or phenyl, wherein the alkyl, cycloalkyl, or phenyl, is unsubstituted or substituted by 1, 2, or 3 halogen or —OH groups. In some embodiments, R$^5$ is C$_6$-C$_{10}$ alkyl that is substituted by 5 to 9 —OH groups; or R$^5$ is C$_{1-10}$ alkyl which is substituted by 1-6 groups selected from —N(R$^e$)$_3$$^+$ and K; or with 2-6 groups selected from —CO$_2$H, —OH, and —N(R$^d$)$_2$; and is optionally further substituted by 1, 2, or 3 R$^f$ groups; and R$^6$ is hydrogen or C$_{1-6}$ alkyl. In some embodiments, R$^5$ is C$_6$-C$_{10}$ alkyl that is substituted by 5 to 9 —OH groups; and R$^6$ is hydrogen or C$_{1-6}$ alkyl. In some embodiments, K is —SO$_2$OH, —P(O)(OH)(R$^d$), —P(O)(OH)(OR$^d$), —CH$_2$P(O)(OH)(OR$^d$), —C(O)NHSO$_2$(R$^d$), or —SO$_2$NHC(O)(R$^d$); and each R$^d$ is independently hydrogen or C$_{1-6}$ alkyl.

In some embodiments of a compound of Formula (V), D is

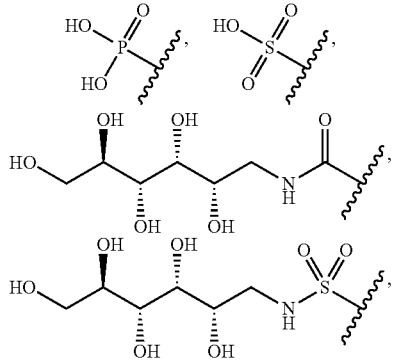

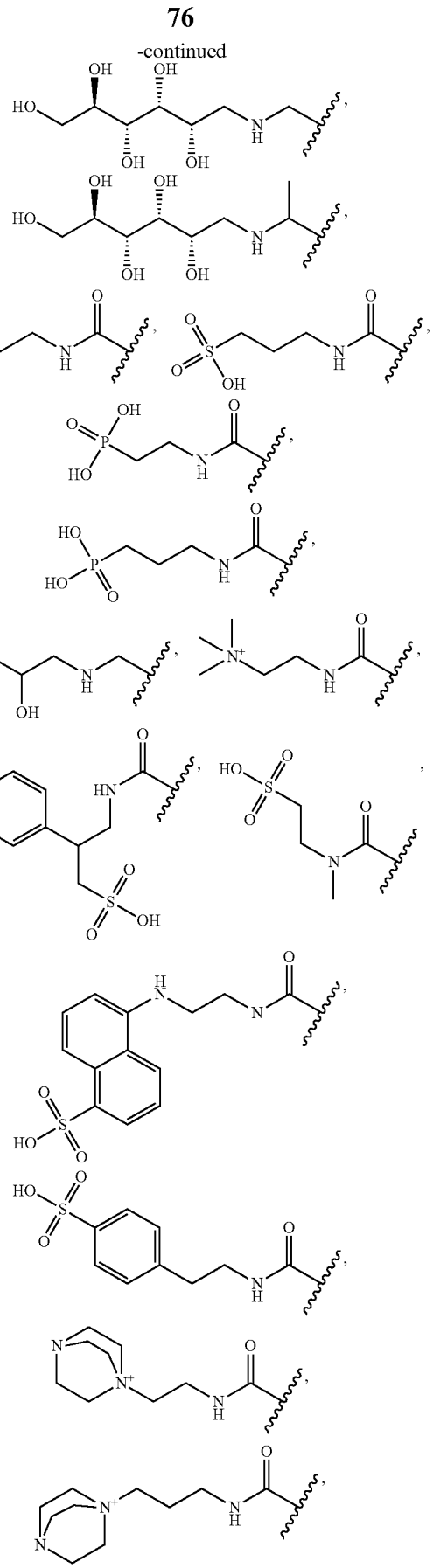

-continued

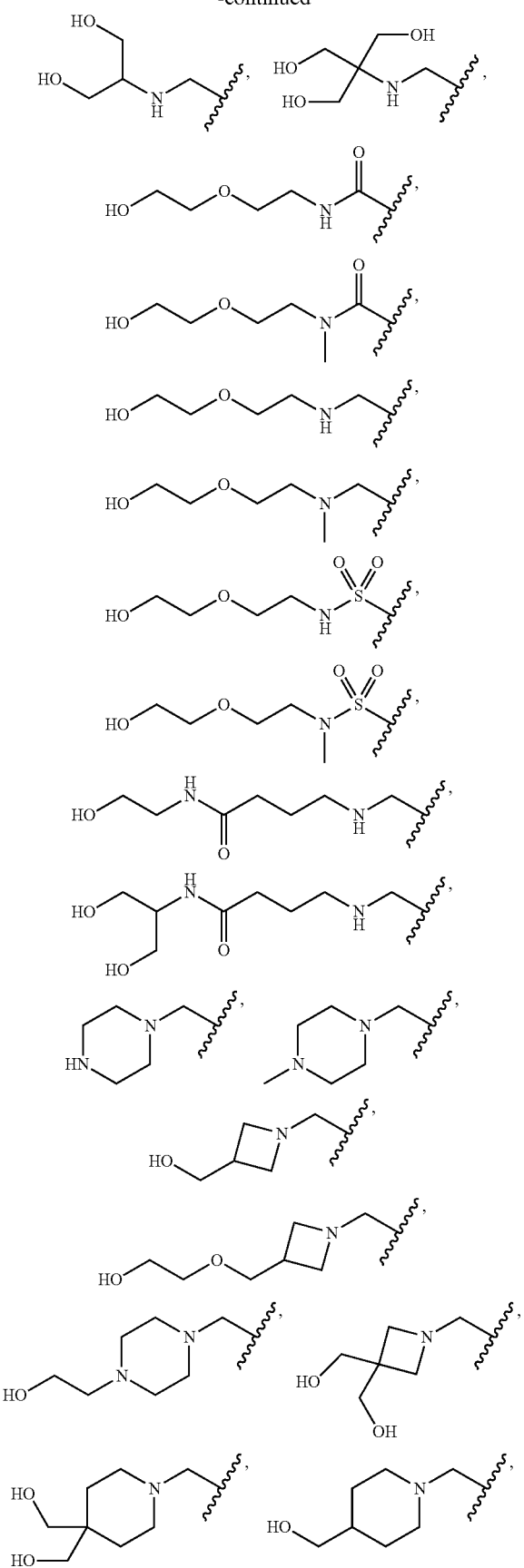

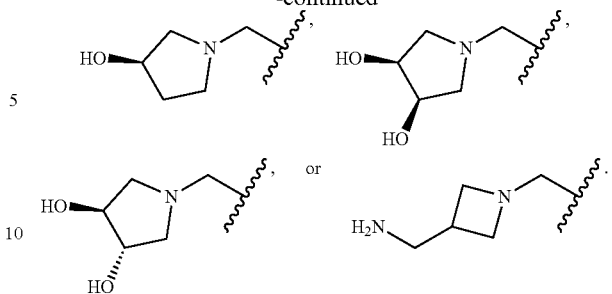

Also disclosed herein, in some embodiment is a compound of Formula (III):

Formula (III)

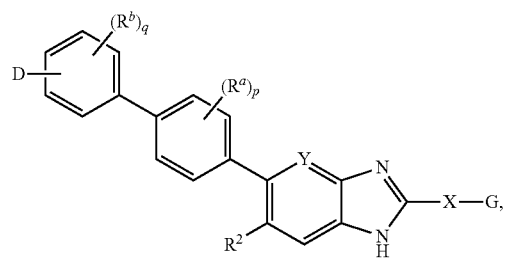

or a pharmaceutically acceptable salt, solvate, stereoisomer, or prodrug thereof, wherein:

X is —O— or —S—;

Y is N or CH;

G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

D is K or —Z—NR$^5$R$^6$;

Z is —(CH$_2$)—, —(CH(CH$_3$)—, —C(=O)—, or —S(=O)$_2$-;

K is —SO$_2$OH, —S(O)OH, —P(O)(OH)(R$^d$), —P(O)(OH)(OR$^d$), —CH$_2$P(O)(OH)(OR$^d$), —B(OR$^d$)(OH), —NHC(O)H, —N(R$^d$)C(O)NHSO$_2$(R$^d$), —C(O)NHSO$_2$(R$^d$), —SO$_2$NHC(O)(R$^d$), —NHC(O)NH(R$^d$), —N(R$^d$)C(=N(R$^d$)N(R$^d$)$_2$, —N(R$^d$)C(=NH)NHC(=NH)NH$_2$,

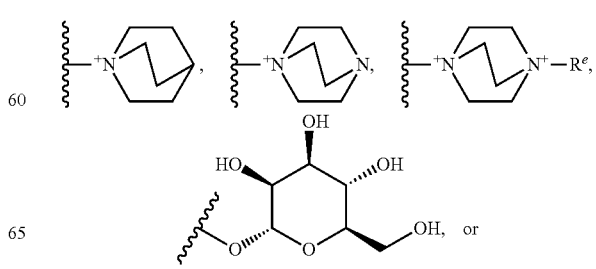

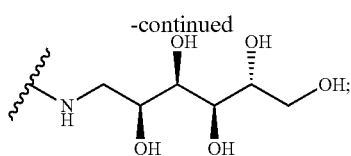

$R^a$ and $R^b$ are each independently halogen, —CN, —OH, —OR$^{13}$, —NR$^{14}$R$^{14}$, —C(O)OR$^{14}$, —C(O)NR$^{14}$R$^{14}$, $C_1$-$C_6$ alkyl, or $C_1$-$C_6$ fluoroalkyl;

each $R^d$ is independently hydrogen or $C_{1-6}$ alkyl;

each $R^e$ is independently $C_{1-6}$ alkyl; each $R^2$ is independently halogen, —CN, $C_1$-$C_4$ alkyl, $C_1$-$C_4$ fluoroalkyl, or $C_3$-$C_6$ cycloalkyl; $R^5$ is $C_6$-$C_{10}$ alkyl that is substituted by 5 to 9 —OH groups;

or $R^5$ is $C_{1-10}$ alkyl which is substituted by 1-6 groups selected from —N(R$^e$)$_3^+$ and K; or with 2-6 groups selected from —CO$_2$H, —OH, and —N(R$^d$)$_2$; and is optionally further substituted by 1, 2, or 3 $R^f$ groups;

each $R^f$ is independently halogen, —CN, —OH, —OR$^{13}$, —NR$^{14}$R$^{14}$, —C(O)OR$^{14}$, —C(O)NR$^{14}$R$^{14}$, —NR$^{14}$C(O)R$^{13}$, —NR$^{14}$C(O)NR$^{14}$R$^{14}$, $C_1$-$C_6$ alkyl, $C_3$-$C_6$ cycloalkyl, or phenyl, wherein the alkyl, cycloalkyl, or phenyl, is unsubstituted or substituted by 1, 2, or 3 halogen or —OH groups;

or $R^5$ is —[(C(R$^d$)$_2$)$_s$—V]$_t$—R$^9$; wherein each V is independently —C(R$^d$)$_2$O—, —C(R$^d$)$_2$NR$^d$—, —N(R$^d$)—C(O)—N(R$^d$)—, or —C(O)N(R$^d$)—;

or $R^5$ is —($C_1$-$C_6$ alkylene)—aryl, or —($C_1$-$C_6$ alkylene)—heteroaryl; wherein the aryl or heteroaryl is substituted by 1-6 groups selected from —CO$_2$H, —OH, —N(R$^d$)$_2$, —N(R$^e$)$_3^+$, and K; and wherein the alkylene is unsubstituted or substituted by 1, 2, or 3 $R^f$ groups;

$R^6$ is hydrogen or $C_{1-6}$ alkyl;

or $R^5$ and $R^6$ are taken together with the nitrogen to which they are attached to form a 3- to 6-membered N-heterocycloalkyl which is unsubstituted or substituted with 1-6 groups selected from —CH$_3$, —CH$_2$OH, —CH$_2$NH$_2$, —CH$_2$CH$_2$OH, —CH$_2$OCH$_2$CH$_2$OH, —N(R$^e$)$_3^+$, and K; or with 2-6 groups selected from —CO$_2$H, —OH, —CH$_2$OH, —CH$_2$NH$_2$, —CH$_2$CH$_2$OH, —CH$_2$OCH$_2$CH$_2$OH, and —N(R$^d$)$_2$;

$R^9$ is hydrogen, $C_{1-8}$ alkyl, phenyl, or naphthyl, wherein the alkyl, phenyl, or naphthyl is unsubstituted or substituted by 1-6 groups selected from —OH, —CO$_2$H, —N(R$^e$)$_2$, —N(R$^e$)$_3^+$, and K;

each $R^{13}$ is independently $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl; and each $R^{14}$ is independently hydrogen, $C_1$-$C_6$ alkyl, $C_2$-$C_6$ alkenyl, $C_2$-$C_6$ alkynyl, $C_1$-$C_6$ fluoroalkyl, $C_3$-$C_6$ cycloalkyl, 3- to 6-membered heterocycloalkyl, phenyl, or monocyclic heteroaryl;

or two $R^{14}$ on the same nitrogen atom are taken together with the nitrogen to which they are attached to form a 3- to 6-membered N-heterocycloalkyl;

p is 0 or 1;

q is 0 or 1;

each s is independently 1-6; and each t is independently 1-6.

In some embodiments, $R^2$ is halogen, —CN, $C_1$-$C_4$ alkyl, or $C_1$-$C_4$ fluoroalkyl. In some embodiments, $R^2$ is —F, —Cl, —CN, methyl, ethyl, n-propyl, i-propyl, n-butyl, i-butyl, sec-butyl, tert-butyl, —CH$_2$F, —CHF2, or —CF$_3$. In some embodiments, $R^2$ is —F, —Cl, —CN, methyl, ethyl, isopropyl, or —CF$_3$. In some embodiments, $R^2$ is —F, —Cl, or —CN. In some embodiments, $R^2$ is —Cl.

In some embodiments, p is 1. In some embodiments, $R^a$ is —F, —Cl, —CN, —OH, —O—($C_1$-$C_6$ alkyl), $C_1$-$C_6$ alkyl, or $C_1$-$C_6$ fluoroalkyl. In some embodiments, $R^a$ is —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF2, or —CF$_3$. In some embodiments, $R^a$ is —F, —Cl, —CN, —OH, —OCH$_3$, —OCF$_3$, methyl, or —CF$_3$.

In some embodiments, p is 0.

In some embodiments, q is 1. In some embodiments, $R^b$ is —F, —Cl, —CN, —OH, —O-($C_1$-$C_6$ alkyl), $C_1$-$C_6$ alkyl, or $C_1$-$C_6$ fluoroalkyl. In some embodiments, $R^b$ is —F, —Cl, —CN, —OH, —OCH$_3$, - OCF$_3$, methyl, ethyl, n-propyl, i-propyl, n-butyl, i-butyl, sec-butyl, tert-butyl, —CH$_2$F, —CHF2, or - CF$_3$. In some embodiments, $R^b$ is —F, —Cl, —CN, —OH, —OCH$_3$, —OCF$_3$, methyl, or —CF$_3$. In some embodiments, $R^b$ is —OH.

In some embodiments, q is 0.

In some embodiments, $R^2$ is —F, —Cl, or —CN; $R^a$ is —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF2, or —CF$_3$; and $R^b$ is —F, —Cl, —CN, —OH, —OCH$_3$, —OCF$_3$, methyl, ethyl, n-propyl, i-propyl, n-butyl, i-butyl, sec-butyl, tert-butyl, —CH$_2$F, —CHF$_2$, or —CF$_3$. In some embodiments, $R^2$ is —Cl; p is 0; q is 0 or 1; and $R^b$ is —OH.

In some embodiments, the compound has the structure of Formula (IV):

Formula (IV)

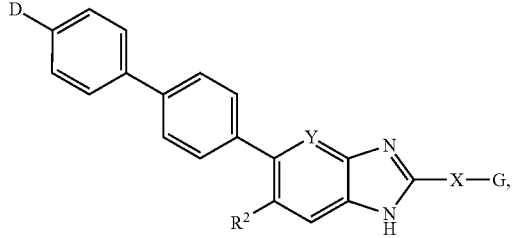

or a pharmaceutically acceptable salt, solvate, stereoisomer, or prodrug thereof.

In some embodiments, X is —O—. In some embodiments, X is —S—.

In some embodiments, G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is monocyclic 3- to 6-membered heterocycloalkyl containing 1 oxygen atom, which is substituted with 1 or 2 substituents selected from —C(O)OH, —OH, and —CH$_2$OH.

In some embodiments, G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH. In some embodiments, G is bicyclic 8- to 10-membered heterocycloalkyl containing 2 oxygen atoms, which is substituted with 1 or 2 substituents selected from —C(O)OH, —OH, and —CH$_2$OH. In some embodiments, G is bicyclic 8- to 10-membered heterocycloalkyl containing 2 oxygen atoms, which is substituted with 1 or 2 substituents selected from —OH and —CH$_2$OH.

In some embodiments, G is bicyclic 8- to 10membered heterocycloalkyl containing 2 oxygen atoms, which is substituted with 1 substituent selected from —OH and —CH₂OH. In some embodiments, G is bicyclic 8- to 10-membered heterocycloalkyl containing 2 oxygen atoms, which is substituted with 1 —OH substituent.

In some embodiments, —X-G is selected from:

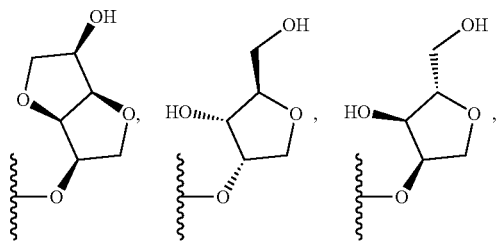

and

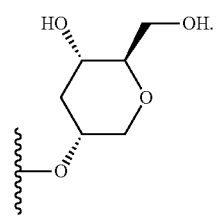

In some embodiments, —X-G is:

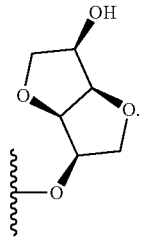 [SMILES: *O[C@@H]1CO[C@H]2[C@@H]1OC[C@H]2O]

In some embodiments, —X-G is:

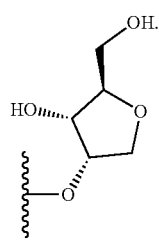

In some embodiments, —X-G is:

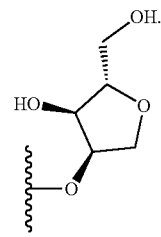 [SMILES: *O[C@@H]1CO[C@@H](CO)[C@@H]1O]

In some embodiments, —X-G is:

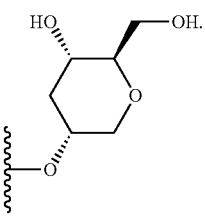 [SMILES: *O[C@H]1CO[C@H](CO)[C@@H](O)C1]

In some embodiments, Y is N. In some embodiments, Y is CH.

In some embodiments, D is K. In some embodiments, K is —SO₂OH, —P(O)(OH)(R$^d$), —P(O)(OH)(OR$^d$), —CH₂P(O)(OH)(OR$^d$), —N(R$^d$)C(O)NHSO₂(R$^d$), —C(O)NHSO₂(R$^d$), —SO₂NHC(O)(R$^d$), —NHC(O)NH(R$^d$),

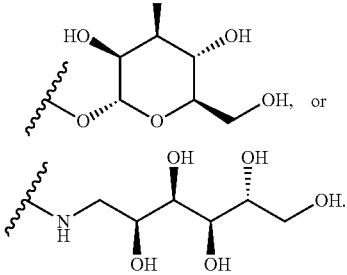

In some embodiments, K is —SO₂OH, —P(O)(OH)(R$^d$), —P(O)(OH)(OR$^d$), —CH₂P(O)(OH)(OR$^d$), —N(R$^d$)C(O)NHSO₂(R$^d$), —C(O)NHSO₂(R$^d$), —SO₂NHC(O)(R$^d$), —NHC(O)NH(R$^d$),

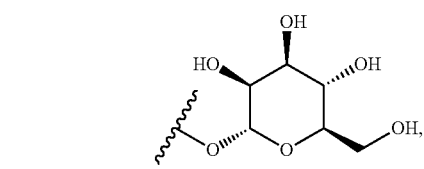 [SMILES: *O[C@H]1O[C@H](CO)[C@@H](O)[C@H](O)[C@@H]1O]

or

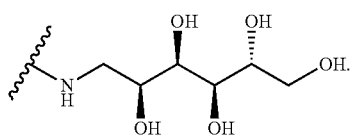 [SMILES: *NC[C@H](O)[C@@H](O)[C@H](O)[C@H](O)CO]

In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$). In some embodiments, each R$^d$ is independently hydrogen or $C_{1-6}$ alkyl. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$); and each R$^d$ is independently hydrogen or $C_{1-6}$ alkyl. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$); and each R$^d$ is independently hydrogen or $C_{1-3}$ alkyl. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$); and each R$^d$ is independently hydrogen or methyl. In some embodiments, K is —SO₂OH, —P(O)(OH)₂, —CH₂P(O)(OH)₂, —P(O)(OH)(Me), —P(O)(OH)(H), or —P(O)(OH)(OMe). In some embodiments, K is —SO₂OH or —P(O)(OH)₂. In some embodiments, K is —SO₂OH. In some embodiments, K is —P(O)(OH)₂.

In some embodiments, D is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$); and each R$^d$ is independently hydrogen or $C_{1-6}$ alkyl. In some embodiments, D is —SO₂OH, —P(O)(OH)₂, —CH₂P(O)(OH)₂, —P(O)(OH)(Me), —P(O)(OH)(H), or —P(O)(OH)(OMe). In some embodiments, D is —SO₂OH or —P(O)(OH)₂. In some embodiments, D is —SO₂OH. In some embodiments, D is —P(O)(OH)₂.

In some embodiments, D is -Z-NR⁵R⁶.

In some embodiments, Z is —(CH₂)—, —C(=O)—, or —S(=O)₂—. In some embodiments, Z is —(CH₂)—. In some embodiments, Z is —(CH(CH₃)—. In some embodiments, Z is —C(=O)— or —S(=O)₂—. In some embodiments, Z is —C(=O)—. In some embodiments, Z is —S(=O)₂—.

In some embodiments, R⁵ is $C_6$-$C_{10}$ alkyl that is substituted by 5 to 9 —OH groups. In some embodiments, R⁵ is $C_6$-$C_{10}$ alkyl that is substituted by 5 —OH groups.

In some embodiments, R⁵ is $C_{1-10}$ alkyl which is substituted by 1-6 groups selected from —N(R$^e$)₃⁺ and K; or with 2-6 groups selected from —CO₂H, —OH, and —N(R$^d$)₂; and is optionally further substituted by 1, 2, or 3 R$^f$ groups; and each R$^f$ is independently halogen, —CN, —OH, —OR¹³, —NR¹⁴R¹⁴, —C(O)OR¹⁴, —C(O)NR¹⁴R¹⁴, —NR¹⁴C(O)R¹⁴, —NR¹⁴C(O)NR¹⁴R¹⁴, $C_1$-$C_6$ alkyl, $C_3$-$C_6$ cycloalkyl, or phenyl, wherein the alkyl, cycloalkyl, or phenyl, is unsubstituted or substituted by 1, 2, or 3 halogen or —OH groups.

In some embodiments, R⁵ is —[(C(R$^d$)₂)$_s$-V]$_t$—R⁹; wherein each V is independently —C(R$^d$)₂O—, —C(R$^d$)₂NR$^d$—, —N(R$^d$)—C(O)—N(R$^d$)—, or —C(O)N(R$^d$)—; each R$^d$ is independently hydrogen or $C_{1-6}$ alkyl; R⁶ is hydrogen or $C_{1-6}$ alkyl; and R⁹ is hydrogen, $C_{1-8}$ alkyl, phenyl, or naphthyl, wherein the alkyl, phenyl, or naphthyl is unsubstituted or substituted by 1-6 groups selected from —OH, —CO₂H, —N(R$^e$)₂, —N(R$^e$)₃⁺, and K. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$). In some embodiments, K is —SO₂OH, —P(O)(OH)₂, —CH₂P(O)(OH)₂, —P(O)(OH)(Me), —P(O)(OH)(H), or —P(O)(OH)(OMe). In some embodiments, K is —SO₂OH or —P(O)(OH)₂. In some embodiments, K is —SO₂OH. In some embodiments, K is —P(O)(OH)₂.

In some embodiments, R⁵ and R⁶ are taken together with the nitrogen to which they are attached to form a 3- to 6-membered N-heterocycloalkyl which is unsubstituted or substituted with 1-6 groups selected from —CH₃, —CH₂OH, —CH₂NH₂, —CH₂CH₂OH, —CH₂OCH₂CH₂OH, —N(R$^e$)₃⁺, and K; or with 2-6 groups selected from —CO₂H, —OH, —CH₂OH, —CH₂NH₂, —CH₂CH₂OH, —CH₂OCH₂CH₂OH, and —N(R$^d$)₂. In some embodiments, R⁵ and R⁶ are taken together with the nitrogen to which they are attached to form a 4- to 6-membered N-heterocycloalkyl which is substituted with 2-4 groups selected from —OH and —CH₂OH. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$). In some embodiments, K is —SO₂OH, —P(O)(OH)₂, —CH₂P(O)(OH)₂, —P(O)(OH)(Me), —P(O)(OH)(H), or —P(O)(OH)(OMe). In some embodiments, K is —SO₂OH or —P(O)(OH)₂. In some embodiments, K is —SO₂OH. In some embodiments, K is —P(O)(OH)₂.

In some embodiments, R⁵ is $C_6$-$C_{10}$ alkyl that is substituted by 5 to 9 —OH groups; or R⁵ is $C_{1-10}$ alkyl which is substituted by 1-6 groups selected from —N(R$^e$)₃⁺ and K; or with 2-6 groups selected from —CO₂H, —OH, and —N(R$^d$)₂; and is optionally further substituted by 1, 2, or 3 R$^f$ groups. In some embodiments, K is —SO₂OH, —P(O)(OH)(R$^d$), —P(O)(OH)(OR$^d$), —CH₂P(O)(OH)(OR$^d$), —C(O)NHSO₂(R$^d$), or —SO₂NHC(O)(R$^d$). In some embodiments, K is —SO₂OH, —P(O)(OH)₂, —CH₂P(O)(OH)₂, —P(O)(OH)(Me), —P(O)(OH)(H), or —P(O)(OH)(OMe). In some embodiments, K is —SO₂OH or —P(O)(OH)₂. In some embodiments, K is —SO₂OH. In some embodiments, K is —P(O)(OH)₂.

In some embodiments, D is

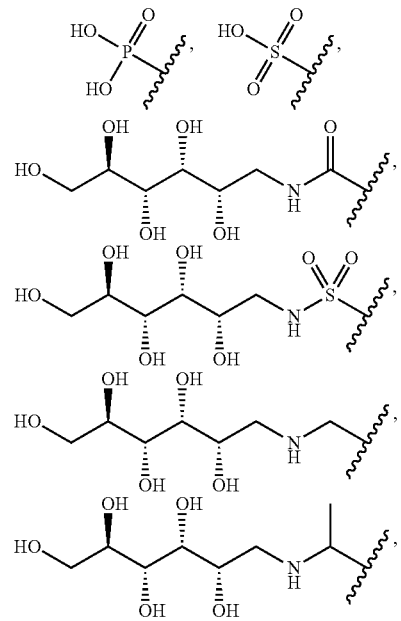

-continued
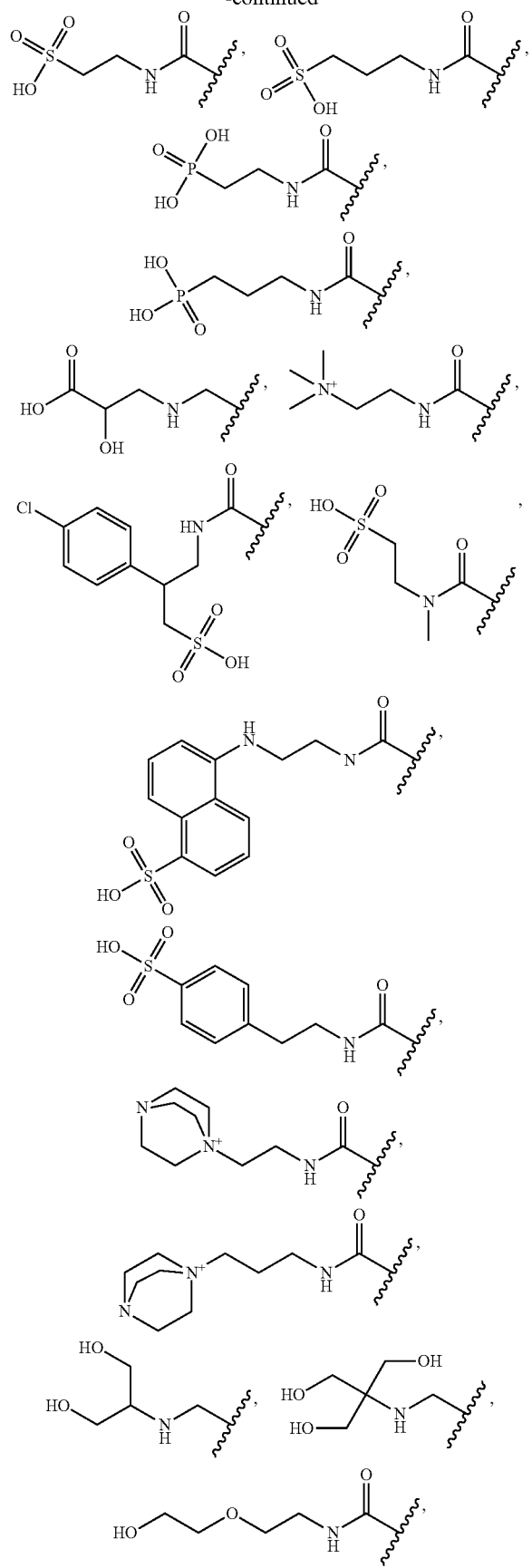
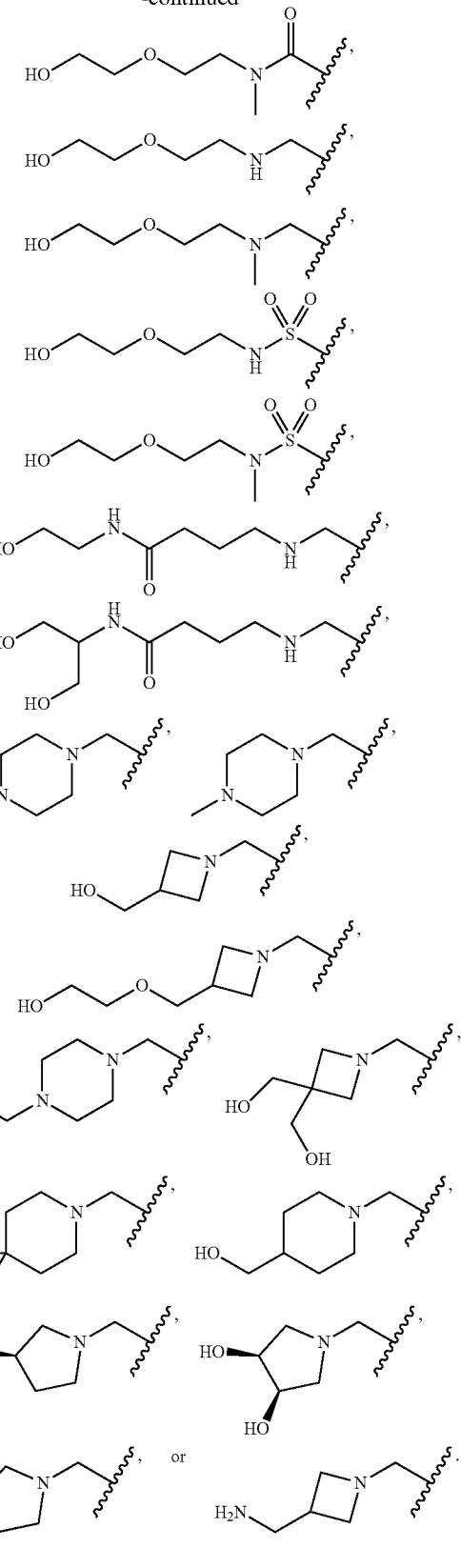
Any combination of the groups described above for the various variables is contemplated herein. Throughout the specification, groups and substituents thereof are chosen by one skilled in the field to provide stable moieties and compounds.

In some embodiments, the compound is a compound in one of the following tables, or a pharmaceutically acceptable salt, solvate, stereoisomer, or prodrug thereof.

TABLE 1

| Cmpd No. | Structure |
|---|---|
| 1 | 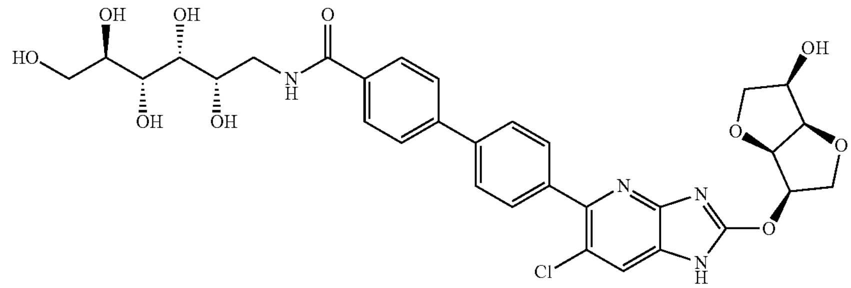 [SMILES: O=C(NC[C@H](O)[C@@H](O)[C@H](O)[C@H](O)CO)c1ccc(-c2ccc(-c3nc4nc(O[C@@H]5CO[C@H]6[C@@H]5OC[C@H]6O)[nH]c4cc3Cl)cc2)cc1] |
| 2 | 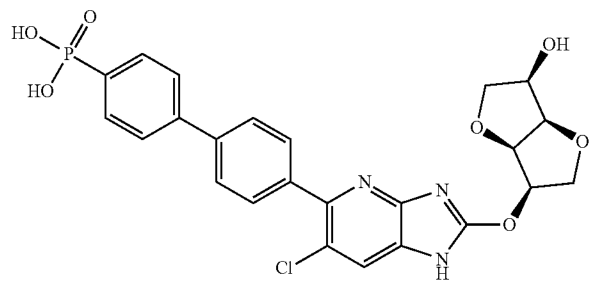 [SMILES: O=P(O)(O)c1ccc(-c2ccc(-c3nc4nc(O[C@@H]5CO[C@H]6[C@@H]5OC[C@H]6O)[nH]c4cc3Cl)cc2)cc1] |
| 3 | 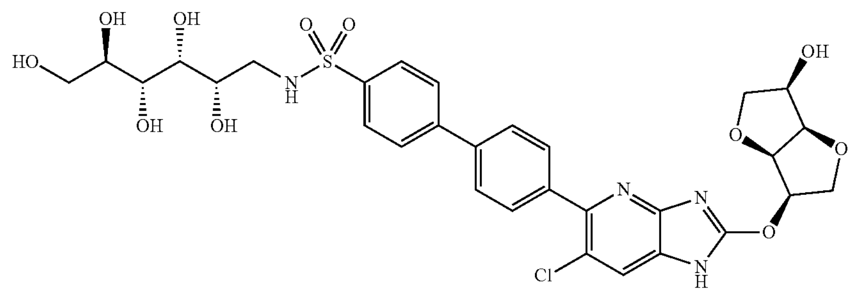 [SMILES: O=S(=O)(NC[C@H](O)[C@@H](O)[C@H](O)[C@H](O)CO)c1ccc(-c2ccc(-c3nc4nc(O[C@@H]5CO[C@H]6[C@@H]5OC[C@H]6O)[nH]c4cc3Cl)cc2)cc1] |
| 4 | 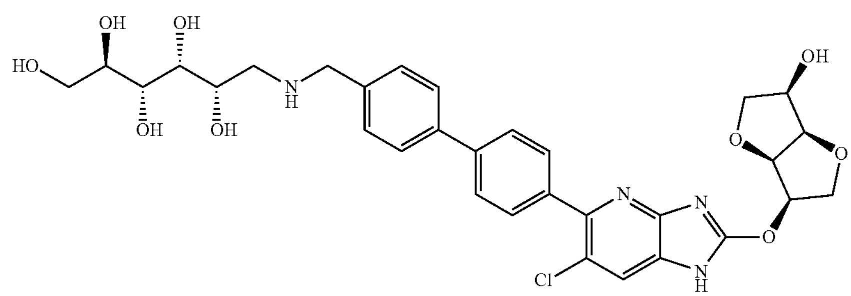 [SMILES: OC[C@@H](O)[C@@H](O)[C@H](O)[C@@H](O)CNCc1ccc(-c2ccc(-c3nc4nc(O[C@@H]5CO[C@H]6[C@@H]5OC[C@H]6O)[nH]c4cc3Cl)cc2)cc1] |
| 5 | 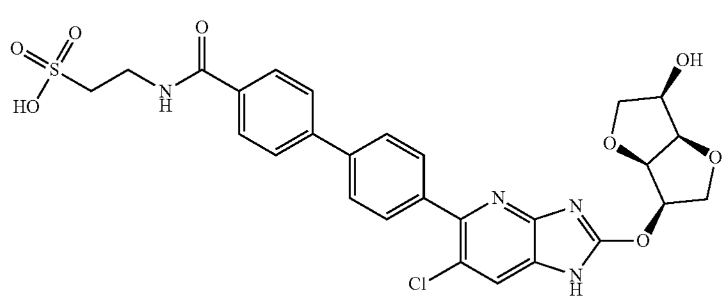 [SMILES: O=C(NCCS(=O)(=O)O)c1ccc(-c2ccc(-c3nc4nc(O[C@@H]5CO[C@H]6[C@@H]5OC[C@H]6O)[nH]c4cc3Cl)cc2)cc1] |

TABLE 1-continued
| Cmpd No. | Structure |
|---|---|
| 6 | 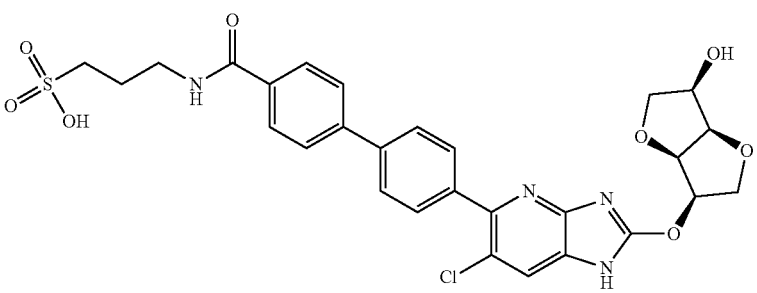 [SMILES: O=C(NCCCS(=O)(=O)O)c1ccc(-c2ccc(-c3nc4nc(O[C@@H]5CO[C@H]6[C@@H]5OC[C@H]6O)[nH]c4cc3Cl)cc2)cc1] |
| 7 | 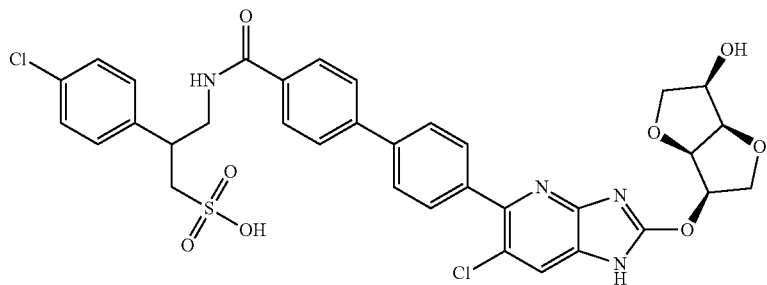 [SMILES: O=C(NCC(CS(=O)(=O)O)c1ccc(Cl)cc1)c1ccc(-c2ccc(-c3nc4nc(O[C@@H]5CO[C@H]6[C@@H]5OC[C@H]6O)[nH]c4cc3Cl)cc2)cc1] |
| 8 | 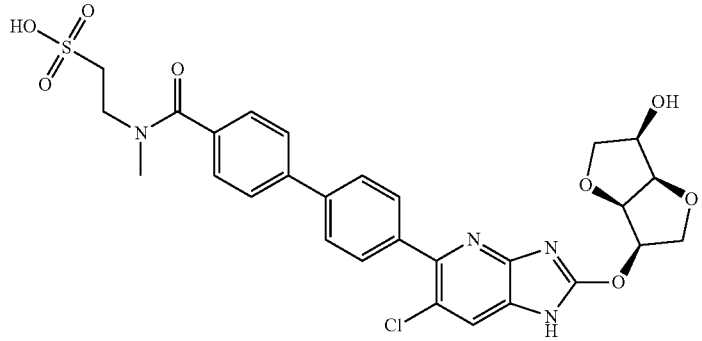 [SMILES: CN(CCS(=O)(=O)O)C(=O)c1ccc(-c2ccc(-c3nc4nc(O[C@@H]5CO[C@H]6[C@@H]5OC[C@H]6O)[nH]c4cc3Cl)cc2)cc1] |
| 9 | 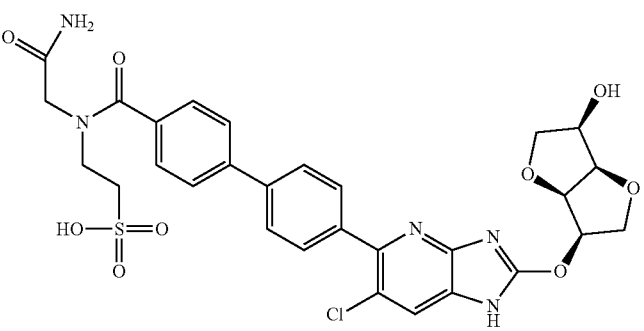 [SMILES: NC(=O)CN(CCS(=O)(=O)O)C(=O)c1ccc(-c2ccc(-c3nc4nc(O[C@@H]5CO[C@H]6[C@@H]5OC[C@H]6O)[nH]c4cc3Cl)cc2)cc1] |
| 10 | 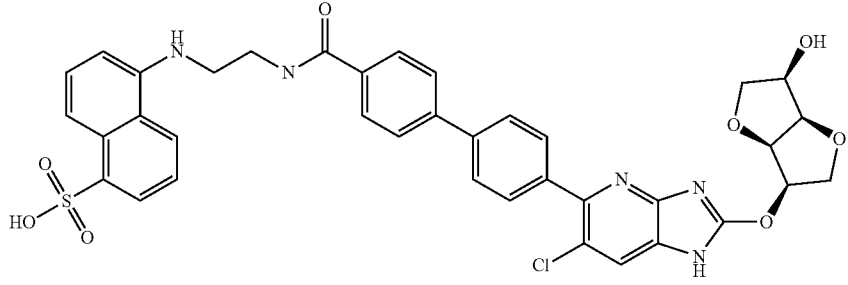 [SMILES: O=C(NCCNc1cccc2c(S(=O)(=O)O)cccc12)c1ccc(-c2ccc(-c3nc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 11 | 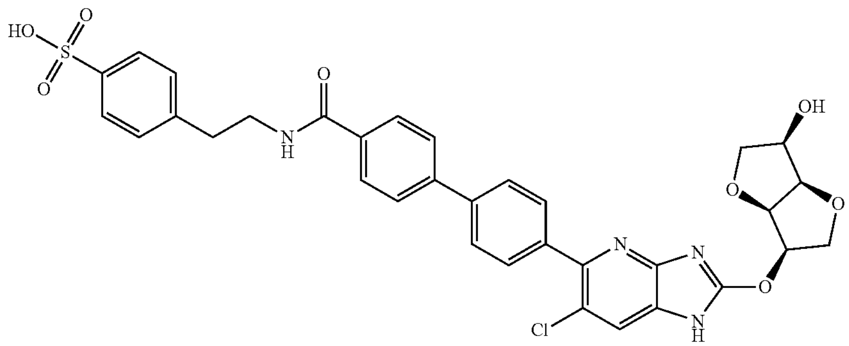 [SMILES: O=C(NCCc1ccc(S(=O)(=O)O)cc1)c1ccc(-c2ccc(-c3nc4nc(O[C@@H]5CO[C@H]6[C@@H]5OC[C@H]6O)[nH]c4cc3Cl)cc2)cc1] |
| 12 | 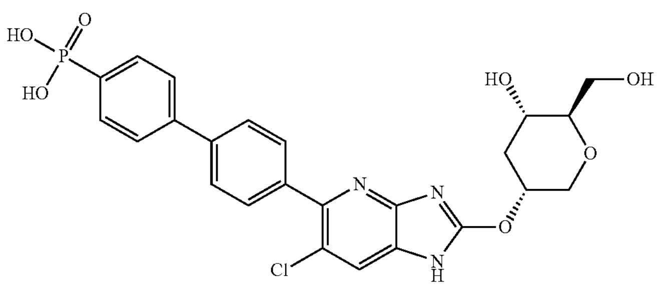 [SMILES: O=P(O)(O)c1ccc(-c2ccc(-c3nc4nc(O[C@H]5CO[C@H](CO)[C@@H](O)C5)[nH]c4cc3Cl)cc2)cc1] |
| 14 | 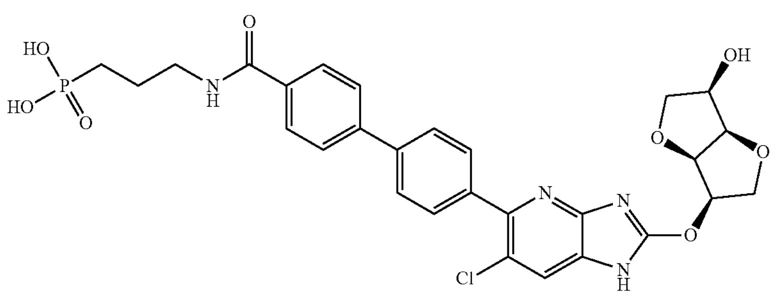 [SMILES: O=C(NCCCP(=O)(O)O)c1ccc(-c2ccc(-c3nc4nc(O[C@@H]5CO[C@H]6[C@@H]5OC[C@H]6O)[nH]c4cc3Cl)cc2)cc1] |
| 22 | 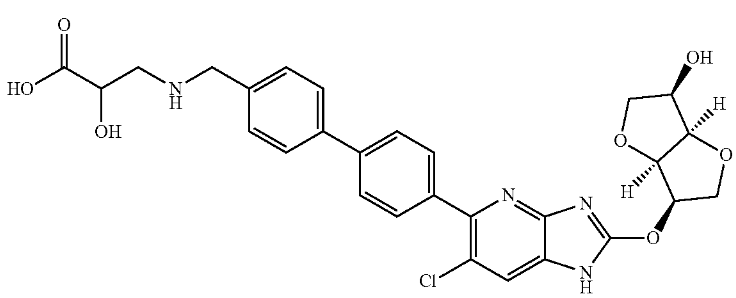 [SMILES: O=C(O)C(O)CNCc1ccc(-c2ccc(-c3nc4nc(O[C@@H]5CO[C@H]6[C@@H]5OC[C@H]6O)[nH]c4cc3Cl)cc2)cc1] |
| 29 | 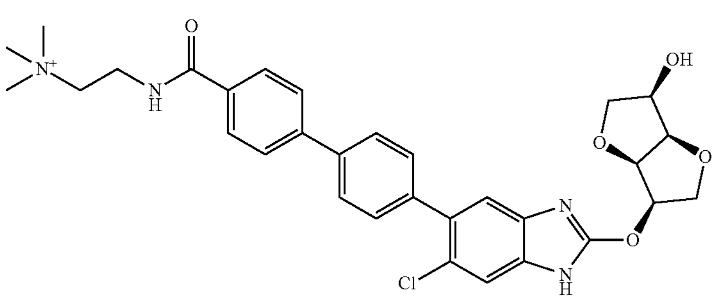 [SMILES: C[N+](C)(C)CCNC(=O)c1ccc(-c2ccc(-c3cc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 30 | 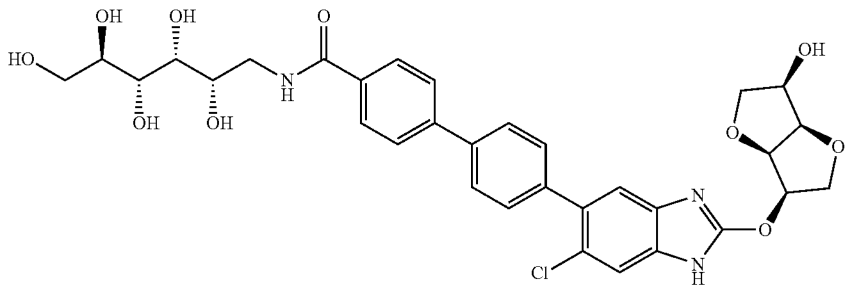 |
| 31 | 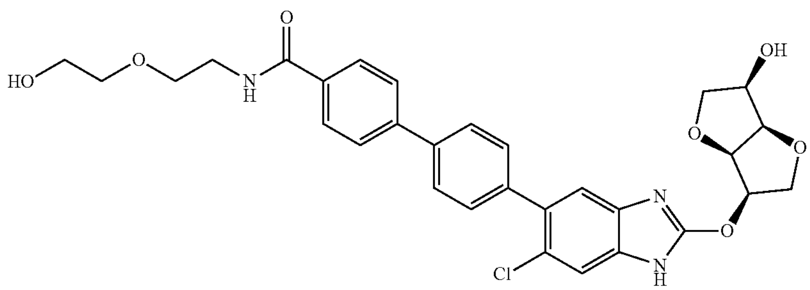 [SMILES: O=C(NCCOCCO)c1ccc(-c2ccc(-c3cc4nc(O[C@@H]5CO[C@H]6[C@@H]5OC[C@H]6O)[nH]c4cc3Cl)cc2)cc1] |
| 32 | 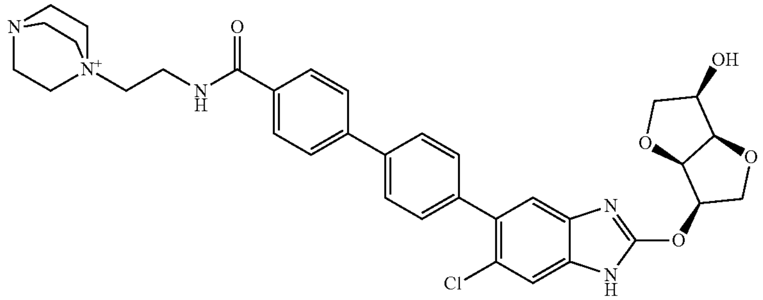 [SMILES: O=C(NCC[N+]12CCN(CC1)CC2)c1ccc(-c2ccc(-c3cc4nc(O[C@@H]5CO[C@H]6[C@@H]5OC[C@H]6O)[nH]c4cc3Cl)cc2)cc1] |
| 33 | 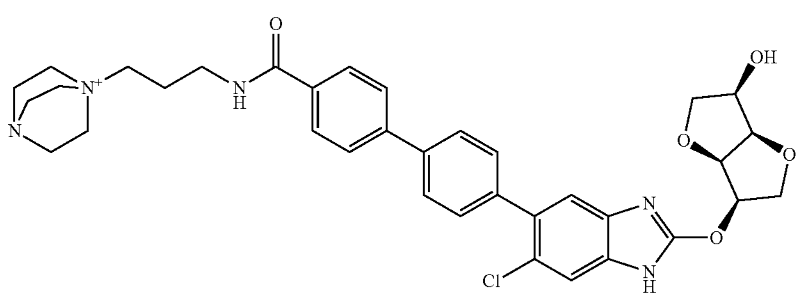 [SMILES: O=C(NCCC[N+]12CCN(CC1)CC2)c1ccc(-c2ccc(-c3cc4nc(O[C@@H]5CO[C@H]6[C@@H]5OC[C@H]6O)[nH]c4cc3Cl)cc2)cc1] |
| 36 | 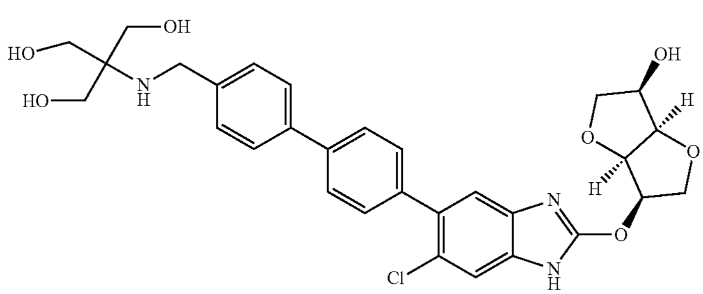 [SMILES: OCC(CO)(CO)NCc1ccc(-c2ccc(-c3cc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 37 | (structure) |
| 38 | (structure) |
| 40 | (structure) |
| 45 | (structure) |
| 48 | (structure) |

TABLE 1-continued
| Cmpd No. | Structure |
|---|---|
| 49 | 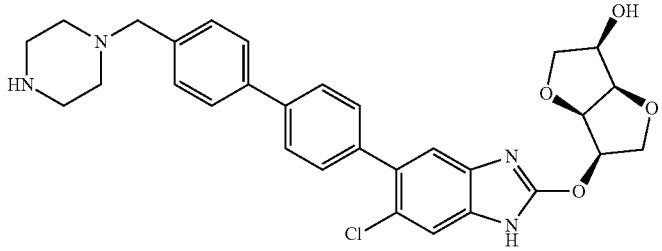 [SMILES: O[C@@H]1CO[C@H]2[C@@H]1OC[C@H]2Oc1nc2cc(-c3ccc(-c4ccc(CN5CCNCC5)cc4)cc3)c(Cl)cc2[nH]1] |
| 50 | 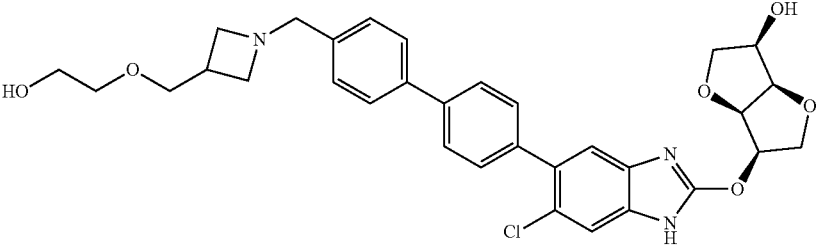 [SMILES: OCCOCC1CN(Cc2ccc(-c3ccc(-c4cc5nc(O[C@@H]6CO[C@H]7[C@@H]6OC[C@H]7O)[nH]c5cc4Cl)cc3)cc2)C1] |
| 51 | 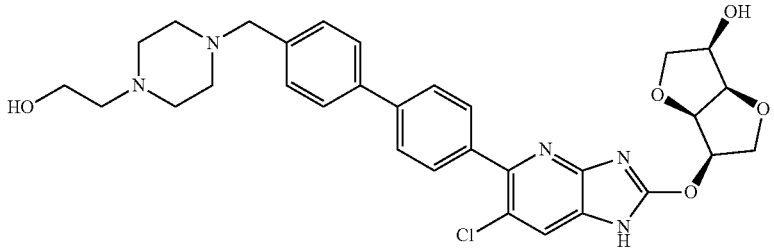 [SMILES: OCCN1CCN(Cc2ccc(-c3ccc(-c4nc5nc(O[C@@H]6CO[C@H]7[C@@H]6OC[C@H]7O)[nH]c5cc4Cl)cc3)cc2)CC1] |
| 52 | 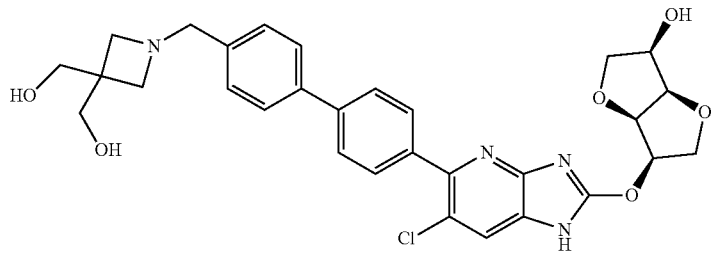 [SMILES: OCC1(CO)CN(Cc2ccc(-c3ccc(-c4nc5nc(O[C@@H]6CO[C@H]7[C@@H]6OC[C@H]7O)[nH]c5cc4Cl)cc3)cc2)C1] |
| 53 | 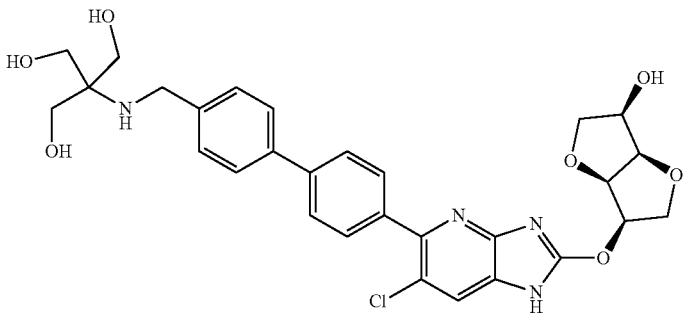 [SMILES: OCC(CO)(CO)NCc1ccc(-c2ccc(-c3nc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 54 | 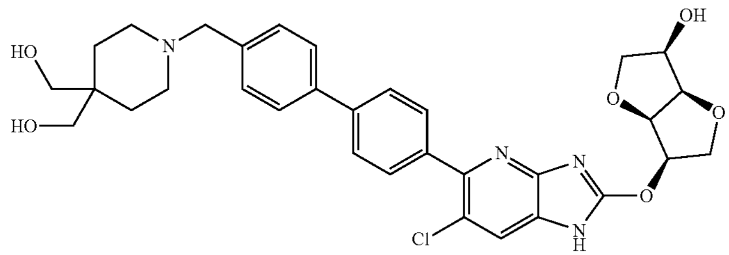 [SMILES: OCC1(CO)CCN(Cc2ccc(-c3ccc(-c4nc5nc(O[C@@H]6CO[C@H]7[C@@H]6OC[C@H]7O)[nH]c5cc4Cl)cc3)cc2)CC1] |
| 55 | 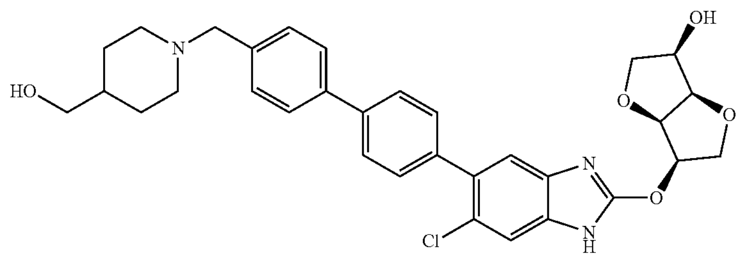 [SMILES: OCC1CCN(Cc2ccc(-c3ccc(-c4cc5nc(O[C@@H]6CO[C@H]7[C@@H]6OC[C@H]7O)[nH]c5cc4Cl)cc3)cc2)CC1] |
| 56 | 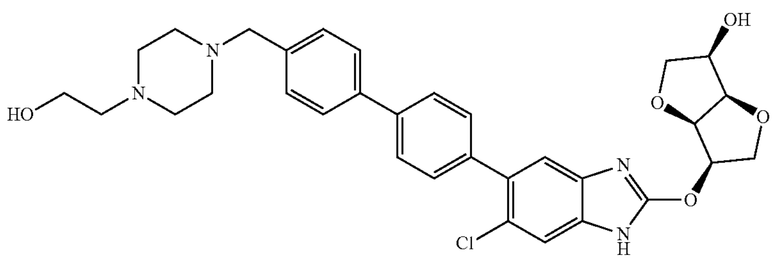 [SMILES: OCCN1CCN(Cc2ccc(-c3ccc(-c4cc5nc(O[C@@H]6CO[C@H]7[C@@H]6OC[C@H]7O)[nH]c5cc4Cl)cc3)cc2)CC1] |
| 57 | 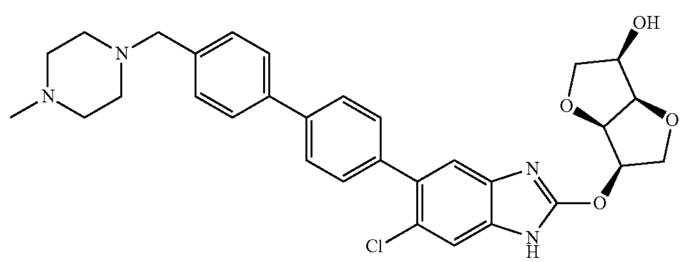 [SMILES: CN1CCN(Cc2ccc(-c3ccc(-c4cc5nc(O[C@@H]6CO[C@H]7[C@@H]6OC[C@H]7O)[nH]c5cc4Cl)cc3)cc2)CC1] |
| 58 | 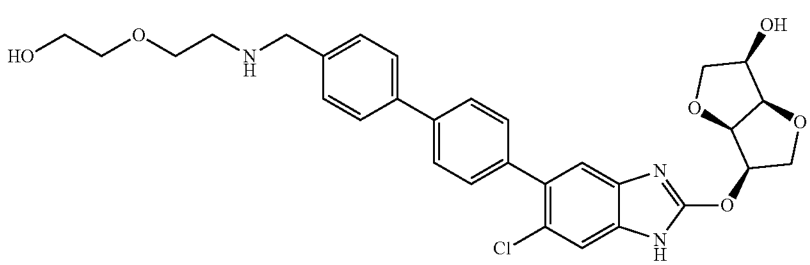 [SMILES: OCCOCCNCc1ccc(-c2ccc(-c3cc4nc(O[C@@H]5CO[C@H]6[C@@H]5OC[C@H]6O)[nH]c4cc3Cl)cc2)cc1] |
| 59 | 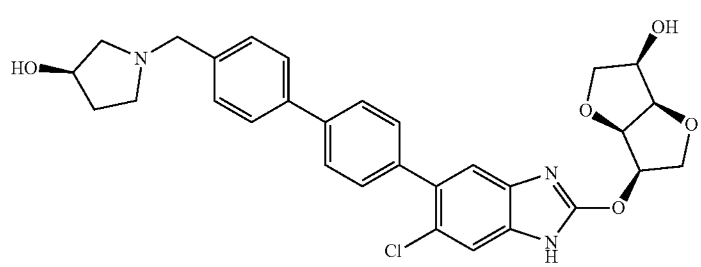 [SMILES: O[C@@H]1CCN(Cc2ccc(-c3ccc(-c4cc5nc(O[C@@H]6CO[C@H]7[C@@H]6OC[C@H]7O)[nH]c5cc4Cl)cc3)cc2)C1] |

TABLE 1-continued

| Cmpd No. | Structure |
|---|---|
| 60 | 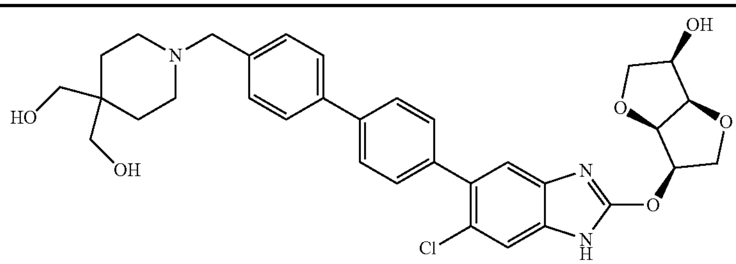 |
| 61 | 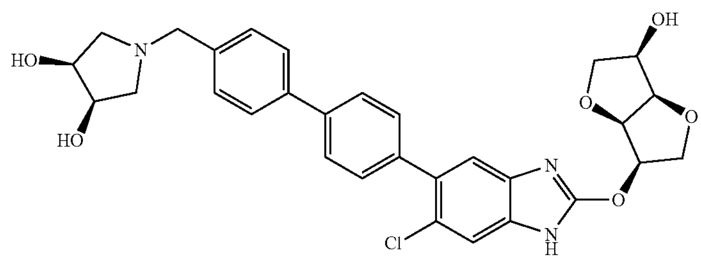 [SMILES: O[C@@H]1CO[C@H]2[C@@H]1OC[C@H]2Oc1nc2cc(-c3ccc(-c4ccc(CN5C[C@@H](O)[C@@H](O)C5)cc4)cc3)c(Cl)cc2[nH]1] |
| 62 | 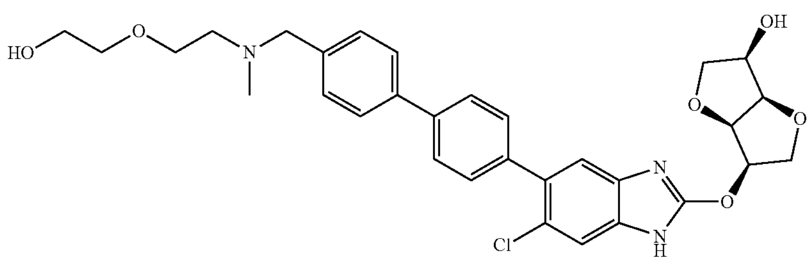 [SMILES: CN(CCOCCO)Cc1ccc(-c2ccc(-c3cc4nc(O[C@@H]5CO[C@H]6[C@@H]5OC[C@H]6O)[nH]c4cc3Cl)cc2)cc1] |
| 63 | 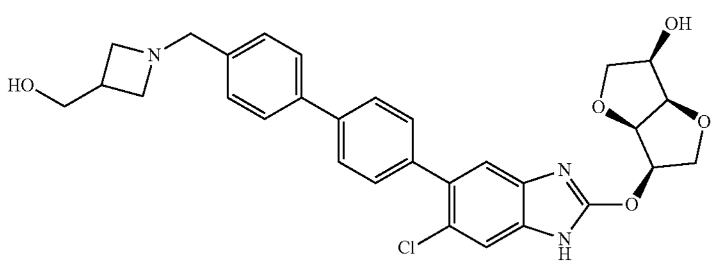 [SMILES: OCC1CN(Cc2ccc(-c3ccc(-c4cc5nc(O[C@@H]6CO[C@H]7[C@@H]6OC[C@H]7O)[nH]c5cc4Cl)cc3)cc2)C1] |
| 64 | 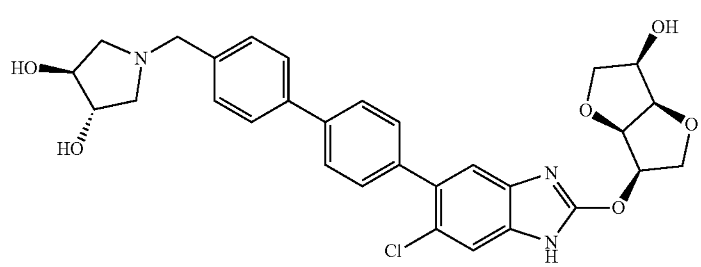 [SMILES: O[C@@H]1CO[C@H]2[C@@H]1OC[C@H]2Oc1nc2cc(-c3ccc(-c4ccc(CN5C[C@H](O)[C@@H](O)C5)cc4)cc3)c(Cl)cc2[nH]1] |
| 65 | 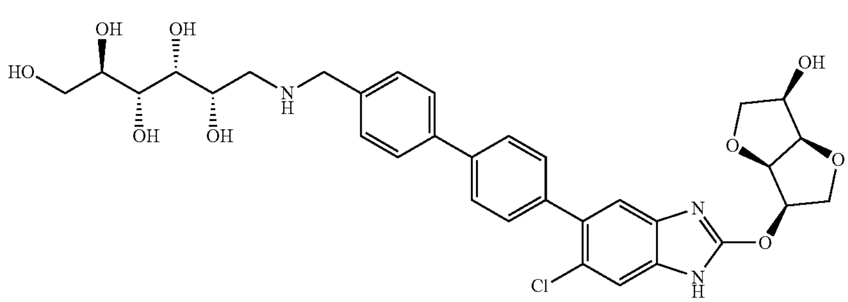 [SMILES: OC[C@@H](O)[C@@H](O)[C@H](O)[C@@H](O)CNCc1ccc(-c2ccc(-c3cc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 66 | 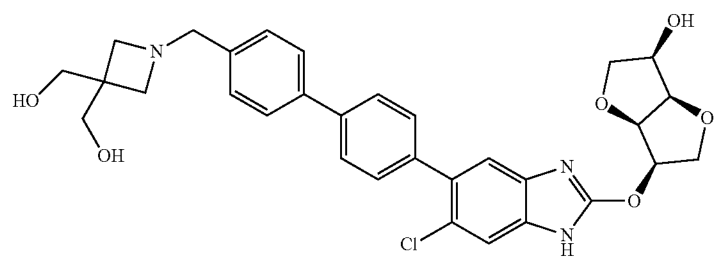 [SMILES: OCC1(CO)CN(Cc2ccc(-c3ccc(-c4cc5nc(O[C@@H]6CO[C@H]7[C@@H]6OC[C@H]7O)[nH]c5cc4Cl)cc3)cc2)C1] |
| 67 | 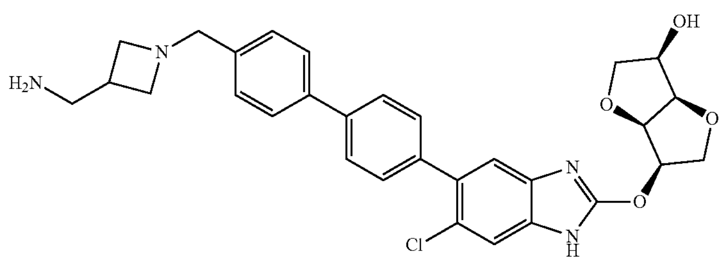 [SMILES: NCC1CN(Cc2ccc(-c3ccc(-c4cc5nc(O[C@@H]6CO[C@H]7[C@@H]6OC[C@H]7O)[nH]c5cc4Cl)cc3)cc2)C1] |
| 68 | 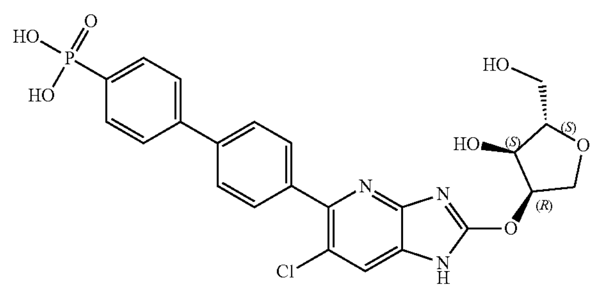 |
| 69 | 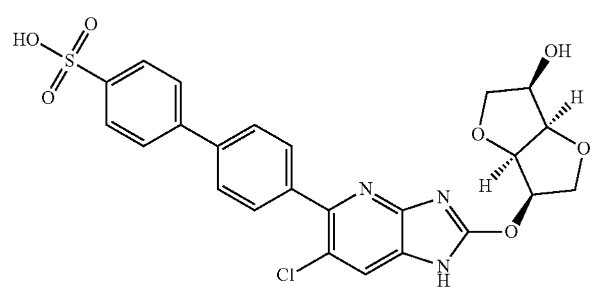 [SMILES: O=S(=O)(O)c1ccc(-c2ccc(-c3nc4nc(O[C@@H]5CO[C@H]6[C@@H]5OC[C@H]6O)[nH]c4cc3Cl)cc2)cc1] |
| 70 | 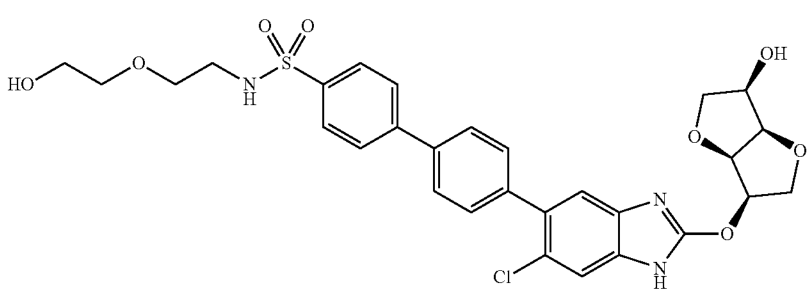 [SMILES: O=S(=O)(NCCOCCO)c1ccc(-c2ccc(-c3cc4nc(O[C@@H]5CO[C@H]6[C@@H]5OC[C@H]6O)[nH]c4cc3Cl)cc2)cc1] |

TABLE 1-continued

| Cmpd No. | Structure |
|---|---|
| 71 | 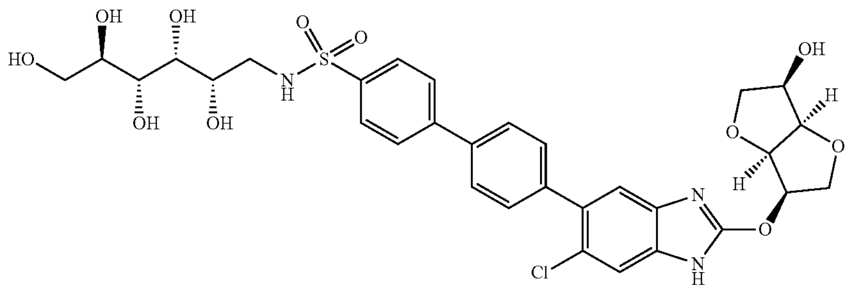 [SMILES: O=S(=O)(NC[C@H](O)[C@@H](O)[C@H](O)[C@H](O)CO)c1ccc(-c2ccc(-c3cc4nc(O[C@@H]5CO[C@H]6[C@@H]5OC[C@H]6O)[nH]c4cc3Cl)cc2)cc1] |
| 72 | 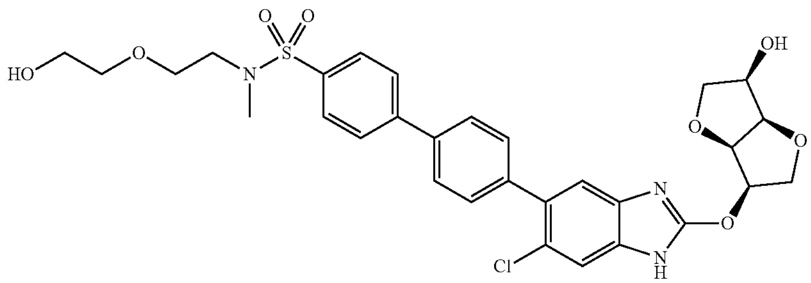 [SMILES: CN(CCOCCO)S(=O)(=O)c1ccc(-c2ccc(-c3cc4nc(O[C@@H]5CO[C@H]6[C@@H]5OC[C@H]6O)[nH]c4cc3Cl)cc2)cc1] |
| 73 | 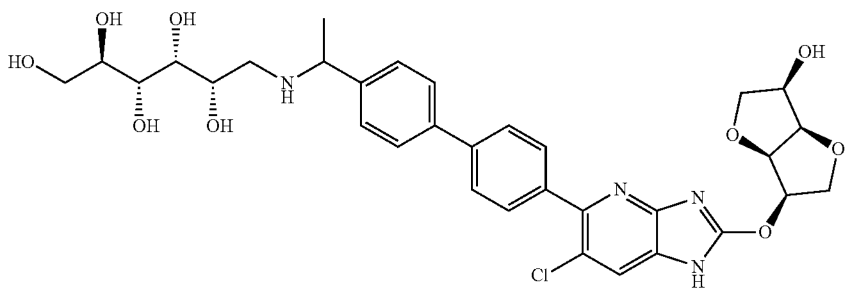 [SMILES: CC(NC[C@H](O)[C@@H](O)[C@H](O)[C@H](O)CO)c1ccc(-c2ccc(-c3nc4nc(O[C@@H]5CO[C@H]6[C@@H]5OC[C@H]6O)[nH]c4cc3Cl)cc2)cc1] |
| 74 | 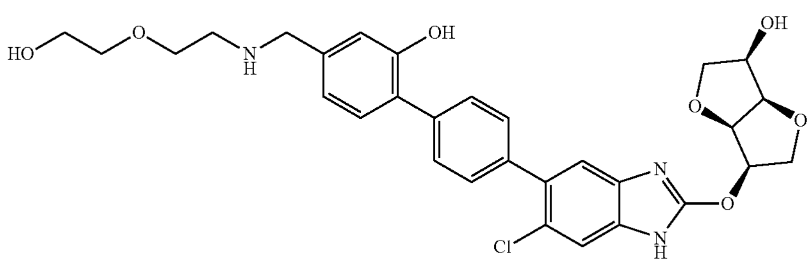 [SMILES: OCCOCCNCc1ccc(-c2ccc(-c3cc4nc(O[C@@H]5CO[C@H]6[C@@H]5OC[C@H]6O)[nH]c4cc3Cl)cc2)c(O)c1] |
| 75 | 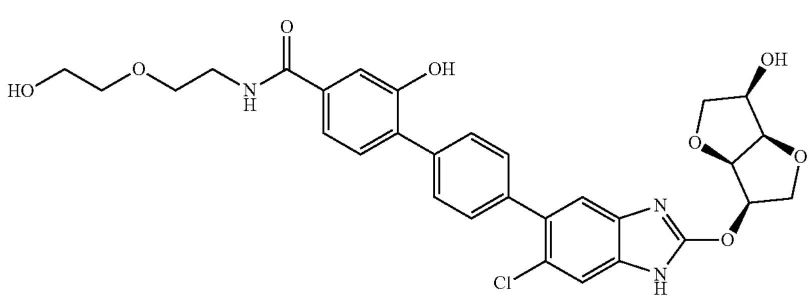 [SMILES: O=C(NCCOCCO)c1ccc(-c2ccc(-c3cc4nc(O[C@@H]5CO[C@H]6[C@@H]5OC[C@H]6O)[nH]c4cc3Cl)cc2)c(O)c1] |

Compounds in Table 1 are named:
1: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(2S,3R,4R,5R)-2,3,4,5,6-pentahydroxyhexyl)-[1,1'-biphenyl]-4-carboxamide;
2: (4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)phosphonic acid;
3: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(2S,3R,4R,5R)-2,3,4,5,6-pentahydroxyhexyl)-[1,1'-biphenyl]-4-sulfonamide;
4: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)hexane-1,2,3,4,5-pentaol;
5: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethane-1-sulfonic acid;
6: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propane-1-sulfonic acid;
7: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)-2-(4-chlorophenyl)propane-1-sulfonic acid;
8: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-methyl-[1,1'-biphenyl]-4-carboxamido)ethane-1-sulfonic acid;
9: 2-(N-(2-amino-2-oxoethyl)-4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethane-1-sulfonic acid;
10: 5 -(2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)amino)naphthalene-1-sulfonic acid;
11: 4-(2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)benzenesulfonic acid;
12: (4'-(6-chloro-2-(((3R,5S,6R)—5-hydroxy-6-(hydroxymethyl)tetrahydro-2H-pyran-3-yl)oxy)-1H-imidazo[4,5-b]pyridin-5-yl)-[1,1'-biphenyl]-4-yl)phosphonic acid;
14: (3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propyl)phosphonic acid;
22: 3-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-hydroxypropanoic acid;
29: 2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)-N,N,N-trimethylethan-1-aminium;
30: 4'-(6-chloro-2-(((3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1'-biphenyl]-4-carboxamide;
31: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-[1,1'-biphenyl]-4-carboxamide;
32: 1-(2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)ethyl)-1,4-diazabicyclo[2.2.2]octan-1-ium;
33: 1-(3-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)propyl)-1,4-diazabicyclo[2.2.2]octan-1-ium;
36: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-2-(hydroxymethyl)propane-1,3-diol;
37: 4-((((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(2-hydroxyethyl)butanamide; 38: 4-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(1,3-dihydroxypropan-2-yl)butanamide;
40: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)propane-1,3-diol;
45: (4'-(6-chloro-2-(((3S,4R,5R)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid;
48: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-carboxamide;
49: (3R,3aR,6R,6aR)-6-(6-chloro-5-(4'-(piperazin-1-ylmethyl)-[1,1'-biphenyl]-4-yl)-1H-benzo[d]imidazol-2-yl)oxy)hexahydrofuro[3,2-b]furan-3-ol;
50: (3R,3aR,6R,6aR)-6-((6-chloro-5-(4'-((3-((2-hydroxyethoxy)methyl)azetidin-1-yl)methyl)-[1,1'-biphenyl]-4-yl)-1H-benzo[d]imidazol-2-yl)oxy)hexahydrofuro[3,2-b]furan-3 -ol;
51: (3R,3aR,6R,6aR)-6-((6-chloro-5-((4'-(4-(2-hydroxyethyl)piperazin-1-yl)methyl)-[1,1'-biphenyl]-4-yl)-1H-imidazo[4,5-b]pyridin-2-yl)oxy)hexahydrofuro[3,2-b]furan-3-ol;
52: (1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)azetidine-3,3 -diyl)dimethanol;
53: 2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-(hydroxymethyl)propane-1,3-diol;
54: (1-((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)piperidine-4,4-diyl)dimethanol;
55: (3R,3aR,6R,6aR)-6-((6-chloro-5-((4'-((4-(hydroxymethyl)piperidin-1-yl)methyl)-[1,1'-biphenyl]-4-yl)-1H-benzo[d]imidazol-2-yl)oxy)hexahydrofuro[3,2-b]furan-3-o;
56: (3R,3aR,6R,6aR)-6-(((6-chloro-5-(4'-((4-(2-hydroxyethyl)piperazin-1-yl)methyl)-[1,1'-biphenyl]-4-yl)-1H-benzo[d]imidazol-2-yl)oxy)hexahydrofuro[3,2-b]furan-3-ol;
57: (3R,3aR,6R,6aR)-6-((6-chloro-5-(4'-((4-methylpiperazin- 1-yl)methyl)-[1,1'-biphenyl]-4-yl)-1H-benzo[d]imidazol-2-yl)oxy)hexahydrofuro[3,2-b]furan-3-ol;
58: (3R,3aR,6R,6aR)-6-((6-chloro-5-(4'-(((2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol;

59: (R)-1-(4'-(6-chloro-2-(((3R,3aR,6R,6aR)-6-hydroxyhexahydrofuro[3,2-b]furan-3-yl)oxy)-1H-benzo[d]imidazol-5-yl)[1,1'-biphenyl]-4-yl)methyl)pyrrolidin-3-ol;

60: (1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)piperidine-4,4-diyl)dimethanol;

61: (3S,4R)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidine-3,4-diol;

62: (3R,3aR,6R,6aR)-6-((6-chloro-5-(4'-(((2-(2-hydroxyethoxy)ethyl)(methyl)amino)methyl)-[1,1'-biphenyl]-4-yl)-1H-benzo[d]imidazol-2-yl)oxy)hexahydrofuro[3,2-b]furan-3-ol;

63: (3R,3aR,6R,6aR)-6-((6-chloro-5-(4'-((3-(hydroxymethyl)azetidin-1-yl)methyl)-[1,1'-biphenyl]-4-yl)-1H-benzo[d]imidazol-2-yl)oxy)hexahydrofuro[3,2-b]furan-3-ol;

64: (3S,4S)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidine-3,4-diol;

65: (2R,3R,4R,5S)-6-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)hexane-1,2,3,4,5-pentaol;

66: (1-((4'-(6-chloro-2-(((3R,3aR,6R,6aR)-6-hydroxyhexahydrofuro[3,2-b]furan-3-yl)oxy)1H-benzo[d]imidazol-5-yl)-[1,1'-biphenyl]-4-yl)methyl)azetidine-3,3-diyl)dimethanol;

67: (3R,3aR,6R,6aR)-6-((5-(4'-((3-(aminomethyl)azetidin-1-yl)methyl)-[1,1'-biphenyl]-4-yl)-6-chloro-1H-benzo[d]imidazol-2-yl)oxy)hexahydrofuro[3,2-b]furan-3-ol;

68: (4'-(6-chloro-2-(((3R,4S,5S)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid;

69: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-sulfonic acid;

70: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-[1,1'-biphenyl]-4-sulfonamide;

71: 4'-(6-chloro-2-(((3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1,1'-biphenyl]-4-sulfonamide;

72: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-sulfonamide;

73: (2R,3R,4R,5S)-6-(1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)ethyl)amino)hexane-1,2,3,4,5-pentaol;

74: (3R,3aR,6R,6aR)-6-((6-chloro-5-(2'-hydroxy-4'-(((2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol;

75: 4'-(6-chloro-2-(((3R,3aR,6R,6aR)-6-hydroxyhexahydrofuro[3,2-b]furan-3-yl)oxy)-1H-benzo[d]imidazol-5-yl)-2-hydroxy-N-(2-(2-hydroxyethoxy)ethyl)-[1,1'-biphenyl]-4-carboxamide.

In some embodiments, the compound is a pharmaceutically acceptable salt of a compound in Table 1.

TABLE 2

| Cmpd No. | Structure |
| --- | --- |
| 13 | 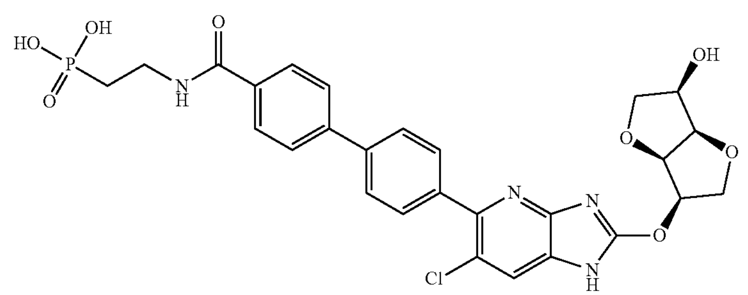 [SMILES: O=C(NCCP(=O)(O)O)c1ccc(-c2ccc(-c3nc4nc(O[C@@H]5CO[C@H]6[C@@H]5OC[C@H]6O)[nH]c4cc3Cl)cc2)cc1] |
| 15 | 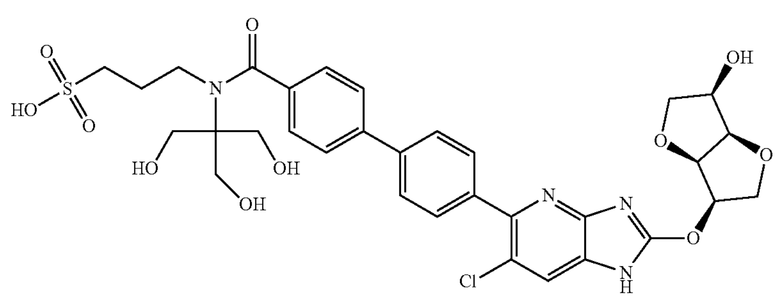 [SMILES: O=C(c1ccc(-c2ccc(-c3nc4nc(O[C@@H]5CO[C@H]6[C@@H]5OC[C@H]6O)[nH]c4cc3Cl)cc2)cc1)N(CCCS(=O)(=O)O)C(CO)(CO)CO] |

TABLE 2-continued

| Cmpd No. | Structure |
|---|---|
| 16 | 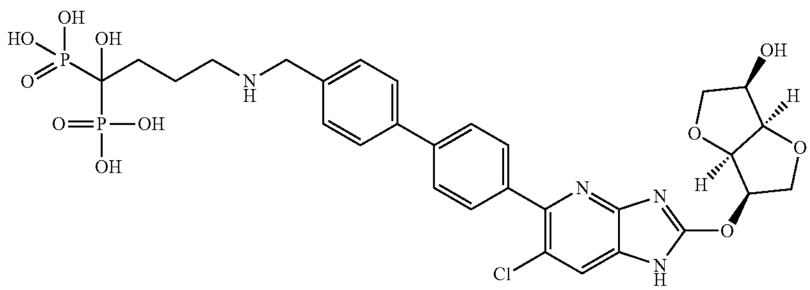 [SMILES: O=P(O)(O)C(O)(CCCNCc1ccc(-c2ccc(-c3nc4nc(O[C@@H]5CO[C@H]6[C@@H]5OC[C@H]6O)[nH]c4cc3Cl)cc2)cc1)P(=O)(O)O] |
| 17 | 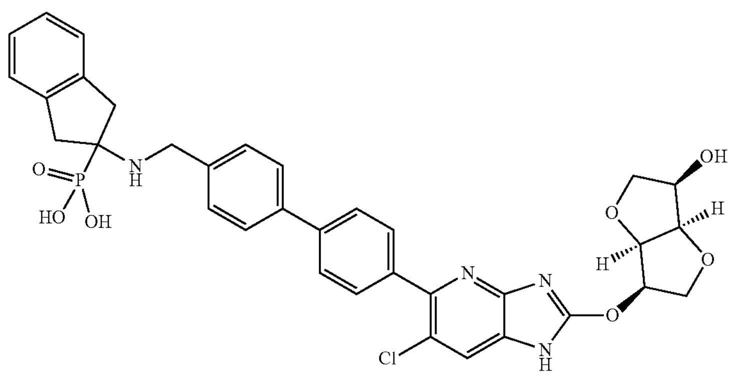 [SMILES: O=P(O)(O)C1(NCc2ccc(-c3ccc(-c4nc5nc(O[C@@H]6CO[C@H]7[C@@H]6OC[C@H]7O)[nH]c5cc4Cl)cc3)cc2)Cc2ccccc2C1] |
| 18 | 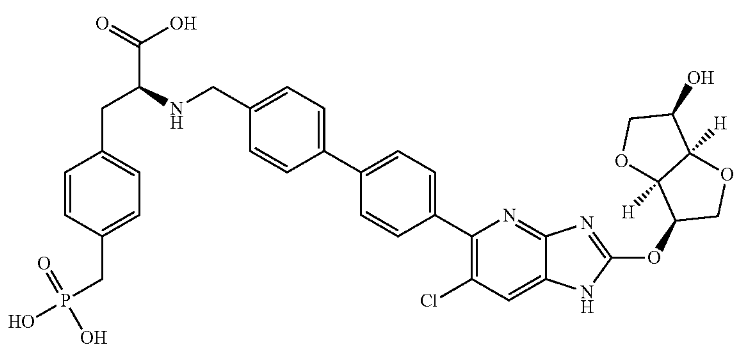 [SMILES: O=C(O)[C@H](Cc1ccc(CP(=O)(O)O)cc1)NCc1ccc(-c2ccc(-c3nc4nc(O[C@@H]5CO[C@H]6[C@@H]5OC[C@H]6O)[nH]c4cc3Cl)cc2)cc1] |
| 19 | 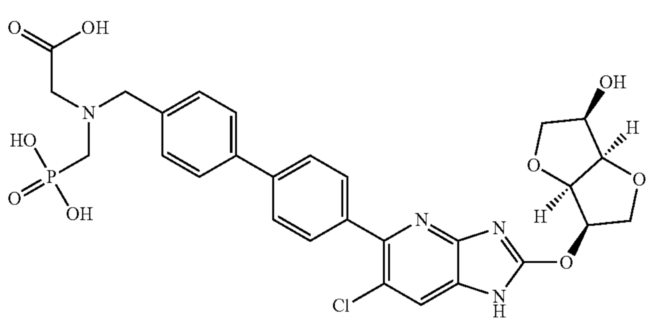 [SMILES: O=C(O)CN(Cc1ccc(-c2ccc(-c3nc4nc(O[C@@H]5CO[C@H]6[C@@H]5OC[C@H]6O)[nH]c4cc3Cl)cc2)cc1)CP(=O)(O)O] |

TABLE 2-continued

| Cmpd No. | Structure |
|---|---|
| 20 | 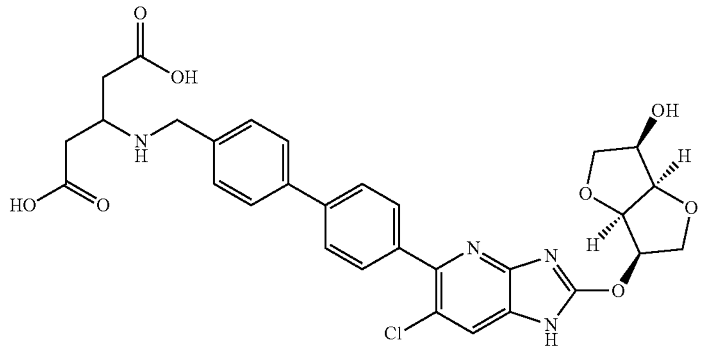 [SMILES: O=C(O)CC(CC(=O)O)NCc1ccc(-c2ccc(-c3nc4nc(O[C@@H]5CO[C@H]6[C@@H]5OC[C@H]6O)[nH]c4cc3Cl)cc2)cc1] |
| 21 | 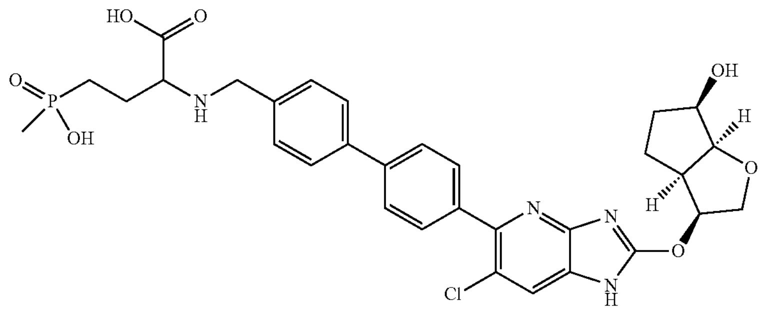 [SMILES: CP(=O)(O)CCC(NCc1ccc(-c2ccc(-c3nc4nc(O[C@@H]5CO[C@H]6[C@@H]5CC[C@H]6O)[nH]c4cc3Cl)cc2)cc1)C(=O)O] |
| 23 | 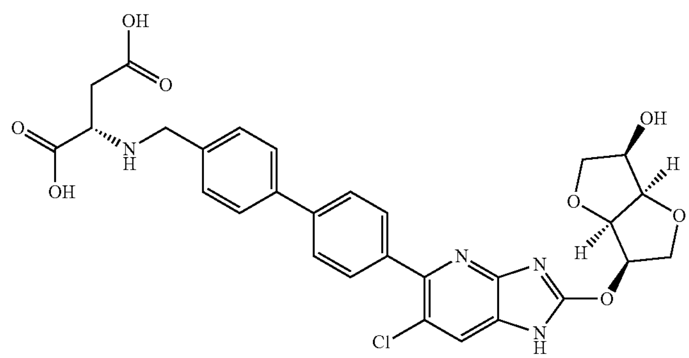 [SMILES: O=C(O)C[C@H](NCc1ccc(-c2ccc(-c3nc4nc(O[C@@H]5CO[C@H]6[C@@H]5OC[C@H]6O)[nH]c4cc3Cl)cc2)cc1)C(=O)O] |
| 24 | 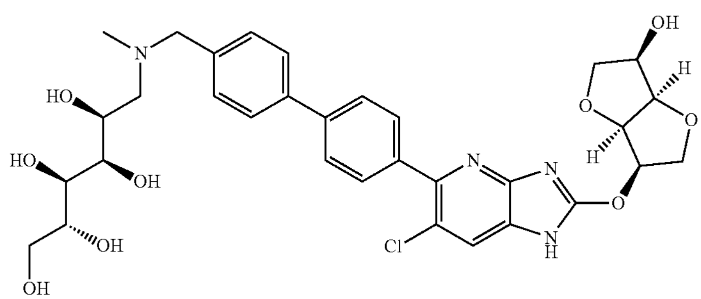 [SMILES: CN(Cc1ccc(-c2ccc(-c3nc4nc(O[C@@H]5CO[C@H]6[C@@H]5OC[C@H]6O)[nH]c4cc3Cl)cc2)cc1)C[C@H](O)[C@@H](O)[C@H](O)[C@H](O)CO] |
| 25 | 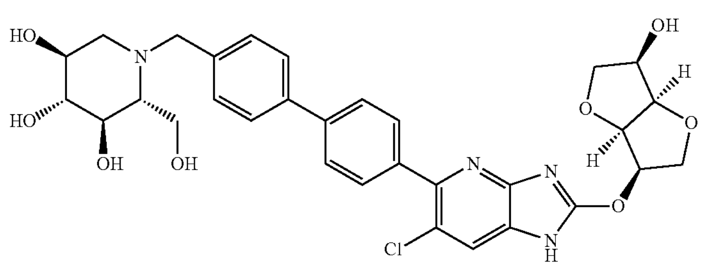 [SMILES: OC[C@@H]1[C@@H](O)[C@H](O)[C@@H](O)CN1Cc1ccc(-c2ccc(-c3nc4nc(O[C@@H]5CO[C@H]6[C@@H]5OC[C@H]6O)[nH]c4cc3Cl)cc2)cc1] |

TABLE 2-continued
| Cmpd No. | Structure |
|---|---|
| 26 | 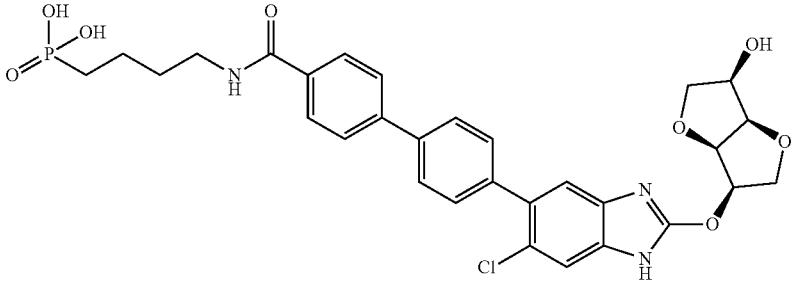 [SMILES: O=C(NCCCCP(=O)(O)O)c1ccc(-c2ccc(-c3cc4nc(O[C@@H]5CO[C@H]6[C@@H]5OC[C@H]6O)[nH]c4cc3Cl)cc2)cc1] |
| 27 | 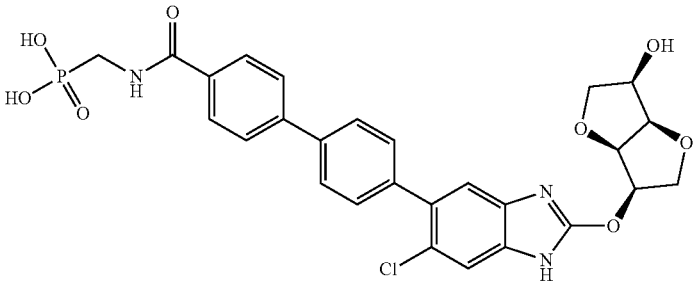 [SMILES: O=C(NCP(=O)(O)O)c1ccc(-c2ccc(-c3cc4nc(O[C@@H]5CO[C@H]6[C@@H]5OC[C@H]6O)[nH]c4cc3Cl)cc2)cc1] |
| 28 | 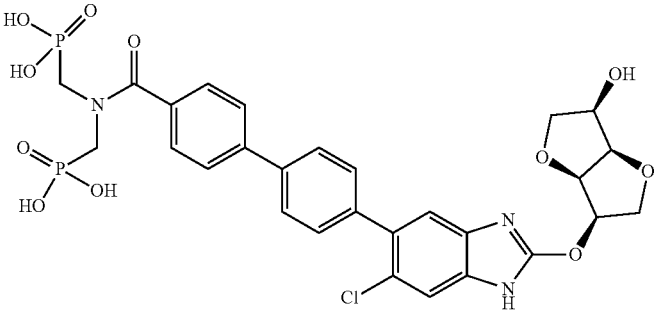 [SMILES: O=C(c1ccc(-c2ccc(-c3cc4nc(O[C@@H]5CO[C@H]6[C@@H]5OC[C@H]6O)[nH]c4cc3Cl)cc2)cc1)N(CP(=O)(O)O)CP(=O)(O)O] |
| 34 | 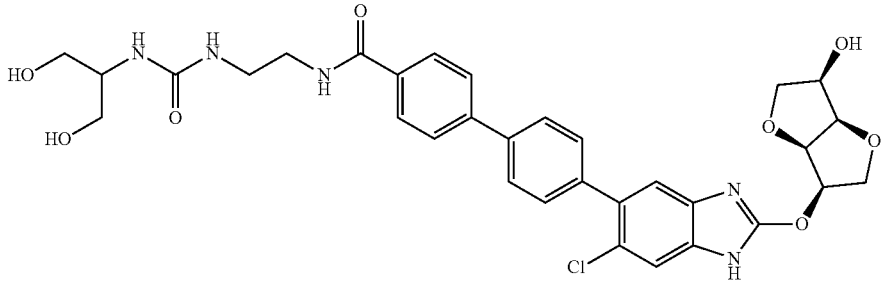 [SMILES: O=C(NCCNC(=O)c1ccc(-c2ccc(-c3cc4nc(O[C@@H]5CO[C@H]6[C@@H]5OC[C@H]6O)[nH]c4cc3Cl)cc2)cc1)NC(CO)CO] |
| 35 | 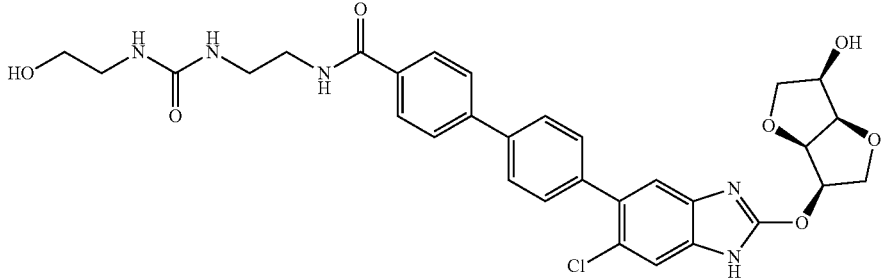 [SMILES: O=C(NCCO)NCCNC(=O)c1ccc(-c2ccc(-c3cc4nc(O[C@@H]5CO[C@H]6[C@@H]5OC[C@H]6O)[nH]c4cc3Cl)cc2)cc1] |

TABLE 2-continued

| Cmpd No. | Structure |
|---|---|
| 39 | 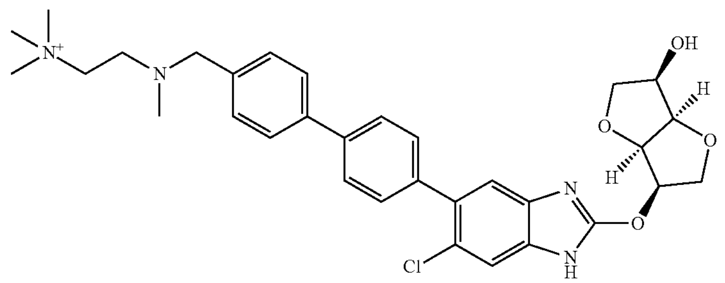 [SMILES: CN(CC[N+](C)(C)C)Cc1ccc(-c2ccc(-c3cc4nc(O[C@@H]5CO[C@H]6[C@@H]5OC[C@H]6O)[nH]c4cc3Cl)cc2)cc1] |
| 41 | 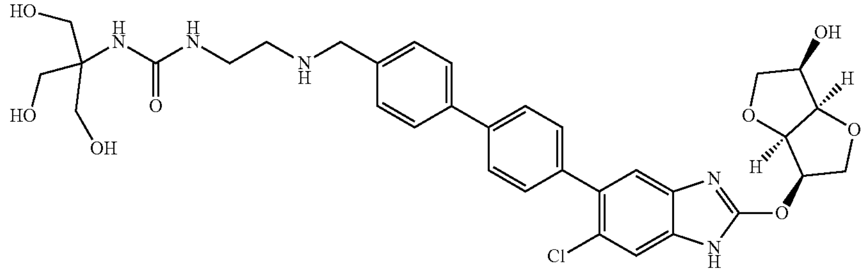 [SMILES: O=C(NCCNCc1ccc(-c2ccc(-c3cc4nc(O[C@@H]5CO[C@H]6[C@@H]5OC[C@H]6O)[nH]c4cc3Cl)cc2)cc1)NC(CO)(CO)CO] |
| 42 | 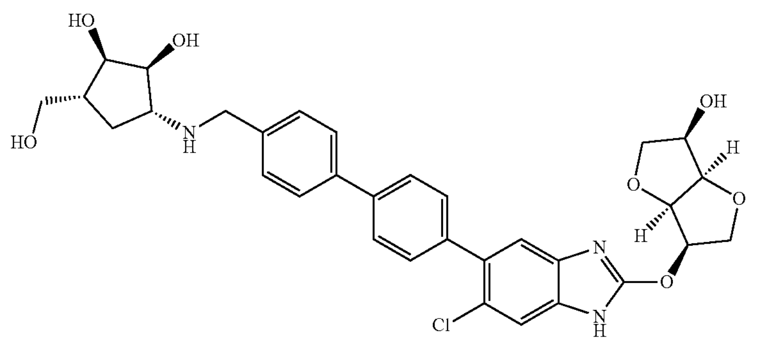 [SMILES: OC[C@H]1C[C@@H](NCc2ccc(-c3ccc(-c4cc5nc(O[C@@H]6CO[C@H]7[C@@H]6OC[C@H]7O)[nH]c5cc4Cl)cc3)cc2)[C@H](O)[C@@H]1O] |
| 43 | 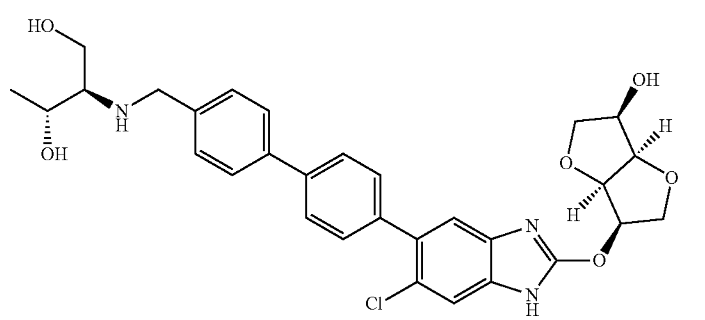 [SMILES: C[C@@H](O)[C@@H](CO)NCc1ccc(-c2ccc(-c3cc4nc(O[C@@H]5CO[C@H]6[C@@H]5OC[C@H]6O)[nH]c4cc3Cl)cc2)cc1] |
| 44 | 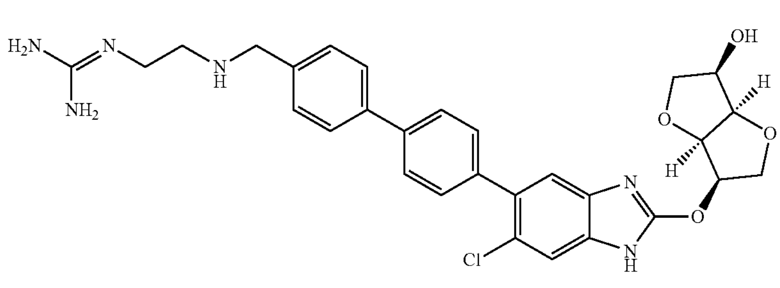 [SMILES: NC(N)=NCCNCc1ccc(-c2ccc(-c3cc4nc(O[C@@H]5CO[C@H]6[C@@H]5OC[C@H]6O)[nH]c4cc3Cl)cc2)cc1] |

TABLE 2-continued

| Cmpd No. | Structure |
|---|---|
| 46 | 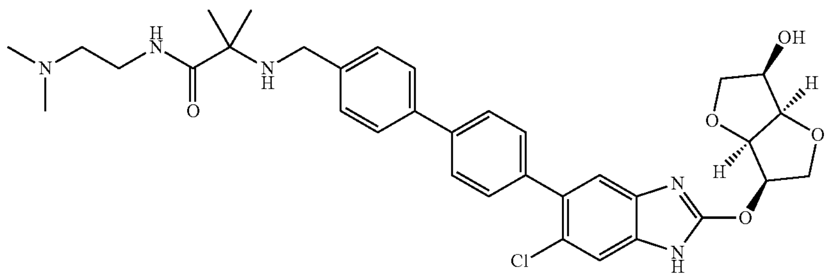 [SMILES: CN(C)CCNC(=O)C(C)(C)NCc1ccc(-c2ccc(-c3cc4nc(O[C@@H]5CO[C@H]6[C@@H]5OC[C@H]6O)[nH]c4cc3Cl)cc2)cc1] |

Compounds in Table 2 are named:

13: (2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)phosphonic acid;

15: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(1,3-dihydroxy-2-(hydroxymethyl)propan-2-yl)-[1,1'-biphenyl]-4-carboxamido)propane-1-sulfonic acid;

16: (4-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-1-hydroxybutane-1,1-diyl)bis(phosphonic acid);

17: (2-(((4'-(6-chloro-2-(((3R,3aR,6R,6aR)-6-hydroxyhexahydrofuro[3,2-b]furan-3-yl)oxy)-1H- imidazo[4,5-b]pyridin-5-yl)-[1,1'-biphenyl]-4-yl)methyl)amino)-2,3-dihydro-1H-inden-2- yl)phosphonic acid;

18: (S)-2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-3-(4-(phosphonomethyl)phenyl)propanoic acid;

19: N-((4'-(6-chloro-2-(((3R,3aR,6R,6aR)-6-hydroxyhexahydrofuro[3,2-b]furan-3-yl)oxy)-1H-imidazo[4,5 -b]pyridin-5-yl)-[1,1'-biphenyl]-4-yl)methyl)-N-(phosphonomethyl)glycine;

20: 3 -(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)pentanedioic acid;

21: 2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-4-(hydroxy(methyl)phosphoryl)butanoic acid;

23: ((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)-L-aspartic acid;

24: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5 -b]pyridin-5-yl)-[1,1'-biphenyl]-4-yl)methyl)(methyl)amino)hexane-1,2,3,4,5-pentaol;

25: (2R,3R,4R,5S)-1-((4'-(6-chloro-2-(((3R,3aR,6R,6aR)-6-hydroxyhexahydrofuro[3,2-b]furan-3 -yl)oxy)-1H-imidazo[4,5 -b]pyridin-5-yl)-[1,1'-biphenyl]-4-yl)methyl)-2-(hydroxymethyl)piperidine- 3,4,5-triol;

26: (4-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)butyl)phosphonic acid;

27: (4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)methyl)phosphonic acid;

28: ((4'-(6-chloro-2-(((3R,3aR,6R,6aR)-6-hydroxyhexahydrofuro[3,2-b]furan-3-yl)oxy)-1H-benzo[d]imidazol-5-yl)-N-(phosphonomethyl)-[1,1'-biphenyl]-4-carboxamido) methyl)phosphonic acid;

34: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(3-(1,3 -dihydroxypropan-2-yl)ureido)ethyl)-[1,1'-biphenyl]-4-carboxamide;

35: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(3-(2-hydroxyethyl)ureido)ethyl)-[1,1'-biphenyl]-4-carboxamide;

39: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)(methyl)amino)-N,N,N-trimethylethan-1-aminium;

41: 1-(2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)ethyl)-3-(1,3-dihydroxy-2-(hydroxymethyl)propan-2-yl)urea;

42: (1R,2S,3R,5R)-3-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-5-(hydroxymethyl)cyclopentane-1,2-diol;

43: (2R,3R)-2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)butane-1,3-diol;

44: 2-(2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)ethyl)guanidine; 46: 2-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(2-(dimethylamino)ethyl)-2-methylpropanamide.

In some embodiments, the compound is a pharmaceutically acceptable salt of a compound in Table 2.

Further Forms of Compounds

Furthermore, in some embodiments, the compounds described herein exist as "geometric isomers." In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

A "tautomer" refers to a molecule wherein a proton shift from one atom of a molecule to another atom of the same molecule is possible. In some embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

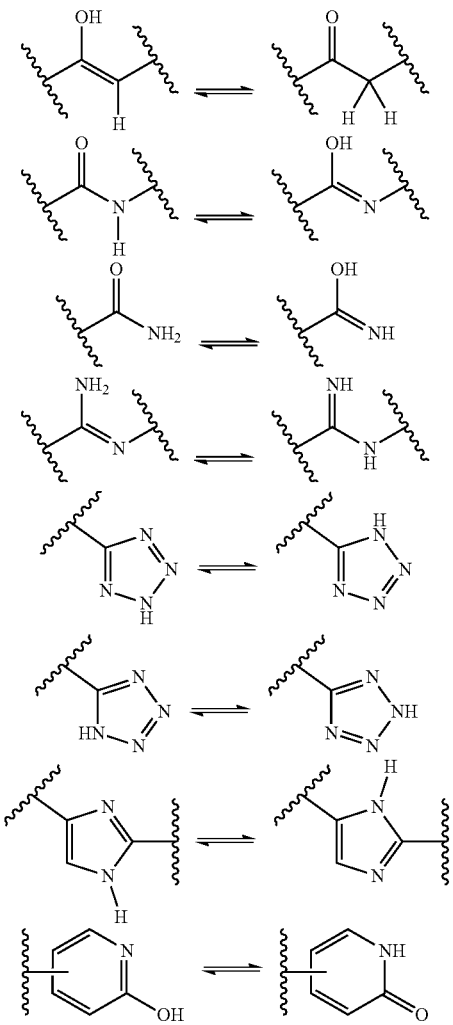

In some situations, the compounds described herein possess one or more chiral centers and each center exists in the (R)- configuration or (S)- configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "positional isomer" refers to structural isomers around a central ring, such as ortho-, meta-, and para-isomers around a benzene ring.

The methods and formulations described herein include the use of crystalline forms (also known as polymorphs), or pharmaceutically acceptable salts of compounds described herein, as well as active metabolites of these compounds having the same type of activity.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S.M. et al., "Pharmaceutical Salts," $Journal\ of\ Pharmaceutical\ Science$, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to an active compound described herein. Thus, the term prodrug refers to a precursor of an active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, carboxy, or mercapto group is bonded to any group that, when the prodrug of the active compound is administered to a mammalian subject, cleaves to form a free hydroxy, free amino, free carboxy, or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or nonstoichiometric amounts of a solvent, and are formed during the process of making with pharmaceutically acceptable solvents such as water, ethanol, and the like. "Hydrates" are formed when the solvent is water, or "alcoholates" are formed when the solvent is alcohol. Solvates of compounds described herein are conveniently prepared or formed during the processes described herein. The compounds provided herein optionally exist in either unsolvated as well as solvated forms.

The compounds disclosed herein, in some embodiments, are used in different enriched isotopic forms, e.g., enriched in the content of $^2H$, $^3H$, $^{11}C$, $^{13}C$ and/or $^{14}C$. In some embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$—or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$) Isotopic substitution with $^2H$, $^3H$, $^{11}C$, $^{13}C$, 14C, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}CL$, $^{37}CL$, $^{79}Br$, $^{81}Br$, $^{125}I$ are all contemplated. All isotopic variations of the compounds of the present invention, whether radioactive or not, are encompassed within the scope of the present invention.

In some embodiments, the compounds disclosed herein have some or all of the $^1H$ atoms replaced with $^2H$ atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

In some embodiments, the compounds described herein, or a pharmaceutically acceptable salt, solvate, stereoisomer, or prodrug thereof, as described herein are substantially pure, in that it contains less than about 5%, or less than about 1%, or less than about 0.1%, of other organic small molecules, such as contaminating intermediates or by-products that are created, for example, in one or more of the steps of a synthesis method. Preparation of the Compounds Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as outlined in the Scheme below.

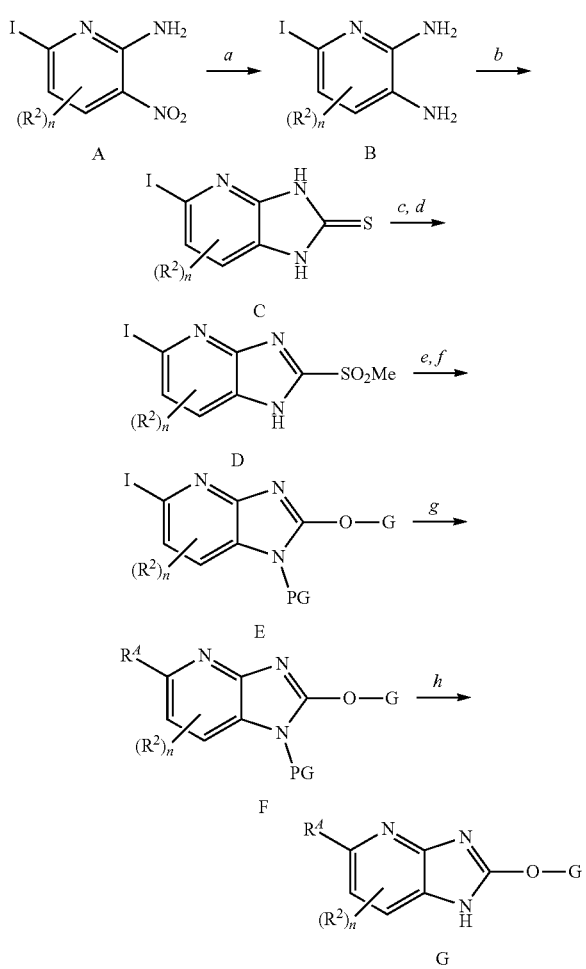

a. SnCl$_2$-2H$_2$O; b. C(S)Cl$_2$; c. CH$_3$I; d. [ox]; e. HO-G; f. protection; g. R$^A$-B(OR$_2$); h. deprotection and optional substituent modification Briefly, nitropyridine compound A is reduced to bis-amino-pyridine compound B. Compound B is treated with thiophosgene to afford compound C. Compound C undergoes a methylation reaction following by oxidation to afford compound D. Compound D is protected with a suitable protecting group, then undergoes a substitution reaction with a suitable alcohol to afford compound E. Aryl iodide E is treated under cross-coupling conditions, for example Suzuki cross- coupling, to arrive at compound F. Finally, protecting group removal yields final compound G. In some instances, additional chemical modification, such as amide formation or reductive amination, is performed on compound F before final deprotection to compound G. In other embodiments, such modifications are performed directly on compound G to provide further compounds.

In some embodiments, compounds described herein are prepared as described as outlined in the Examples.

Pharmaceutical Compositions

In some embodiments, disclosed herein is a pharmaceutical composition comprising an AMPK activator described herein, or a pharmaceutically acceptable salt, solvate, stereoisomer, or prodrug thereof, and at least one pharmaceutically acceptable excipient. In some embodiments, the AMPK activator is combined with a pharmaceutically suitable (or acceptable) carrier (also referred to herein as a pharmaceutically suitable (or acceptable) excipient, physiologically suitable (or acceptable) excipient, or physiologically suitable (or acceptable) carrier) selected on the basis of a chosen route of administration, e.g., oral administration, and standard pharmaceutical practice.

Examples of suitable aqueous and non-aqueous carriers which are employed in the pharmaceutical compositions include water, ethanol, polyols (such as glycerol, propylene glycol, polyethylene glycol, and the like), and suitable mixtures thereof; vegetable oils, such as olive oil; and injectable organic esters, such as ethyl oleate and cyclodextrins. Proper fluidity is maintained, for example, by the use of coating materials, such as lecithin; by the maintenance of the required particle size, in the case of dispersions; and by the use of surfactants. Combination Therapies In some embodiments, it is appropriate to administer at least one compound described herein, or a pharmaceutically acceptable salt, solvate, stereoisomer, or prodrug thereof, in combination with one or more other therapeutic agents.

In some embodiments, a compound described herein, or a pharmaceutically acceptable salt, solvate, stereoisomer, or prodrug thereof, is administered in combination with one or more anti- inflammatory agents. Examples of anti-inflammatory agents to be used in combination with a compound described herein, or a pharmaceutically acceptable salt, solvate, stereoisomer, or prodrug thereof, include, but are not limited to: aminosalicylates such as balsalazide, mesalamine, olsalazine, and sulfalazine; corticosteroids such as budesonide, prednisone, prednisolone, methylprednisolone, dexamethasone, and betamethasone; anti-TNF alpha agents such as infliximab, adalimumab, certolizumab pegol, golimumab, and PRX-106; anti-IL-12 and/or 23 agents such as ustekinumab, guselkumab, brazikumab, mirikizumab, risankizumab, and PTG-200; anti-integrin agents such as natalizumab, vedolizumab, etrolizumab, SHP 647 (PF-00547659), alicaforsen, abrilumab, AJM300, and PTG-100; JAK inhibitors such as tofacitinib, filgotinib, peficitinib, itacitinib, ABT-494, and TD- 1473; S1P1R modulators such as ozanimod, amiselimod, etrasimod, and CBP-307; salicylates such as aspirin, salicylic acid, gentisic acid, choline magnesium salicylate, choline salicylate, choline magnesium salicylate, choline salicylate, magnesium salicylate, sodium salicylate, and diflunisal; COX inhibitors such as carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, and meloxicam; COX-2 specific inhibitors such as, but not limited to, celecoxib, rofecoxib, valdecoxib, parecoxib, etoricoxib, lumiracoxib, CS-502, JTE-522, L-745 337, and NS398; and IL-22 agents such as RG-7880. In some embodiments, a compound described herein, or a pharmaceutically acceptable salt, solvate, stereoisomer, or prodrug thereof, is administered in combination with a aminosalicylate, a corticosteroid, an anti-TNF alpha agent, an anti-IL-12 and/or NB-23 agent, an anti-integrin agent, a JAK inhibitor, a S1P1R modulator, a salicylate, a COX inhibitor, a COX-2 specific inhibitor, an interleukin-22 (IL-22) agent, or a combination thereof.

In some embodiments, a compound described herein, or a pharmaceutically acceptable salt, solvate, stereoisomer, or prodrug thereof, is administered in combination with one or more agents that improve gastrointestinal barrier function. Examples of agents that improve gastrointestinal barrier function to be used in combination with a compound described herein, or a pharmaceutically acceptable salt, solvate, stereoisomer, or prodrug thereof, include, but are not limited to: HIF-PH inhibitors such as DS-1093, TRC-160334, and GB-004; MC1R agonists such as PL-8177; EZH2 inhibitors such as IMU-856; and DPP-4 inhibitors such as sitagliptin, vildagliptin, saxagliptin, linagliptin, gemigliptin, teneligliptin, alogliptin, trelagliptin, omarigliptin, evogliptin, gosogliptin, and dutogliptin. In some embodiments, a compound described herein, or a pharmaceutically acceptable salt, solvate, stereoisomer, or prodrug thereof, is administered in combination with a hypoxia-inducible factor-prolyl hydroxylase (HIF-PH) inhibitor, a melanocortin-1 receptor (MC1R) agonist, an enhancer of zeste homolog 2 (EZH2) inhibitor, or combinations thereof.

In some embodiments, a compound described herein, or a pharmaceutically acceptable salt, solvate, stereoisomer, or prodrug thereof, is administered in combination with a glucagon-like peptide (GLP)-1 agonist, a GLP-2 agonist, a GLP-1/2 co-agonist, a peroxisome proliferator-activator receptor (PPAR) agonist, a Farsnenoid X receptor (FXR) agonist, a TGR5 agonist, a GPR40 agonist, a GPR119 agonist, an SSTR5 antagonist, an SSTR5 inverse agonist, an acetyl-CoA carboxylase (ACC) inhibitor, a stearoyl-CoA desaturase 1 (SCD-1) inhibitor, a dipeptidyl peptidase 4 (DPP-4) inhibitor, or combinations thereof. In some embodiments, the pharmaceutical composition comprises one or more anti-diabetic agents. In some embodiments, the pharmaceutical composition comprises one or more anti-obesity agents. In some embodiments, the pharmaceutical composition comprises one or more agents to treat nutritional disorders.

Examples of a GLP-1 agonist to be used in combination with a compound described herein, or a pharmaceutically acceptable salt, solvate, stereoisomer, or prodrug thereof, include: exenatide, liraglutide, taspoglutide, lixisenatide, albiglutide, dulaglutide, semaglutide, OWL833 and ORMD 0901.

Examples of a GLP-2 agonist to be used in combination with a compound described herein, or a pharmaceutically acceptable salt, solvate, stereoisomer, or prodrug thereof, include: tedaglutide, glepaglutide (ZP1848), elsiglutide (ZP1846), apraglutide (FE 203799), HM-15912, NB-1002, GX-G8, PE-0503, and SAN-134, and those described in WO-2011050174, WO-2012028602, WO-2013164484, WO-2019040399, WO-2018142363, WO-2019090209, WO-2006117565, WO-2019086559, WO-2017002786, WO-2010042145, WO-2008056155, WO-2007067828, WO-2018229252, WO-2013040093, WO-2002066511, WO-2005067368, WO-2009739031, WO-2009632414, and WO-2008028117

Examples of a GLP-1/2 co-agonist to be used in combination with a compound described herein, or a pharmaceutically acceptable salt, solvate, stereoisomer, or prodrug thereof, include ZP-GG-72 and those described in WO-2018104561, WO-2018104558, WO-2018103868, WO-2018104560, WO-2018104559, WO-2018009778, WO-2016066818, and WO-2014096440..

Examples of a PPAR agonist to be used in combination with a compound described herein, or a pharmaceutically acceptable salt, solvate, stereoisomer, or prodrug thereof, include: elafibranor (GFT505), lanifibranor, pioglitazone, rosiglitazone, saroglitazar, seladelpar, and GW501516.

Examples of a FXR agonist to be used in combination with a compound described herein, or a pharmaceutically acceptable salt, solvate, stereoisomer, or prodrug thereof, include: obeticholic acid, NGM-282, EYP001, GS-9674, tropifexor (LJN452), and LMB-763.

Examples of a TGR5 agonist to be used in combination with a compound described herein, or a pharmaceutically acceptable salt, solvate, stereoisomer, or prodrug thereof, include: INT-777, XL-475, SRX-1374, RDX-8940, RDX-98940, SB-756050, and those disclosed in WO-2008091540, WO-2010059853, WO-2011071565, WO-2018005801, WO-2010014739, WO-2018005794, WO-2016054208, WO-2015160772, WO-2013096771, WO-2008067222, WO-2008067219, WO-2009026241, WO-2010016846, WO-2012082947, WO-2012149236, WO-2008097976, WO-2016205475, WO-2015183794, WO-2013054338, WO-2010059859, WO-2010014836, WO-2016086115, WO-2017147159, WO-2017147174, WO-2017106818, WO-2016161003, WO-2014100025, WO-2014100021, WO-2016073767, WO-2016130809, WO-2018226724, WO-2018237350, WO-2010093845, WO-2017147137, WO-2015181275, WO-2017027396, WO-2018222701, WO-2018064441, WO-2017053826, WO-2014066819, WO-2017079062, WO-2014200349, WO-2017180577, WO-2014085474.

Examples of a GPR40 agonist to be used in combination with a compound described herein, or a pharmaceutically acceptable salt, solvate, stereoisomer, or prodrug thereof, include: fasiglifam, MR-1704, SCO-267, SHR-0534, HXP-0057-SS, LY-2922470, P-11187, JTT-851, ASP- 4178, AMG-837, ID-11014A, HD-C$_{715}$, CNX-011-67, JNJ-076, TU-5113, HD-6277, MK-8666, LY-2881835, CPL-207-280, ZYDG-2, and those described in US-07750048, WO-2005051890, WO-2005095338, WO-2006011615, WO-2006083612, WO-2006083781, WO-2007088857, WO-2007123225, WO-2007136572, WO-2008054674, WO-2008054675, WO-2008063768, WO-2009039942, WO-2009039943, WO-2009054390, WO-2009054423, WO-2009054468, WO-2009054479, WO-2009058237, WO-2010085522, WO-2010085525, WO-2010085528, WO-2010091176, WO-2010123016, WO-2010123017, WO-2010143733, WO-2011046851, WO-2011052756, WO-2011066183, WO-2011078371, WO-2011161030, WO-2012004269, WO-2012004270, WO-2012010413, WO-2012011125, WO-2012046869, WO-2012072691, WO-2012111849, WO-2012147518, WO-2013025424, WO-2013057743, WO-2013104257, WO-2013122028, WO-2013122029, WO-2013128378, WO-2013144097, WO-2013154163, WO-2013164292, WO-2013178575, WO-2014019186, WO-2014073904, WO-2014082918, WO-2014086712, WO-2014122067, WO-2014130608, WO-2014146604, WO-2014169817, WO-2014170842, WO-2014187343, WO-2015000412, WO-2015010655, WO-2015020184, WO-2015024448, WO-2015024526, WO-2015028960, WO-2015032328, WO-2015044073, WO-2015051496, WO-2015062486, WO-2015073342, WO-2015078802, WO-2015084692, WO-2015088868, WO-2015089809, WO-2015097713, WO-2015105779, WO-2015105786, WO-2015119899, WO-2015176267, WO-201600771, WO-2016019587, WO-2016022446, WO-2016022448, WO-2016022742, WO-2016032120, WO-2016057731, WO-2017025368, WO-2017027309, WO-2017027310, WO-2017027312, WO-2017042121, WO-2017172505, WO-2017180571, WO-2018077699, WO-2018081047, WO-2018095877, WO-2018106518, WO-2018111012, WO-2018118670, WO-2018138026, WO-2018138027, WO-2018138028, WO-2018138029, WO-2018138030, WO-2018146008, WO-2018172727, WO-2018181847, WO-2018182050, WO-2018219204, WO-2019099315, and WO-2019134984.

Examples of a GPR119 agonist to be used in combination with a compound described herein, or a pharmaceutically acceptable salt, solvate, stereoisomer, or prodrug thereof, include: DS-8500a, HD-2355, LC34AD3, PSN-491, HM-47000, PSN-821, MBX-2982, GSK-1292263, APD597, DA-1241, and those described in WO-2009141238, WO-2010008739, WO-2011008663, WO-2010013849, WO-2012046792, WO-2012117996, WO-2010128414, WO-2011025006, WO-2012046249, WO-2009106565, WO-2011147951, WO-2011127106, WO-2012025811, WO-2011138427, WO-2011140161, WO-2011061679, WO-2017175066, WO-2017175068, WO-2015080446, WO-2013173198, US-20120053180, WO-2011044001, WO-2010009183, WO-2012037393, WO-2009105715, WO-2013074388, WO-2013066869, WO-2009117421, WO-201008851, WO-2012077655, WO-2009106561, WO-2008109702, WO-2011140160, WO-2009126535, WO-2009105717, WO-2013122821, WO-2010006191, WO-2009012275, WO-2010048149, WO-2009105722, WO-2012103806, WO-2008025798, WO-2008097428, WO-2011146335, WO-2012080476, WO-2017106112, WO-2012145361, WO-2012098217, WO-2008137435, WO-2008137436, WO-2009143049, WO-2014074668, WO-2014052619, WO-2013055910, WO-2012170702, WO-2012145604, WO-2012145603, WO-2011030139, WO-2018153849, WO-2017222713, WO-2015150565, WO-2015150563, WO-2015150564, WO-2014056938, WO-2007120689, WO-2016068453, WO-2007120702, WO-2013167514, WO-2011113947, WO-2007003962, WO-2011153435, WO-2018026890, WO-2011163090, WO-2011041154, WO-2008083238, WO-2008070692, WO-2011150067, and WO-2009123992.

Examples of a SSTR5 antagonist or inverse agonist to be used in combination with a compound described herein, or a pharmaceutically acceptable salt, solvate, stereoisomer, or prodrug thereof, include those described in: WO-03104816, WO-2009050309, WO-2015052910, WO-2011146324, WO-2006128803, WO-2010056717, WO-2012024183, and WO-2016205032.

Examples of an ACC inhibitor to be used in combination with a compound described herein, or a pharmaceutically acceptable salt, solvate, stereoisomer, or prodrug thereof, include: firsocostat, GS-834356, and PF-05221304.

Examples of a SCD-1 inhibitor to be used in combination with a compound described herein, or a pharmaceutically acceptable salt, solvate, stereoisomer, or prodrug thereof, include aramchol.

Examples of a DPP-4 inhibitor to be used in combination with a compound described herein, or a pharmaceutically acceptable salt, solvate, stereoisomer, or prodrug thereof, include: sitagliptin, vildagliptin, saxagliptin, linagliptin, gemigliptin, teneligliptin, alogliptin, trelagliptin, omarigliptin, evogliptin, gosogliptin, and dutogliptin.

Examples of anti-diabetic agents to be used in combination with a compound described herein, or a pharmaceutically acceptable salt, solvate, stereoisomer, or prodrug thereof, include: GLP-1 receptor agonists such as exenatide, liraglutide, taspoglutide, lixisenatide, albiglutide, dulaglutide, semaglutide, OWL833 and ORMD 0901; SGLT2 inhibitors such as dapagliflozin, canagliflozin, empagliflozin, ertugliflozin, ipragliflozin, luseogliflozin, remogliflozin, sergliflozin, sotagliflozin, and tofogliflozin; biguinides such as metformin; insulin and insulin analogs.

Examples of anti-obesity agents to be used in combination with a compound described herein, or a pharmaceutically acceptable salt, solvate, stereoisomer, or prodrug thereof, include: GLP-1 receptor agonists such as liraglutide, semaglutide; SGLT1/2 inhibitors such as LIK066, pramlintide and other amylin analogs such as AM-833, AC2307, and BI 473494; PYY analogs such as NN-9747, NN-9748, AC-162352, AC-163954, GT-001, GT-002, GT-003, and RHS-08; GIP receptor agonists such as APD-668 and APD-597; GLP-1/GIP co-agonists such as tirzepatide (LY329176), BHM-089, LBT-6030, CT-868, SCO-094, NNC-0090-2746, RG-7685, NN-9709, and SAR-438335; GLP-1/glucagon co-agonist such as cotadutide (MEDI0382), BI 456906, TT-401, G-49, H&D-001A, ZP-2929, and HM-12525A; GLP-1/GIP/glucagon triple agonist such as SAR-441255, HM-15211, and NN-9423; GLP-1/secretin co-agonists such as GUB06-046; leptin analogs such as metreleptin; GDF15 modulators such as those described in WO-2012138919, WO-2015017710, WO-2015198199, WO-2017147742 and WO-2018071493; FGF21 receptor modulators such as NN9499, NGM386, NGM313, BFKB8488A (RG7992), AKR-001, LLF-580, CVX-343, LY-2405319, BIO89-100, and BMS-986036; MC4 agonists such as setmelanotide; MetAP2 inhibitors such as ZGN-1061; ghrelin receptor modulators such as HM04 and AZP-531; and oxytocin analogs such as carbetocin.

Examples of agents for nutritional disorders to be used in combination with a compound described herein, or a pharmaceutically acceptable salt, solvate, stereoisomer, or prodrug thereof, include: GLP-2 receptor agonists such as tedaglutide, glepaglutide (ZP1848), elsiglutide (ZP1846), apraglutide (FE 203799), HM-15912, NB-1002, GX-G8, PE-0503, SAN-134, and those described in WO-2011050174, WO-2012028602, WO-2013164484, WO-2019040399, WO-2018142363, WO-2019090209, WO-2006117565, WO-2019086559, WO-2017002786, WO-2010042145, WO-2008056155, WO-2007067828, WO-2018229252, WO-2013040093, WO-2002066511, WO-2005067368, WO-2009739031, WO-2009632414, and WO-2008028117; and GLP-1/GLP-2 receptor co-agonists such as ZP-GG-72 and those described in WO-2018104561, WO-2018104558, WO-2018103868, WO-2018104560, WO-2018104559, WO-2018009778, WO-2016066818, and WO-2014096440.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt, solvate, stereoisomer, or prodrug thereof, is co-administered with one or more additional therapeutic agents, wherein the compound described herein, or a pharmaceutically acceptable salt, solvate, stereoisomer, or prodrug thereof, and the additional therapeutic agent(s) modulate different aspects of the disease, disorder or condition being treated, thereby providing a greater overall benefit than administration of either therapeutic agent alone. In some embodiments, the additional therapeutic agent(s) is a glucagon-like peptide (GLP)-1 agonist, a GLP-2 agonist, a GLP-1/2 co-agonist, a peroxisome proliferator-activator receptor (PPAR) agonist, a Farsnenoid X receptor (FXR) agonist, a stearoyl-CoA desaturase 1 (SCD-1) inhibitor, a dipeptidyl peptidase 4 (DPP-4) inhibitor, or a combination thereof. In some embodiments, the second therapeutic agent is an anti-inflammatory agent. In some embodiments, the additional therapeutic agent(s) is an aminosalicylate, a corticosteroid, an anti-TNF alpha agent, an anti-IL-12 and/or 23 agent, an anti-integrin agent, a JAK inhibitor, a S1P1R modulator, a salicylate, a COX inhibitor, a COX-2 specific inhibitor, an IL-22 agent, or a combination thereof. In some embodiments, the second therapeutic agent is an agent that improves gastrointestinal barrier function. In some embodiments, the additional therapeutic agent(s) is a HIF-PH inhibitor, an MC1R agonist, an EZH2 inhibitor, or a combination thereof.

In some embodiments, the overall benefit experienced by the patient is additive of the two (or more) therapeutic agents. In other embodiments, the patient experiences a synergistic benefit of the two (or more) therapeutic agents.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or pharmaceutically acceptable salts, solvates, stereoisomers, or prodrugs thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease.

In some embodiments, a compound described herein, or a pharmaceutically acceptable salt thereof, is administered in combination with anti-inflammatory agent, anti-cancer agent, immunosuppressive agent, steroid, non-steroidal anti-inflammatory agent, antihistamine, analgesic, hormone blocking therapy, radiation therapy, monoclonal antibodies, or combinations thereof.

EXAMPLES

List of Abbreviations

As used above, and throughout the description of the invention, the following abbreviations, unless otherwise indicated, shall be understood to have the following meanings:

| | |
|---|---|
| ACN or MeCN | acetonitrile |
| AcOH or HOAc | acetic acid |
| AcCl | acetyl chloride |
| ADP | adenosine diphosphate |
| AMP | adenosine monophosphate |
| AMPK | 5' AMP-activated protein kinase or adenosine 5'-monophosphate-activated protein kinase |
| ATP | adenosine triphosphate |
| aq | aqueous |
| BPD | bis(pinacolato)diboron |
| DBU | 1,8-diazabicyclo[5.4.0]undec-7-ene |
| DCM | dichloromethane |
| DIEA or DIPEA | N,N-diisopropylethylamine |

| | |
|---|---|
| DMAP | 4-dimethylaminopyridine |
| DME | dimethoxyethane |
| DMF | dimethylformamide |
| DMSO | dimethyl sulfoxide |
| DMTMM | 4-(4,6-dimethoxy-1,3,5-triazin-2-yl)-4-methyl-morpholinium chloride |
| eq | equivalent(s) |
| Et | ethyl |
| EtOH | ethanol |
| EtOAc or EA | ethyl acetate |
| FA | formic acid |
| h, hr(s) | hour(s) |
| HATU | 1-[Bis(dimethylamino)methylene]-1H-1,2,3-triazolo[4,5-b]pyridinium 3-oxide hexafluorophosphate |
| HPLC | high performance liquid chromatography |
| KOAc | potassium acetate |
| LCMS | liquid chromatography-mass spectrometry |
| Me | methyl |
| MeOH | methanol |
| MeI | methyl iodide |
| min(s) | minute(s) |
| MS | mass spectroscopy or molecular sieves |
| NCS | N-chlorosuccinimide |
| NMR | nuclear magnetic resonance |
| Oxone | potassium peroxysulfate |
| Pd(dppf)Cl$_2$ | [1,1'-bis(diphenylphosphino)ferrocene]-dichloropalladium(II) |
| Pd(dppf)Cl'2•CH$_2$Cl$_2$ | [1,1'-bis(diphenylphosphino)ferrocene]-dichloropalladium(II) dichloromethane complex |
| RP-MPLC | reverse phase medium pressure liquid chromatography |
| SEM | 2-(trimethylsilyl)ethoxymethyl |
| SEM-Cl | 2-(trimethylsilyl)ethoxymethyl chloride |
| rt or RT | room temperature |
| TBS | tert-butyldimethylsilyl |
| TBS-Cl | tert-butyldimethylsilyl chloride |
| TMSBr | trimethylsilyl bromide |
| tBu | tert-butyl |
| tBu$_3$P•Pd•G2 | chloro[(tri-tert-butylphosphine)-2-(2-aminobiphenyl)] palladium(II) |
| TEA | triethylamine |
| TFA | trifluoroacetic acid |
| THF | tetrahydrofuran |
| TLC | thin layer chromatography |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-((2S,3R,4R,5R)-2,3,4,5,6-pentahydroxyhexyl)-[1,1'-biphenyl]-4-carboxamide (Compound 1)

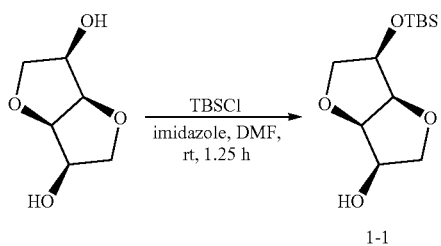

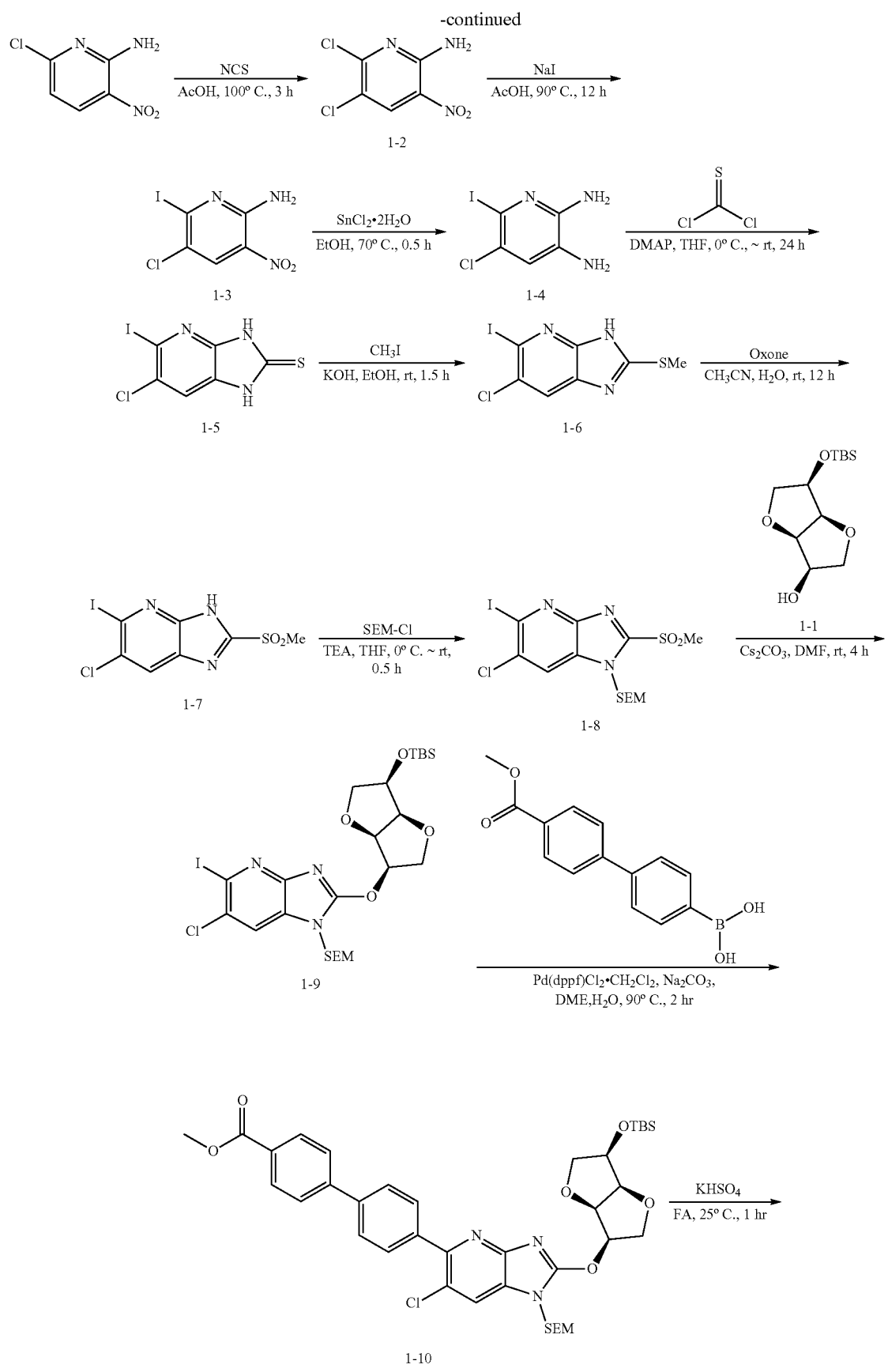

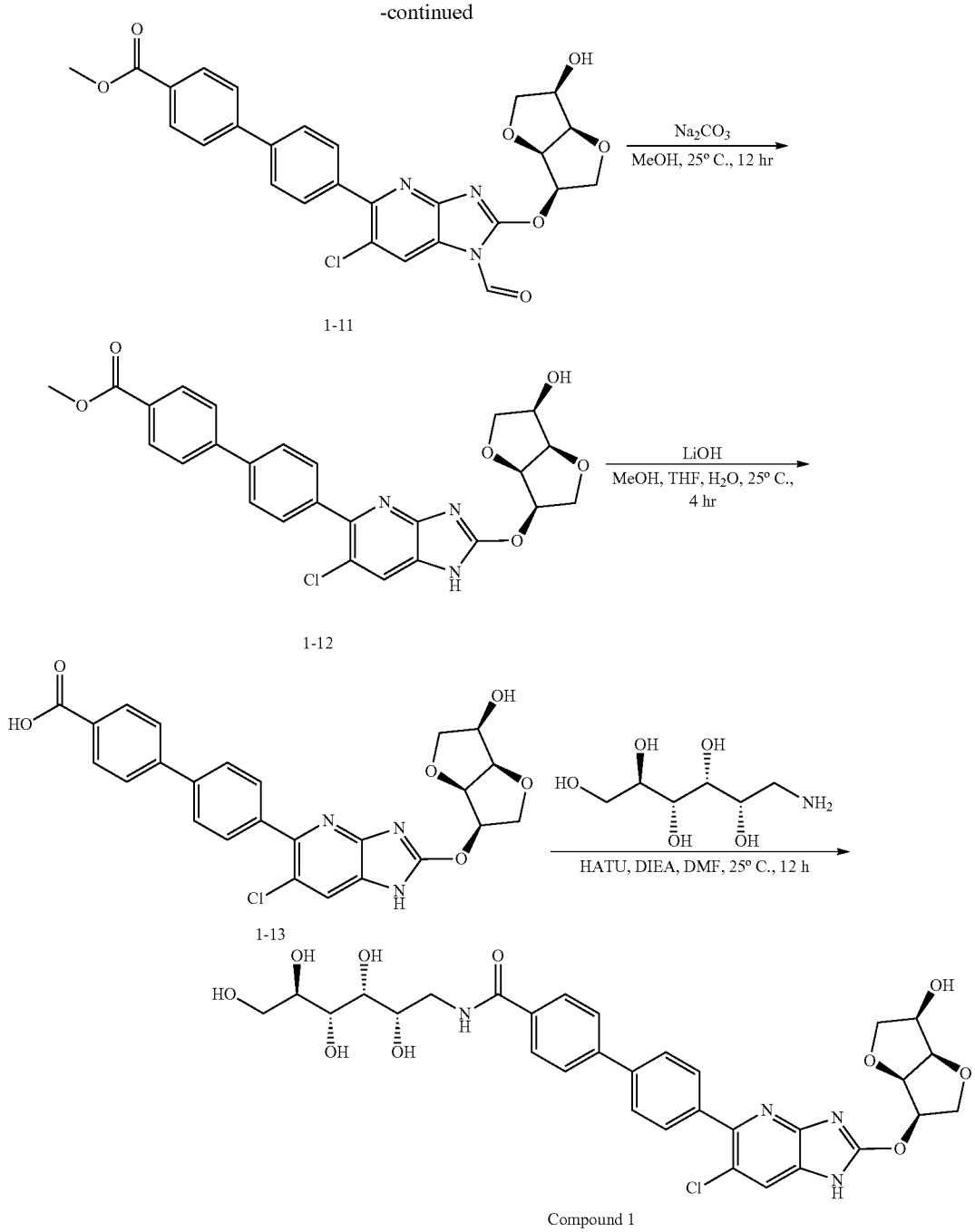

Compound 1

Step 1: (3R,3aR,6R,6aS)-6-(tert-butyldimethylsilyl)oxy) hexahydrofuro[3,2-b]furan-3-ol(1-1): To a solution of (3R, 3aR,6R,6aR)-2,3,3a,5,6,6a-hexahydrofuro[3,2-b]furan-3,6-diol (24 g, 0.16 mol, 1 eq) and imidazole (25 g, 0.37 mmol, 2.25 eq) in DMF (240 mL) was added TBSCl (27 g, 0.18 mol, 22 mL, 1.1 eq). The mixture was stirred at room temperature for 1.25 hrs. The mixture was poured into water (200 mL) and then extracted with ethyl acetate (3×300 mL). The combined organic layers were washed with saturated brine (2×100 mL), then concentrated in vacuo. The residue was purified by column chromatography (SiO$_2$, petroleum ether : ethyl acetate=5:1 to 1:1) to give 1-1 (18 g, 43% yield) as a white solid. $^1$H-NMR (CD$_3$OD, 400 MHz): δ 4.52 (t, J=5.6 Hz, 1H), 4.43 (t, J=5.2 Hz, 1H), 4.27 (q, J=5.2 Hz, 1H), 4.23-4.17 (m, 1H), 3.99-3.93 (m, 2H), 3.78-3.73 (m, 2H), 3.19 (d, J=9.2 Hz, 1H), 0.92 (s, 9H), 0.13 (s, 3H), 0.12 (s, 3H).

Step 2: 5,6-dichloro-3-nitropyridin-2-amine (1-2): To a solution of 6-chloro-3-nitro-pyridin-2-amine (50 g, 0.29 mol, 1 eq) in AcOH (250 mL) was added NCS (46 g, 0.35 mmol, 1.2 eq). The mixture was stirred at 100° C. for 3 hrs. The mixture was cooled to room temperature, then filtered. The filter cake was washed with ethanol (100 mL), then dried in vacuo to give 1-2 (48 g, crude) as a yellow solid. LCMS (ES$^+$): m/z (M+H)$^+$=207.9.

Step 3: 5-chloro-6-iodo-3-nitropyridin-2-amine (1-3): To a solution of 1-2 (48 g, 0.23 mol, 1 eq) in AcOH (250 mL) was added NaI (73 g, 0.48 mol, 2.1 eq). The mixture was stirred at 90 °C. for 12 hrs. The mixture was poured into water (500 mL), then filtered. The filter cake was washed with water (200 mL), then dried in vacuo to give 1-3 (60 g, crude) as a yellow solid. LCMS (ES$^+$): m/z (M+H)$^+$=299.8.

Step 4: 5-chloro-6-iodopyridine-2,3-diamine (1-4): To a solution 1-3 of (60 g, 0.20 mol, 1 eq) in EtOH (300 mL) was added $SnCl_2 \cdot 2HO$ (0.18 kg, 0.80 mol, 4 eq). The mixture was stirred at 70° C. for 0.5 hr. To the mixture was added water (450 mL) and KF (0.18 kg), and the mixture was stirred for 0.5 h, then extracted with ethyl acetate (2×100 mL). The organic phase was washed with saturated brine (2×50 mL), then concentrated in vacuo. The residue was purified by column chromatography ($SiO_2$, petroleum ether : ethyl acetate=2:1 to 0:1) to give 1-4 (41 g, 73% yield, 96% purity) as an off-white solid. LCMS (ES$^+$): m/z (M+H)$^+$= 269.9.

Step 5: 6-chloro-5-iodo-1H-imidazo[4,5-b]pyridine-2 (3H)-thione (1-5): To a solution of 1-4 (20 g, 74 mmol, 1 eq) and DMAP (26 g, 0.22 mol, 2.9 eq) in THF (400 mL) was added dropwise thiocarbonyl dichloride (12 g, 0.10 mol, 8.0 mL, 1.4 eq) at 0° C. under $N_2$. The mixture was stirred at room temperature for 24 hr. To the reaction mixture was added ethyl acetate (2000 mL) and 2 N aqueous HCl (200 mL). The organic layer was washed with saturated brine (2×300 mL), then concentrated in vacuo to give 1-5 (17 g) as a yellow solid. LCMS (ES$^+$): m/z (M+H)$^+$=311.8.

Step 6: 6-chloro-5-iodo-2-(methylthio)-3H-imidazo[4,5-b]pyridine (1-6): A solution of 1-5 (22 g, 70 mmol, 1 eq) and KOH (4.7 g, 84 mmol, 1.2 eq) in EtOH (440 mL) was stirred at room temperature for 0.5 hr. MeI (10.0 g, 70 mmol, 4.4 mL, 1 eq) was added, and the reaction was stirred at room temperature for another 1 hr. The reaction mixture was concentrated in vacuo to give a residue, then ethyl acetate (300 mL) was added followed by 2 N aqueous HCl (50 mL). The organic layer was washed with saturated brine (2×50 mL), then concentrated in vacuo. The residue was purified by column chromatography ($SiO_2$, petroleum ether : ethyl acetate=5:1 to 1:1) to give 1-6(16 g, 48% yield, 68% purity) as a yellow solid. added m/z (M+H)$^+$=325.8.

Step 7: 6-chloro-5-iodo-2-(methylsulfonyl)-3H-imidazo[4,5-b]pyridine (1-7): To a solution of 1-6 (16 g, 49 mmol, 1 eq) in ACN (320 mL) and $H_2O$ (320 mL) was added Oxone (66 g, 0.11 mmol, 2.2 eq). The mixture was stirred at room temperature for 12 hrs. The mixture was extracted with ethyl acetate (3×400 mL). The combined organic layers were washed with saturated $Na_2SO_3$ solution (2×200 mL) and brine (2×200 mL), then concentrated in vacuo to give 1-7 (16 g) as a yellow solid which was used for next step directly. LCMS (ES$^+$): m/z (M+H)$^+$=357.8.

Step 8: 6-chloro-5-iodo-2-(methylsulfonyl)-1-((trimethylsilyl)ethoxy)methyl)-1H-imidazo[4,5-b]pyridine (1-8): SEM-Cl (7.3 g, 44 mmol, 7.7 mL, 1 eq) was added dropwise to a THF (310 mL) solution of 1-7 (16 g, 44 mmol, 1 eq) and TEA (6.6 g, 65 mmol, 9.1 mL, 1.5 eq) at 0° C. under nitrogen. The reaction mixture was stirred at room temperature for 0.5 hr. The mixture was poured into water (100 mL) and then extracted with ethyl acetate (2×200 mL). The combined organic layers were washed with saturated brine (2×100 mL), then concentrated in vacuo. The residue was purified by column chromatography ($SiO_2$, petroleum ether : ethyl acetate=10:1 to 5:1) to give 1-8 (12 g, 56% yield, 98% purity) as a yellow solid. LCMS (ES$^+$): m/z (M+Na)$^+$=510.0.

Step 9: 2-(((3R,3aR,6R,6aS)-6-(tert-butyldimethylsilyl)oxy)hexahydrofuro[3,2-b]furan-3-yl)oxy)-6-chloro-5-iodo-1-((trimethylsilyl)ethoxy)methyl)-1H-imidazo[4,5-b]pyridine (1-9): To a solution of 1-8 (12 g, 25 mmol, 1 eq) and 1-1 (8.0 g, 31 mmol, 1.2 eq) in DMF (125 mL) was added $C_{s2}CO_3$ (17 g, 51 mmol, 2 eq) under $N_2$. The mixture was stirred at room temperature for 4 hrs. The mixture was poured into water (100 mL) and then extracted with ethyl acetate (2×200 mL). The combined organic layers were washed with saturated brine (2×50 mL), then concentrated in vacuo. The residue was purified by column chromatography ($SiO_2$, petroleum ether : ethyl acetate=20:1 to 5:1) to give 1-9 (10 g, 53% yield, 90% purity) as a yellow solid. LCMS (ES$^+$): m/z (M+H)$^+$=668.2. $^1$H-NMR (DMSO-d$_6$, 400 MHz): δ 8.07 (s, 1H), 5.50 -5.46 (m, 1H), 5.37 (s, 2H), 4.82 (t, J=5.2 Hz, 1H), 4.37-4.35 (m, 2H), 4.32- 4.23 (m, 2H), 4.00-3.94 (m, 1H), 3.79 -3.71 (m, 2H), 3.61 (t, J=8.4 Hz, 1H), 0.87 (s, 9H), 0.08- 0.05 (m, 8H), −0.07 (s, 9H).

Step 10: methyl 4'-(2-(((3R,3aR,6R,6aS)-6-((tert-butyldimethylsilyl)oxy) hexahydrofuro[3,2-b]furan-3-yl)oxy)-6-chloro-1-((2-(trimethylsilyl)ethoxy)methyl)-1H-imidazo[4,5-b]pyridin-5-yl)-[1,1'-biphenyl]-4-carboxylate (1-10): To a solution of 1-9 (0.50 g, 0.75 mmol) and (4'-(methoxycarbonyl)-[1,1'-biphenyl]-4-yl)boronic acid (0.23 g, 0.90 mmol) in DME (10 mL) and $H_2O$ (2 mL) was added Pd(dppf)Cl$_2$CH$_2$Cl$_2$ (0.12 g, 0.15 mmol) and $Na_2CO_3$ (0.24 g, 2.2 mmol) under $N_2$. The mixture was stirred at 90° C. for 2 hr. The reaction mixture was quenched by addition water (30 mL) and extracted with ethyl acetate (20 mL×3). The combined organic layers were washed with saturated brine (10 mL×3), dried over $Na_2SO_4$, filtered, and concentrated under reduced pressure to give 1-10 (0.55 g, 89% yield, 91% purity) as a yellow solid. LCMS (ES$^+$): m/z (M+H)$^+$=752.2.

Step 11: methyl 4'-(6-chloro-1-formyl-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxylate (1-11): To a solution of 1-10 (0.55 g, 0.73 mmol) in HCOOH (16 mL) was added saturated aqueous KHSO$_4$ solution (0.1 g, 0.73 mmol, 43 uL). The mixture was stirred at 25° C. for 1 hr. The reaction mixture was quenched by addition water 20 mL and extracted with ethyl acetate (10 mL×3). The combined organic layers were washed with saturated brine 10 mL, dried over $Na_2SO_4$, filtered, and concentrated under reduced pressure to give 1-11 (0.44 g) as a yellow solid. LCMS (ES$^+$): m/z (M+H)$^+$=536.2

Step 12: methyl 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'biphenyl]-4-carboxylate (1-12): To a solution of 1-11 (0.44 g, 0.82 mmol) in MeOH (10 mL) was added $Na_2CO_3$ (0.14 g, 1.6 mmol). The mixture was stirred at 25° C. for 12 hr to give a yellow methanolic solution of 1-12 (0.40 g, 95.92% yield). The mixture was used for the next step without work-up and purification. LCMS (ES$^+$): m/z m/z (M+H)$^+$=508.0.

Step 13: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxylic acid (1-13): To a solution of 1-12 (50 mg, 0.79 mmol) in MeOH (2 mL), THF (2 mL) and $H_2O$ (2 mL) was added LiOH·$H_2O$ (7.5 mg, 1.6 mmol). The mixture was stirred at 25° C. for 4 hr. The reaction mixture was quenched by addition 2N HCl (5 mL), then diluted with ethyl acetate (20 mL) and extracted with ethyl acetate (20 mL×2). The combined organic layers were washed with saturated brine (15 mL×2), dried over $Na_2SO_4$, filtered, and concentrated under reduced pressure to give a residue. The residue was purified by prep-HPLC (column: Waters Xbridge C18 150×50 mm×10 μm; mobile phase: [A: water (0.225% FA); B: ACN]; B%: 68% - 98%, 10 min) and lyophilized to give 1-—(6.05 mg, 11.78% yield, 97.35% purity) as a white solid. LCMS (ES+): m/z (M+H)+=494.3. $^1$H-NMR (DMSO-$d_6$, 400 MHz): δ 8.05 (d, J=8.4 Hz, 2H), 7.93 (s, 1H) 7.87-7.83 (m, 4H), 7.78-7.63 (m, 2H), 5.48 (q, J=6.4 Hz, 1H), 4.99 (s, 1H), 4.84 (t, J=5.2 Hz, 1H), 4.36 (t, J=4.8 Hz, 1H), 4.14-4.10 (m, 2H), 3.91 (t, $J_1$=9.6 Hz, $J_2$=5.6 Hz, 1H), 3.79 (t, J=7.2 Hz, 1H), 3.46-3.42 (m, 1H).

Step 14: 4'-(6-chloro-2-(((3R,3aR,6R,6aR)-6-hydroxy-hexahydrofuro[3,2-b]furan-3-yl)oxy)-1H-imidazo[4,5-b]pyridin-5-yl)-N-(2S,3R,4R,5R)-2,3,4,5,6-pentahydroxy-hexyl)-[1,1'-biphenyl]-4-carboxamide (Compound 1): To a solution of 1-—(50 mg, 0.10 mmol) in DMF (1 mL) was added HATU (46 mg, 0.12 mmol), DIPEA (26 mg, 0.20 mmol, 35 uL), and (2R,3R,4R,5S)-6-aminohexane-1,2,3,4,5-pentaol (18 mg, 0.10 mmol). The mixture was stirred at 25° C. for 12 hr. The reaction mixture was filtered to give a solution. The solution was purified by prep-HPLC (column: Phenomenex Synergi C18 150×25 mm×10 μm; mobile phase: [A: water (0.225% FA); B: ACN]; B%: 14%-47%, 10 min) and lyophilized to give Compound 1 (17.22 mg, 24.88% yield, 96.10% purity) as a white solid. LCMS (ES+): m/z (M+H)+=657.3. $^1$H-NMR (CD$_3$OD, 400 MHz): δ7.96-7.94 (m, 2H), 7.84 (s, 1H), 7.81-7.77 (m, 6H), 5.55 (q, J=5.6 Hz, 1H), 4.97 (t, J=5.2 Hz, 1H), 4.47 (t, J=4.8 Hz, 1H), 4.30-4.26(m, 1H), 4.18-4.12 (m, 2H), 4.02-4.00 (m, 1H), 3.92-3.89 (m, 1H), 3.86-3.84 (m, 1H), 3.82-3.78 (m, 1H), 3.74-3.72 (m, 2H), 3.69-3.62 (m, 2H), 3.60-3.49 (m, 2H).

Example 2: (4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)phosphonic acid (Compound 2)

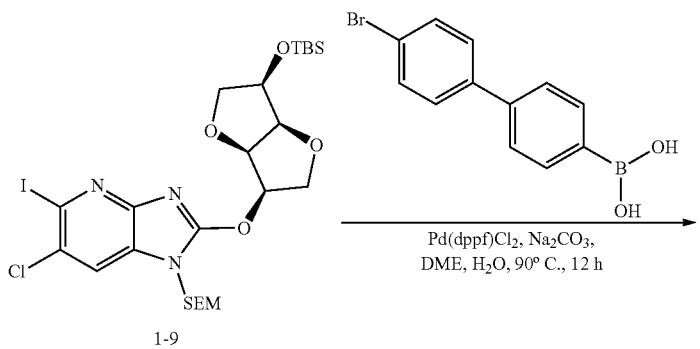

1-9

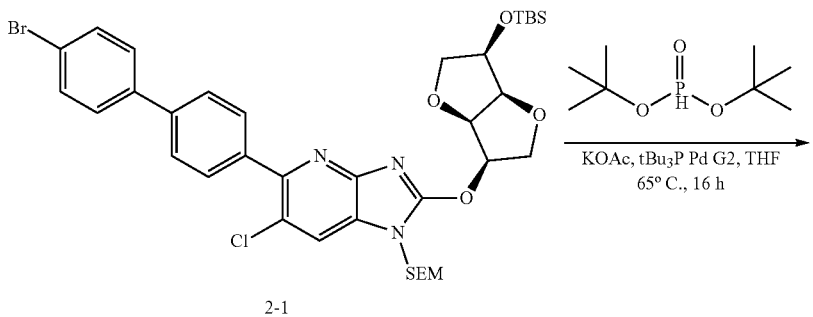

2-1

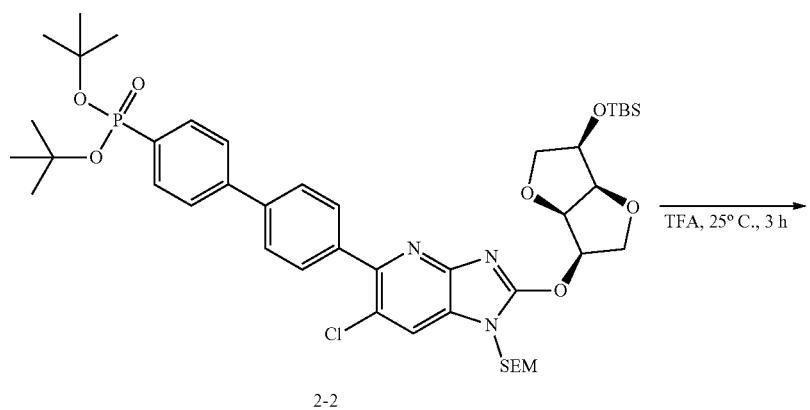

2-2

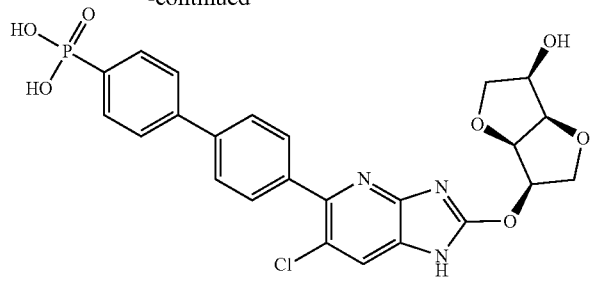

Compound 2

Step 1: 5-(4'-bromo-[1,1'-biphenyl]-4-yl)-2-(((3R,3aR, 6R,6aS)-6-(tert-butyldimethylsilyl)oxy) hexahydrofuro[3,2-b]furan-3-yl)oxy)-6-chloro-1-((2-(trimethylsilyl)ethoxy)methyl)-1H-imidazo[4,5-b]pyridine (2-1): To a solution of 1-9 (0.20 g, 0.30 mmol) and (4'-bromo-[1,1'-biphenyl]-4-yl)boronic acid (99 mg, 0.36 mmol) in DME (3.0 mL) and $H_2O$ (0.60 mL) was added Pd(dppf)$Cl_2$·$CH_2Cl_2$ (49 mg, 60 µmol) and $Na_2CO_3$ (95 mg, 0.90 mmol) under $N_2$. The mixture was stirred at 90° C. for 12 hours. The reaction mixture was quenched by addition water (30 mL) and extracted with ethyl acetate (20 mL×3). The combined organic layers were washed with saturated brine (30 mL), dried over $Na_2SO_4$, filtered, and concentrated under reduced pressure to give a residue. The residue was purified by column chromatography ($SiO_2$, petroleum ether : ethyl acetate=20:1 to 10:1) to give 2-1 (0.16 g, 0.19 mmol, 65% yield, 94% purity) as a yellow oil. $^1$H NMR (400 MHz, $CDCl_3$) δ=7.86 (s, 1H), 7.83 (m, 2H), 7.64 (m, 2H), 7.59 (m, 2H), 7.53 (m, 2H), 5.55 (m, 3H), 4.96 (t, J=10.4 Hz, 1H), 4.43 (t, J=10.0 Hz, 1H), 4.33 (m, 1H), 4.17 (dd, $J_1$=1.2 Hz, $J_2$=1.2 Hz, 2H), 3.86 (m, 1H), 3.74 (m, 2H), 3.66 (t, J=16.4 Hz, 1H), 0.94 (s, 9H), 0.15 (s, 2H), 0.13 (t, J=6.0 Hz, 6H), −0.64 (s, 9H).

Step 2: di-tert-butyl (4'-(2-(((3R,3aR,6R,6aS)-6-(tert-butyldimethylsilyl)oxy)hexahydrofuro [3,2-b]furan-3-yl)oxy)-6-chloro-1-((2-(trimethylsilyl)ethoxy)methyl)-1H-imidazo[4,5-b]pyridin-5-yl)-[1,1'-biphenyl]-4-yl)phosphonate (2-2): To a solution of 2-1 (0.13 g, 0.17 mmol) and di-tert-butyl phosphonate (0.16 g, 0.84 mmol) in THF (4.0 mL) was added KOAc (50 mg, 0.50 mmol) and $tBu_3P$·Pd·$G_2$ (7.5 mg, 15 µmol) in a glove box. Then the mixture was stirred at 65° C. for 16 hours. The reaction mixture was filtered to give a residue. The residue was purified by prep-TLC ($SiO_2$, petroleum ether : ethyl acetate=1:1) to give 2-2 (60 mg, 59 µmmol, 35% yield, 87% purity) as a yellow oil. $^1$H NMR (400 MHz, $CDCl_3$) δ=7.86 (s, 4H), 7.81 (m, 1H), 7.71 (m, 4H), 6.10 (s, 2H), 5.56 (m, 3H), 4.97 (t, J=10.4 Hz, 1H), 4.44 (m, 1H), 4.34 (m, 1H), 4.18 (m, 2H), 3.85 (m, 1H), 3.66 (m, 1H), 1.51 (s, 18H), 0.94 (s, 9H), 0.15 (s, 2H), 0.13 (t, J=6.0 Hz, 6H), −0.64 (s, 9H).

Step 3: (4'-(6-chloro-2-(((3R,3aR,6R,6aR)-6-hydroxy-hexahydrofuro[3,2-b]furan-3-yl)oxy)-1H-imidazo[4,5-b]pyridin-5-yl)-[1,1'-biphenyl]-4-yl)phosphonic acid (Compound 2): A solution of 2-2 (55 mg, 54 µmol) in TFA (0.50 mL) was stirred at 25° C. for 3 hours. The reaction mixture was concentrated under reduced pressure at 25° C. to give a residue. The residue was purified by prep-HPLC (column: UniSil 3-100 C18 Ultra 150×25 mm×3 µm; mobile phase: [A: water (0.225% FA); B: ACN]; B%: 18%-48%, 10 min) to give Compound 2 (5.4 mg, 17% yield, 96% purity, formic acid salt) as a white solid. $^1$H NMR (400 MHz, DMSO-$d_6$) δ=7.91 (m, 1H), 7.77 (m, 8H), 5.48 (m, 1H), 4.84 (t, J=10.0 Hz, 1H), 4.37 (t, J=9.6 Hz, 1H), 4.14 (m, 2H), 3.91 (m, 1H), 3.80 (m, 1H), 3.46 (m, 1H).

Example 3: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-((2S,3R,4R,5R)-2,3,4,5,6-pentahydroxyhexyl)-[1,1'-biphenyl]-4-sulfonamide (Compound 3)

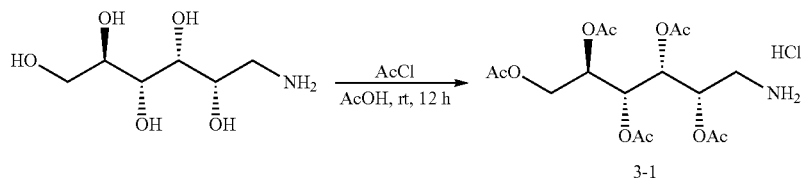

3-1

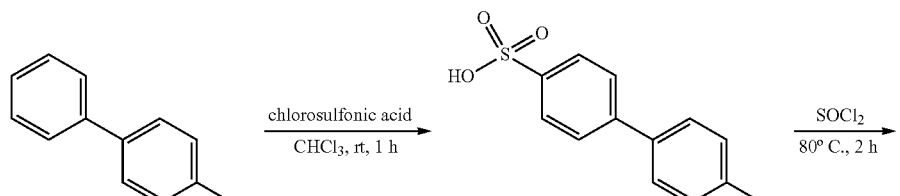

3-2

-continued
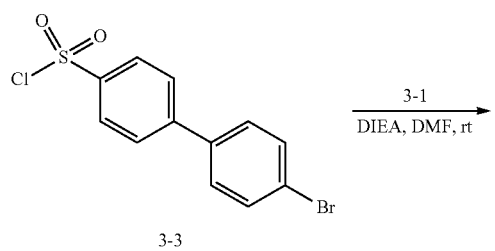
3-3
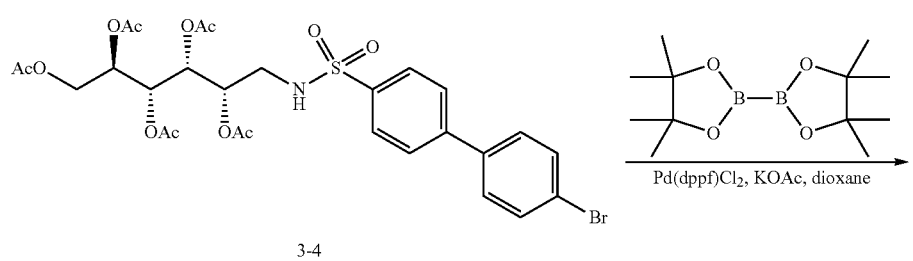
3-4
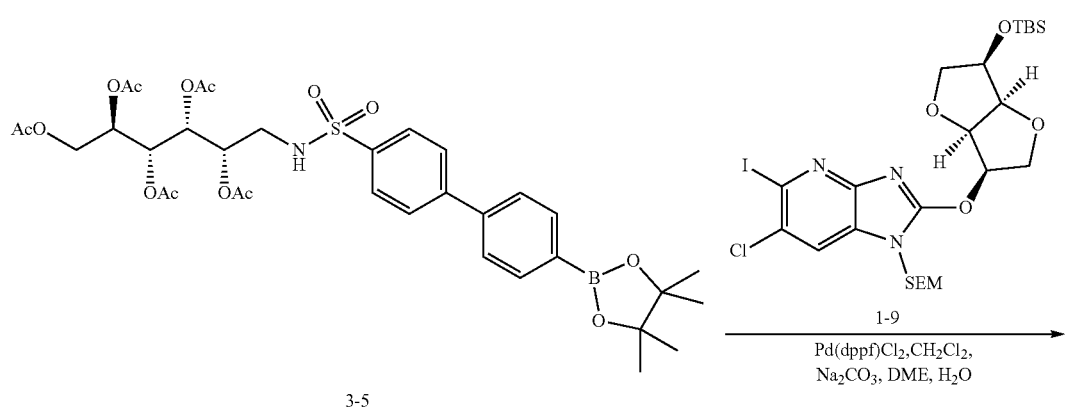
3-5
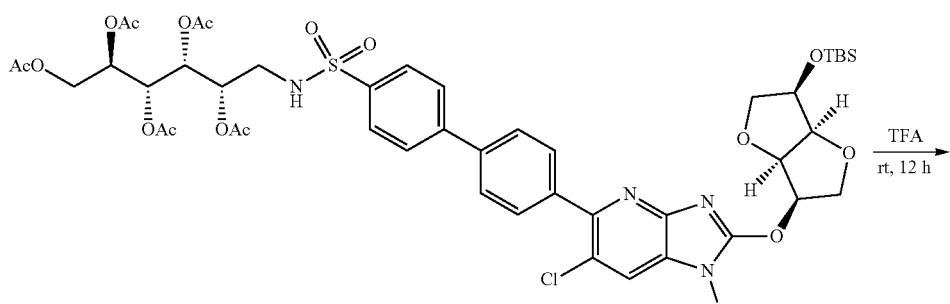
3-6
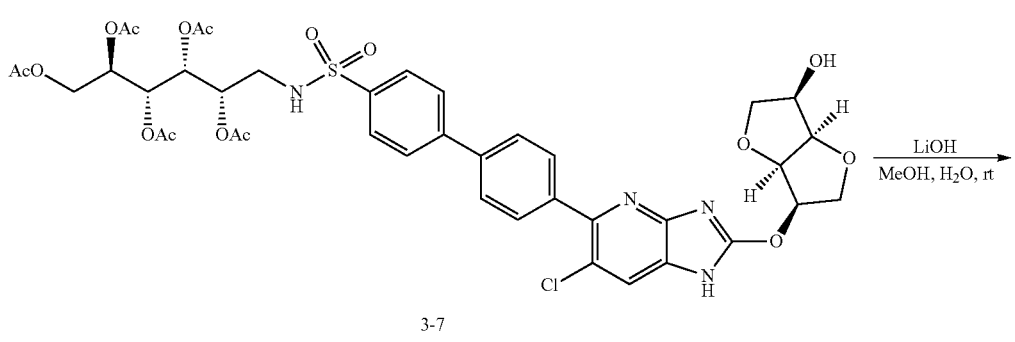
3-7

-continued

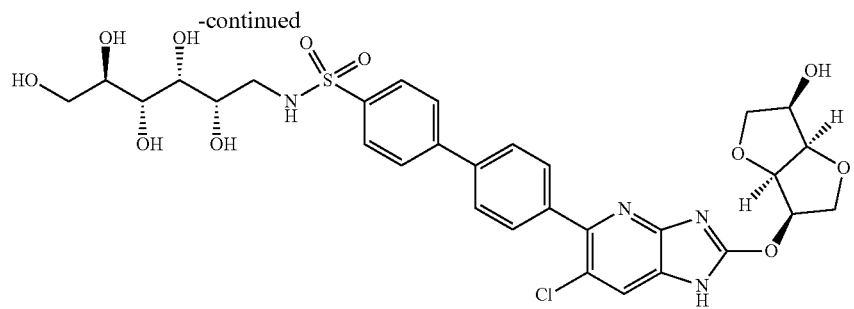

Compound 3

Step 1: (2R,3R,4R,5S)-6-aminohexane-1,2,3,4,5-pentayl pentaacetate HCl salt (3-1): To a mixture of (2R,3R,4R,5S)-6-aminohexane-1,2,3,4,5-pentol (1.0 g, 5.5 mmol, 1.0 eq) in AcOH (10 mL) was added acetyl chloride (8.7 g, 0.11 mol, 7.9 mL, 20 eq) at 0° C. under $N_2$. The mixture was stirred at 25° C. for 12 hr. The mixture was concentrated and the residue was triturated with EtOH and filtered to give 3-1 (1.7 g, 3.9 mmol, 70% yield, HCl salt) as a white solid. $^1$NMR (400 MHz, DMSO-$d_6$) δ 8.17 (br s, 3H), 5.34-5.26 (m, 2H), 5.23-5.14 (m, 1H), 5.05-4.96 (m, 1H), 4.23 (dd, J=2.8, 12.4 Hz, 1H), 4.08 (dd, J=6.4, 12.4 Hz, 1H), 3.01 (br s, 2H), 2.11 (s, 3H), 2.05 (d, J=8.4 Hz, 6H), 1.99 (d, J=4.4 Hz, 6H).

Step 2: 4'-bromo-[1,1'-biphenyl]-4-sulfonic acid (3-2): To a mixture of 1-bromo-4- phenylbenzene (3.0 g, —mmol, 1.0 eq) in CHC—(5 mL) was added sulfurochloridic acid (1.9 g, 16 mmol, 1.1 mL, 1.3 eq) under $N_2$. The mixture was stirred at 25° C. for 1 hr. The mixture was concentrated, washed with cold $CHCl_3$, and filtered to give 3-2 (4.0 g, —mmol, 99% yield) as a white solid. $^1$H NMR (400 MHz, DMSO-$d_6$) δ 7.70-7.66 (m, 2H), 7.66-7.59 (m, 6H).

Step 3: 4'-bromo-[1,1'-biphenyl]-4-sulfonyl chloride (3-3): A solution of 3-2 (4.0 g, —mmol, 1.0 eq) in $SOCl_2$ (40 mL) was stirred at 80° C. for 2 hr. The mixture was poured into ice water and filtered to give 3-3 (3.6 g, 11 mmol, 85% yield) as a white solid. $^1$H NMR (400 MHz, DMSO-$d_6$) δ 7.71-7.67 (m, 2H), 7.65-7.60 (m, 6H).

Step 4: (2R,3R,4R,5S)-6-(4'-bromo-[1,1'-biphenyl]-4-ylsulfonamido)hexane-1,2,3,4,5-pentayl pentaacetate (3-4): To a solution of 3-3 (1.2 g, 3.7 mmol, 1.0 eq) and 3-1 (1.6 g, 3.7 mmol, 1.0 eq, HCl) in DMF (20 mL) was added DIEA (1.9 g, 15 mmol, 2.6 mL, 4.0 eq), and the mixture was stirred at 25° C. for 12 hr. The mixture was poured into water and extracted with ethyl acetate (100 mL×2). The combined organic phase was washed with brine (100 mL), dried with anhydrous $Na_2SO_4$, filtered, and concentrated in vacuum. The residue was purified by column chromatography (SiO$_2$, petroleum ether : ethyl acetate=10:1 to 1:1) to give 3-4 (2.4 g, 3.5 mmol, 93% yield) as a white solid. $^1$H NMR (400 MHz, DMSO-$d_6$) δ 8.01 (s, 1H), 7.94-7.88 (m, 2H), 7.86-7.81 (m, 2H), 7.71 (s, 4H), 5.33 (br t, J=6.4 Hz, 2H), 4.97 (br d, J=6.0 Hz, 2H), 4.20 (br d, J=11.6 Hz, 1H), 4.05-3.98 (m, 1H), 2.97 (br s, 2H), 2.06 (s, 3H), 1.98 (br d, J=8.0 Hz, 12H).

Step 5: (2R,3R,4R,5S)-6-(4'-(4,4,5,5-tetramethyl-1,3,2-dioxaborolan-2-yl)-[1,1'-biphenyl]-4-ylsulfonamido) hexane-1,2,3,4,5-pentayl pentaacetate (3-5): To a solution of 3-4 (1.5 g, 2.2 mmol, 1.0 eq) and bis(pinacolato)diboron (0.67 g, 2.6 mmol, 1.2 eq) in dioxane (15 mL) was added Pd(dppf)Cl$_2$ (80 mg, 0.11 mmol, 0.050 eq) and KOAc (1.3 g, —mmol, 6.0 eq), and the mixture was stirred at 80° C. for 12 hr. The mixture was poured into water and extracted with ethyl acetate (100 mL×2). The combined organic phase was washed with brine (100 mL), dried with anhydrous $Na_2SO_4$, filtered, and concentrated in vacuum. The residue was purified by column chromatography (SiO$_2$, petroleum ether : ethyl acetate=10:1 to 1:1) to give 3-5 (1.3 g, 1.8 mmol, 81% yield) as a white solid. $^1$H NMR (400 MHz, CDCl$_3$) δ 7.93 (dd, J=5.2, 8.4 Hz, 4H), 7.76 (d, J=8.4 Hz, 2H), 7.62 (d, J=8.0 Hz, 2H), 5.49-5.41 (m, 2H), 5.11-5.00 (m, 2H), 4.94 (dd, J=5.2, 8.0 Hz, 1H), 4.29-4.21 (m, 1H), 4.18-4.08 (m, 1H), 3.39 (ddd, J=5.6, 8.4, 14.0 Hz, 1H), 3.08 (td, J=5.2, 14.0 Hz, 1H), 2.12 (s, 3H), 2.09-2.05 (m, 9H), 2.04 (s, 3H), 1.38 (s, 12H).

Step 6: (2R,3R,4R,5S)-6-(4'-(2-(((3R,3aR,6R,6aS)-6-(tert-butyldimethylsilyl)oxy)hexahydrofuro[3,2-b]furan-3-yl)oxy)-6-chloro-1-((2-(trimethylsilyl)ethoxy)methyl)-1H-imidazo[4,5-b]pyridin-5-yl)-[1,1'-biphenyl]-4-ylsulfonamido)hexane-1,2,3,4,5-pentayl pentaacetate (3-6): To a solution of 1-9 (0.3 g, 0.45 mmol, 1.0 eq) and 3-5 (0.40 g, 0.54 mmol, 1.2 eq) in DME (5.0 mL) and H$_2$O (1.0 mL) was added Na$_2$CO$_3$ (0.14 g, 1.4 mmol, 3.0 eq) and Pd(dppf) Cl$_2$·CH$_2$Cl$_2$ (73 mg, 90 μmol, 0.20 eq). The mixture was stirred at 90° C. for 1.5 hr. The mixture was filtered and concentrated. The residue was purified by column chromatography (SiO$_2$, petroleum ether : ethyl acetate=100:1 to 1:1) to give 3-6 (0.40 g, 0.35 mmol, 78% yield) as a white solid.

Step 7: (2R,3R,4R,5S)-6-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-ylsulfonamido)hexane-1,2,3,4,5-pentayl pentaacetate (3-7): A solution of 3-6 (0.40 g, 0.35 mmol, 1.0 eq) in TFA (10 mL) was stirred at 25° C. for 12 hr. The mixture was concentrated and purified by column chromatography (SiO$_2$, ethyl acetate : methanol=100:1 to 5:1) to give 3-7 (0.30 g, 0.33 mmol, 95% yield) as a white solid.

Step 8: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-((2S,3R,4R,5R)-2,3,4,5,6-pentahydroxyhexyl)-[1,1'-biphenyl]-4-sulfonamide (Compound 3): To a solution of 3-7 (0.20 g, 0.22 mmol, 1.0 eq) in MeOH (2.0 mL) and H$_2$O (1.0 mL) was added LiOH·H$_2$O (56 mg, 1.3 mmol, 6.0 eq), and the mixture was stirred at 25° C. for 3 hr. The mixture was concentrated, and the residue was purified by prep-HPLC (column: Phenomenex Luna C18 200×40 mm×10 μm; mobile phase: [A: water (0.2% FA); B: ACN]; B%: 20%-50%, 8 min) to give Compound 3 (50 mg, 32% yield, 99% purity) as a white solid. LCMS (ES$^+$): m/z (M+H)$^+$=693.2. $^1$H NMR (400 MHz, CD$_3$OD) δ 8.01-7.96 (m, 2H), 7.93-7.88 (m, 2H), 7.80 (s, 5H), 5.55 (br d, J=5.2 Hz, 1H), 4.97 (t, J=5.2 Hz, 1H), 4.47 (t, J=5.2 Hz, 1H), 4.32-4.25 (m, 1H), 4.21-4.08 (m, 2H), 3.90 (t, J=7.6 Hz, 1H), 3.87-3.74 (m, 3H), 3.71-3.65 (m, 1H), 3.64-3.57 (m, 3H), 3.16 (dd, J=4.8, 13.2 Hz, 1H), 2.97 (dd, J=7.2, 13.2 Hz, 1H).

Example 4: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)hexane-1,2,3,4,5-pentaol (Compound 4)
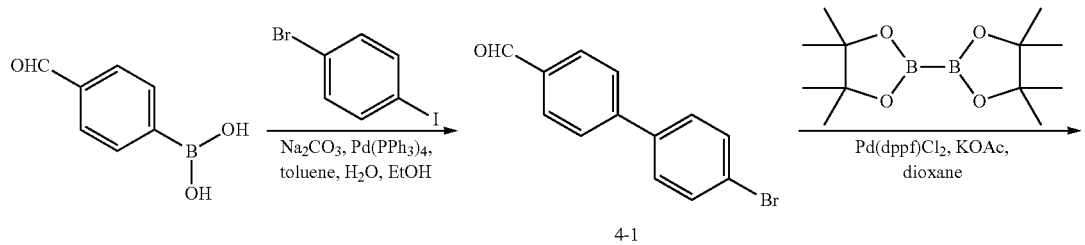
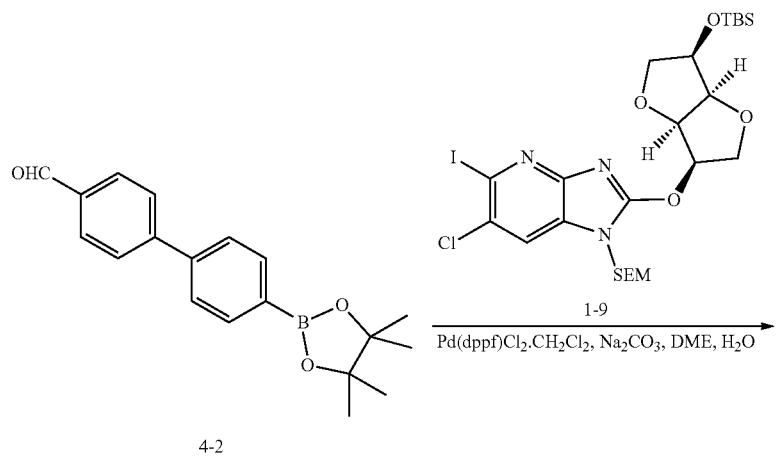
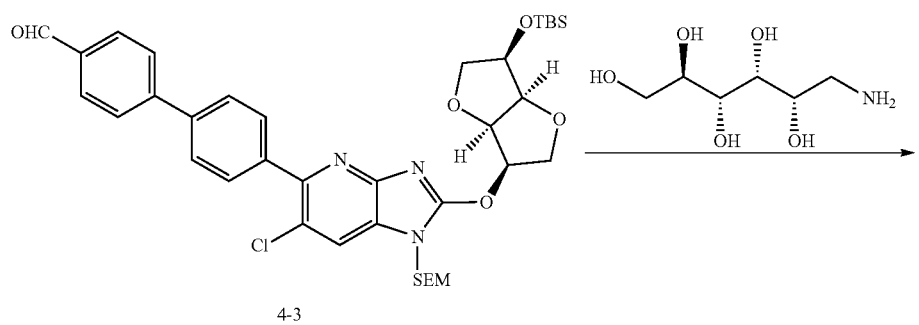
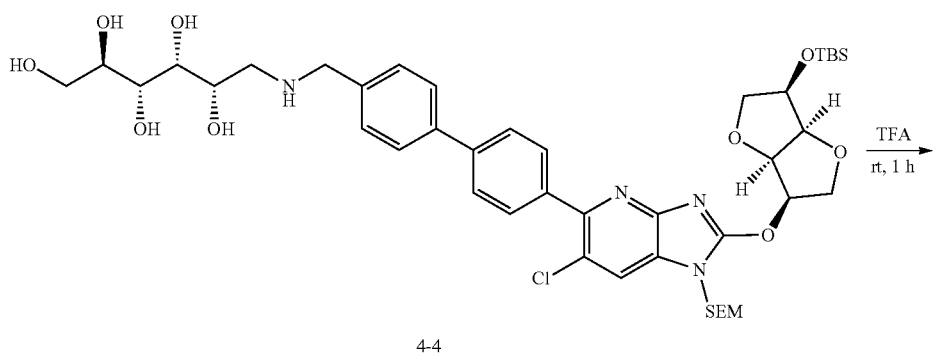

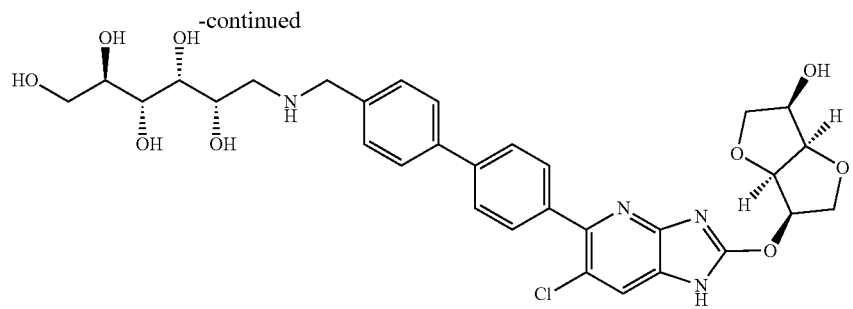

Compound 4

Step 1: 4'-bromo-[1,1'-biphenyl]-4-carbaldehyde (4-1): To a mixture of 1-bromo-4-iodo-benzene (6.0 g, 21 mmol, 1.0 eq), Pd(PPh$_3$)$_4$ (1.2 g, 1.1 mmol, 0.050 eq), and Na$_2$CO$_3$ (2.0 M, 11 mL, 1.0 eq) in toluene (60 mL) was added (4-formylphenyl)boronic acid (3.5 g, 23 mmol, 1.1 eq) in ethanol (20 mL) under Ar, and the mixture was stirred at 110° C. for 3 hours. The mixture was poured into water and extracted with ethyl acetate (100 mL×2). The combined organic phase was washed with brine (100 mL), dried with anhydrous Na$_2$SO$_4$, filtered, and concentrated in vacuum. The residue was purified by column chromatography (SiO$_2$, petroleum ether : ethyl acetate=100:1 to 10:1) to give 4-1 (3.0 g, 11 mmol, 54% yield) as a white solid. $^1$H NMR (400 MHz, CDCl$_3$) δ 10.07 (s, 1H), 7.97 (d, J=8.4 Hz, 2H), 7.73 (d, J=8.0 Hz, 2H), 7.62 (d, J=8.8 Hz, 2H), 7.54-7.49 (m, 2H).

Step 2: 4'-(4,4,5,5-tetramethyl-1,3,2-dioxaborolan-2-yl)-[1,1'-biphenyl]-4-carbaldehyde (4-2): To a solution of bis(pinacolato)diboron (1.3 g, 5.1 mmol, 1.2 eq) and 4-(4-bromophenyl)benzaldehyde 4-1 (1.1 g, 4.2 mmol, 1.0 eq) in dioxane (10 mL) was added Pd(dppf)Cl$_2$ (0.15 g, 0.21 mmol, 0.050 eq) and KOAc (2.5 g, 25 mmol, 6.0 eq), and the mixture was stirred at 80° C. for 12 hr. The mixture was poured into water and extracted with ethyl acetate (100 mL×2). The combined organic phase was washed with brine (100 mL), dried with anhydrous Na$_2$SO$_4$, filtered, and concentrated in vacuum. The residue was purified by column chromatography (SiO$_2$, petroleum ether : ethyl acetate=100:1 to 10:1) to give 4-2 (1.2 g, 3.9 mmol, 92% yield) as a white solid. $^1$H NMR (400 MHz, CDCl$_3$) δ 10.07 (s, 1H), 7.97 (br d, J=8.4 Hz, 2H), 7.93 (br d, J=8.0 Hz, 2H), 7.79 (d, J=8.4 Hz, 2H), 7.66 (d, J=8.0 Hz, 2H), 1.38 (s, 12H).

Step 3: 4'-(2-(((3R,3aR,6R,6aS)-6-(tert-butyldimethylsilyl)oxy)hexahydrofuro[3,2-b]furan-3-yl)oxy)-6-chloro-1-((2-(trimethylsilyl)ethoxy)methyl)-1H-imidazo[4,5-b]pyridin-5-yl)-[1,1'-biphenyl]-4-carbaldehyde (4-3): To a solution of 4-2 (0.28 g, 0.90 mmol, 1.2 eq) and 1-9 (0.50 g, 0.75 mmol, 1.0 eq) in DME (5.0 mL) and H$_2$O (1.0 mL) was added Na$_2$CO$_3$ (0.24 g, 2.3 mmol, 3.0 eq) and Pd(dppf)Cl$_2$·CH$_2$Cl$_2$ (0.12 g, 0.15 mmol, 0.20 eq) under N$_2$, and the mixture was stirred at 90° C. for 1.5 hr. The mixture was filtered and concentrated. The residue was purified by column chromatography (SiO$_2$, petroleum ether : ethyl acetate=100:1 to 1:1) to give 4-3 (0.42 g, 0.58 mmol, 78% yield) as a white solid. $^1$H NMR (400 MHz, CDCl$_3$) δ 10.09 (s, 1H), 7.99 (d, J=8.4 Hz, 2H), 7.94-7.85 (m, 3H), 7.83 (d, J=8.4 Hz, 2H), 7.79-7.69 (m, 2H), 5.64-5.43 (m, 3H), 4.97 (t, J=5.2 Hz, 1H), 4.43 (t, J=4.8 Hz, 1H), 4.38-4.29 (m, 1H), 4.18 (d, J=6.0 Hz, 2H), 3.90-3.82 (m, 1H), 3.80-3.72 (m, 2H), 3.67 (t, J=8.4 Hz, 1H), 1.02-0.95 (m, 2H), 0.95-0.93 (m, 9H), 0.16-0.13 (m, 6H), 0.07-0.23 (m, 9H).

Step 4: (2R,3R,4R,5S)-6-(((4'-(2-(((3R,3aR,6R,6aS)-6-(tert-butyldimethylsilyl)oxy)hexahydrofuro[3,2-b]furan-3-yl)oxy)-6-chloro-1-(2-(trimethylsilyl)ethoxy)methyl)-1H-imidazo[4,5-b]pyridin-5-yl)-[1,1'-biphenyl]-4-yl)methyl)amino)hexane-1,2,3,4,5-pentaol (4-4): To a solution of (2R,3R,4R,5S)-6-aminohexane-1,2,3,4,5-pentol (65 mg, 0.36 mmol, 1.3 eq) in AcOH (42 mg, 0.69 mmol, 40 uL, 2.5 eq) and MeOH (2.0 mL) was added a solution of 4-3 (0.20 g, 0.28 mmol, 1.0 eq) in DCM (1.0 mL). After stirring for 1 h, NaBH3CN (35 mg, 0.55 mmol, 2.0 eq) was added, and the mixture was stirred at 25° C. for 12 hr. The mixture was concentrated and the residue triturated with water to give 4-4 (0.24 g) as a white solid.

Step 5: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)hexane-1,2,3,4,5-pentaol (Compound 4): A solution of 4-4 (0.24 g, 0.28 mmol, 1.0 eq) in TFA (5.0 mL) was stirred at 25° C. for 1 hr. The mixture was concentrated and purified by prep-HPLC (column: Phenomenex Luna C18 200×40 mm×10 μm; mobile phase: [A: water (0.2% FA); B: ACN]; B%: 10%-50%, 8 min) to give Compound 4 (60 mg, 35% yield, formic acid salt) as a white solid. LCMS (ES$^+$): m/z (M+H)$^+$=643.2. $^1$H NMR (400 MHz, CD$_3$OD) δ 8.51 (s, 1H), 7.83-7.78 (m, 1H), 7.83-7.78 (m, 2H), 7.75 (s, 4H), 7.59 (d, J=8.4 Hz, 2H), 5.54 (q, J=5.6 Hz, 1H), 4.96 (t, J=5.2 Hz, 1H), 4.46 (t, J=5.2 Hz, 1H), 4.32-4.23 (m, 3H), 4.19-4.14 (m, 1H), 4.13-4.06 (m, 2H), 3.93-3.87 (m, 1H), 3.85 (d, J=3.6 Hz, 1H), 3.77 (dd, J=2.8, 10.6 Hz, 1H), 3.72-3.56 (m, 4H), 3.22-3.17 (m, 2H).

Example 5: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-ylcarboxamido)ethanesulfonic acid (Compound 5)

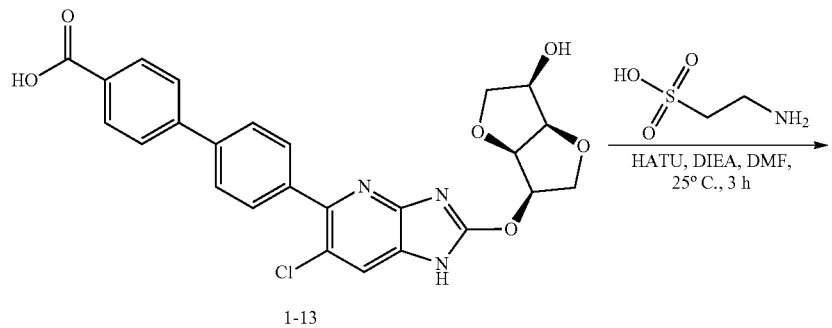

1-13

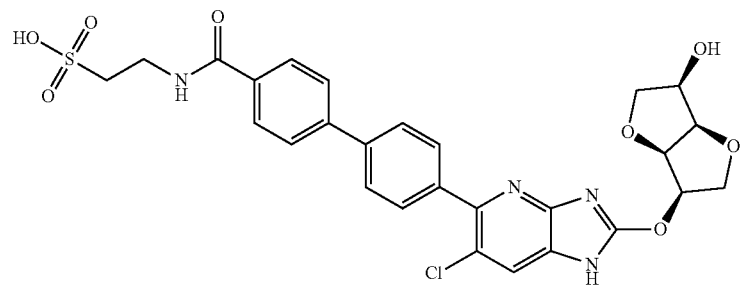

Compound 5

Step 1: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-ylcarboxamido)ethanesulfonic acid (Compound 5): To a solution of 1—(30 mg, 60 umol, 1 eq) in DMF (1 mL) was added 2-aminoethanesulfonic acid (8.4 mg, 67 umol, 8.4 uL, 1.1 eq), HATU (35 mg, 91 umol, 1.5 eq) and DIPEA (16 mg, 121 umol, 21 uL, 2 eq), and the reaction was stirred at 25° C. for 3 hours. The reaction mixture was filtered. The filter cake was purified by prep-HPLC (column: Phenomenex Gemini-NX C18 75×30 mm×3 um; mobile phase: [A: water (0.225% FA); B: ACN]; B%: 20%-50%, 7 min) and lyophilized to give Compound 5 (38 mg, 58 umol, 96% yield, 98.11% purity, FA salt) as a yellow oil. LCMS (ES$^+$) m/z (M+H)$^+$=601.0; HPLC: Rt=1.718 min, 98.11% purity. $^1$H NMR (400 MHz, DMSO-d$_6$) δ 8.59 (t, J=5.2 Hz, 1H), 7.95 (s, 1H), 7.90 (s, 2H), 7.87-7.82 (m, 4H), 7.79 -7.75 (m, 2H), 5.54-5.45 (m, 1H), 4.84 (t, J=5.2 Hz, 1H), 4.36 (t, J=4.8 Hz, 1H), 4.17-4.10 (m, 2H), 3.95-3.88 (m, 2H), 3.81-3.77 (m, 2H), 3.582-3.534 (m, 2H), 3.45 (br d, J=8.8 Hz, 2H), 2.71 (t, J=7.2 Hz, 2H).

Example 6: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propane-1-sulfonic acid (Compound 6)

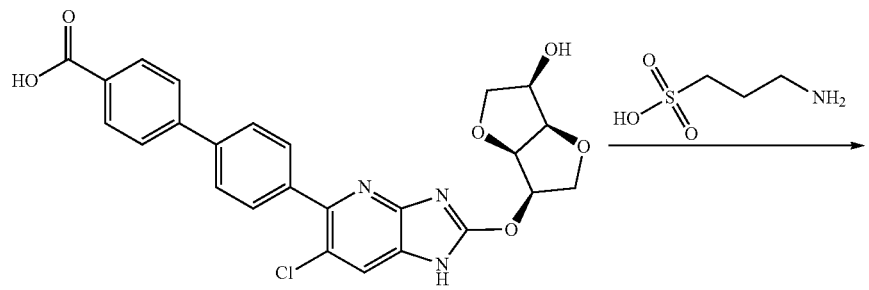

1-13

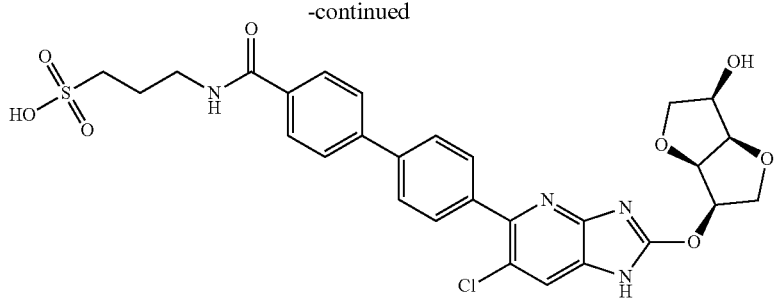

Compound 6

Compound 6 is synthesized using methods analogous to those described in Example 5. LCMS (ES+) m/z (M+H)+= 615.1; 1H NMR (400 MHz, DMSO-d6) δ 8.77-8.68 (m, 1H), 7.96 (s, 3H), 7.88-7.80 (m, 4H), 7.78 (s, 2H), 5.52-5.45 (m, 1H), 4.84 (t, J=5.2 Hz, 1H), 4.36 (t, J=4.8 Hz, 1H), 4.19-4.08 (m, 2H), 3.96-3.88 (m, 1H), 3.79 (t, J=7.2 Hz, 1H), 3.46-3.42 (m, 3H), 3.370-3.339 (m, 3H), 2.56-2.52 (m, 2H), 1.90-1.82 (m, 2H).

Example 7: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)-2-(4-chlorophenyl)propane-1-sulfonic acid (Compound 7)

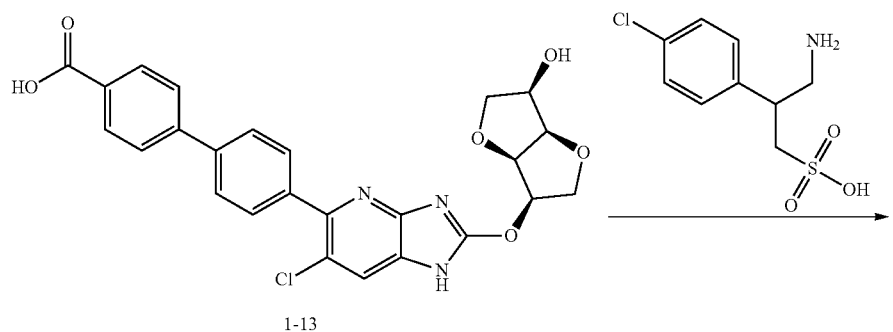

1-13

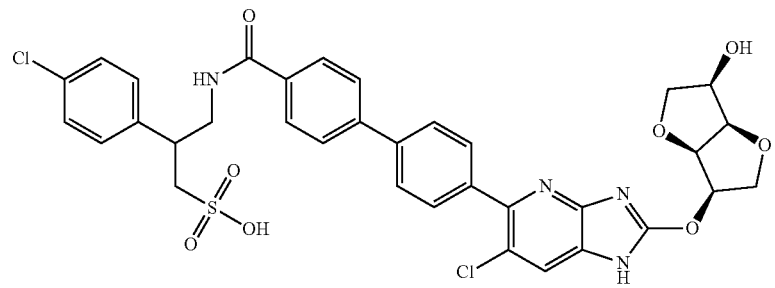

Compound 7

Compound 7 is synthesized using methods analogous to those described in Example 5. LCMS (ES−) m/z (M-H)−= 723.0; 1H NMR (400 MHz, DMSO-d6) δ 9.00-8.93 (m, 1H), 7.97-7.87 (m, 3H), 7.85-7.79 (m, 4H), 7.78-7.73 (m, 2H), 7.34-7.26 (m, 4H), 5.53-5.44 (m, 1H), 4.84 (t, J=5.2 Hz, 1H), 4.36 (t, J=4.8 Hz, 1H), 4.18-4.09 (m, 2H), 3.96-3.89 (m, 1H), 3.79 (t, J=7.2 Hz, 1H), 3.70-3.52 (m, 3H), 3.46-3.41 (m, 4H), 3.11-2.99 (m, 1H), 2.79-2.70 (m, 1H).

Example 8: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-methyl-[1,1'-biphenyl]4-carboxamido)ethane-1-sulfonic acid (Compound 8)

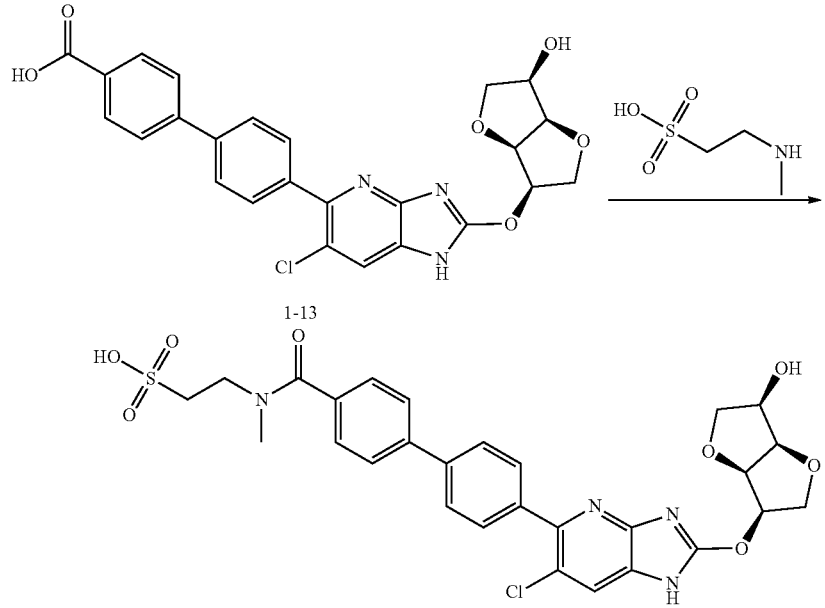

Compound 8

Compound 8 is synthesized using methods analogous to those described in Example 5. LCMS (ES$^+$) m/z (M+H)$^+$= 615.3. $^1$H NMR (400 MHz, DMSO-d$_6$) δ 7.94 (s, 1H), 7.84-7.74 (m, 6H), 7.51 (s, 2H), 5.48 (q, J=6.0 Hz, 1H), 4.99 (d, J=2.8 Hz, 1H), 4.84 (t, J=5.2 Hz, 1H), 4.36 (t, J=4.8 Hz, 1H), 4.12 (dd, J$_1$=9.6 Hz, J$_2$=6.0 Hz, 2H), 3.91 (dd, J$_1$=9.6 Hz, J$_2$=6.0 Hz, 1H), 3.79 (t, J=7.2 Hz, 1H), 3.74-3.60 (m, 1H), 3.53 (d, J=8.8 Hz, 1H), 3.46-3.40 (m, 1H), 2.96 (s, 3H), 2.82 -2.68 (m, 2H).

Example 9: 2-(N-(2-amino-2-oxoethyl)-4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethane-1-sulfonic acid (Compound 9)

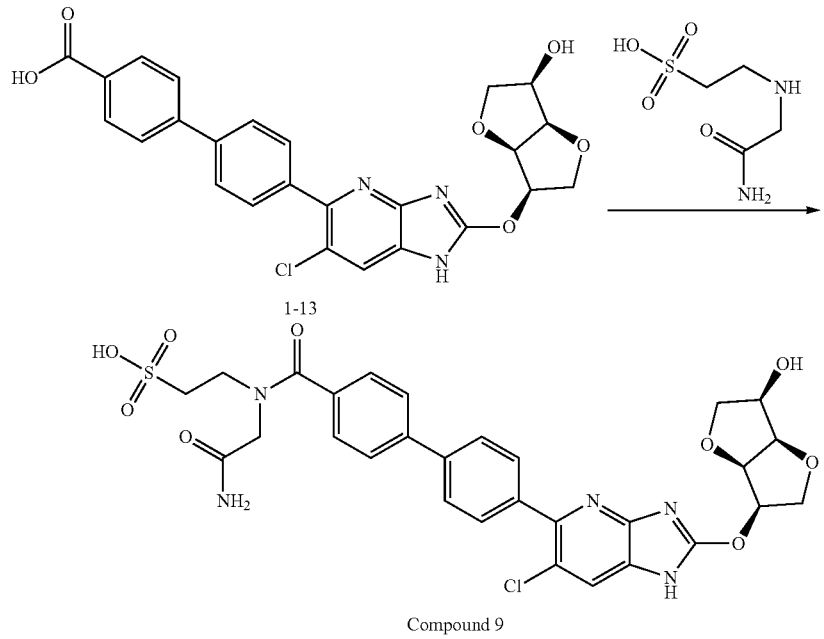

Compound 9

Compound 9 is synthesized using methods analogous to those described in Example 5. LCMS (ES$^+$) m/z (M+H)$^+$= 679.4. $^1$H NMR (400 MHz, CD$_3$OD) δ 7.90 (br s, 1H), 7.76 (br s, 6H), 7.65 (br d, J=7.2 Hz, 1H), 7.57 (br d, J=7.6 Hz, 1H), 5.60-5.53 (m, 1H), 4.97 (t, J=5.2 Hz, 1H), 4.47 (t, J=4.8 Hz, 1H), 4.32-4.22 (m, 2H), 4.20-4.08 (m, 3H), 3.96-3.81 (m, 3H), 3.60 (t, J=8.4 Hz, 1H), 3.26 (br t, J=6.0 Hz, 1H), 3.19-3.04 (m, 1H).

Example 10: 5-((2'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)amino)naphthalene-1-sulfonic acid (Compound 10)

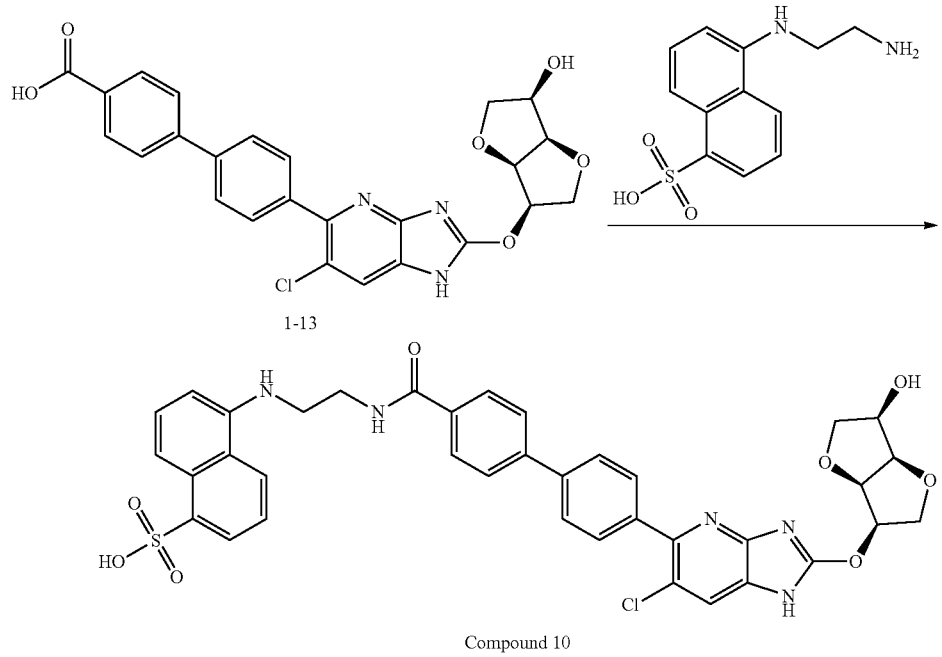

Compound 10

Compound 10 is synthesized using methods analogous to those described in Example 5. LCMS (ES$^+$) m/z (M+H)$^+$= 742.3. $^1$H NMR (400 MHz, CD$_3$OD) δ 8.24-8.11 (m, 3H), 7.98-7.91 (m, 2H), 7.83-7.74 (m, 7H), 7.42 (t, J=8.0 Hz, 2H), 6.82-6.73 (m, 1H), 5.58-5.49 (m, 1H), 4.96 (br t, J=4.8 Hz, 1H), 4.49-4.43 (m, 1H), 4.31-4.24 (m, 1H), 4.20-4.13 (m, 1H), 4.13-4.07 (m, 1H), 3.90 (t, J=7.6 Hz, 1H), 3.83-3.76 (m, 2H), 3.63-3.52 (m, 3H).

Example 11: 4-(2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)benzenesulfonic acid (Compound 11)

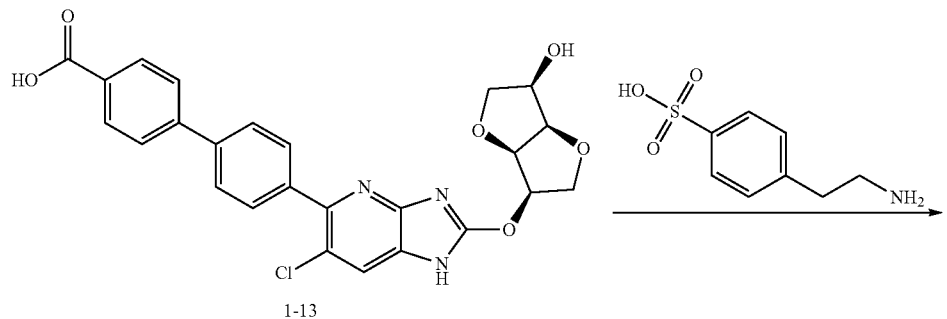

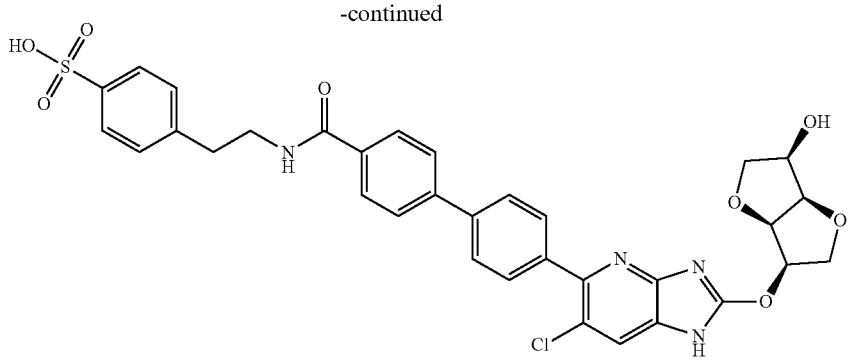
Compound 11
Compound 11 is synthesized using methods analogous to those described in Example 5. LCMS (ES$^+$) m/z (M+H)$^+$= 677.0. $^1$H NMR (400 MHz, CD$_3$OD) δ 7.91-7.85 (m, 2H), 7.84 (s, 1H), 7.81-7.74 (m, 8H), 7.35 (d, J=8.4 Hz, 2H), 5.58-5.51 (m, 1H), 4.97 (t, J=5.2 Hz, 1H), 4.47 (t, J=5.2 Hz, 1H), 4.32-4.25 (m, 1H), 4.20-4.14 (m, 1H), 4.14-4.08 (m, 1H), 3.94-3.87 (m, 1H), 3.69-3.57 (m, 3H), 3.00 (t, J=7.2 Hz, 2H).
Example 12: (4'-(6-chloro-2-(((3R,5S,6R)-5-hydroxy-6-(hydroxymethyl)tetrahydro-2H-pyran-3-yl)oxy)-1H-imidazo[4,5b]pyridin-5-yl)-[1,1'-biphenyl]-4-yl)phosphonic acid (Compound 12)
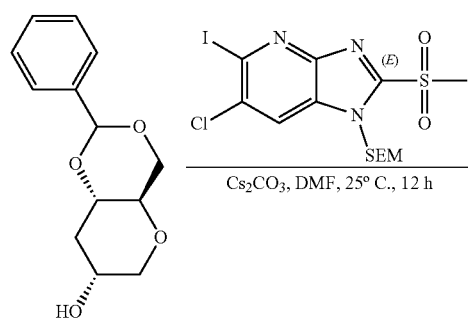
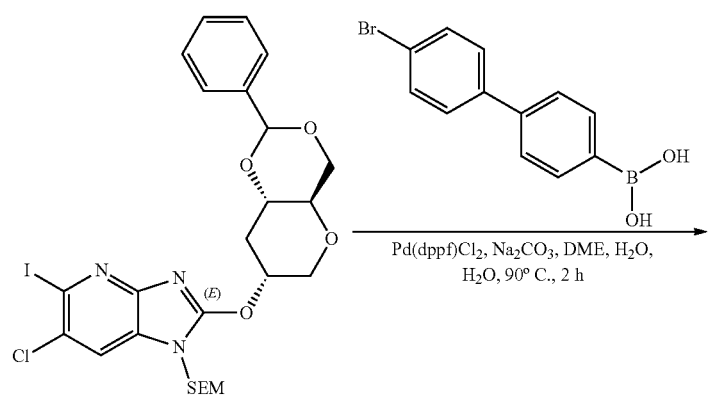
12-1

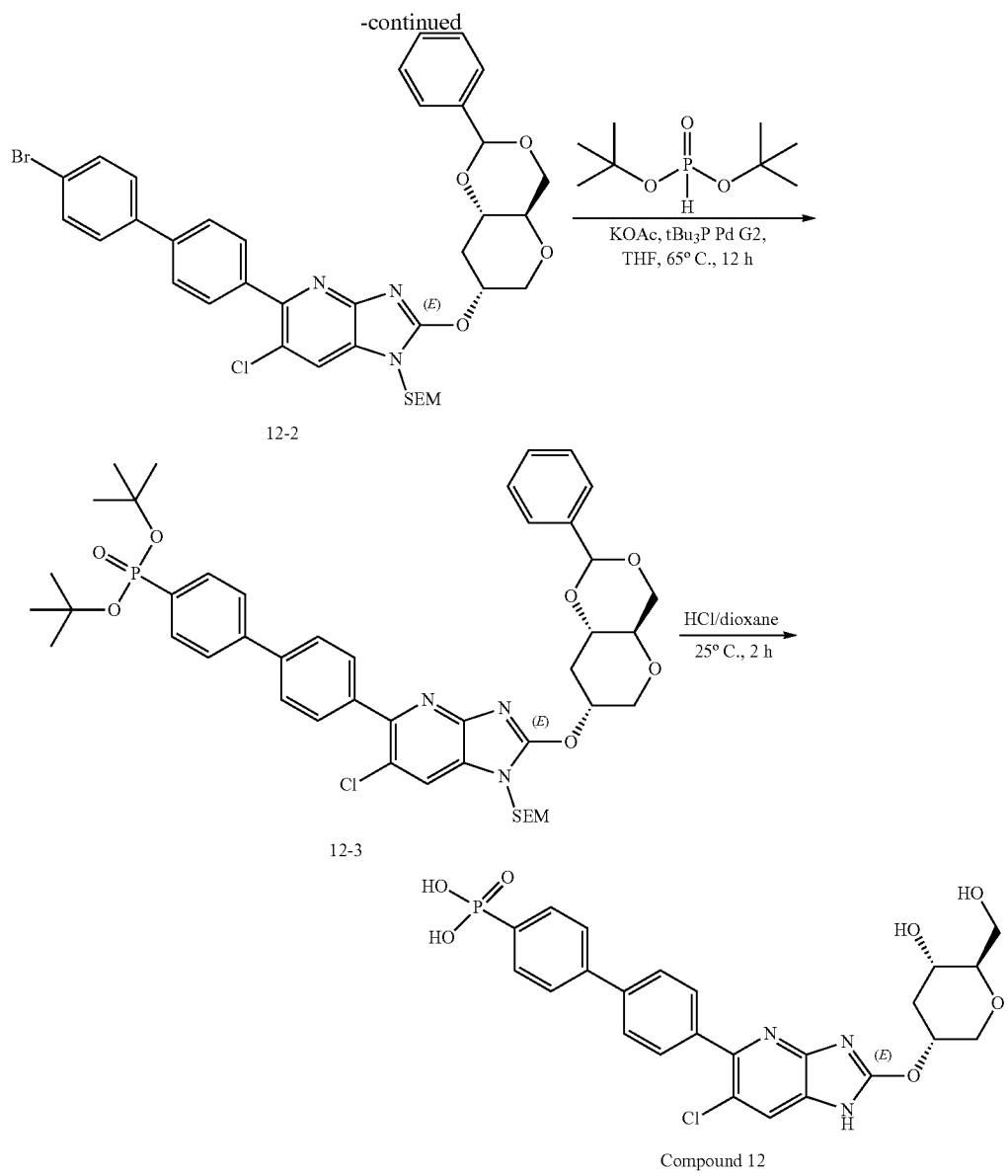

Step 1: 6-chloro-5-iodo-2-(((4aR,7R,8aS)-2-phenylhexahydropyrano[3,2-d][1,3]dioxin-7-yl)oxy)-1-(2-(trimethylsilyl)ethoxy)methyl)-1H-imidazo[4,5-b]pyridine (12-1): To a solution of 2-[(6-chloro-5-iodo-2-methylsulfonyl-imidazo[4,5-b]pyridin-1-yl)methoxy]ethyl-trimethyl-silane (1.8 g, 3.69 mmol, 1 eq) and (4aR,7R,8aS)-2-phenyl-4,4a,6,7,8,8a-hexahydropyrano[3,2-d][1,3]dioxin-7-ol (1.05 g, 4.4 mmol, 1.2 eq) in DMF (18 mL) was added $Cs_2CO_3$ (2.4 g, 7.4 mmol, 2 eq). The mixture was stirred at 25° C. for 12 hours. The reaction mixture was partitioned between EA (100 mL) and water (10 mL). The organic phase was separated, washed with brine (25 mL×2), dried over $Na_2SO_4$, filtered and concentrated under reduced pressure to give a residue. The residue was purified by column chromatography ($SiO_2$, Petroleum ether/Ethyl acetate, 100/1 to 10/1 gradient) to give 12-1 (1.8 g, 76% yield) as a yellow solid. LCMS (ES+) m/z $(M+H)^+$=644.0.

Step 2: 5-(4'-bromo-[1,1'-biphenyl]-4-yl)-6-chloro-2-(((4aR,7R,8aS)-2-phenylhexahydropyrano[3,2-d][1,3]dioxin-7-yl)oxy)-1-((2-(trimethylsilyl)ethoxy)methyl)-1H-imidazo[4,5-b]pyridine (12-2): To a solution of 12-1 (100 mg, 155 umol, 1 eq) and [4-(4-bromophenyl)phenyl]boronic acid (47 mg, 171 umol, 1.1 eq) in DME (1.6 mL) and $H_2O$ (0.4 mL) was added $Pd(dppf)Cl_2$ (6 mg, 7.8 umol, 0.05 eq) and $Na_2CO_3$ (33 mg, 311 umol, 2 eq). The mixture was stirred at 90° C. for 2 hours. The mixture was poured into 10 mL of $H_2O$ and extracted with EA (10 mL×3). The combined organic layer was washed with water (10 mL×2) and brine (10 mL×2), dried over $Na_2SO_4$ and concentrated in vacuo. The residue was purified by flash silica gel chromatography (ISCO®; 4 g SepaFlash® Silica Flash Column, Eluent of 0% to 10% MeOH/DCM @ 20 mL/min) to give 12-2 (80 mg, 63% yield, 92% purity) as a yellow solid. LCMS (ES+) m/z $(M+H)^+$=750.0. $^1$H NMR (400 MHz, $CDCl_3$) δ 7.88 (s, 1H), 7.85-7.81 (m, 2H), 7.67-7.63 (m, 2H), 7.62-7.58 (m, 2H), 7.55-7.49 (m, 4H), 7.42-7.36 (m, 3H), 5.59 (s, 1H), 5.49 (s, 2H), 5.46-5.38 (m, 1H), 4.48-4.33 (m, 2H), 3.79-3.67 (m, 4H), 3.57-3.49 (m, 1H), 3.47-3.38 (m, 1H), 2.97-2.85 (m, 1H), 2.03-1.91 (m, 1H), 0.99-0.91 (m, 2H), −0.01-0.08 (m, 9H).

Step 3: di-tert-butyl (4'-(6-chloro-2-(((4aR,7R,8aS)-2-phenylhexahydropyrano[3,2-d][1,3]dioxin-7-yl)oxy)-1-((2-trimethylsilyl)ethoxy)methyl)-1H-imidazo[4,5-b]pyridin-5-yl)-[1,1'-biphenyl]-4-yl)phosphonate (12-3): To a mixture of 12-2 (80 mg, 107 umol, 1 eq) and 2-tert-butoxyphosphonoyloxy-2-methyl-propane (104 mg, 534 umol, 5 eq) in THF (1 mL) was added KOAc (31 mg, 320 umol, 3 eq) and tBu₃P·Pd·G₂ (6 mg, 11 umol, 0.1 eq) in a glovebox. Then the mixture was stirred at 65° C. for 12 hours. The reaction mixture was filtered, and the filtrate was concentrated. The residue was purified by flash silica gel chromatography (ISCO®; 4 g SepaFlash® Silica Flash Column, Eluent of 0% to 50% Ethyl acetate/Petroleum ether gradient @ 12 mL/min) to give 12-3 (65 mg, 64% yield, 91% purity) as a colorless oil. LCMS (ES+) m/z (M+H)⁺=862.5.

Step 4: (4'-(6-chloro-2-(((3R,5S, 6R)-5-hydroxy-6-(hydroxymethyl)tetrahydro-2H-pyran-3-yl)oxy)-1H-imidazo[4,5-b]pyridin-5-yl)-[1,1'-biphenyl]-4-yl)phosphonic acid (Compound 12): A mixture of 12-3 (60 mg, 70 umol, 1 eq) in HCl/dioxane (4 M, 522 uL, 30 eq) was stirred at 25° C. for 2 hours. The mixture was concentrated in vacuo. The residue was purified by prep-HPLC (column: Phenomenex Synergi C18 150×25 mm×10 um; mobile phase: [water (0.225% FA); B: ACN]; B%: 9%-39%, 10 min) and lyophilized to give Compound 12 (8.52 mg, 22% yield, 95% purity, FA salt) as a white solid. LCMS (ES+) m/z (M+H)⁺=532.2. ¹H NMR (400 MHz, CD₃OD) δ 7.97-7.89 (m, 2H), 7.84 (s, 1H), 7.82-7.74 (m, 6H), 5.21-5.09 (m, 1H), 4.41-4.33 (m, 1H), 3.94-3.88 (m, 1H), 3.71-3.60 (m, 2H), 3.42-3.36 (m, 1H), 3.22-3.14 (m, 1H), 2.83-2.73 (m, 1H), 1.80-1.65 (m, 1H).

Example 13: (3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propyl)phosphonic acid (Compound 14)

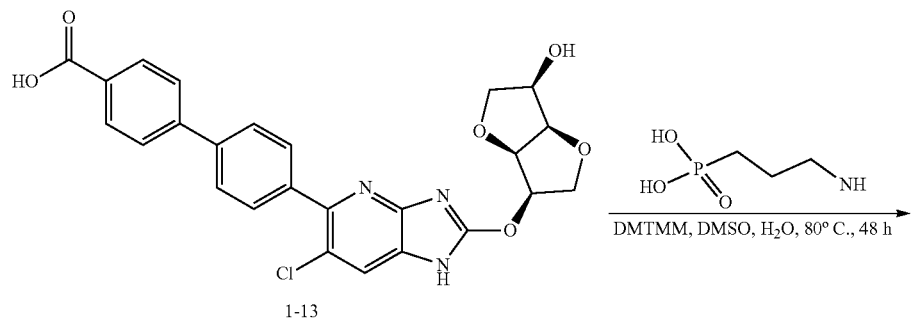

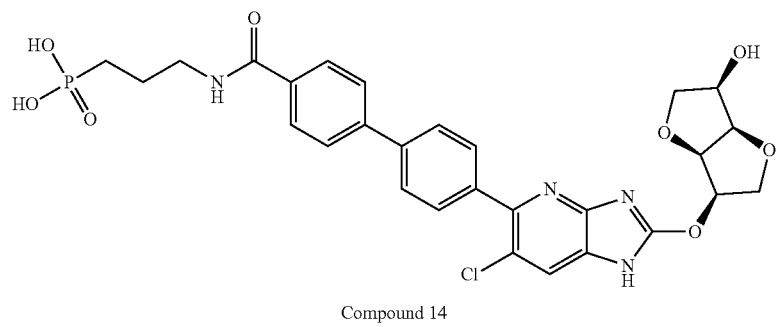

Compound 14

To a solution of 1-—(0.10 g, 0.2 mmol) in H₂O (2 mL) and DMSO (2 mL) was added (3-aminopropyl)phosphonic acid (56 mg, 0.41 mmol) and DMTMM (0.17 g, 0.61 mmol). The mixture was stirred at 80° C. for 48 hours. The reaction mixture was purified by prep-HPLC (column: Phenomenex Synergi C18 150×25 mm×10 um; mobile phase: [A: water (0.225% FA), B: ACN]; B%: 25%-55%) and further purified by prep-HPLC (column: 3_Phenomenex Luna C18 75×30 mm×3 um; mobile phase: [A: water (0.05% HCl), B: ACN]; B%: 19%-39%) to give Compound 14 (5.5 mg, 4% yield) as a white solid. LCMS: (ES+) m/z (M+H)+=615.2. ¹H NMR (400 MHz, CD₃OD) δ=8.15 (s, 1H), 7.96 (d, J=8.4 Hz, 2H), 7.89-7.83 (m, 3H), 7.83-7.75 (m, 3H), 5.62 (q, J=5.2 Hz, 1H), 4.98 (t, J=5.4 Hz, 1H), 4.47 (t, J=5.0 Hz, 1H), 4.34-4.24 (m, 1H), 4.22-4.09 (m, 2H), 3.93-3.85 (m, 1H), 3.59 (t, J=8.6 Hz, 1H), 3.50 (t, J=6.8 Hz, 2H), 2.02-1.89 (m, 2H), 1.87-1.74 (m, 2H).

Example 14: 2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)-N,N,N-trimethylethan-1-aminium bicarbonate (Compound 29)

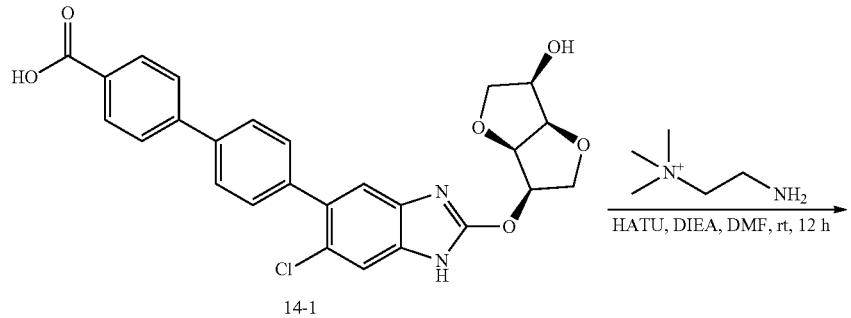

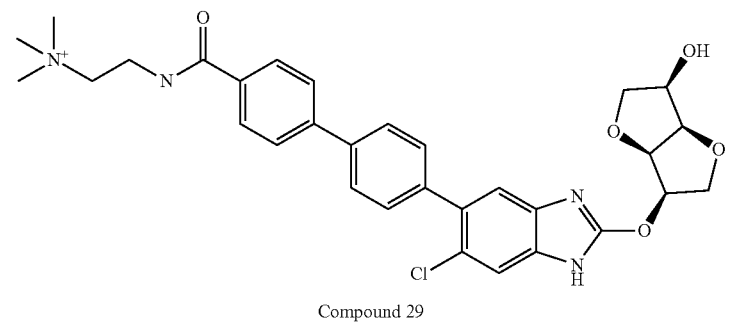

Compound 29

14-1 was synthesized using methods analogous to those described in Example 1, for Compound 1-13. LCMS: (ES+) m/z (M+H)+=493.2.; ¹H NMR (400 MHz, DMSO-d₆) δ 12.32 (s, 1H), 8.04 (d, J=8.4 Hz, 2H), 7.86 (d, J=8.4 Hz, 2H), 7.81 (d, J=8.4 Hz, 2H), 7.55 (d, J=8.4 Hz, 2H), 7.45-7.29 (m, 2H), 5.44 (q, J=6.0 Hz, 1H), 4.98 (s, 1H), 4.83 (t, J=4.8 Hz, 1H), 4.36 (t, J=4.8 Hz, 1H), 4.14-4.10 (m, 2H), 3.90-3.87 (m, 1H), 3.79 (t, J=7.6 Hz, 1H), 3.44 (t, J=8.8 Hz, 1H).

To a solution of 14-1 (50 mg, 0.10 mmol, 1 eq) in DMF (1 mL) was added HATU (77 mg, 0.20 mmol, 2 eq), DIEA (26 mg, 0.20 mmol, 35uL, 2 eq) and 2-aminoethyl (trimethyl)ammonium chloride hydrochloride (36 mg, 0.20 mmol, 2 eq). The mixture was stirred at 25° C. for 12 hours. The reaction mixture was purified by prep-HPLC (column: Phenomenex Gemini-NX C18 75×30 mm×3 um; mobile phase: [A: water (10 mMNH₄HCO₃), B: ACN]; B%: 12%-42%) to give Compound 29 (bicarbonate salt, 21 mg, 34% yield) as a white solid. LCMS: (ES+) m/z (M)+=577.2. ¹H-NMR (400 MHz, CD₃OD) δ=7.95 (d, J=8.4 Hz, 2H), 7.83 (d, J=8.4 Hz, 2H), 7.74 (d, J=8.4 Hz, 2H), 7.54 (d, J=8.4 Hz, 2H), 7.46 (s, 1H), 7.32 (s, 1H), 5.50-5.40 (m, 1H), 4.96-4.93 (m, 3H), 4.47 (t, J=4.8 Hz, 1H), 4.33-4.25 (m, 1H), 4.20-4.13 (m, 1H), 4.10-7.05 (m, 1H), 3.91 (s, 3H), 3.64-3.58 (m, 3H), 3.26 (s, 9H).

Example 15: 4'-(6-chloro-2-(((3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1,1'-biphenyl]-4-carboxamide (Compound 30)

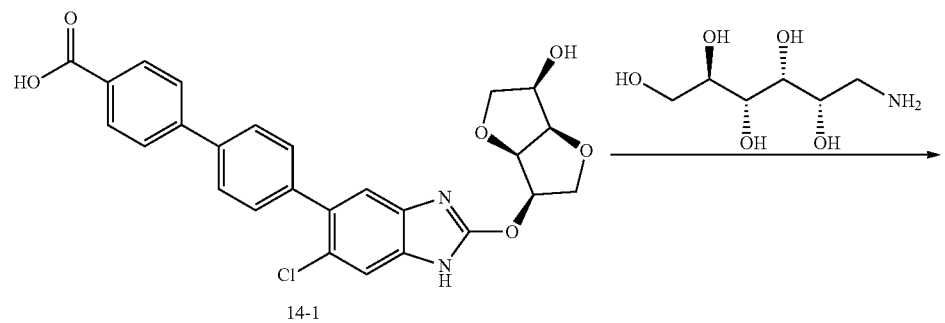

-continued

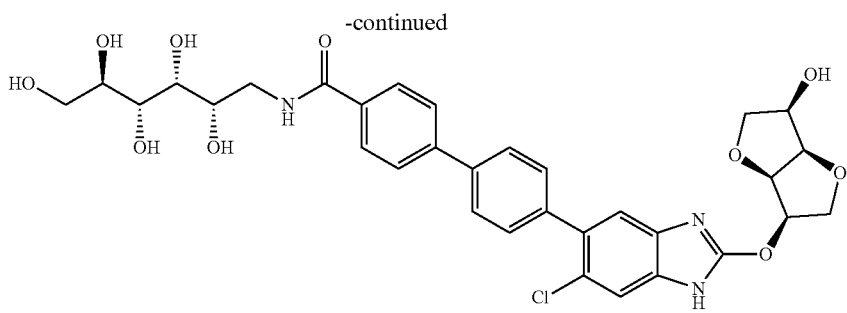

Compound 29

Compound 30 is synthesized using methods analogous to those described in Example 14. LCMS: (ES+) m/z (M+H)+= 656.1. $^1$H NMR (400 MHz, CD$_3$OD) δ 7.95 (d, J=8.4 Hz, 2H), 7.80 (d, J=8.4 Hz, 2H), 7.74 (d, J=8.0 Hz, 2H), 7.54 (d, J=8.4 Hz, 2H), 7.47 (s, 1H), 7.33 (s, 1H), 5.44 (q, J=5.2 Hz, 1H), 4.95-4.93 (m, 2H), 4.47 (t, J=4.8 Hz, 1H), 4.31-4.24 (m, 1H), 4.20-4.14 (m, 1H), 4.13-4.07 (m, 1H), 4.06-3.97 (m, 1H), 3.95-3.87 (m, 1H), 3.86-3.76 (m, 2H), 3.75-3.58 (m, 5H). 3.55-3.45 (m, 1H).

Example 16: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-[1,1'-biphenyl]-4-carboxamide (Compound 31)

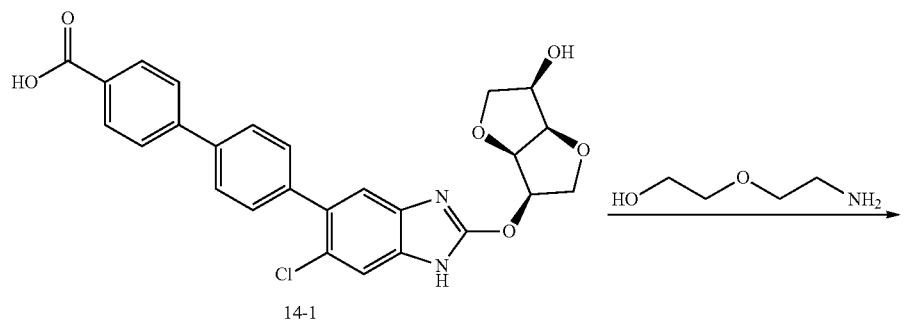

Compound 31

Compound 31 was synthesized using methods analogous to those described in Example 14. LCMS: (ES+) m/z (M)+= 580.2. $^1$H NMR (400 MHz, CD$_3$OD) δ=7.94 (d, J=8.0 Hz, 2H), 7.83-7.69 (m, 4H), 7.57-7.50 (m, 2H), 7.47 (s, 1H), 7.32 (d, J=3.2 Hz, 1H), 5.50-5.40 (m, 1H), 4.95 (t, J=5.6 Hz, H), 4.47 (t, J=5.2 Hz, 1H), 4.33-4.25 (m, 1H), 4.20-4.12 (m, 1H), 4.11-4.04 (m, 1H), 3.91 (t, J=7.5 Hz, 1H), 3.73-3.66 (m, 4H), 3.65-3.57 (m, 5H).

Example 17: 1-(2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)ethyl)-1,4-diazabicyclo[2.2.2]octan-1-ium formate (Compound 32)

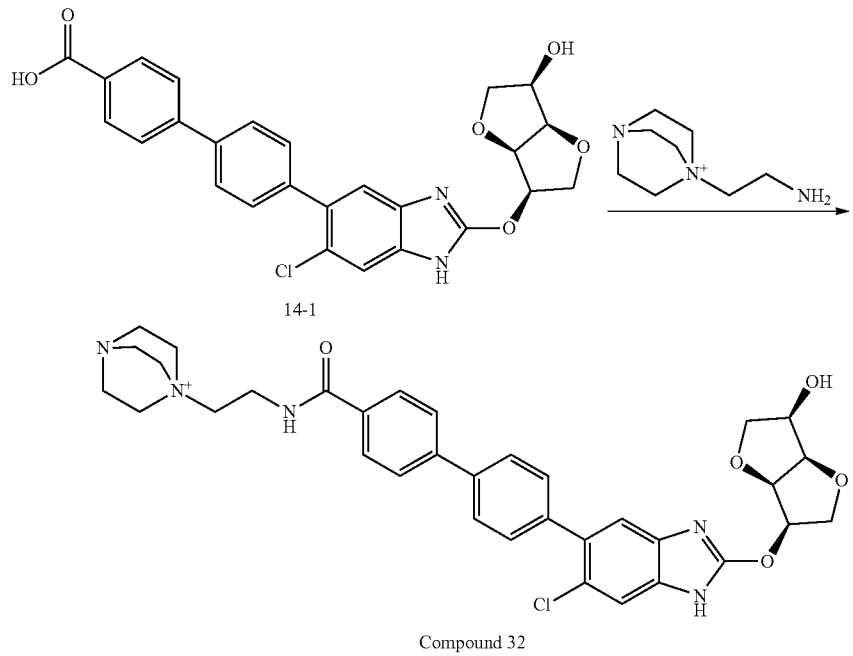

Compound 32 was synthesized as the formate salt using methods analogous to those described in Example 14. LCMS: (ES+) m/z (M+H)+=719.4. $^1$H NMR (400 MHz, DMSO-$d_6$) δ=8.98 (br s, 1H), 8.24 (d, J=8.4 Hz, 2H), 7.89 (d, J=8.4 Hz, 2H), 7.87-7.77 (m, 5H), 5.51 (q, J=6.3 Hz, 1H), 4.85 (t, J=5.0 Hz, 1H), 4.53 (s, 2H), 4.42 (t, J=4.9 Hz, 1H), 4.24-4.15 (m, 2H), 3.93 (dd, J=6.4, 9.4 Hz, 1H), 3.86-3.74 (m, 6H), 3.51 (t, J=8.4 Hz, 1H), 3.36 (br s, 4H), 2.78-2.70 (m, 3H), 2.18-2.05 (m, 2H).

Example 18: 1-(3-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)propyl)-1,4-diazabicyclo[2.2.2]octan-1-ium trifluoroacetate (Compound 33)

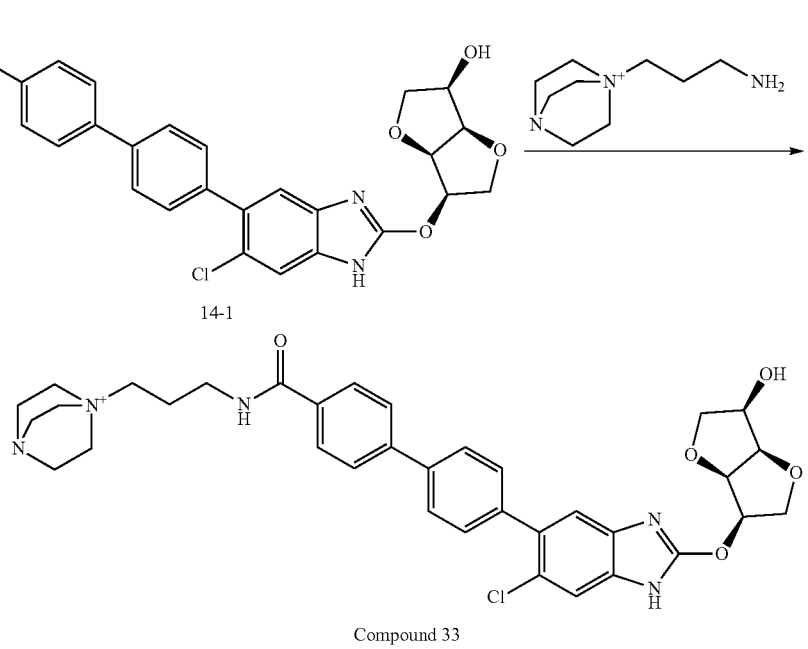

Compound 33 was synthesized as the trifluoroacetate salt using methods analogous to those described in Example 14. LCMS: (ES+) m/z (M+H)+=644.3. 1H NMR (400 MHz, CD₃OD) δ 7.96 (d, J=8.4 Hz, 2H), 7.82 (d, J=8.4 Hz, 2H), 7.76 (d, J=8.0 Hz, 2H), 7.57-7.51 (m, 3H), 7.39 (s, 1H), 5.51-5.43 (m, 1H), 4.98 (t, J=5.2 Hz, 1H), 4.47 (t, J=4.8 Hz, 1H), 4.32-4.24 (m, 1H), 4.15 (m, 2H), 3.95-3.85 (m, 1H), 3.59 (t, J=8.4 Hz, 1H), 3.55-3.50 (m, 2H), 3.49-3.42 (m, 6H), 3.42-3.36 (m, 2H), 3.30-3.23 (m, 6H), 2.20-2.07 (m, 2H).

Example 20: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-carboxamide (Compound 48)

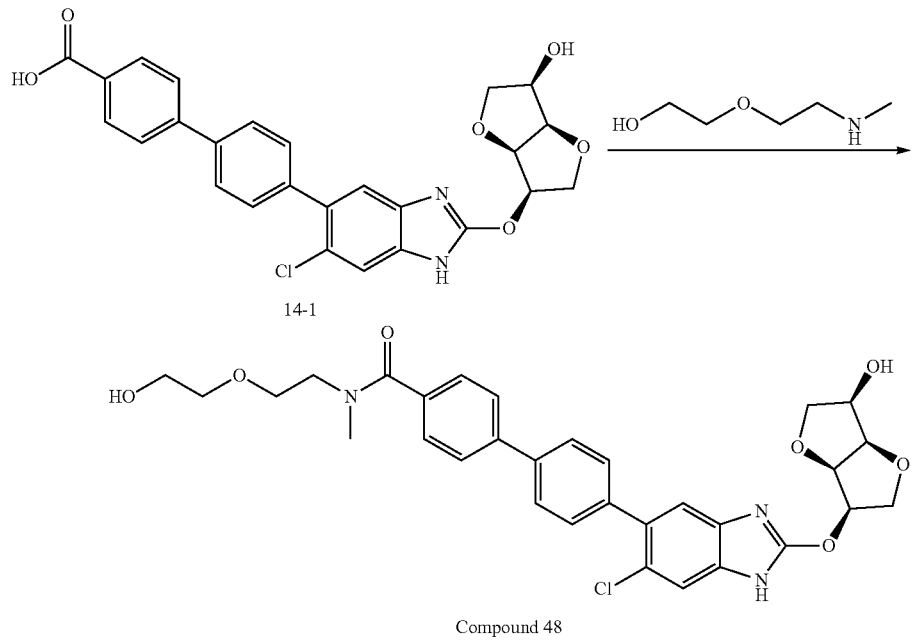

Compound 48 was synthesized using methods analogous to those described in Example 14. LCMS: (ES+) m/z (M)+= 594.5. ¹H NMR (400 MHz, CD₃OD) δ=7.82-7.69 (m, 4H), 7.60-7.51 (m, 4H), 7.49 (s, 1H), 7.34 (s, 1H), 5.46 (q, J=5.4 Hz, 1H), 4.96 (t, J=5.2 Hz, 1H), 4.47 (t, J=5.0 Hz, 1H), 4.32-4.25 (m, 1H), 4.13 (qd, J=10.2, 5.2 Hz, 2H), 3.91 (dd, J=8.2, 6.8 Hz, 1H), 3.79 (br s, 2H), 3.74-3.55 (m, 6H), 3.50 (br s, 1H), 3.14 (br d, J=6.88 Hz, 3H).

Example 21: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carbaldehyde (Intermediate 21-1)

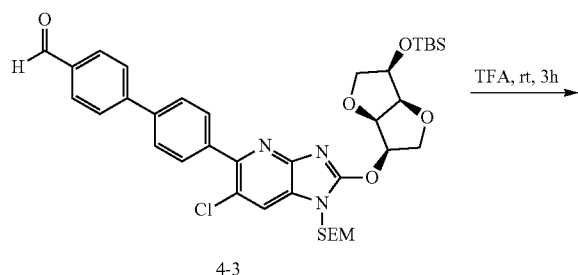

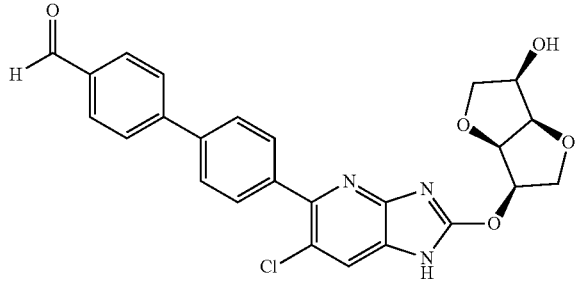

Step 1: A solution of 4-3 (2.3 g, 3.2 mmol, 1 eq) in TFA (23 mL) was stirred at 25° C. for 3 hrs. The mixture was concentrated in vacuo to give a residue. The residue was purified by prep- HPLC (column: Phenomenex luna C18 150×40 mm×15 um; mobile phase: [water (0.225% FA)-ACN]; B%: 30%-60%, 11 min) to give intermediate 21-1 (0.84 g, 50% yield) as a white solid. LCMS: (ES+) m/z (M+H)+=478.0. ¹H NMR (400 MHz, DMSO-d₆) δ 10.08 (s, 1H), 8.05-7.86 (m, 7H), 7.81-7.79 (m, 2H), 5.51-5.46 (m, 1H), 4.99 (d, J=6.8 Hz, 1H), 4.84 (t, J=4.8 Hz, 1H), 4.36 (t, J=4.8 Hz, 1H), 4.18-4.09 (m, 2H), 3.94-3.90 (m, 1H), 3.81-3.77 (m, 1H), 3.44 (t, J=4.4 Hz, 1H).

Example 22: 3-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-hydroxypropanoic acid (Compound 22)

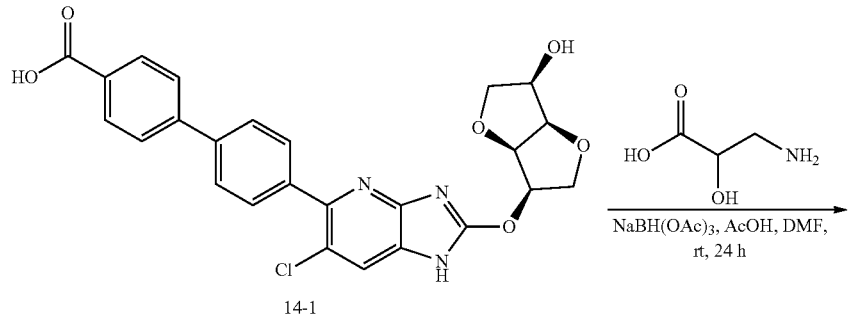

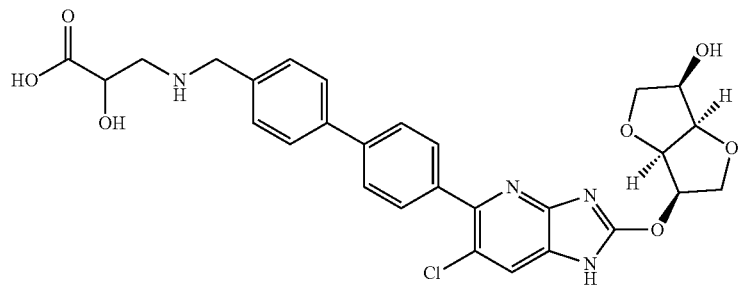

Compound 22

Step 1: To a solution of 21-1 (50 mg, 0.11 mmol) and 3-amino-2-hydroxypropanoic acid (14 mg, 0.14 mmol) in DMF (0.5 mL) was added AcOH (31 mg, 0.52 mmol). The mixture was stirred at 25° C. for 12 hrs. Then NaBH(OAc)₃ (33 mg, 0.16 mmol) was added. The mixture was stirred at 25° C. for another 12 hrs. The mixture was filter, and the organic phase was collected and then purified by prep-HPLC (column: Shim-pack C18 150×25×10 um; mobile phase: [A: water (0.225% FA), B:ACN]; B%: 16% -36%) to give Compound 22 (30 mg, 48% yield) as a white solid. LCMS: (ES+) m/z (M+H)+=567.2. ¹H NMR (400 MHz, CD₃OD) δ=8.34 (s, 1H), 7.82 (br d, J=2.4 Hz, 2H), 7.80 (s, 1H), 7.75 (s, 4H), 7.61 (br d, J=8.0 Hz, 2H), 5.55 (br d, J=5.4 Hz, 1H), 4.97 (t, J=5.0 Hz, 2H), 4.47 (t, J=4.8 Hz, 1H), 4.33-4.26 (m, 3H), 4.18-4.09 (m, 3H), 3.90 (dd, J=7.0, 8.4 Hz, 1H), 3.60 (t, J=8.6 Hz, 1H), 3.13 (dd, J=8.2, 12.4 Hz, 1H).

Example 23: (3R,3aR,6R,6aR)-6-((6-chloro-5-(4'-(piperazin-1-ylmethyl)-[1,1'-biphenyl]-4-yl)-1H-benzo[d]imidazol-2-yl)oxy)hexahydrofuro[3,2-b]furan-3-ol (Compound 49)

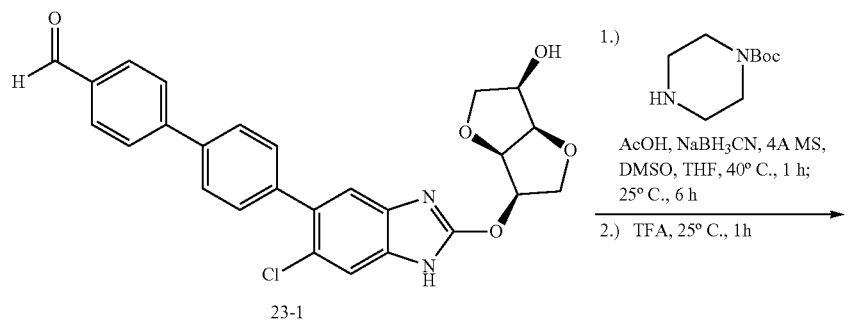

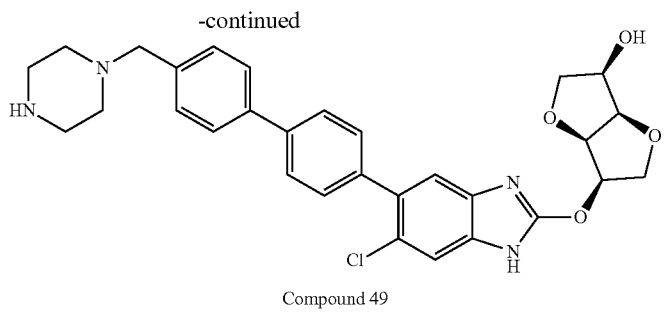

Compound 49

23-1 was synthesized using methods analogous to those described in Examples 4 and 21. LCMS: (ES+) m/z (M+H)+ =477.0. $^1$H NMR (400 MHz, DMSO-$d_6$) δ 10.07 (s, 1H), 8.04-7.98 (m, 4H), 7.86 (d, J=8.4 Hz, 2H), 7.58 (d, J=8.4 Hz, 2H), 7.45-7.32 (m, 2H), 5.44 (q, J=6.0 Hz, 1H), 4.99 (d, J=4.8 Hz, 1H), 4.83 (t, J=5.2 Hz, 1H), 4.36 (t, J=5.2 Hz, 1H), 4.14-4.10 (m, 2H), 3.90-3.87 (m, 1H), 3.79 (t, J=7.2 Hz, 1H), 3.44 (t, J=8.4 Hz, 1H).

Step 1: A mixture of 23-1 (0.30 g, 0.63 mmol), tert-butyl piperazine-1-carboxylate (0.12 g, 0.63 mmol), AcOH (0.11 g, 1.9 mmol) and 4 Å MS (0.5 g) in THF (5 mL) and DMSO (1 mL) was stirred at 40° C. for 1 hr. Then to the mixture was added NaBH(OAc)$_3$ (0.27 g, 1.3 mmol), and the mixture was stirred at 25° C. for 6 hrs. The reaction mixture was quenched by addition of saturated aqueous NH$_4$Cl (20 mL) and then extracted with THF (20 mL×3). The combined organic layers were dried over anhydrous sodium sulfate, filtered and concentrated under reduced pressure to give tert-butyl 4-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)piperazine-1-carboxylate (0.40 g, crude) as yellow solid. LCMS: (ES+) m/z (M+H)+=647.2.

Step 2: A mixture of tert-butyl 4-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)piperazine-1-carboxylate (0.40 g, 0.46 mol) and TFA (3 mL) was stirred at 25° C. for 1 hr. The reaction mixture was concentrated under vacuum to give a residue. The residue was purified by prep-HPLC (column: Phenomenex Gemini 150×25 mm×10 um; mobile phase: [A: water (0.225% FA), B: ACN]; B%: 5%-35%) to give Compound 49 (0.16 g, 60% yield) as an off-white solid. LCMS: (ES+) m/z (M+H)+=547.4. $^1$H NMR (400 MHz, CD$_3$OD) δ=8.52 (s, 1H), 7.68 (d, J=8.0 Hz, 4H), 7.57-7.39 (m, 5H), 7.32 (s, 1H), 5.45 (q, J=5.2 Hz, 1H), 4.95 (t, J=5.2 Hz, 1H), 4.47 (t, J=5.2 Hz, 1H), 4.28 (ddd, J=5.2, 6.8, 8.8 Hz, 1H), 4.20-4.13 (m, 1H), 4.11-4.03 (m, 1H), 3.91 (dd, J=6.9, 8.0 Hz, 1H), 3.67 (s, 2H), 3.61 (t, J=8.8 Hz, 1H), 3.26-3.16 (m, 4H), 2.72 (br d, J=4.4 Hz, 4H).

Example 24: (3R,3aR,6R,6aR)-6-((6-chloro-5-(4'-((2-hydroxyethoxy)methyl)azetidin-1-yl)methyl)-[1,1'-biphenyl]-4-yl)-1H-benzo[d]imidazol-2-yl)oxy)hexahydrofuro[3,2-b]furan-3-ol (Compound 50)

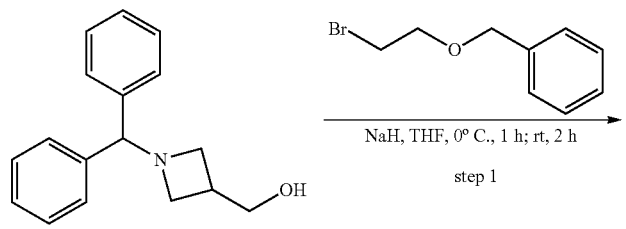

step 1

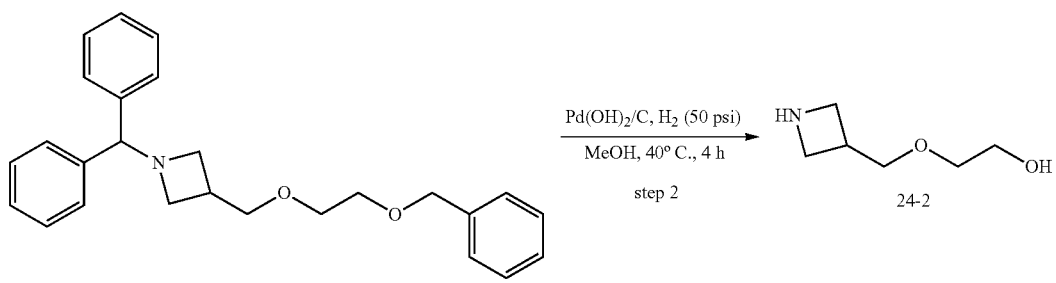

24-1

24-2

-continued

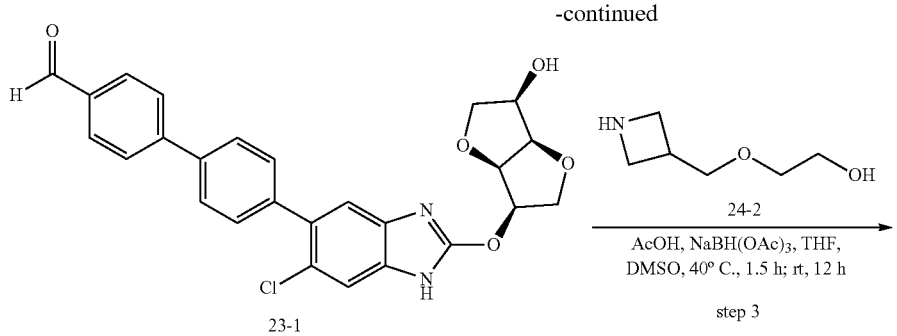

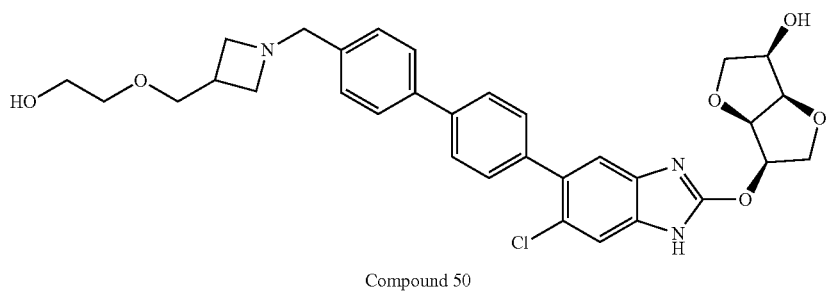

Compound 50

Step 1: To a solution of (1-benzhydrylazetidin-3-yl)methanol (2.5 g, 9.9 mmol, 1 eq) in THF (25 mL) was added NaH (0.79 g, 20 mmol, 60% purity, 2 eq) in portions at 0° C. The mixture was stirred at 0° C. for 1 hr. Then 2-bromoethoxymethylbenzene (2.4 g, 11 mmol, 1.8 mL, 1.1 eq) was added dropwise at 0° C. The mixture was stirred at 25° C. for 2 hrs. The residue was quenched by water (20 mL), then extracted with EA (50 mL×3). The combined organic layers were washed with saturated brine (30 mL×2), dried over anhydrous $Na_2SO_4$, filtered and concentrated under reduced pressure to give a residue. The residue was purified by column chromatography ($SiO_2$, Petroleum ether/Ethyl acetate=20/1 to 1/1) to give 24-1 (1.6 g, 41% yield) as a yellow oil. LCMS: (ES+) m/z (M+H)+=388.3. $^1$H NMR (400 MHz, $CDCl_3$) δ 7.35-7.30 (m. 1H), 7.33 (d, J=7.2 Hz, 3H), 7.27 (br d, J=3.24 Hz, 3H), 7.23-7.16 (m, 5H), 7.15-7.07 (m, 3H), 4.50 (s, 2H), 4.29-4.25 (m, 1H), 3.58-3.51 (m, 6H), 3.28-3.16 (m, 2H), 2.90-2.76 (m, 2H), 2.73-2.59 (m, 1H).

Step 2: To a solution of 24-1 (1.6 g, 4.1 mmol, 1 eq) in MeOH (16 mL) was added 20% Pd(OH)$_2$/C (1.0 g) under $N_2$. The suspension was degassed under vacuum and purged with H2 several times. The mixture was stirred under $H_2$ (50 psi) at 40° C. for 4 hours. The reaction mixture was filtered and concentrated under reduced pressure to give 24-2 (0.75 g, crude) as a gray oil. $^1$H NMR (400 MHz, $CD_3OD$) δ 3.72-3.65 (m, 4H), 3.62-3.58 (m, 2H), 3.57-3.51 (m, 3H), 3.49-3.42 (m, 2H), 3.01-2.85 (m, 1H).

Step 3: A mixture of 23-1 (0.45 g, 0.94 mmol, 1 eq), 24-2 (0.25 g, 1.9 mmol, 2 eq), and AcOH (0.17 g, 2.8 mmol, 3 eq) in THF (2.5 mL) and DMSO (2.5 mL) was stirred at 40° C. for 1.5 hrs. Then to the mixture was added NaBH(OAc)$_3$ (0.60 g, 2.8 mmol, 3 eq), and the mixture stirred at 25° C. for 12 hrs. The reaction mixture was quenched by addition of water (5 mL) and then purified by prep-HPLC (column: YMC Triart C18 250×50 mm×7 um; mobile phase: [A: water (10 mM $NH_4HCO_3$), B: ACN]; B%: 31%-61%) to give Compound 50 (0.17 g, 29% yield) as a white solid. LCMS: (ES+) m/z (M+H)+=592.1. $^1$H NMR (400 MHz, DMSO-d$_6$) δ 7.71 (d, J=8.0 Hz, 2H), 7.66 (d, J=8.0 Hz, 2H), 7.53-7.46 (m, 3H), 7.39-7.33 (m, 2H), 7.31-7.27 (m, 1H), 5.43 (q, J=6.0 Hz, 1H), 5.01-4.93 (m, 1H), 4.82 (t, J=4.8 Hz,1H), 4.70-4.45 (m, 1H), 4.36 (t, J=4.8 Hz, 1H), 4.13-4.11 (m, 2H), 3.89-3.87 (m, 1H), 3.79 (t, J=7.6 Hz, 1H), 3.58-3.53 (m, 4H), 3.49-3.47 (m, 2H), 3.44-3.39 (m, 4H), 3.29-3.24 (m, 4H), 2.91 (t, J=6.4 Hz, 2H), 2.63-2.57 (m, 1H).

Example 25: (3R,3aR,6R,6aR)-6-((6-chloro-5-(4'-((4-(2-hydroxyethyl)piperazin-1-yl)methyl)-[1,1'-biphenyl]-4-yl)-1H-imidazo[4,5-b]pyridin-2-yl)oxy)hexahydrofuro[3,2-b]furan-3-ol (Compound 51)

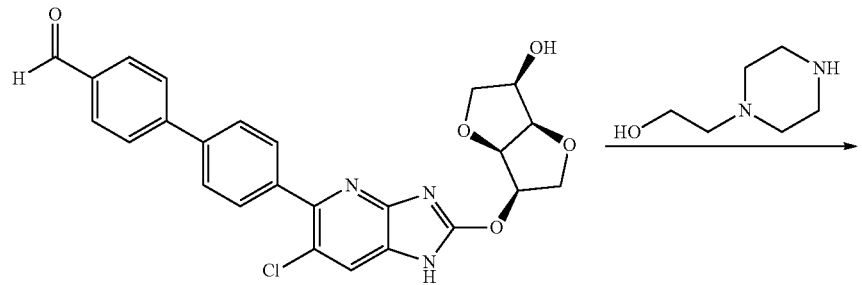

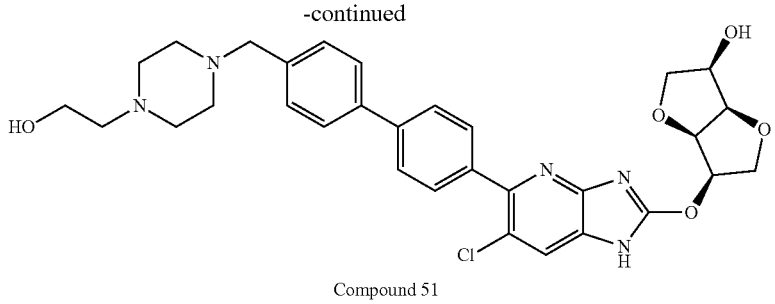

Compound 51

Compound 51 was synthesized using methods analogous to those described in Example 24. LCMS: (ES+) m/z (M+H)+=592.2. $^1$H NMR (400 MHz, DMSO-d$_6$) δ 13.36-12.09 (m, 1H), 7.93 (s, 1H), 7.83-7.62 (m, 6H), 7.40 (d, J=8.1 Hz, 2H), 5.48 (q, J=5.9 Hz, 1H), 4.99 (br d, J=6.6 Hz, 1H), 4.84 (t, J=5.0 Hz, 1H), 4.36 (br t, J=4.8 Hz, 2H), 4.23-4.07 (m, 2H), 3.91 (dd, J=5.9, 9.5 Hz, 1H), 3.79 (t, J=7.4 Hz, 1H), 3.57-3.39 (m, 6H), 2.47-2.31 (m, 9H).

Example 26: (1-((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)azetidine-3,3-diyl)dimethanol (Compound 52)

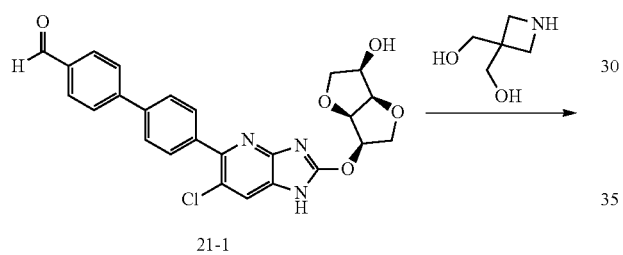

21-1

Example 27: 2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-(hydroxymethyl)propane-1,3-diol (Compound 53)

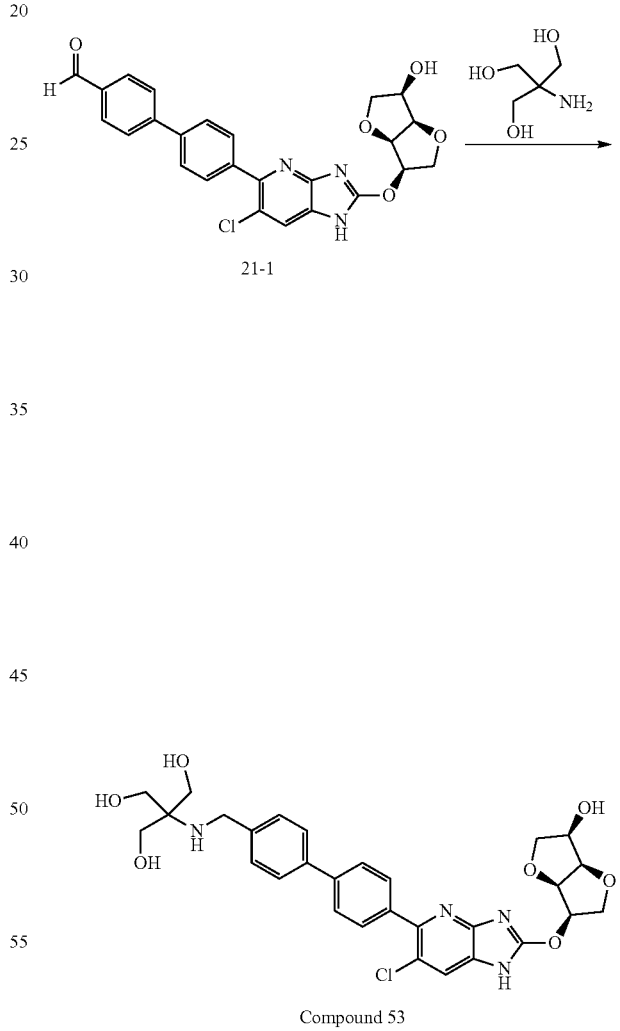

Compound 52

Compound 52 was synthesized using methods analogous to those described in Example 24. LCMS: (ES+) m/z (M+H)+=579.2. $^1$H NMR (400 MHz, CD$_3$OD) δ=7.80 (s, 1H), 7.76-7.63 (m, 6H), 7.42 (d, J=8.3 Hz, 2H), 5.53 (q, J=5.5 Hz, 1H), 4.96 (t, J=5.2 Hz, 1H), 4.47 (t, J=4.9 Hz, 1H), 4.28 (ddd, J=5.2, 6.7, 8.7 Hz, 1H), 4.22-4.04 (m, 2H), 3.90 (dd, J=6.8, 8.2 Hz, 1H), 3.78 (s, 2H), 3.69 (s, 4H), 3.60 (t, J=8.6 Hz, 1H), 3.25 (s, 4H).

Compound 53

Compound 53 was synthesized using methods analogous to those described in Example 24. LCMS: (ES+) m/z (M+H)+=583.0. $^1$H NMR (400 MHz, CD$_3$OD) δ 7.85-7.71 (m, 7H), 7.61 (d, J=8.4 Hz, 2H), 5.60-5.49 (m, 1H), 4.96 (t, J=5.2 Hz, 1H), 4.71 (t, J=5.2 Hz, 1H), 4.33-4.24 (m, 3H), 4.20-4.14 (m, 1H), 4.14-4.07 (m, 1H), 3.94-3.87 (m, 1H), 3.80 (s, 6H), 3.60 (t, J=8.8 Hz, 1H).

Example 28: (1((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)piperidine-4,4-diyl)dimethanol (Compound 54)

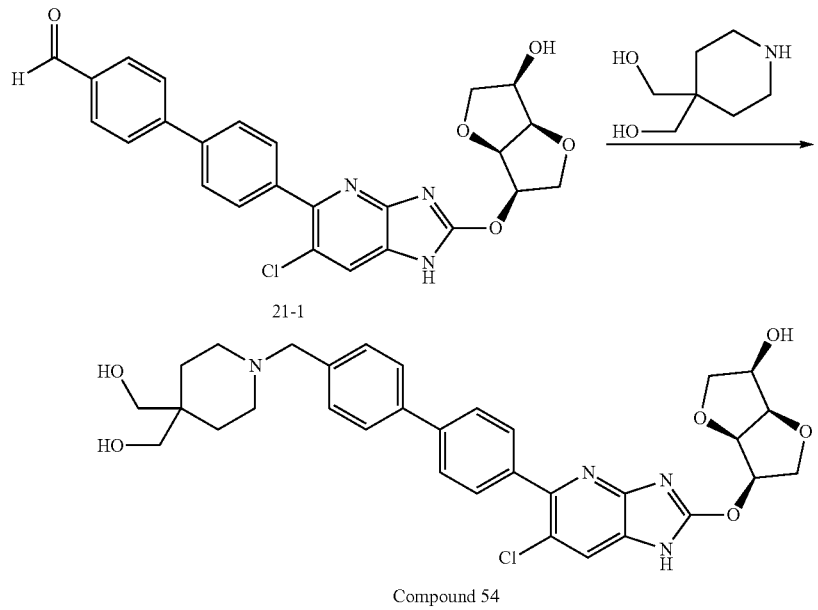

Compound 54

Compound 54 was synthesized using methods analogous to those described in Example 24. LCMS: (ES+) m/z (M+H)+=607.0. $^1$H NMR (400 MHz, CD$_3$OD) δ 8.50 (br s, 1H), 7.84-7.78 (m, 3H), 7.76 (s, 4H), 7.57 (d, J=8.4 Hz, 2H), 5.55 (q, J=5.2 Hz, 1H), 4.97 (t, J=4.8 Hz, 1H), 4.47 (t, J=5.2 Hz, 1H), 4.32-4.26 (m, 1H), 4.19-4.15 (m, 3H), 4.13-4.09 (m, 1H), 3.90 (dd, J=7.2, 8.4 Hz, 1H), 3.60 (t, J=8.4 Hz, 1H), 3.55-3.48 (m, 4H), 3.15-3.05 (m, 4H), 1.73 (br t, J=5.6 Hz, 4H)

Example 29: (3R,3aR,6R,6aR)-6-((6-chloro-5-(4'((4-(hydroxymethyl)piperidin-1-yl)methyl)-[1,1'-biphenyl]-4-yl)-1H-benzo[d]imidazol-2-yl)oxy)hexahydrofuro[3,2-b]furan-3-ol (Compound 55)

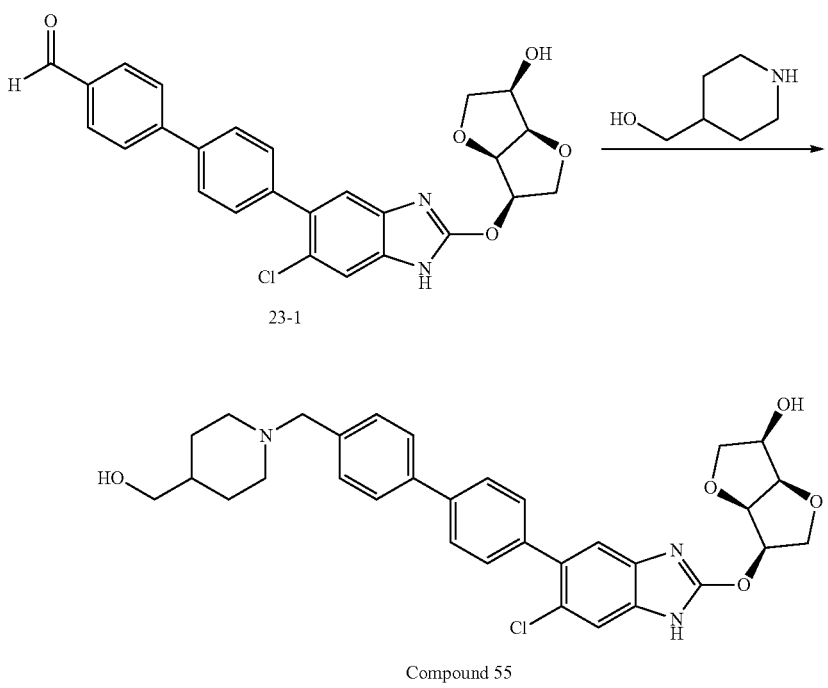

Compound 55

Compound 55 was synthesized using methods analogous to those described in Example 24. LCMS: (ES+) m/z (M+H)+=576.1. $^1$H NMR (400 MHz, CD$_3$OD) δ 7.72-7.61 (m, 4H), 7.56 -7.40 (m, 5H), 7.32 (s, 1H), 5.45 (q, J=5.6 Hz, 1H), 4.94 (t, J=5.2 Hz, 1H), 4.47 (t, J=5.0 Hz, 1H), 4.28 (ddd, J=5.2, 6.8, 8.8 Hz, 1H), 4.21-4.11 (m, 1H), 4.11-4.04 (m, 1H), 3.91 (dd, J=6.8, 8 Hz, 1H), 3.65-3.56 (m, 3H), 3.40 (d, J=6.4 Hz, 2H), 2.98 (br d, J=11.6 Hz, 2H), 2.14-2.03 (m, 2H), 1.75 (br d, J=12.4 Hz, 2H), 1.55-1.42 (m, 1H), 1.36-1.23 (m, 2H).

Example 30: (3R,3aR,6R,6aR)-6-(6-chloro-5-(4'-((4-(2-hydroxyethyl)piperazin-1-yl)methyl)-[1,1'-biphenyl]-4-yl)-1H-benzo[d]imidazol-2-yl)oxy)hexahydrofuro[3,2-b]furan-3-ol (Compound 56)

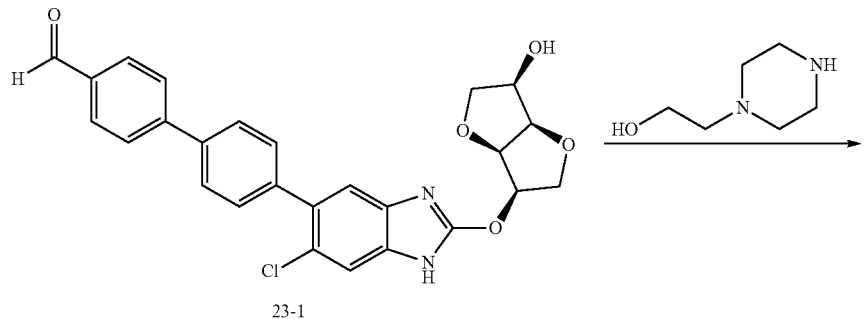

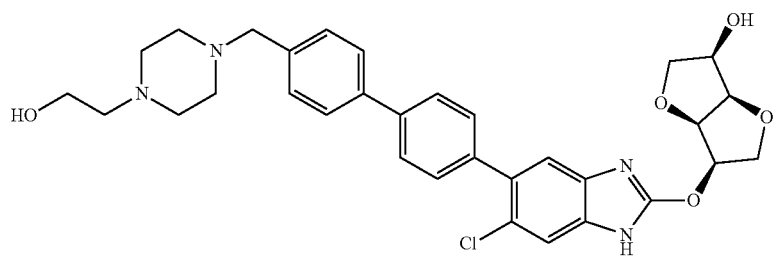

Compound 56

Compound 56 was synthesized using methods analogous to those described in Example 24. LCMS: (ES+) m/z (M+H)+=591.1. $^1$H NMR (400 MHz, DMSO-d$_6$) δ=7.73 (d, J=8.4 Hz 2H), 7.68 (d, J=8.4 Hz 2H), 7.51 (d, J=8.4 Hz 2H), 7.35 (d, J=8.4 Hz, 2H), 7.34-7.25 (m, 2H), 5.43 (q, J=6.0 Hz, 1H), 5.00 (d, J=6.8 Hz, 1H), 4.83 (t, J=5.2 Hz, 1H), 4.39-4.36 (m, 2H), 4.14-4.10 (m, 2H), 3.90-3.79 (m, 2H), 3.50-3.32 (m, 5H), 2.52-2.27 (m, 9H).

Example 31: (3R,3aR,6R,6aR)-6-((6-chloro-5-(4'-((4-methylpiperazin-1-yl)methyl)-[1,1'-biphenyl]-4-yl)-1H-benzo[d]imidazol-2-yl)oxy)hexahydrofuro[3,2-b]furan-3-ol (Compound 57)

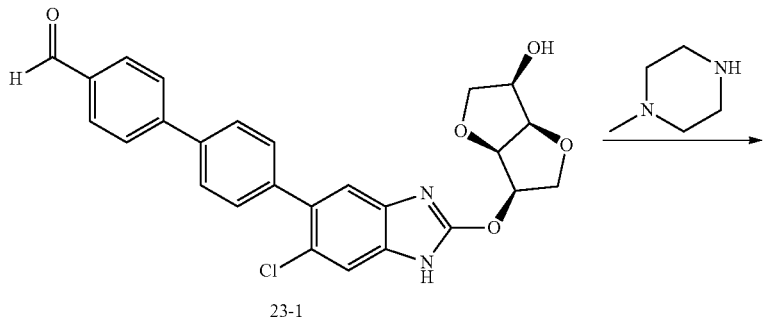

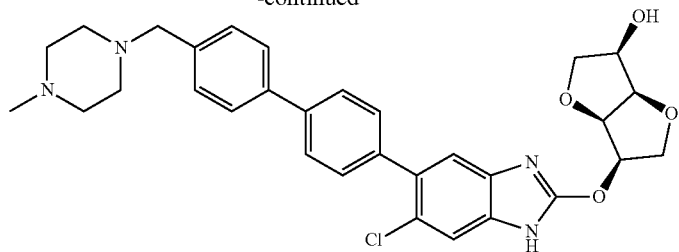

Compound 57

Compound 57 was synthesized using methods analogous to those described in Example 24. LCMS: (ES+) m/z (M+H)+=561.4. $^1$H NMR (400 MHz, CD$_3$OD) δ 7.67 (t, J=8 Hz, 4H), 7.52 -7.42 (m, 5H), 7.32 (s, 1H), 5.45 (q, J=5.2 Hz, 1H), 4.95 (t, J=5.2 Hz, 1H), 4.47 (t, J=5.2 Hz, 1H), 4.28 (ddd, J=5.2, 6.8, 8.8 Hz, 1H), 4.19-4.14 (m, 1H), 4.11-4.05 (m, 1H), 3.91 (dd, J=6.8, 8.0 Hz, 1H), 3.63-3.57 (m, 3H), 2.82-2.34 (m, 8H), 2.30 (s, 3H).

Example 32: (3R,3aR,6R,6aR)-6-((6-chloro-5-(4'-(((2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol (Compound 58)

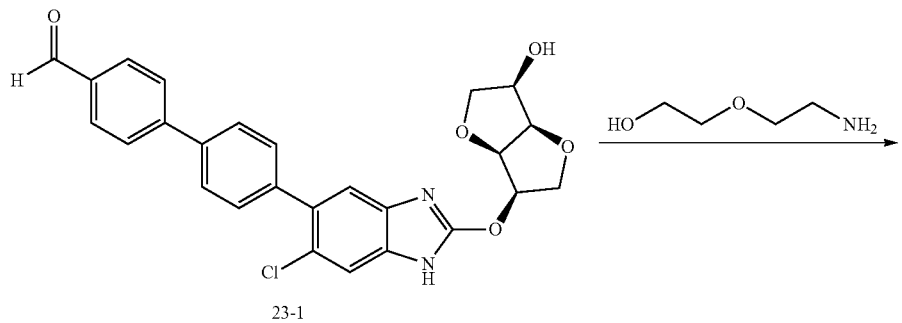

23-1

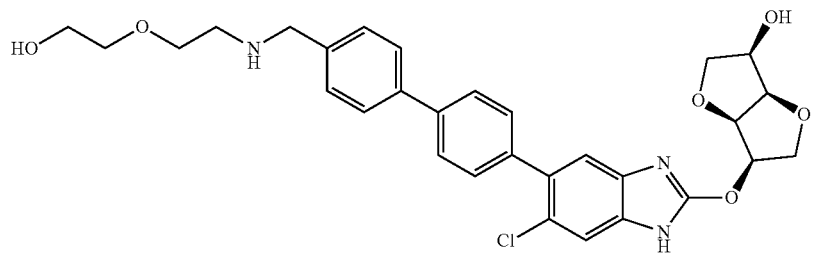

Compound 58

Compound 58 was synthesized using methods analogous to those described in Example 24. LCMS: (ES+) m/z (M+H)+=566.4. $^1$H NMR (400 MHz, CD$_3$OD) δ 7.68 (dd, J=8.2, 2.4 Hz, 4 H), 7.54-7.43 (m, 5H), 7.32 (s, 1H), 5.45 (q, J=5.6 Hz, 1H), 4.98-4.94 (m, 1H), 4.47 (t, J=5.0 Hz, 1H), 4.33-4.25 (m, 1H), 4.20-4.13 (m, 1H), 4.11-4.05 (m, 1H), 3.91 (t, J=7.4 Hz, 1H), 3.86 (s, 2H), 3.71-3.66 (m, 2H), 3.66-3.62 (m, 2H), 3.61 (s, 1H), 3.57-3.52 (m, 2H), 2.84 (t, J=5.2 Hz, 2H).

Example 33: (R)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidin-3-ol (Compound 59)

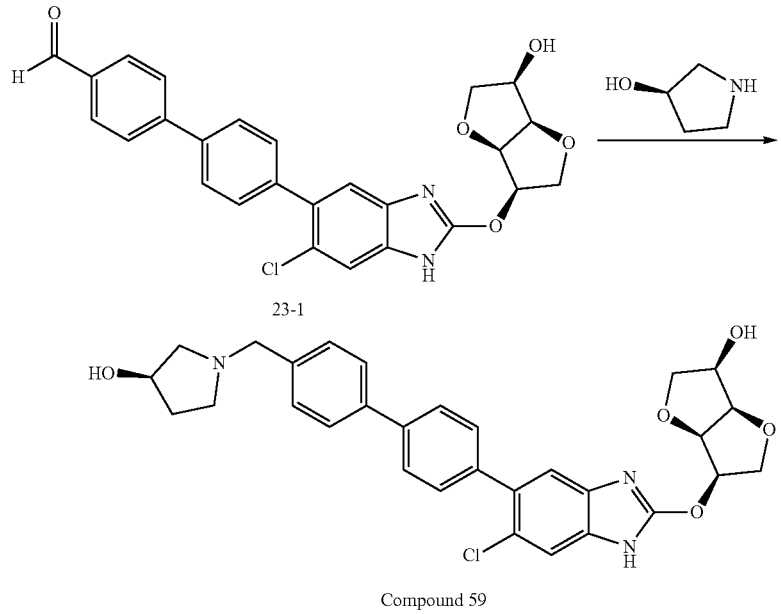

Compound 59 was synthesized using methods analogous to those described in Example 24. LCMS: (ES+) m/z (M+H)+=548.0. $^1$H NMR (400 MHz, CD$_3$OD) δ=7.67 (t, J=8.0 Hz, 4H), 7.56-7.42 (m, 5H), 7.32 (s, 1H), 5.45 (q, J=5.6 Hz, 1H), 4.95 (t, J=5.2 Hz, 1H), 4.47 (t, J=5.0 Hz, 1H), 4.40-4.34 (m, 1H), 4.32-4.24 (m, 1H), 4.20-4.03 (m, 2H), 3.91 (dd, J=8.2, 6.8 Hz, 1H), 3.78-3.55 (m, 3H), 2.92-2.73 (m, 2H), 2.65-2.49 (m, 2H), 2.26-2.07 (m, 1H), 1.76-1.74 (m, 1H).

Example 34: (1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)piperidine-4,4-diyl)dimethanol (Compound 60)

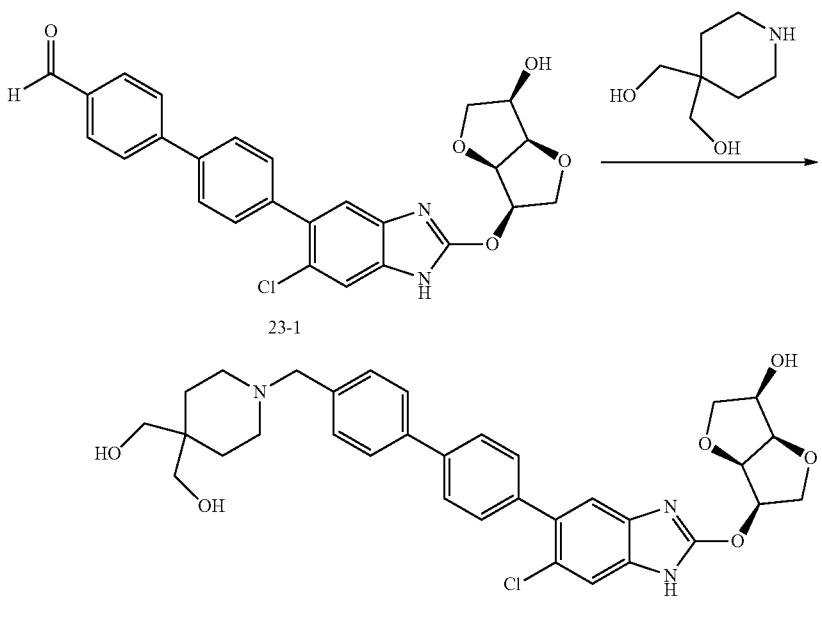

Compound 60 was synthesized using methods analogous to those described in Example 24. LCMS: (ES+) m/z (M+H)+=606.2. $^1$H NMR (400 MHz, CD$_3$OD) δ 7.67 (t, J=8.0 Hz, 4H), 7.49 (d, J=8.0 Hz, 2H), 7.46 (s, 1H), 7.43 (d, J=8.0 Hz, 2H), 7.32 (s, 1H), 5.45 (q, J=5.6 Hz, 1H), 4.94 (t, J=5.2 Hz, 1H), 4.47 (t, J=5.0 Hz, 1H), 4.28 (ddd, J=5.3, 6.8, 8.8 Hz, 1H), 4.20-4.04 (m, 2H), 3.91 (dd, J=6.8, 8.2 Hz, 1H), 3.66-3.56 (m, 3H), 3.49 (s, 4H), 2.51 (br t, J=5.6 Hz, 4H), 1.54 (br t, J=5.6 Hz, 4H).

Example 35: (3S,4R)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidine-3,4-diol (Compound 61)

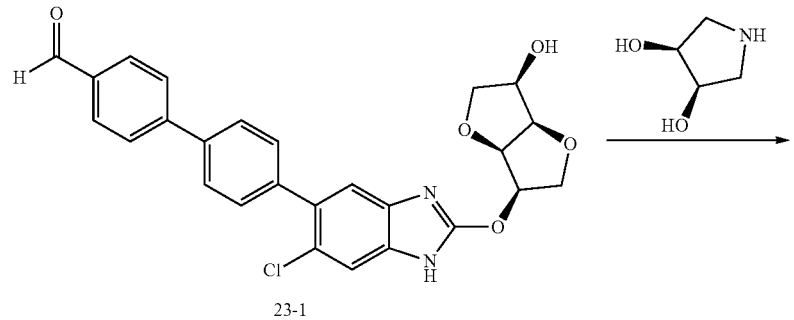

23-1

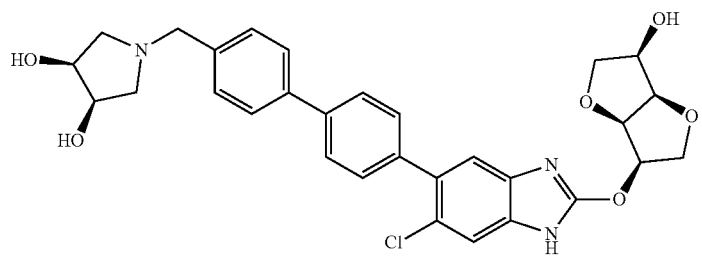

Compound 61

Compound 61 was synthesized using methods analogous to those described in Example 24. LCMS: (ES+) m/z (M+H)+=564.1. $^1$H NMR (400 MHz, CD$_3$OD) δ 7.75-7.62 (m, 4H), 7.60 -7.42 (m, 5H), 7.32 (br d, J=2.4 Hz, 1H), 5.45 (q, J=5.2 Hz, 1H), 4.95 (t, J=5.2 Hz, 1H), 4.47 (t, J=4.8 Hz, 1H), 4.29-4.27 (m, 1H), 4.20-4.12 (m, 3H), 4.11-4.05 (m, 1H), 3.91 (dd, J=8.4, 6.8 Hz, 1H), 3.75 (s, 2H), 3.61 (t, J=8.6 Hz, 1H), 3.02-2.99 (m, 2H), 2.67-2.57 (m, 2H).

Example 36: (3R,3aR,6R,6aR)-6-((6-chloro-5-(4'-(((2-(2-hydroxyethoxy)ethyl)(methyl)amino)methyl)-[1,1'-biphenyl]-4-yl)-1H-benzo[d]imidazol-2-yl)oxy)hexahydrofuro[3,2-b]furan-3-ol (Compound 62)

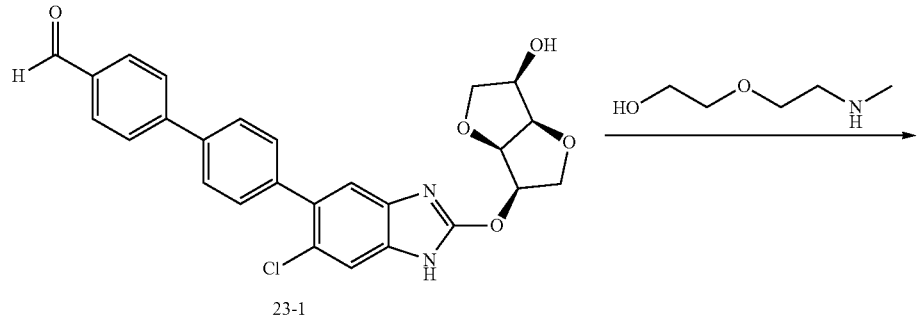

23-1

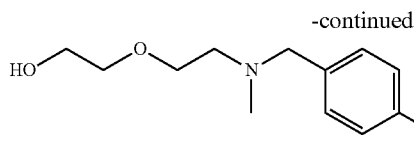

Compound 62

Compound 62 was synthesized using methods analogous to those described in Example 24. LCMS: (ES+) m/z (M+H)+=580.5. $^1$H NMR (400 MHz, CD$_3$OD) δ 8.50 (s, 1H) 7.79 (br d, J=8.0 Hz, 2H) 7.72 (br d, J=8.0 Hz, 2H) 7.58 (br d, J=8.0 Hz, 2H) 7.53 (br d, J=8.0 Hz, 2H) 7.47 (br s, 1H) 7.32 (br s, 1H) 5.45 (q, J=5.2 Hz, 1H) 4.95 (br t, J=5.2 Hz, 1H) 4.47 (br t, J=4.8 Hz, 1H) 4.33-4.21 (m, 3H) 4.19-4.13 (m, 1H) 4.12-4.06 (m, 1H) 3.91 (br t, J=7.6 Hz, 1H) 3.85-3.78 (m, 2H) 3.76-3.70 (m, 2H) 3.65-3.56 (m, 3H) 3.28-3.15 (m, 2H) 2.84-2.66 (m, 3H).

Example 37: (3R,3aR,6R,6aR)-6-((6-chloro-5-(4'((3-(hydroxymethyl)azetidin-1-yl)methyl)-[1,1'-biphenyl]-4-yl)-1H-benzo[d]imidazol-2-yl)oxy)hexahydrofuro[3,2-b]furan-3-ol (Compound 63)

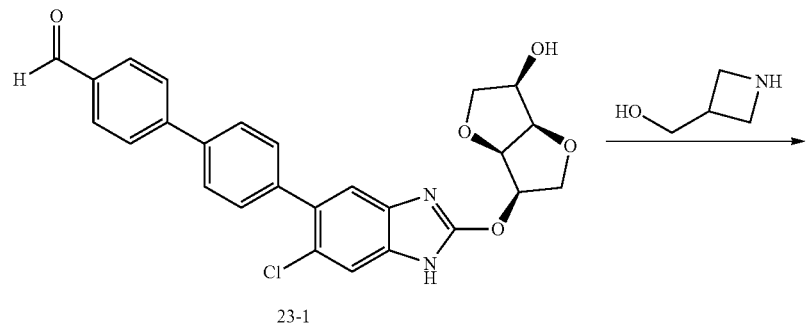

23-1

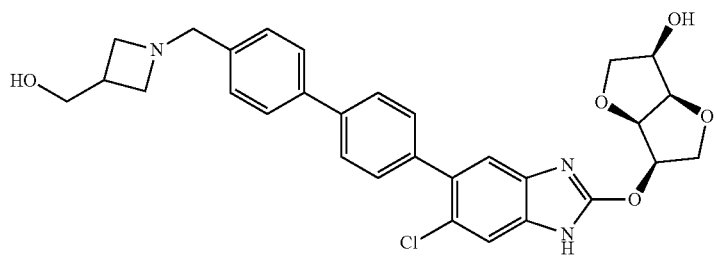

Compound 63

Compound 62 was synthesized using methods analogous to those described in Example 24. LCMS: (ES+) m/z (M)+= 548.1. $^1$H NMR (400 MHz, CD$_3$OD) δ 7.70-7.64 (m, 4H), 7.50 (d, J=8.4 Hz, 2H), 7.46 (s, 1H), 7.40 (d, J=8.0 Hz, 2H), 7.32 (s, 1H), 5.45 (q, J=5.6 Hz, 1H), 4.95 (t, J=5.2 Hz, 1H), 4.47 (t, J=4.9 Hz, 1H), 4.29-4.27 (m, 1H), 4.19-4.14 (m, 1H), 4.11-4.06 (m, 1H), 3.91 (dd, J=7.2, 8.8 Hz, 1H), 3.71 (s, 2H), 3.66 (d, J=6.4 Hz, 2H), 3.60 (t, J=8.4 Hz, 1H), 3.46 (t, J=8.0 Hz, 2H), 3.18-3.11 (m, 2H), 2.74-2.67 (m, 1H).

Example 38: (3S,4S)-1-((4'-(6-chloro-2-(43R,3aR,6R,6aR)-6-hydroxyhexahydrofuro [3,2-b]furan-3-yl)oxy)-1H-benzo[d]imidazol-5-yl)-[1,1'-biphenyl]-4-yl)methyl)pyrrolidine-3,4-diol (Compound 64)

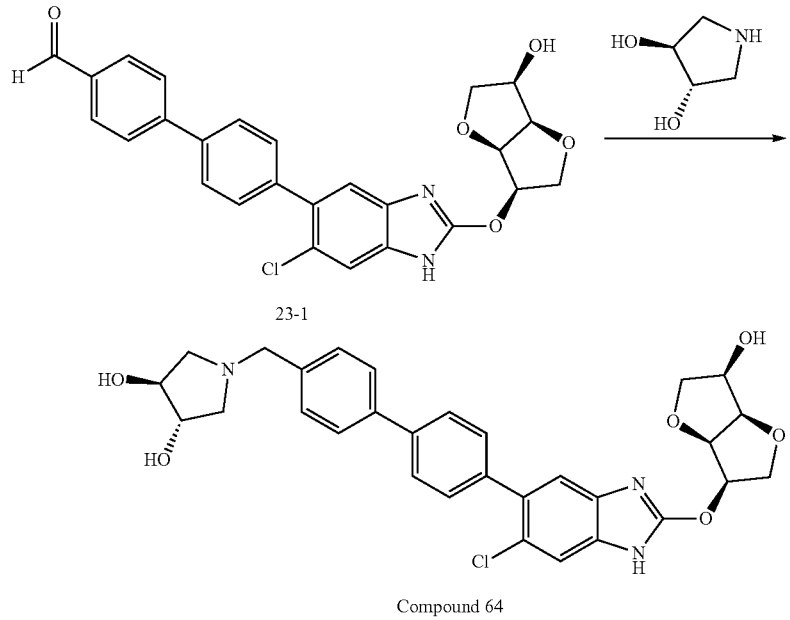

Compound 64 was synthesized using methods analogous to those described in Example 24. LCMS: (ES+) m/z (M+H)+=564.4. $^1$H NMR (400 MHz, DMSO-$d_6$) δ=12.24 (br s, 1H) 7.74 (d, J=8.4 Hz, 2H) 7.68 (d, J=8.4 Hz, 2H) 7.51 (d, J=8.4 Hz, 3H) 7.41 (d, J=8.4 Hz, 2H) 7.19-7.37 (m, 1H) 5.44 (q, J=6.0 Hz, 1H) 4.97 (d, J=6.8 Hz, 1H) 4.80-4.87 (m, 3H) 4.37 (t, J=4.8 Hz, 1H) 4.09 -4.20 (m, 2H) 3.84-3.92 (m, 3H) 3.79 (t, J=7.2 Hz, 1H) 3.61 -3.69 (m, 1H) 3.50 -3.56 (m, 1H) 3.44 (t, J=8.4 Hz, 1H) 2.80 (dd, J=9.6, 6.0 Hz, 2H) 2.31-2.39 (m, 2H).

Example 39: (2R,3R,4R,5S)-6-(((4'-(6-chloro-2-(((3R,3aR,6R,6aR)-6-hydroxyhexahydrofuro[3,2-b]furan-3-yl)oxy)-1H-benzo [d]imidazol-5-yl)-[1,1'-biphenyl]-4-yl) methyl)amino)hexane-1,2,3,4,5-pentaol (Compound 65)

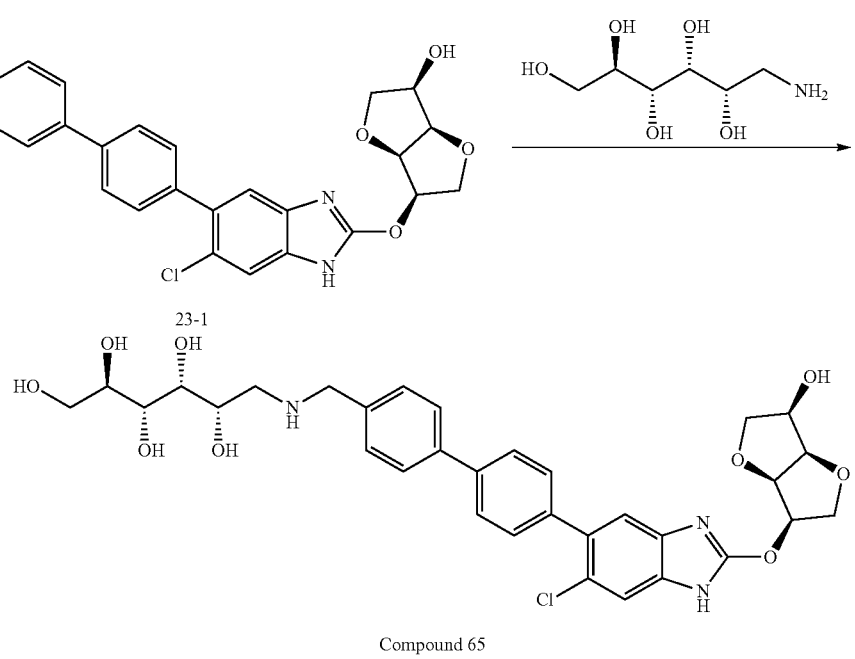

Compound 65 was synthesized using methods analogous to those described in Example 24. LCMS: (ES+) m/z (M+H)+=642.3. ¹H NMR (400 MHz, CD₃OD) δ 8.51 (s, 1H), 7.79 (d, J=8.0 Hz, 2H), 7.72 (d, J=8.4 Hz, 2H), 7.59 (br d, J=8.0 Hz, 2H), 7.53 (d, J=8.0 Hz, 2H), 7.47 (br s, 1H), 7.32 (s, 1H), 5.45 (q, J=5.2 Hz, 1H), 4.95 (t, J=5.2 Hz, 1H), 4.47 (t, J=4.8 Hz, 1H), 4.38-4.20 (m, 3H), 4.19-4.13 (m, 1H), 4.12-3.99 (m, 2H), 3.91 (t, J=7.6 Hz, 1H), 3.85 (br d, J=4.4 Hz, 1H), 3.78 (dd, J=10.4, 2.8 Hz, 1H), 3.74-3.55 (m, 4H), 3.25-3.03 (m, 2H).

Example 40: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-2-(hydroxymethyl)propane-1,3-diol (Compound 36)

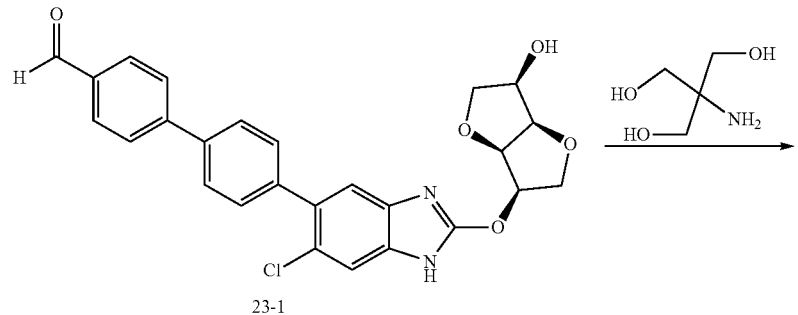

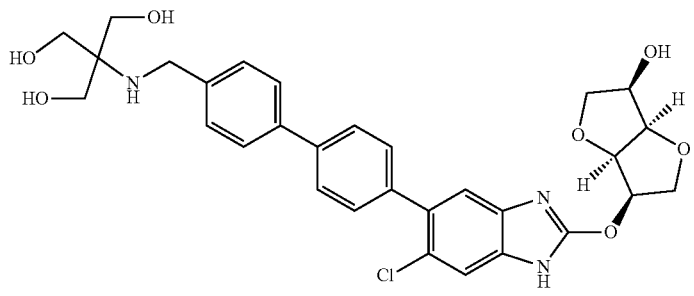

Compound 36

Compound 36 was synthesized using methods analogous to those described in Example 24. LCMS (ES+) m/z (M+H)+=582.1. ¹H NMR (400 MHz, CD₃OD) δ 8.54 (s, 1H), 7.74 (d, J=8 Hz, 2H), 7.70 (d, J=8.0 Hz, 2H), 7.58 (d, J=8.4 Hz, 2H), 7.51 (d, J=8.0 Hz, 2H), 7.46 (s, 1H), 7.32 (br s, 1H), 5.45 (q, J=5.2 Hz, 1H), 4.95 (t, J=5.2 Hz, 1H), 4.47 (t, J=4.8 Hz, 1H), 4.33-4.25 (m, 1H), 4.20 (s, 2H), 4.19-4.13 (m, 1H), 4.11-4.05 (m, 1H), 3.91 (dd, J=7.2, 8.0 Hz, 1H), 3.78 (s, 6H), 3.61 (t, J=8.8 Hz, 1H).

Example 41: (1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)azetidine-3,3-diyl)dimethanol (Compound 66)

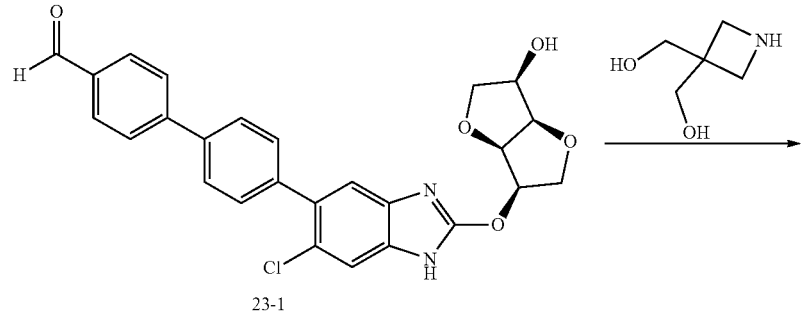

-continued

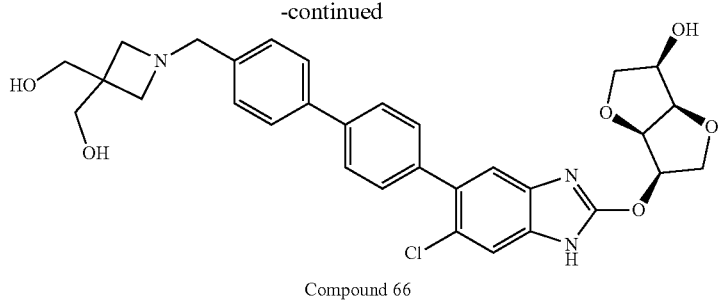

Compound 66

Compound 66 was synthesized using methods analogous to those described in Example 24. LCMS: (ES+) m/z (M+H)+=578.2. $^1$H NMR (400 MHz, CD$_3$OD) δ 7.71-7.61 (m, 4H), 7.48 (d, J=8.0 Hz, 2H), 7.46 (s, 1H), 7.40 (d, J=8.0 Hz, 2H), 7.31 (s, 1H), 5.45 (q, J=5.2 Hz, 1H), 4.94 (t, J=5.2 Hz, 1H), 4.47 (t, J=5.2 Hz, 1H), 4.29-4.27 (m, 1H), 4.20-4.12 (m, 1H), 4.11-4.04 (m, 1H), 3.90 (dd, J=6.8, 8.0 Hz, 1H), 3.77-3.67 (m, 6H), 3.60 (t, J=8.6 Hz, 1H), 3.20 (s, 4H).

Example 42: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)propane-1,3-diol (Compound 40)

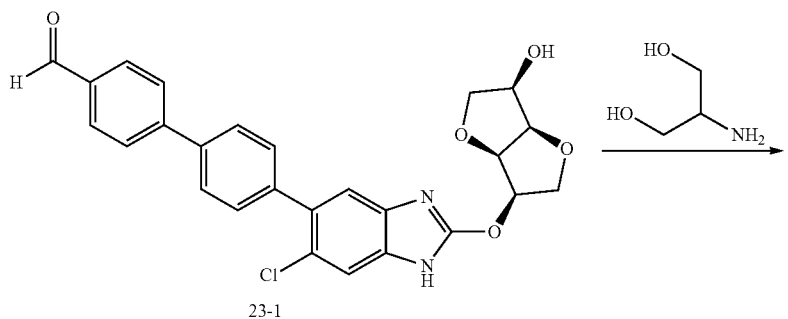

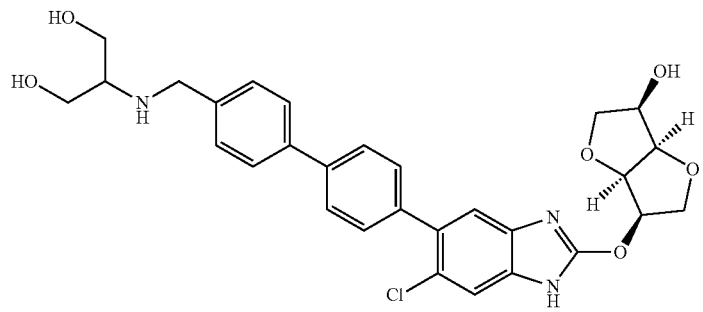

Compound 40

Compound 40 was synthesized using methods analogous to those described in Example 24. LCMS: (ES+) m/z (M+H)+=522.2. $^1$H NMR (400 MHz, CD$_3$OD) δ 7.75 (d, J=8.4 Hz, 2H), 7.70 (d, J=8.4 Hz, 2H), 7.57 (d, J=8.2 Hz, 2H), 7.52 (d, J=8.4 Hz, 2H), 7.47 (s, 1H), 7.32 (br s, 1H), 5.45 (d, J=5.2 Hz, 1H), 4.59 (br s, 3H), 4.47 (t, J=4.8 Hz, 1H), 4.30-4.28 (m, 1H), 4.21 (s, 2H), 4.19-4.13 (m, 1H), 4.11-4.05 (m, 1H), 3.91 (dd, J=6.8, 8.2 Hz, 1H), 3.83-3.78 (m, 2H), 3.77-3.70 (m, 2H), 3.61 (t, J=8.6 Hz, 1H), 3.12 (t, J=5.2 Hz, 1H).

Example 43: 4-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(2-hydroxyethyl)butanamide (Compound 37)

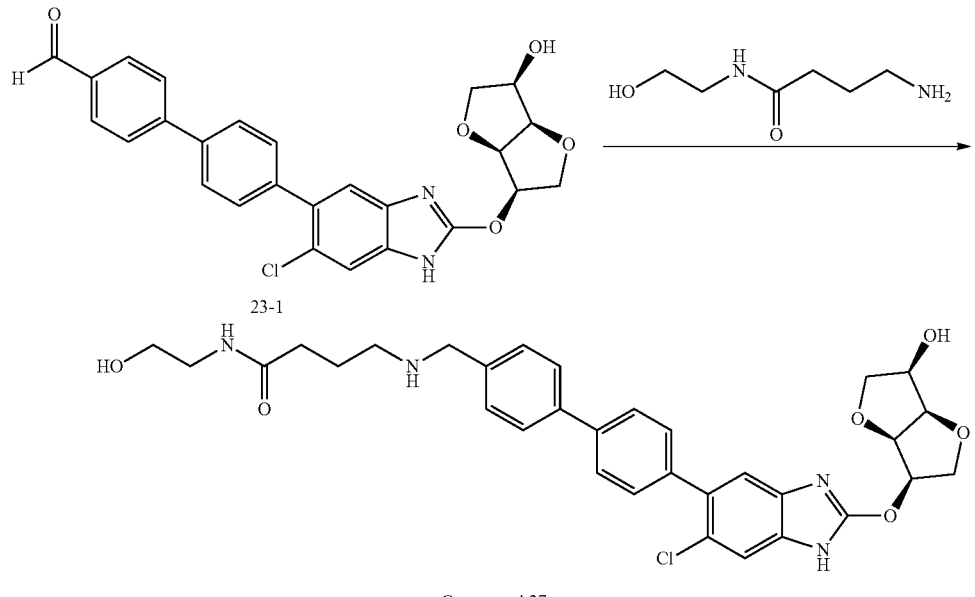

Compound 37 was synthesized using methods analogous to those described in Example 24. LCMS: (ES+) m/z (M+H)+=607.2. $^1$ NMR (400 MHz, CD$_3$OD) δ 7.81 (d, J=8.4 Hz, 2H), 7.73 (d, J=8.4 Hz, 2H), 7.61 (d, J=8.0 Hz, 2H), 7.54 (d, J=8.0 Hz, 2H), 7.50 (s, 1H), 7.36 (s, 1H), 5.46 (q, J=5.2 Hz, 1H), 4.97 (t, J=5.2 Hz, 1H), 4.47 (t, J=5.2 Hz, 1H), 4.30-4.26 (m, 3H), 4.15-4.13 (m, 2H), 3.90 (dd, J1=8.4 Hz, J2=6.8 Hz, 1H), 3.63-3.60 (m, 3H), 3.35-3.31 (m, 2H), 3.15 (t, J=7.2 Hz, 2H), 2.44 (t, J=6.8 Hz, 2H), 2.01 (t, J=6.8 Hz, 2H).

Example 44: 4-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(1,3-dihydroxypropan-2-yl)butanamide (Compound 38)

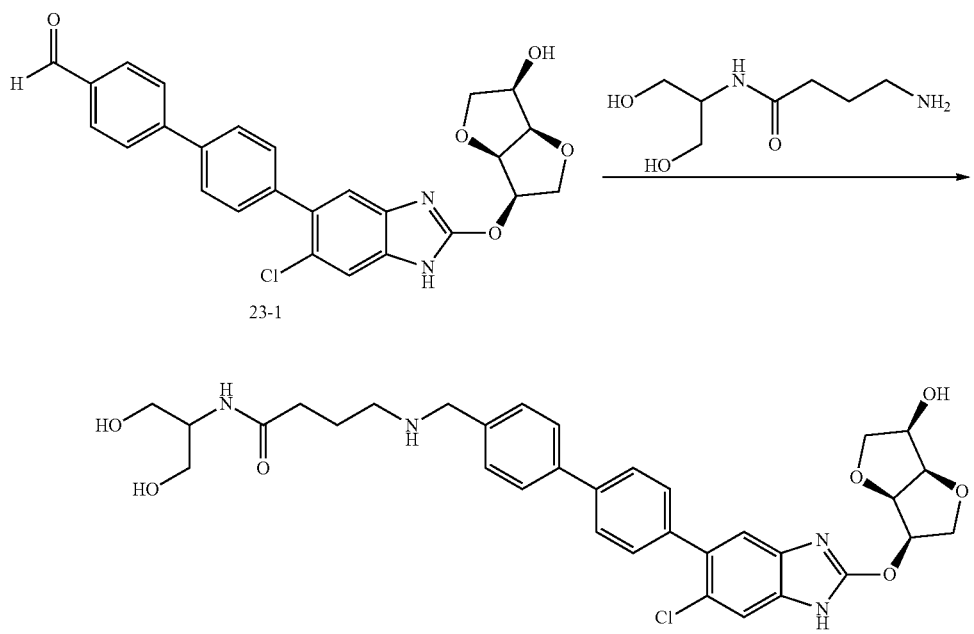

Compound 38 was synthesized using methods analogous to those described in Example 24. LCMS: (ES+) m/z (M+H)+=637.2. $^1$H NMR (400 MHz, CD$_3$OD) δ 7.81 (d, J=8.4 Hz, 2H), 7.75 (d, J=8.4 Hz, 2H), 7.62 (d, J=8.0 Hz, 2H), 7.59 (s, 1H), 7.55 (d, J=8.0 Hz, 2H), 7.43 (s, 1H), 5.48 (q, J=5.2 Hz, 1H), 5.01 (t, J=5.2 Hz, 1H), 4.47 (t, J=5.2 Hz, 1H), 4.30-4.26 (m, 3H), 4.15-4.13 (m, 2H), 4.02-3.94 (m, 1H), 3.88 (t, J=6.8 Hz, 2H), 3.65-3.58 (m, 5H), 3.16 (t, J=7.2 Hz, 2H), 2.47 (t, J=6.8 Hz, 2H), 2.01 (t, J=6.8 Hz, 2H).

Example 45: (3R,3aR,6R,6aR)-6-((5-(4'-((3-(aminomethyl)azetidin-1-yl)methyl)-[1,1'-biphenyl]-4-yl)-6-chloro-1H-benzo[d]imidazol-2-yl)oxy)hexahydrofuro[3,2-b]furan-3-ol (Compound 67)

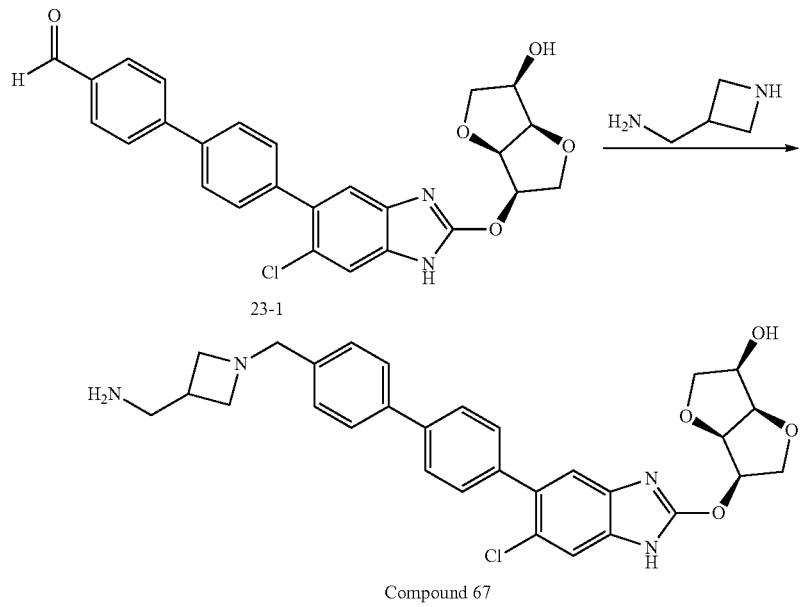

Compound 67

Compound 67 was synthesized using methods analogous to those described in Example 24. LCMS: (ES+) m/z (M+H)+=547.4. $^1$H NMR (400 MHz, DMSO-d$_6$) δ 7.71 (d, J=8.0 Hz, 2H), 7.65 (d, J=8.0 Hz, 2H), 7.48 (d, J=8.0 Hz, 2H), 7.44 (s, 1H) 7.35 (d, J=8.0 Hz, 2H), 7.30 (s, 1H), 5.42 (q, J=6.0 Hz, 1H), 4.82 (t, J=5.2 Hz, 1H), 4.36 (br t, J=4.8 Hz, 1H), 4.07-4.18 (m, 3H), 3.87-3.85 (m, 1H), 3.78 (br t, J=7.2 Hz, 1H), 3.56 (s, 2H), 3.43 (t, J=8.4 Hz, 1H), 3.22 (br t, J=7.2 Hz, 2H), 2.87 (br t, J=6.0 Hz, 2H), 2.61-2.81 (m, 2H), 2.30-2.43 (m, 1H).

Example 46: Synthesis and purification of dimethyl (4'-(6-chloro-2-(((4aR,7S,7aR)-2,2-di-tert-butyltetrahydro-4H-furo[3,2-d][1,3,2]dioxasilin-7-yl)oxy)-1-((2-(trimethylsilyl)ethoxy)methyl)-1H-imidazo[4,5-b]pyridin-5-yl)-[1,1'-biphenyl]-4-yl)phosphonate (Intermediate 46-7A) and dimethyl (4'-(6-chloro-2-(((4aS,7R,7aS)-2,2-di-tert-butyltetrahydro-4H-furo[3,2-d][1,3,2]dioxasilin-7-yl)oxy)-1-((2-(trimethylsilyl)ethoxy)methyl)-1H-imidazo[4,5-b]pyridin-5-yl)-[1,1'-biphenyl]-4-yl)phosphonate (Intermediate 46-7B)

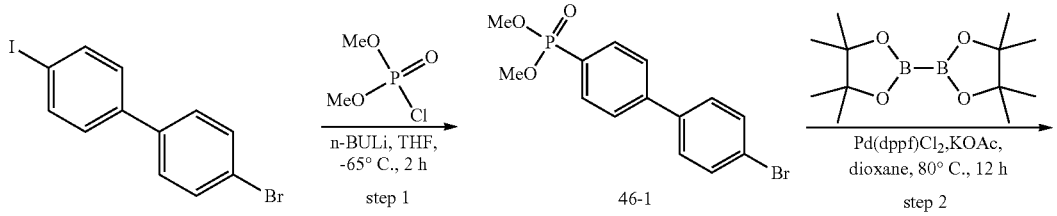

-continued
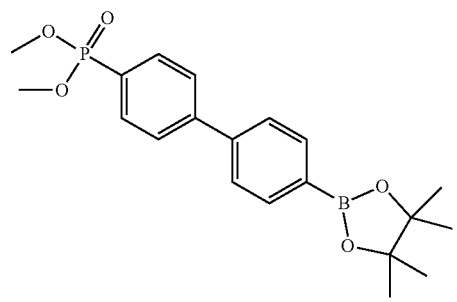
46-2
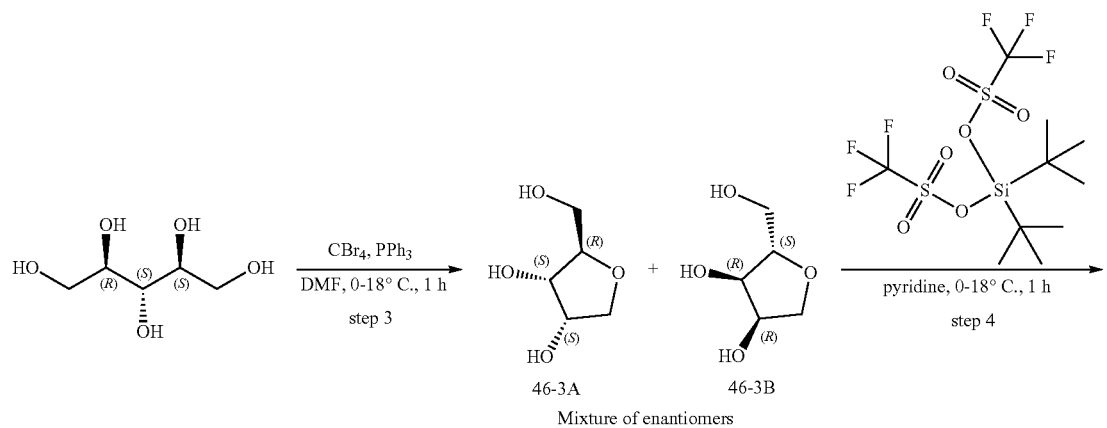
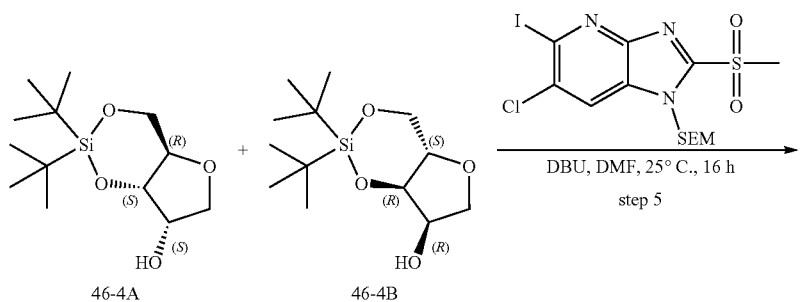
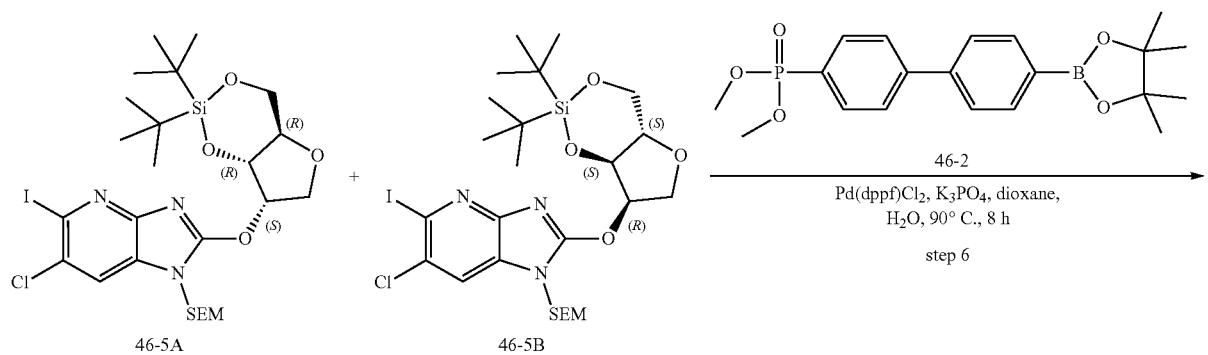

-continued

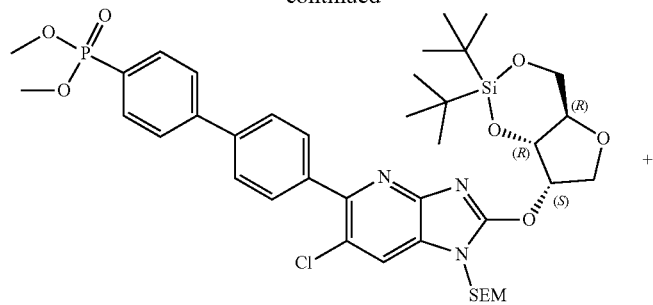
46-6A

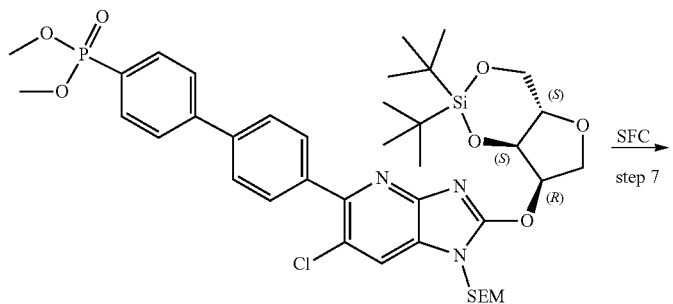
46-6B

SFC
step 7

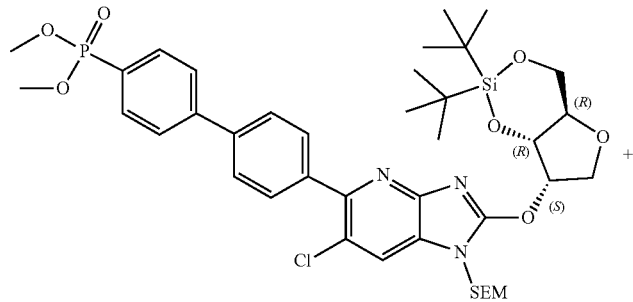
46-7A

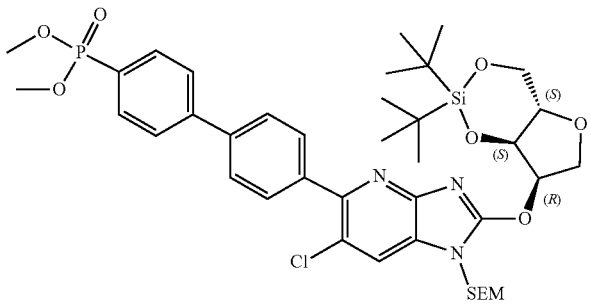
46-7B

Step 1: A mixture of 4-bromo-4'-iodo-1,1'-biphenyl (3.0 g, 8.4 mmol, 1.0 eq) in THF (50 mL) was degassed and purged with $N_2$ 3 times, and then the mixture was cooled to −65° C. n-BuLi (2.5 M, 3.3 mL, 1.0 eq) was added, and the mixture was stirred at −65° C. under $N_2$ atmosphere. Dimethyl phosphorochloridate (1.2 g, 8.4 mmol, 0.90 mL, 1.0 eq) in THF (3 mL) was added, and the mixture was stirred at −65° C. for 2 hours under $N_2$ atmosphere. The reaction mixture was quenched by addition of water (20 mL) at −50° C., then was added EtOAc (100 mL), and the pH adjusted to 7 by addition of aqueous HCl (1M). The reaction mixture was partitioned. The organic phase was separated, washed with brine (15 mL), dried over $Na_2SO_4$, filtered and concentrated under reduced pressure to give a residue. The residue was purified by column chromatography ($SiO_2$, Petroleum ether: Ethyl acetate=1: 0 to 1: 1) to give 46-1 as the crude product. The crude product was purified by RP-MPLC (column: Welch Xtimate C18 100×25 mm×3 um; mobile phase: [A: water (0.025% FA), B: ACN]; B%: 30%-50%) to give 46-1 (0.54 g, 19% yield) as a yellow solid. LCMS: (ES+) m/z (M+H)+=340.9, 342.9. $^1$H NMR (400 MHz, $CDCl_3$) δ 7.88 (dd, J=8.4, 13.2 Hz, 2H), 7.70 -7.63 (m, 2H), 7.61 (d, J=8.4 Hz, 2H), 7.48 (d, J=8.8 Hz, 2H), 3.82 (s, 3H), 3.79 (s, 3H).

Step 2: A mixture of 46-1 (0.50 g, 1.5 mmol, 1.0 eq), 4,4,4',4',5,5,5',5'-octamethyl --2,2'-bi(1,3,2-dioxaborolane) (1.1 g, 4.4 mmol, 3.0 eq), KOAc (0.72 g, 7.3 mmol, 5.0 eq), and Pd(dppf)Cl$_2$·CH$_2$Cl$_2$ (0.12 g, 0.15 mmol, 0.10 eq) in dioxane (20 mL) was degassed and purged with N$_2$ 3 times, and then the mixture was stirred at 80° C. for 12 hours under N$_2$ atmosphere. The reaction mixture was filtered and concentrated under reduced pressure to give a residue. The residue was purified by column chromatography (SiO$_2$, Petroleum ether: Ethyl acetate=20: 1 to 1:3) to give 46-2 (0.50 g, 88% yield) as a yellow solid. LCMS: (ES+) m/z (M+H)+=389.1. $^1$H NMR (400 MHz, CDCl$_3$) δ 7.95-7.82 (m, 4H), 7.72 (dd, J=3.6, 8.4 Hz, 2H), 7.62 (d, J=8.0 Hz, 2H), 3.80 (s, 3H), 3.78 (s, 3H), 1.37 (s, 12H).

Step 3: To a solution of (2R,3S,4S)-pentane-1,2,3,4,5-pentaol (4.0 g, 26 mmol, 1.0 eq) and CB$_{R4}$ (—g, 39 mmol, 1.5 eq) in DMF (40 mL) was added PPh$_3$ (10 g, 39 mmol, 1.5 eq) in DMF (10 mL) at 0° C. The mixture was stirred at 18° C. for 1 hour. The reaction mixture was concentrated under reduced pressure to give a residue. The residue was purified by column chromatography (SiO$_2$, Petroleum ether: Ethyl acetate=1: 2 to 0: 1, then Ethyl acetate: Methanol=20:1 to 5:1) to give a racemic mixture of 46-3A and 46-3B (1.6 g, 45% yield) as a colorless oil. $^1$H NMR (400 MHz, CD$_3$OD) δ 4.18-4.09 (m, 1H), 4.05-3.93 (m, 2H), 3.80-3.67 (m, 3H), 3.60-3.51 (m, 1H).

Step 4: To a solution of a mixture of 46-3A and 46-3B (1.6 g, 12 mmol, 1.0 eq) in pyridine (12 g, 0.15 mol, 12 mL, 12 eq) was added di-tert-butylsilanediyl bis(trifluoromethanesulfonate) (5.4 g, 12 mmol, 1.0 eq) at 0° C. through an injection syringe over a period of 10 mins. The mixture was warmed to 18° C. slowly and stirred at 18° C. for 1 hour. The solvent was removed in vacuo, and the residue was partitioned between water (35 mL) and DCM (100 mL). The organic layer was dried over anhydrous sodium sulfate, filtered and concentrated under reduced pressure to give a residue. The residue was purified by column chromatography (SiO$_2$, Petroleum ether: Ethyl acetate=100: 1 to 5: 1) to give a mixture of 46-4A and 46-4B (2.3 g, 68% yield) as a white solid. $^1$H NMR (400 MHz, CD$_3$CN) δ 4.37-4.31 (m, 1H), 4.25 (br s, 1H), 4.14 (dd, J=4.0, 10.1 Hz, 1H), 3.90-3.76 (m, 3H), 3.72 (d, J=10.0 Hz, 1H), 3.03 (s, 1H), 1.96 (td, J=2.4, 4.8 Hz, 2H), 1.07 (s, 9H), 1.04 (s, 9H).

Step 5: To a solution of a mixture of 46-4A and 46-4B (0.30 g, 1.1 mmol, 1.1 eq), 6-chloro-5-iodo-2-(methylsulfonyl)-1-((2-(trimethyl silyl)ethoxy)methyl)-1H-imidazo[4,5-b]pyridine (0.50 g, 1.0 mmol, 1.0 eq), and 4 Å MS (1.0 g) in DMF (15 mL) was added DBU (0.23 g, 1.5 mmol, 0.23 mL, 1.5 eq). The mixture was stirred at 25° C. for 16 hours. The reaction mixture was filtered, quenched by addition of water (15 mL), and then extracted with DCM (50 mL×2). The combined organic layers were washed with brine (15 mL), dried over Na$_2$SO$_4$, filtered and concentrated under reduced pressure to give a residue. The residue was purified by column chromatography (SiO$_2$, Petroleum ether: Ethyl acetate=1: 0 to 20: 1) to give a racemic mixture of 46-5A and 46-5B (0.31 g, 43% yield) as a white solid. LCMS: (ES+) m/z (M+H)+=682.0. $^1$H NMR (400 MHz, CDCl$_3$) δ 7.78 (s, 1H), 5.73 (t, J=4.4 Hz, 1H), 5.57-5.52 (m, 1H), 5.42 (d, J=11.2 Hz, 1H), 4.53-4.46 (m, 2H), 4.18-4.11 (m, 2H), 4.05 (dt, J=4.4, 10.0 Hz, 1H), 3.99-3.85 (m, 2H), 3.73-3.61 (m, 2H), 1.08 (s, 9H), 1.02 (s, 9H), 0.97-0.92 (m, 2H), 0.04-0.02 (m, 9H).

Step 6: To a solution of mixture of 46-5A and 46-5B (0.30 g, 0.44 mmol, 1.0 eq) and 46-2 (0.25 g, 0.66 mmol, 1.5 eq) in dioxane (10 mL), H$_2$O (2 mL) was added K$_3$PO$_4$ (0.47 g, 2.2 mmol, 5.0 eq) and Pd(dppf)Cl$_2$ (64 mg, 88 umol, 0.20 eq) in the glovebox. The mixture was stirred at 90° C. for 8 hours. The reaction mixture was filtered and concentrated under reduced pressure to give a residue. The residue was purified by column chromatography (SiO$_2$, Petroleum ether: Ethyl acetate=10: 1 to 1: 1) and then by prep-TLC (SiO$_2$, Petroleum ether: Ethyl acetate=1: 2) to give a mixture of 46-6A and 46-6B (0.18 g, 50% yield) as a yellow oil. LCMS: (ES+) m/z (M+H)+=816.2. $^1$H NMR (400 MHz, CDCl$_3$) δ 7.98-7.88 (m, 5H), 7.84-7.78 (m, 2H), 7.75 (d, J=8.4 Hz, 2H), 5.80 (t, J=4.4 Hz, 1H), 5.64 (d, J=11.2 Hz, 1H), 5.50 (d, J=11.2 Hz, 1H), 4.62-4.47 (m, 2H), 4.26-4.17 (m, 2H), 4.16-4.06 (m, 1H), 4.04-3.97 (m, 1H), 3.86 (d, J=11.2 Hz, 6H), 3.80-3.68 (m, 2H), 1.12 (s, 9H), 1.07 (s, 9H), 0.99 (dd, J=6.8, 9.6 Hz, 2H), 0.00 (s, 9H).

Step 7: The racemic mixture of 46-6A and 46-6B was separated and purified by prep-HPLC (column: DAICEL CHIRALPAK IG (250 mm×30 mm,10 um); mobile phase: [A: water (0.1% NH$_3$·H$_2$O), B: EtOH]; B%: 45%) to give 46-7A and 46-7B.

46-7A (Peak 1) (100 mg, 45% yield) as a yellow oil. LCMS: (ES$^+$) m/z (M+H)$^+$=816.2. SFC: tR=1.336 min. $^1$H NMR (400 MHz, CDCl$_3$) δ 8.03 (s, 1H), 7.96-7.85 (m, 5H), 7.80-7.74 (m, 2H), 7.71 (d, J=8.4 Hz, 2H), 5.77 (t, J=4.4 Hz, 1H), 5.60 (d, J=11.2 Hz, 1H), 5.47 (d, J=11.2 Hz, 1H), 4.59-4.44 (m, 2H), 4.22-4.12 (m, 2H), 4.07 (dt, J=4.8, 10.0 Hz, 1H), 4.00-3.91 (m, 1H), 3.82 (d, J=11.2 Hz, 6H), 3.77-3.66 (m, 2H), 1.08 (s, 9H), 1.03 (s, 9H), 0.95 (dd, J=6.8, 9.5 Hz, 2H), —0.04 (s, 9H).

46-7B (Peak 2) (90 mg, 41% yield) as a yellow oil. LCMS: (ES$^+$) m/z (M+H)$^+$=816.2. SFC: tR=1.474 min. $^1$H NMR (400 MHz, CDCl$_3$) δ 7.96-7.84 (m, 5H), 7.77 (dd, J=4.0, 8.0 Hz, 2H), 7.71 (d, J=8.4 Hz, 2H), 5.77 (t, J=4.4 Hz, 1H), 5.60 (d, J=11.2 Hz, 1H), 5.47 (d, J=11.2 Hz, 1H), 4.57-4.44 (m, 2H), 4.22-4.12 (m, 2H), 4.07 (dt, J=4.8, 9.6 Hz, 1H), 3.99-3.92 (m, 1H), 3.82 (d, J=11.2 Hz, 6H), 3.75-3.66 (m, 2H), 1.08 (s, 9H), 1.03 (s, 9H), 0.95 (dd, J=6.8, 9.6 Hz, 2H), –0.04 (s, 9H).

Example 47: (4'-(6-chloro-2-(((3S,4R,5R)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid; (Compound 45)

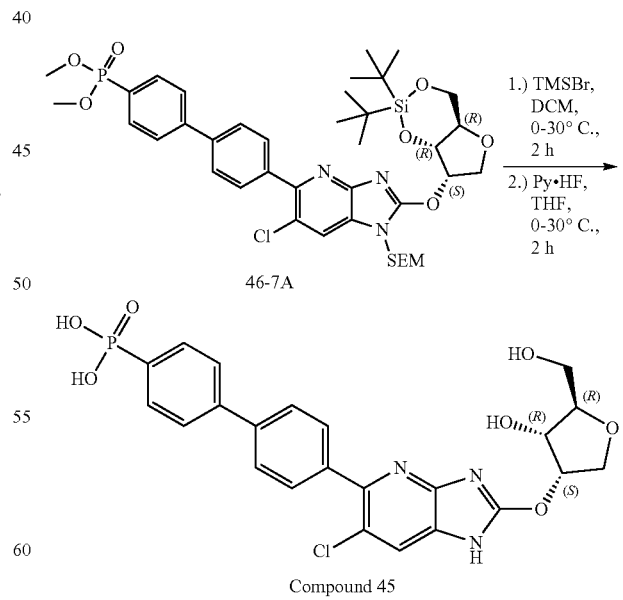

Compound 45

Step 1: To a solution of 46-7A (Peak 1) (60 mg, 73 umol, 1.0 eq) in DCM (10 mL) was added TMSBr (0.56 g, 3.67 mmol, 0.48 mL, 50 eq) at 0° C. The mixture was stirred at 30° C. for 2 hours. The reaction mixture was concentrated under reduced pressure to give the intermediate (50 mg, crude) as a yellow oil, which was used into the next step without further purification. LCMS: (ES+) m/z (M+H)+= 658.3.

Step 2: To a solution of the intermediate obtained in the previous step (50 mg, 76 umol, 1.0 eq) in THF (8 mL) was added pyridine hydrofluoride (45 mg, 0.45 mmol, 41 uL, 6.0 eq) in THF (0.20 mL) at 0° C. under $N_2$. The mixture was stirred at 0-30° C. for 2 hours. The reaction mixture was concentrated under reduced pressure to give a residue. The residue was purified by prep-HPLC (column: Welch Xtimate C18 100×25 mm×3 um; mobile phase: [A: water (0.05% HCl), B: ACN];

B%: 10%-30%) to give Compound 45 (14 mg, 34% yield) as a white solid. LCMS: (ES+) m/z (M+H)+=518.0. $^1$H NMR (400 MHz, DMSO-$d_6$) δ 7.95 (s, 1H), 7.89-7.75 (m, 9H), 5.55-5.49 (m, 1H), 5.33 (t, J=5.2 Hz, 1H), 4.53 (q, J=5.2 Hz, 1H), 4.29 (dd, J=5.2, 6.8 Hz, 1H), 4.21 (dd, J=4.8, 10.4 Hz, 1H), 4.10-4.03 (m, 1H), 3.93 (dd, J=3.2, 10.4 Hz, 1H), 3.81-3.75 (m, 1H).

Example 48: (4'-(6-chloro-2-(((3R,4S,5S)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid (Compound 68)

Compound 68 was synthesized using 46-7B obtained from Example 46 and using methods analogous to those described in Example 47. LCMS: (ES+) m/z (M+H)+= 518.0. $^1$H NMR (400 MHz, DMSO-$d_6$) δ 8.02 (s, 1H), 7.97-7.76 (m, 9H), 5.63-5.56 (m, 1H), 5.40 (t, J=5.2 Hz, 1H), 4.60 (q, J=5.2 Hz, 1H), 4.36 (dd, J=5.2, 6.8 Hz, 1H), 4.28 (dd, J=4.8, 10.4 Hz, 1H), 4.17-4.11 (m, 1H), 4.00 (br dd, J=3.2, 10.4 Hz, 1H).

Example 49: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-sulfonic acid (Compound 69)

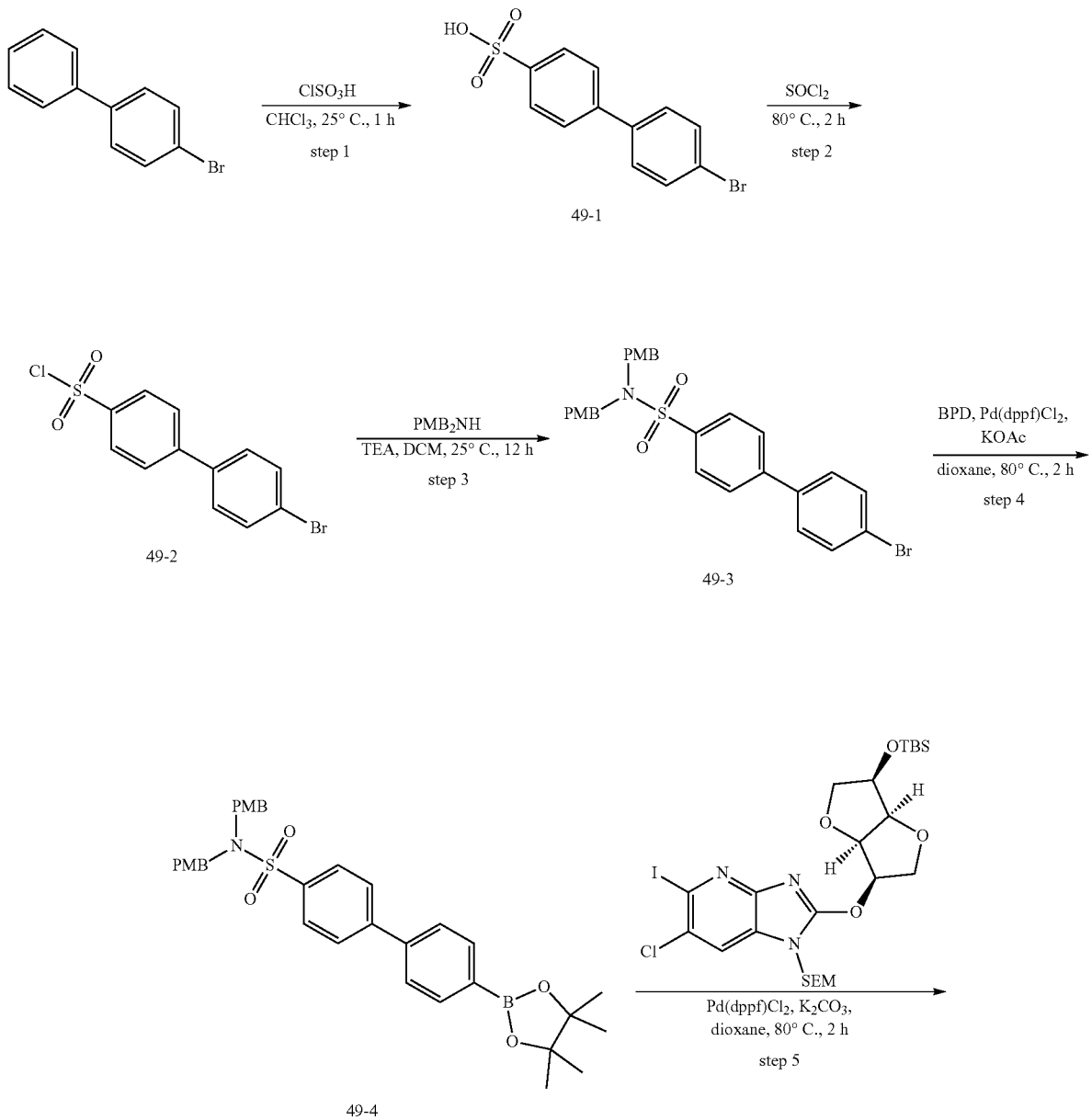

-continued

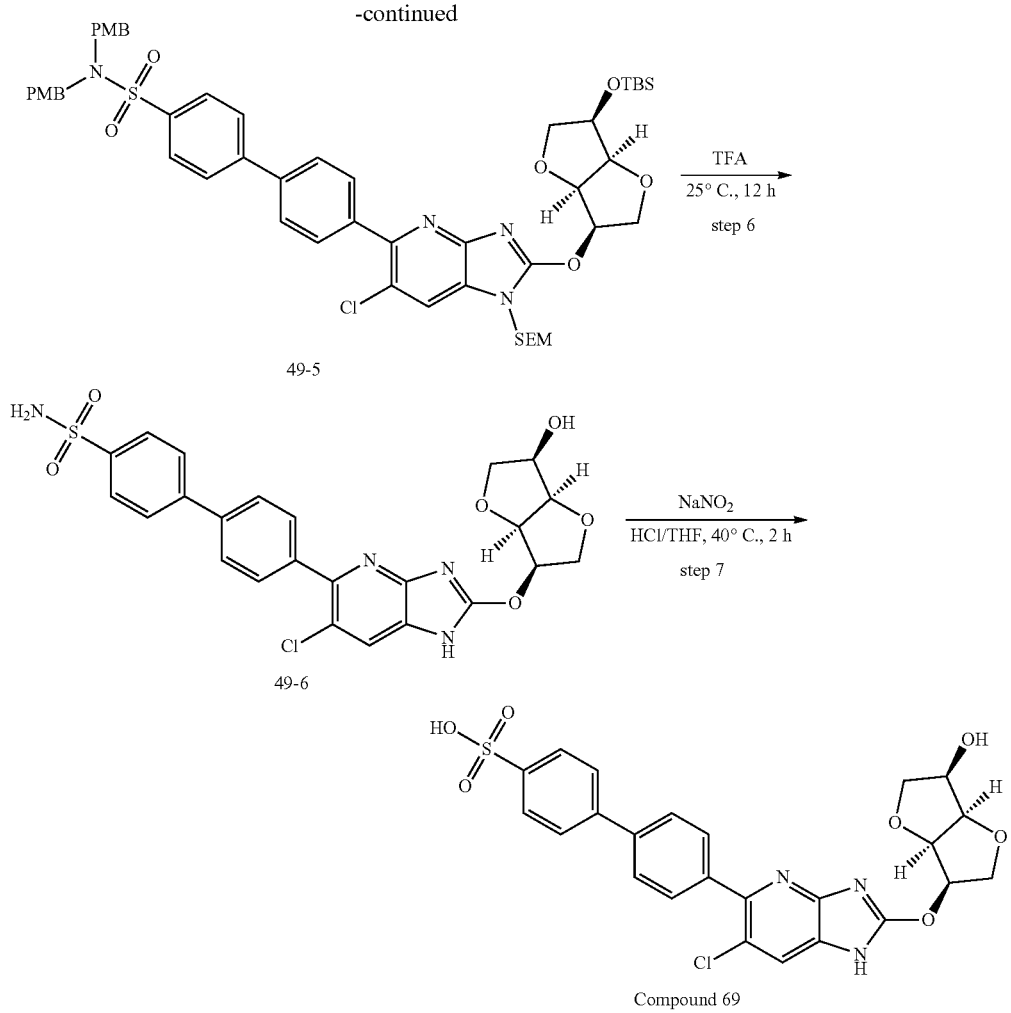

Step 1: To a solution of 1-bromo-4-phenyl-benzene (1 g, 4.3 mmol, 1 eq) in CHCl₃ (4 mL) was added chlorosulfonic acid (0.63 g, 5.4 mmol, 0.36 mL, 1.3 eq). The mixture was stirred at 25° C. for 1 hour. The resulting precipitate was collected by vacuum filtration, washed with DCM at 0° C., then dried to give 49-1 (0.82 mg, crude) as a black brown solid. LCMS: (ES-) m/z (M-1)-=313.0.

Step 2: A mixture of 49-1 (0.49 g, 1.6 mmol, 1 eq) in SOCl₂ (4.9 mL) was stirred at 80 ° C. for 2 hours. The reaction mixture was concentrated under reduced pressure to give 49-2 (0.49 mg, crude) as a black brown solid.

Step 3: To a solution of 49-2 (0.49 g, 1.5 mmol, 1 eq) in DCM (5 mL) was added TEA (0.30 g, 3.0 mmol, 0.41 mL, 2 eq) and 1-(4-methoxyphenyl)-N-[(4-methoxyphenyl)methyl]methanamine (0.46 g, 1.8 mmol, 1.2 eq). The mixture was stirred at 25° C. for 12 hours. The reaction was quenched by addition of H₂O (3 mL) and then extracted with EA (9 mL×3). The combined organic phase was dried over anhydrous Na₂SO₄, filtered and concentrated under pressure to give 49-3 (0.83 g, crude) as a black brown oil. LCMS: (ES+) m/z (M+H)+=574.2.

Step 4: To a solution of 49-3 (0.83 mg, 1.5 mmol, 1 eq) in dioxane (8.3 mL) was added Pd(dppf)Cl₂·CH₂Cl₂ (0.12 g, 0.15 mmol, 0.1 eq), BPD (0.57 g, 2.3 mmol, 1.5 eq) and KOAc (0.37 g, 3.8 mmol, 2.5 eq). The mixture was stirred at 80° C. for 2 hours. The reaction was quenched by addition of H₂O (10 mL) and then extracted with EA (30 mL×3). The combined organic phase was dried over anhydrous Na₂SO₄, filtered and concentrated under pressure to give 49-4 (1.9 g, crude) as a black brown solid. LCMS: (ES+) m/z (M+H)+=622.4.

Step 5: To a solution of 49-4 (2 g, 3.4 mmol, 2 eq) in dioxane (20 mL) was added 2-[[2-[[(3R,3aR,6R,6aS)-6-[tert-butyl(dimethyl)silyl]oxy-2,3,3a,5,6,6a-hexahydrofuro[3,2-b]furan-3-yl]oxy]-6-chloro-5-iodo-imidazo[4,5-b]pyridin-1-yl]methoxy]ethyl-trimethyl-silane (1.1 g, 1.7 mmol, 1 eq), K₂CO₃ (0.46 g, 3.3 mmol, 2 eq) and Pd(dppf)Cl₂·CH₂Cl₂ (0.14 g, 0.17 mmol, 0.1 eq). The mixture was stirred at 80° C. for 2 hours. The reaction was quenched by addition of H₂O (30 mL) and then extracted with EA (30 mL×3). The combined organic phase was dried over anhydrous Na₂SO₄, filtered and concentrated under pressure. The residue was purified by flash silica gel chromatography (ISCO®; 25 g SepaFlash® Silica Flash Column, Eluent of 0-70% Ethyl acetate/Petroleum ether gradient) to give 49-5 (1.8 g, 72% yield) as a yellow solid. LCMS: (ES+) m/z (M+H)+=1013.6.

Step 6: A mixture of 49-5 (1.7 g, 1.7 mmol, 1 eq) in TFA (18 mL) was stirred at 25° C. for 12 hours. The reaction mixture was concentrated under reduced pressure to give 49-6 (1.3 g, crude) as a black brown solid. LCMS: (ES+) m/z (M+H)+=529.2.

Step 7: To a solution of 49-6 (0.40 g, 0.76 mmol, 1 eq) in conc. HCl (12M in H$_2$O, 3.3 mL)/THF (3.5 mL) was added NaNO$_2$ (0.13 g, 1.9 mmol, 2.5 eq). The mixture was stirred at 40° C. for 2 hours. The reaction was quenched by addition of saturated aqueous Na$_2$CO$_3$ solution and then extracted with THF (10 mL×3). The combined organic phase was washed with H$_2$O (10 mL), dried over anhydrous Na$_2$SO$_4$, filtered and concentrated under pressure. The mixture was further purification by prep-HPLC (column: Welch Xtimate C18 150×25 mm×5 um; mobile phase: [A: water (0.05% HCl), B: ACN]; B%: 12%-42%) and then lyophilized to give Compound 69 (7.9 mg, —umol, 1% yield, HCl) as a white solid. LCMS: (ES+) m/z (M+H)+=530.2. $^1$H NMR (400 MHz, DMSO-d$_6$) δ ppm 7.96 (s, 1H), 7.81-7.72 (m, 4H), 7.71 (s, 4H), 5.49 (q, J=5.6 Hz, 1H), 4.84 (t, J=5.2 Hz, 1H), 4.37 (br s, 1H), 4.16 (br s, 1H), 4.09 (br s, 1H), 3.95-3.91 (m, 1H), 3.79 (t, J=7.2 Hz, 1H), 3.44 (t, J=8.4 Hz, 1H).

Example 50: 4'-(6-chloro-(((3R,3aR,6R,6aR)-6-hydroxy-hexahydrofuro[3,2-b]furan-3-yl)oxy)-1H-benzo [d]imidazol-5-yl)-N-(2-(2-hydroxyethoxy)ethyl)-[1,1'-biphenyl]-4-sulfonamide (Compound 70)

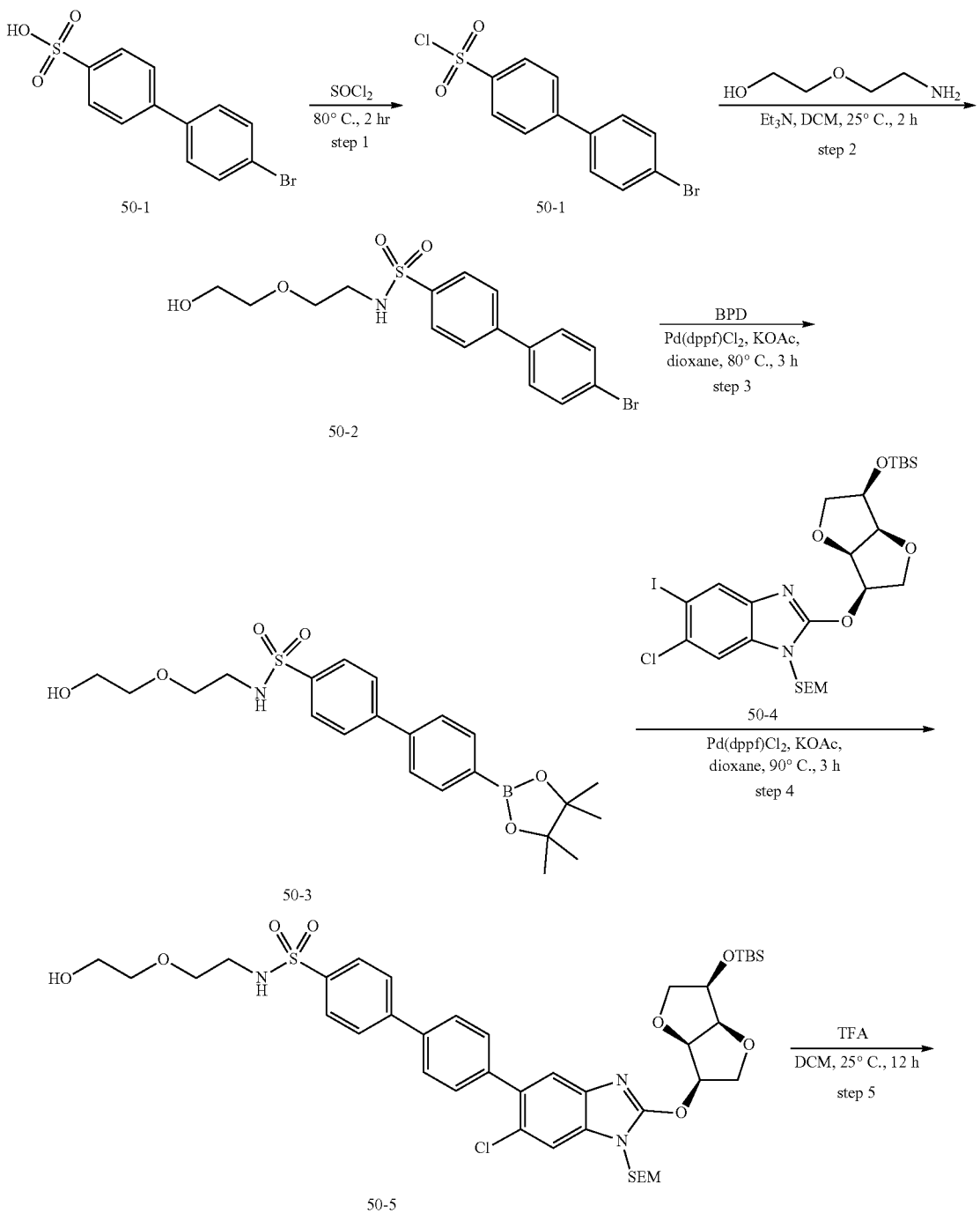

-continued

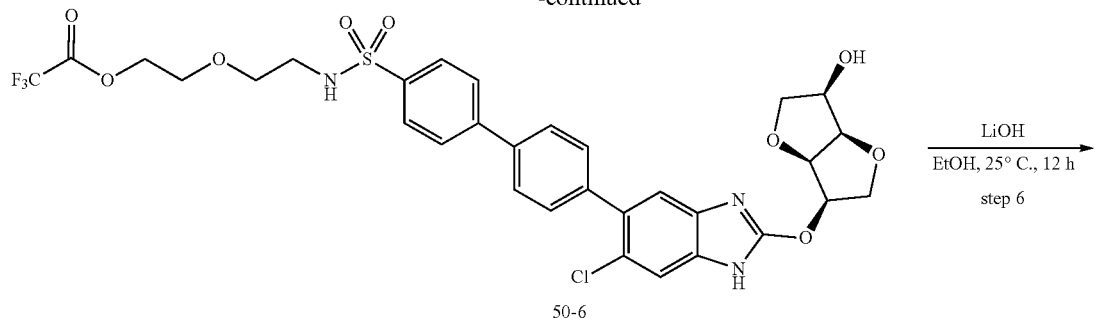

50-6

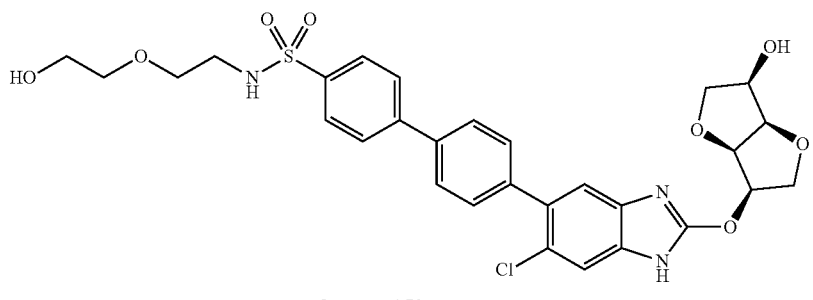

Compound 70

Step 1: A mixture of 4'-bromo-[1,1'-biphenyl]-4-sulfonic acid (2.0 g, 6.4 mmol, 1 eq) in SOCl₂ (20 mL) was stirred at 80° C. for 2 hours. The reaction mixture was concentrated in vacuo to give 50-1 (2.0 g, crude) as a brown solid.

Step 2: A mixture of 50-1 (2.0 g, 6.0 mmol, 1 eq), 2-(2-aminoethoxy)ethanol (0.71 g, 6.6 mmol, 0.67 mL, 1.1 eq), and TEA (1.8 g, 18 mmol, 2.5 mL, 3 eq) in DCM (20 mL) was stirred at 25° C. for 2 hours. The mixture was poured into water (20 mL) and then extracted with ethyl acetate (20 mL×2). The combine organic layers were washed with saturated brine (20 mL×2) and concentrated in vacuo to give 50-2 (2.4 g, crude) as a brown solid. LCMS: (ES+) m/z (M+H)+=400.2.

Step 3: A mixture of 50-2 (2.3 g, 5.8 mmol, 1 eq), BPD (2.2 g, 8.6 mmol, 1.5 eq), Pd(dppf)Cl₂·CH₂Cl₂ (0.71 g, 0.87 mmol, 0.15 eq) and KOAc (1.7 g, 17 mmol, 3 eq) in dioxane (25 mL) was degassed and purged with N2 3 times, and then the mixture was stirred at 80° C. for 3 hours under N₂ atmosphere. The mixture was poured into water (30 mL), then extracted with ethyl acetate (2×30 mL). The combine organic layers were washed with saturated brine (2×30 mL) and concentrated in vacuo. The residue was purified by column chromatography (SiO₂, Petroleum ether/Ethyl acetate=50:1 to 1:1) to afford 50-3 (2.1 g, 81% yield) as a brown solid. LCMS: (ES+) m/z (M+H)+=448.2.

Step 4: A mixture of 50-3 (1.5 g, 3.4 mmol, 1 eq) , 50-4 (2.7 g, 4.0 mmol, 1.2 eq; synthesized by procedures analogous to those described in Example 1), Pd(dppf)Cl₂ (0.55 g, 0.75 mmol, 0.1 eq), KOAc (1.0 g, 10 mmol, 3 eq) and H₂O (4 mL) in dioxane (20 mL) was degassed and purged with N₂ 3 times. The mixture was stirred at 90° C. for 3 hours under N₂ atmosphere. The mixture was poured into water (30 mL), then extracted with ethyl acetate (2×30 mL). The combine organic layers were washed with saturated brine (2×30 mL) and concentrated in vacuo. The residue was purified by column chromatography (SiO₂, Petroleum ether/ Ethyl acetate=50:1 to 0:1) to afford 50-5 (2.1 g, 81% yield) as a brown solid. LCMS: (ES+) m/z (M+H)+=448.2.

Step 5: A solution of 50-5 (0.5 g, 0.59 mmol, 1 eq) and TFA (3.8 g, 34 mmol, 2.5 mL, 58 eq) in DCM (5 mL) was stirred at 25° C. for 12 hours. The mixture was concentrated in vacuo to give 50-6 (0.75 g, crude) as a black solid. LCMS: (ES+) m/z (M+H)+=712.1.

Step 6: A solution of 50-6 (0.42 g, 0.51 mmol, 1 eq, TFA salt), LiOH·H2O (64 mg, 1.5 mmol, 3 eq) and H₂O (1.6 mL) in EtOH (8 mL) was stirred at 25° C. for 6 hours. The reaction mixture was concentrated in vacuo. The residue was purified by Prep-HPLC (column: Phenomenex luna C18 150×25 mm×10 um; mobile phase: [A: water (0.225% FA), B: ACN]; B%: 27%-57%) to afford Compound 70 (68 mg, 21% yield) as a yellow solid. LCMS: (ES+) m/z (M+H)+= 616.2. ¹H NMR (400 MHz, DMSO-d₆) δ 12.25 (s, 1H), 7.98 (d, J=8.0 Hz, 2H), 7.90 (d, J=8.0 Hz, 2H), 7.82 (d, J=8.0 Hz, 2H), 7.75 (s, 1H), 7.58 (d, J=8.0 Hz, 2H), 7.55-7.22 (m, 2H), 5.54-5.38 (m, 1H), 4.98 (d, J=6.8 Hz, 1H), 4.83 (t, J=4.8 Hz, 1H), 4.55 (t, J=5.2 Hz, 1H), 4.37 (t, J=4.8 Hz, 1H), 4.23-4.09 (m, 2H), 3.95-3.85 (m, 1H), 3.95-3.85 (m, 1H), 3.84-3.74 (m, 1H), 3.48-3.35 (m, 7H), 2.89-3.03 (q, J=5.2 Hz, 2H).

Example 51: 4'-(6-chloro-2—O(3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1,1'-biphenyl]-4-sulfonamide (Compound 71)

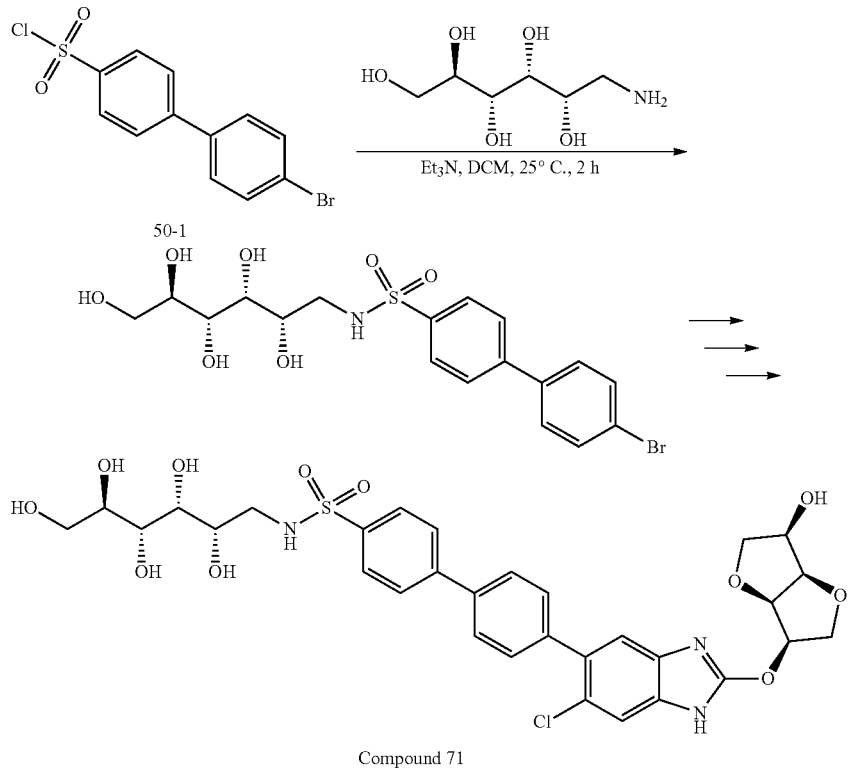

Compound 71

Compound 71 was synthesized using methods analogous to those described in Example 50. LCMS: (ES+) m/z (M)+= 692.2. $^1$H NMR (400 MHz, DMSO-$d_6$) δ 12.39-12.17 (m, 1H) 7.98-7.93 (m, 2H) 7.92-7.87 (m, 2H) 7.83 (d, J=8.0 Hz, 2H) 7.57 (br d, J=8.0 Hz, 2H) 7.52 (br d, J=5.2 Hz, 1H) 5.48-5.38 (m, 1H) 4.97 (d, J=6.8 Hz, 1H) 4.86-4.73 (m, 2H) 4.47 (d, J=5.6 Hz, 1H) 4.39-4.26 (m, 4H) 4.19-4.09 (m, 2H) 3.94-3.84 (m, 1H) 3.79 (t, J=7.2Hz, 1H) 3.69-3.59 (m, 3H) 3.58-3.52 (m, 1H) 3.44 (br t, J=8.4 Hz, 3H) 3.37 (br dd, J=10, 5.2 Hz, 4H).

Example 52: 4'-(6-chloro-2-0 (3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-sulfonamide (Compound 72)

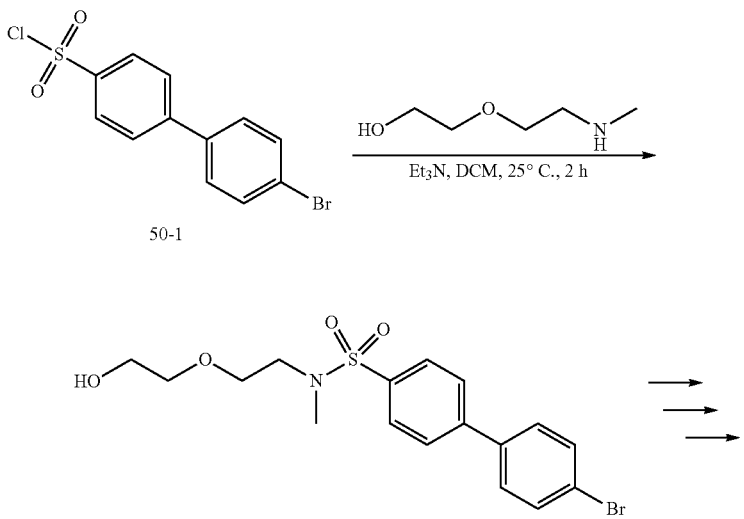

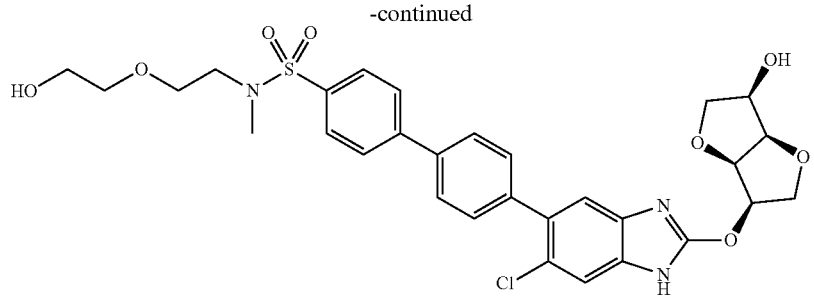
Compound 72
Compound 77 was synthesized using methods analogous to those described in Example 50. LCMS: (ES+) m/z (M+H)+=630.1. $^1$ NMR (400 MHz, DMSO-d$_6$) δ 12.30 (s, 1H), 8.00 (d, J=8.4 Hz, 2H), 7.92-7.79 (q, 4H), 7.60 (d, J=8.4 Hz, 2H), 7.40 (s, 1H), 7.15 (s, 1H), 5.45 (s, 1H), 5.00 (d, J=6.8 Hz, 1H), 4.80 (t, J=4.8 Hz, 1H), 4.58 (t, J=5.2 Hz, 1H), 4.37 (t, J=4.8 Hz, 1H), 4.26-4.06 (m, 2H), 3.95-3.74 (m, 2H), 3.57 (t, J=5.6 Hz, 2H), 3.50-3.44 (m, 3H), 3.43-3.38 (m, 2H), 3.22 (t, J=4.2 Hz, 2H), 2.80 (s, 3H).
Example 53: (2R,3R,4R,5S)-6-(1-(4'-(6-chloro-2-(((3R,3aR,6R,6aR)-6-hydroxyhexahydrofuro[3,2-b]furan-3-yl)oxy)-1H-imidazo[4,5-13]pyridin-5-yl)-[1,1'-biphenyl]-4-yl)ethyl)amino)hexane-1,2,3,4,5-pentaol (Compound 73)
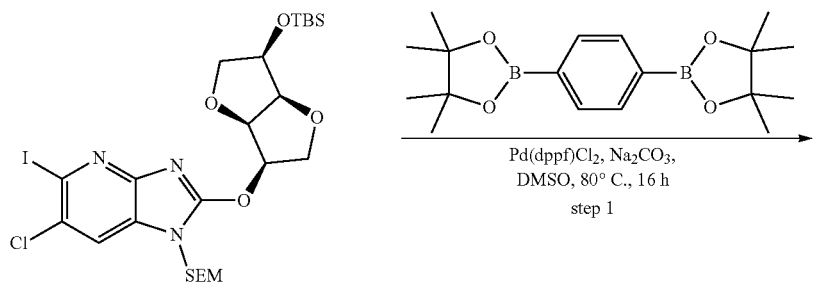
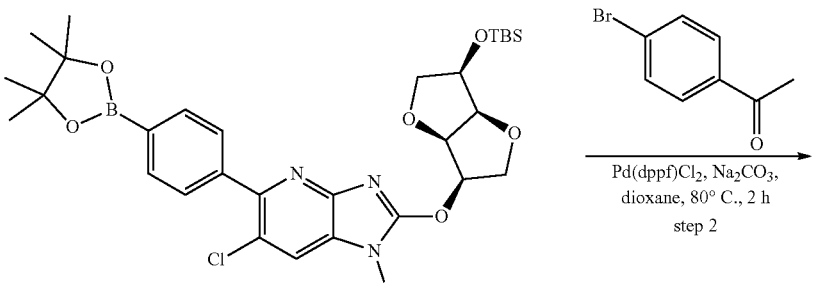
53-1
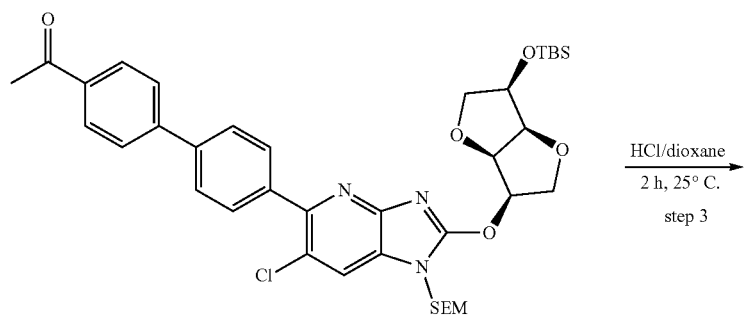
53-2

-continued

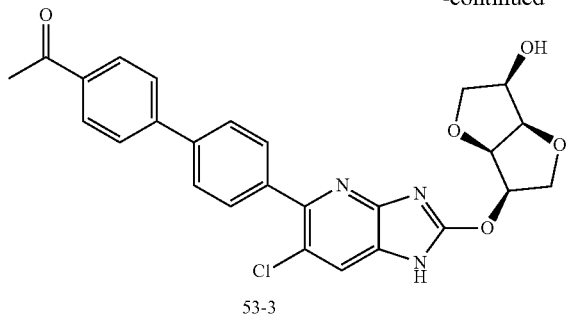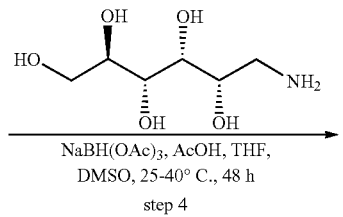

53-3

NaBH(OAc)₃, AcOH, THF,
DMSO, 25-40° C., 48 h step 4

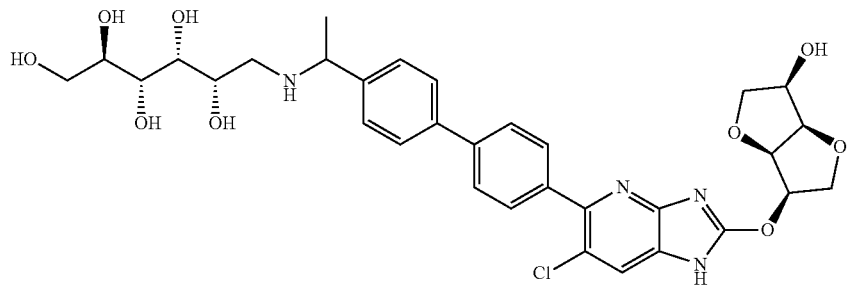

Compound 73

Step 1: A mixture of 2-[[2-[[(3R,3aR,6R,6aS)-6-[tert-butyl(dimethyl)silyl]oxy-2,3,3a,5,6,6a-hexahydrofuro[3,2-b]furan-3-yl]oxy]-6-chloro-5-iodo-imidazo [4,5-b]pyridin-1-yl]methoxy]ethyl-trimethyl-silane (1.5 g, 2.25 mmol, 1 eq) and 4,4,5,5-tetramethyl-2-[4-(4,4,5,5-tetramethyl-1,3,2-dioxaborolan-2-yl)phenyl]-1,3,2-dioxaborolane (889 mg, 2.69 mmol, 1.2 eq) in DMSO (15 mL) was degassed and purged with N₂ 3 times. Then to the mixture was added Na₂CO₃ (661 mg, 6.24 mmol, 2.8 eq) and Pd(dppf)Cl₂.CH₂Cl₂ (183 mg, 225 umol, 0.1 eq). The mixture was stirred at 80° C. for 16 hours under N₂ atmosphere. The reaction mixture was quenched by addition of H₂O (50 mL) and extracted with EA (50 mL×3). The combined organic layers were washed with saturated aqueous NaCl (50 mL×2), dried over Na₂SO₄, filtered and concentrated under reduced pressure to give a residue. The residue was purified by column chromatography (SiO₂, Petroleum ether/Ethyl acetate=4/1 to 3/1) to give 53-1 (730 mg, 44% yield) as a brown oil. LCMS: (ES+) m/z (M)+=744.2.

Step 2: To a solution of 53-1 (400 mg, 537 umol, 1 eq) and 1-(4-bromophenyl)ethanone (128 mg, 645 umol, 1.2 eq) in dioxane (4 mL) and H₂O (1.0 mL) was added K2CO₃ (371 mg, 2.69 mmol, 5 eq) and Pd(dppf)Cl₂.CH₂Cl₂ (88 mg, 107 umol, 0.2 q). The mixture was stirred at 80° C. for 2 hours. The reaction mixture was quenched by addition of H₂O (30 mL) and extracted with EA (20 mL×3). The combined organic layers were washed with saturated aqueous NaCl (20 mL×2), dried over Na₂SO₄, filtered and concentrated under reduced pressure to give a residue. The residue was purified by column chromatography (SiO₂, Petroleum ether/ Ethyl acetate=5/1 to 4/1) to give 53-2 (232 mg, 59% yield) as a brown oil. LCMS: (ES+) m/z (M)+=736.3.

Step 3: A solution of 53-2 (230 mg, 312 umol, 1 eq) in HCl/dioxane (4 M, 1.95 mL, 25 eq) was stirred at 25° C. for 2 hours. The reaction mixture was quenched by addition of H₂O (20 mL), and then the pH was adjusted to 7 with saturated aqueous Na₂CO₃ solution. The combined organic layers were washed with EA (20 mL×3), dried over Na₂SO₄, filtered and concentrated under reduced pressure to give 53-3 (113 mg, crude) as yellow solid, which was used into the next step without further purification.

Step 4: To a solution of 53-3 (190 mg, 386 umol, 1 eq) and (2R,3R,4R,5S)-6-aminohexane-1,2,3,4,5-pentaol (280 mg, 1.54 mmol, 4 eq) in THF (5 mL) and DMSO (5 mL) was added AcOH (70 mg, 1.16 mmol, 66 uL, 3 eq) and NaBH(OAc)₃ (164 mg, 772 umol, 2 eq). The mixture was stirred at 25-40° C. for 48 hours. The reaction solution was concentrated under reduced pressure to remove THF and filtered, and then the mixture was purified by prep-HPLC (column: Phenomenex Synergi Polar-RP 100×25 mm×4 um; mobile phase: [A: water (0.225% FA), B: ACN]; B%: 10%-40%) to give Compound 73 (35.37 mg, 58% yield) as a white solid. LCMS: (ES+) m/z (M)+=657.1. ¹H NMR (400 MHz, CD₃OD) δ 8.53 (s, 1H), 7.85-7.71 (m, 7H), 7.57 (d, J=8.2 Hz, 2H), 5.55 (q, J=5.2 Hz, 1H), 4.97 (t, J=5.2 Hz, 1H), 4.47 (t, J=4.8 Hz, 1H), 4.39-4.24 (m, 2H), 4.21-4.14 (m, 1H), 4.14-4.08 (m, 1H), 4.06-3.95 (m, 1H), 3.93-3.86 (m, 1H), 3.84-3.73 (m, 2H), 3.70-3.57 (m, 4H), 3.09-3.02 (m, 1H), 3.00-2.86 (m, 1H), 1.67 (d, J=6.8 Hz, 3H).

Example 54: (3R,3aR,6R,6aR)-6-(6-chloro-5-(2'-hydroxy-4'-((2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol (Compound 74)

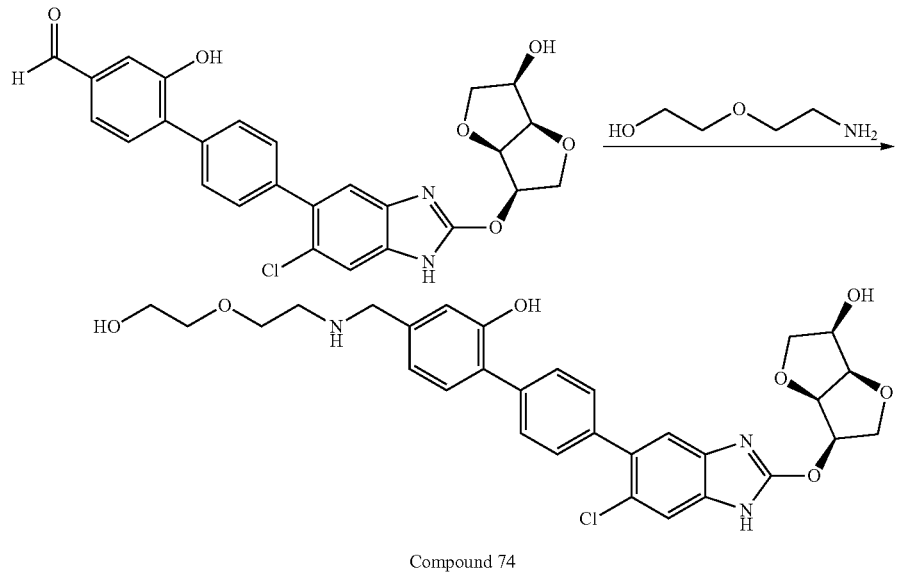

Compound 74

Compound 74 was synthesized using methods analogous to those described in Example 53. LCMS: (ES+) m/z (M)+= 582.4. $^1$H NMR (400 MHz, CD$_3$OD) δ 8.53-8.38 (m, 1H), 7.63 (d, J=8.0 Hz, 2H), 7.53-7.38 (m, 4H), 7.36-7.26 (m, 1H), 7.10-7.00 (m, 2H), 5.45 (q, J=5.2 Hz, 1H), 4.94 (t, J=5.2 Hz, 1H), 4.47 (t, J=5.2 Hz, 1H), 4.33-4.25 (m, 1H), 4.22-4. —(m, 3H), 4.11 -4.04 (m, 1H), 3.91 (dd, J=8.4, 6.8 Hz, 1H), 3.81-3.70 (m, 4H), 3.65-3.57 (m, 3H), 3.29-3.25 (m, 2H).

Example 55: 4'-(6-chloro-2-(((3R,3aR,6R,6aR)-6-hydroxyhexahydrofuro[3,2-b]furan-3-yl)oxy)-1H-benzo[d]imidazol-5-yl)-2-hydroxy-N-(2-(2-hydroxyethoxy)ethyl)-[1,1'-biphenyl]-4-carboxamide (Compound 75)

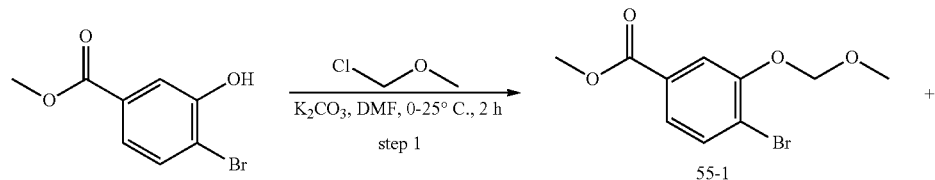

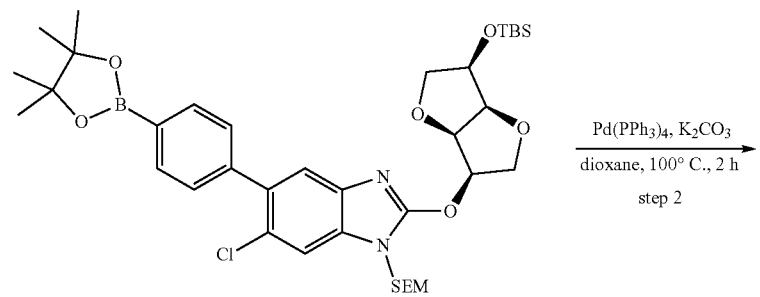

-continued
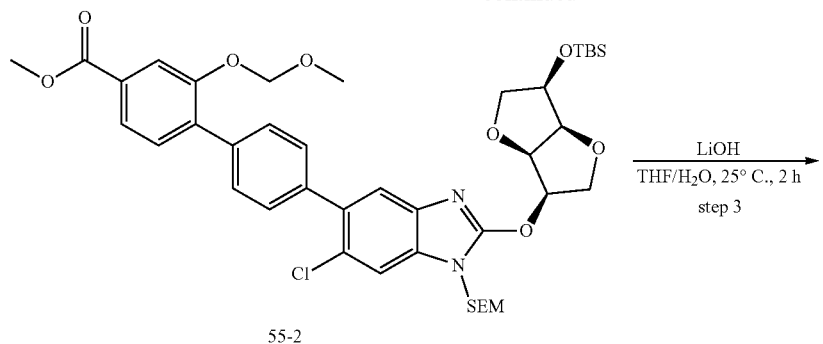
55-2
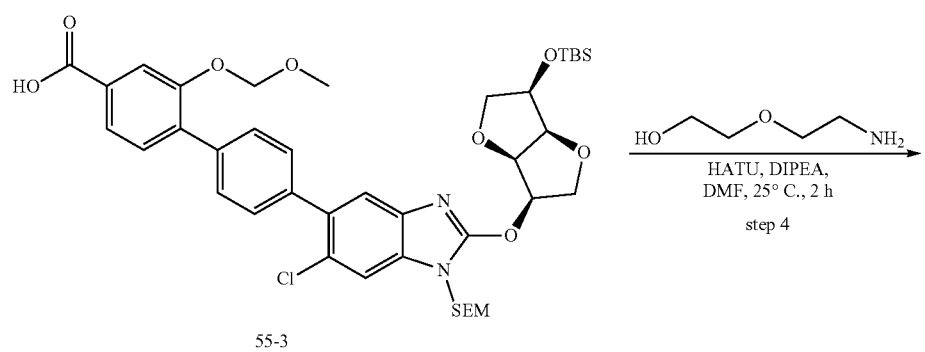
55-3
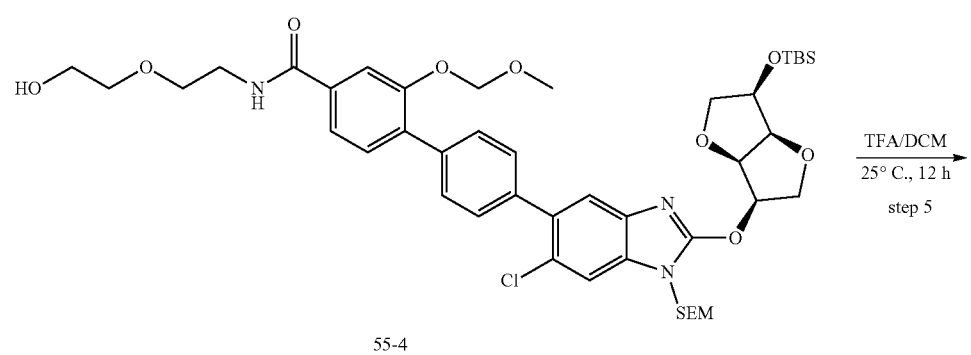
55-4
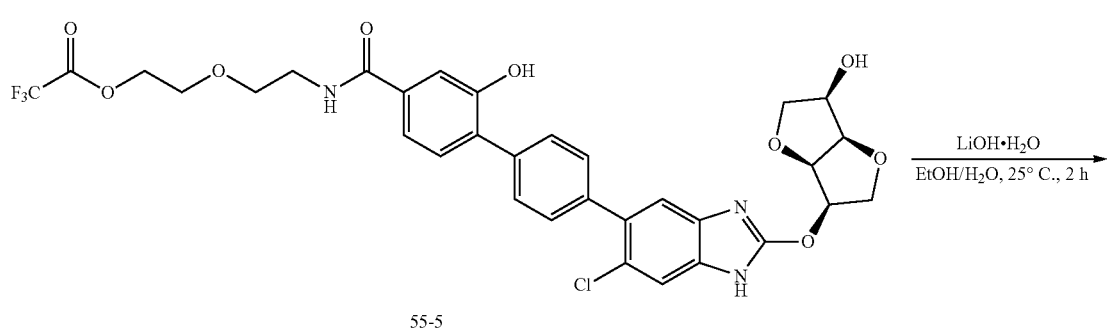
55-5
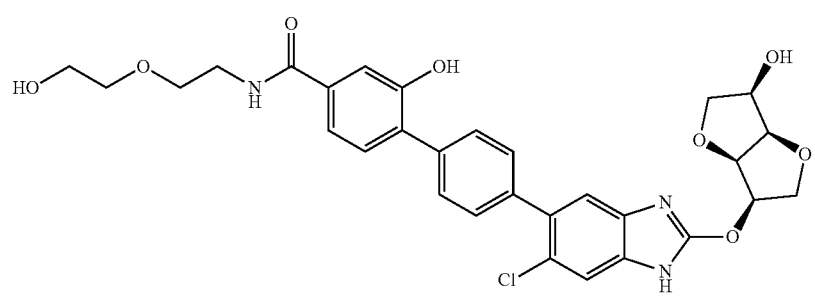
Compound 75

Step 1: To a solution of methyl 4-bromo-3-hydroxybenzoate (2.5 g, 11 mmol, 1 eq) in DMF (30 mL) was added K2CO3 (3.1 g, 23 mmol, 2.1 eq). Then chloro(methoxy)methane (1.3 g, 16 mmol, 1.2 mL, 1.5 eq) was added dropwise at 0° C. The mixture was stirred at 25° C. for 2 hours. The reaction was quenched by addition of H$_2$O (15 mL) and then extracted with EA (15 mL×3). The combined organic phase was washed with saturated brine (15 mL×2), dried over anhydrous Na$_2$SO$_4$, filtered and concentrated under pressure. The residue was purified by flash silica gel chromatography (ISCO®; 20 g SepaFlash® Silica Flash Column, Eluent of 0-50% Ethyl acetate/Petroleum ether gradient) to give 55-1 (1.6 g, 54% yield) as a colorless oil. $^1$H NMR (400 MHz, CDCl$_3$) δ ppm 7.77 (d, J=2.0 Hz, 1H), 7.59-7.65 (m, 1H), 7.55 (dd, J=8.0, 2.0 Hz, 1H), 5.30 (s, 2H), 3.90 (s, 3H), 3.53 (s, 3H).

Step 2: To a solution of 55-1 (1.2 g, 1.6 mmol, 1 eq) and 2-(((3R,3aR,6R,6aS)-6-(tert-butyldimethylsilyl)oxy)hexahydrofuro[3,2-b]furan-3-yl)oxy)-6-chloro-5-(4-(4,4,5,5-tetramethyl-1,3,2-dioxaborolan-2-yl)phenyl)-1-(2-(trimethylsilyl)ethoxy)methyl)-1H-benzo[d]imidazole (prepared with procedures analogous to Example 53 for compound 53-1) (0.53 g, 1.9 mmol, 1.2 eq) in dioxane (12 mL) was added Pd(PPh$_3$)$_4$ (0.28 g, 0.24 mmol, 0.15 eq) and K$_2$CO$_3$ (0.67 mg, 4.8 mmol, 3 eq). The mixture was stirred at 100° C. for 2 hours. The reaction was quenched by addition of H$_2$O (10 mL) and then extracted with DCM (12 mL×3). The combined organic phase was washed with saturated brine (10 mL×2), dried over anhydrous Na$_2$SO$_4$, filtered and concentrated under pressure. The residue was purified by flash silica gel chromatography (ISCO®; 24 g SepaFlash® Silica Flash Column, Eluent of 0-45% Ethyl acetate/Petroleum ethergradient) to give 55-2 (0.47 g, 23% yield) as a colorless oil. LCMS: (ES+) m/z (M+H)+=811.6.

Step 3: To a solution of 55-2 (0.47 g, 0.58 mmol, 1 eq) in THF (4.7 mL)/H$_2$O (0.94 mL) was added LiOH·H2O (49 mg, 1.16 mmol, 2 eq). The mixture was stirred at 25° C. for 2 hours. The reaction was adjusted to pH 6 with 1M aqueous HCl solution, then extracted with EA (7 mL×3). The combined organic phase was washed with saturated brine (7 mL×2), dried over anhydrous Na$_2$SO$_4$, filtered and concentrated under pressure. The crude product (50 mg) was further purification by pre-HPLC (column: Phenomenex luna C18 150×25 mm×10 um; mobile phase: [A: water (0.225% FA), B: ACN]; B%: 80%-100%) to give 55-3 (0.48 g, 59% yield) as a colorless oil. LCMS: (ES+) m/z (M+H)+=797.6.

Step 4: To a solution of 55-3 (0.48 g, 0.59 mmol, 1 eq) in DMF (4 mL) was added HATU (0.34 g, 0.9 mmol, 1.5 eq), 2-(2-aminoethoxy)ethanol (75 mg, 0.72 mmol, 71 uL, 1.2 eq) and DIPEA (0.23 g, 1.8 mmol, 0.31 mL, 3 eq). The mixture was stirred at 25° C. for 2 hours. The reaction was quenched by addition of H$_2$O and then extracted with EA (8 mL×3). The combined organic phase was washed with saturated brine (8 mL×2), dried over anhydrous Na$_2$SO$_4$, filtered and concentrated under pressure to give 55-4 (0.46 g, crude) as a yellow oil. LCMS: (ES+) m/z (M+H)+=884.5.

Step 5: A mixture of 55-4 (0.45 mg, 0.51 mmol, 1 eq) in DCM (0.5 mL)/TFA (0.1 mL) was stirred at 25° C. for 12 hours. The reaction mixture was directly concentrated under reduced pressure to give 55-5 (0.55 g, crude) as a red oil. LCMS: (ES+) m/z (M+H)+=692.2.

Step 6: To a solution of 55-5 (0.55 g, 0.80 mmol, 1 eq) in EtOH (5 mL)/H$_2$O (1 mL) was added LiOH·H2O (0.10 g, 2.4 mmol, 3 eq). The mixture was stirred at 25° C. for 2 hours. The reaction mixture was directly concentrated under reduced pressure. The mixture was further purification by prep-HPLC (column: Phenomenex luna C18 150×25 mm×10 um; mobile phase: [A: water (0.225% FA), B: ACN]; B%: 20%-50%) to give Compound 75 (76 mg, 15% yield) as a white solid. LCMS: (ES+) m/z (M+H)+=596.2. $^1$-E1 NMR (400 MHz, DMSO-d$_6$) δ 12.26 (br s, 1H), 9.91 (s, 1H), 8.43 (t, J=5.6 Hz, 1H), 7.74-7.33 (m, 9H), 5.49-5.41 (m, 1H), 4.97 (br d, J=6.4 Hz, 1H), 4.83 (t, J=5.2 Hz, 1H), 4.61 (br t, J=5.2 Hz, 1H), 4.41-4.33 (m, 1H), 4.18-4.08 (m, 2H), 3.88 (dd, J=9.2, 6.4 Hz, 1H), 3.83-3.75 (m, 1H), 3.57-3.43 (m, 4H), 3.48-3.41 (m, 5H).

II. Biological Evaluation Example A-1: In Vitro pAMPK1 Kinase Activation Assay

Compound effect on AMPK enzyme activation was determined in a cell-free format with a 12-point concentration curve. The ADP-Glo detection system was used to determine phosphorylation of a SAMS peptide substrate. Recombinant AMPK α1/β1/γ1 complex was pre-activated by phosphorylation with CAMKK2 followed by incubated with compound for 15 minutes prior to the SAMS phosphorylation reaction. Activity curves and EC$_{50}$ values were fitted by interpolation to an ATP:ADP standard curve as indicated by the ADP-Glo manufacturer using Prism software.

Results for exemplary compounds are shown in Table A.

TABLE A

| Compound | EC$_{50}$ (nM)[a] |
|---|---|
| 1 | 0.05 |
| 2 | 1.4 |
| 3 | 0.09 |
| 4 | 0.1 |
| 5 | 0.86 |
| 6 | 0.62 |
| 7 | 1.22 |
| 8 | 1.78 |
| 9 | 1.61 |
| 10 | 0.40 |
| 11 | 0.46 |
| 12 | 152 |
| 14 | 0.50 |
| 22 | 0.63 |
| 29 | 0.56 |
| 30 | 0.65 |
| 31 | 0.85 |
| 32 | 0.76 |
| 33 | 0.96 |
| 36 | 0.84 |
| 37 | 3.6 |
| 38 | 2.4 |
| 40 | 1.08 |
| 45 | >10000 |
| 48 | 1.16 |
| 49 | 1.76 |
| 50 | 1.46 |
| 51 | 0.72 |
| 52 | 0.81 |
| 53 | 0.23 |
| 54 | 0.57 |
| 55 | 2.22 |
| 56 | 0.93 |
| 57 | 0.89 |
| 58 | 0.93 |
| 59 | 1.04 |
| 60 | 0.85 |
| 61 | 1.36 |
| 62 | 1.30 |
| 63 | 1.09 |
| 64 | 1.40 |
| 65 | 0.77 |
| 66 | 0.80 |
| 67 | 0.93 |
| 68 | >10000 |
| 69 | 1.84 |
| 70 | 1.51 |
| 71 | 0.63 |
| 72 | 1.38 |

TABLE A-continued

| Compound | $EC_{50}$ (nM)$^a$ |
|---|---|
| 73 | 1.33 |
| 74 | 0.15 |
| 75 | 0.37 |
| MK-8722 | 10.4 |
| 60 | 0.85 |

The compounds of the present invention are one to two orders of magnitude more active than the clinically investigated systemic AMPK activator, MK-8722 (*Science* 2017, 357 (6350):507-511).

Example A-2: Pharmacokinetic Assays
Oral Bioavailability

Selected compounds were tested for pharmacokinetics in C57BL/6 mice. Compounds 1, 4, 31, 32, 40, 55, 57 and 60 were dosed IV at 1 mg/kg as a formulation of 0.2 mg/mL in 5% DMSO+30% PEG400+65% water and were dosed PO at 30 mg/kg as a formulation of 3 mg/mL in 0.25% MC+5% Tween 80+0.02% SDS. Compound 2 was dosed IV at 1 mg/kg as a formulation of 0.2 mg/mL in 5% ethanol +95% saline and was dosed PO at 30 mg/kg as a formulation of 3 mg/mL in 0.25% MC+5% Tween 80+0.02% SDS.

Compounds 1, 2, 4, and 32 were shown to have oral bioavailability of less than 1%; Compounds 31, 40, and 57 were shown to have oral bioavailability of less than 10%; and Compounds 55 and 60 were shown to have oral bioavailability of less than 15%.

Following IV administration, Compounds 4 and 32 have a volume of distribution<1 L/kg, and Compounds 1, 2, 31, 40, 55, 57, and 60 have a volume of distribution of <5 L/kg. Additionally, the half-life for Compound 4 was shown to be 1.4 h and for Compound 31 was shown to be 1.7 h. Half-lives for the other compounds tested were between 2 and 6 hours. This indicates that a smaller portion of the absorbed dose makes it into tissues and that any absorbed dose is eliminated rather quickly for the compounds of the present invention, such as Compound 4, which in turn have a greatly reduced risk of causing systemic AMPK activation compared to the systemic AMPK activator MK-8722, which has an oral bioavailability of 82% (*Science* 2017, 357 (6350):507-511).

Example A-3: Permeability Assessment in the Caco-2 Cell Monolayer

Caco-2 cells purchased from ATCC were seeded onto polyethylene membranes (PET) in 96-well BD Insert plates at $1\times10^5$ cells/cm$^2$, and refreshed medium every 4-5 days until to the 21$^{st}$ to 28$^{th}$ day for confluent cell monolayer formation. The transport buffer in the study was HBSS with 10 mM HEPES at pH 7.40±0.05. Test compounds were tested at 2 µM bi-directionally in duplicate. Digoxin was tested at 10 µM bi-directionally in duplicate, while nadolol and metoprolol were tested at 2 µM in A to B direction in duplicate. Final DMSO concentration was adjusted to less than 1%.

The plate was incubated for 2 hours in $CO_2$ incubator at 37±1° C., with 5% $CO_2$ at saturated humidity without shaking. All samples were mixed with acetonitrile containing internal standard and were centrifuged at 4000 rpm for 10 min. Subsequently, 100 µL supernatant solution was diluted with 100 µL distilled water for LC/MS/MS analysis. Concentrations of test and control compounds in starting solution, donor solution, and receiver solution were quantified by LC/MS/MS, using peak area ratio of analyte/internal standard.

Results for exemplary compounds are shown in Table B.

TABLE B

| Compound | Mean $P_{app}$ ($10^{-6\ cm/s}$) A to B | B t oA | Efflux Ratio | Mean Recovery (%) A to B | B to A |
|---|---|---|---|---|---|
| Nadolol (control: low permeability) | 0.08 | ND | — | 97.74 | ND |
| Metoprolol (control: high permeability) | 16.37 | ND | — | 90.00 | ND |
| Digoxin (Pgp substrate) | <0.03 | 12.70 | >437.79 | <90.79 | 92.23 |
| Compound 1 | <0.25 | 0.73 | >2.90 | <82.61 | 89.90 |
| Compound 4 | <0.480 | 0.710 | >1.48 | <99.6 | 102.1 |
| Compound 31 | 0.115 | 31.7 | 275 | 83.2 | 97.8 |

Compounds 1 and 31 were shown to have a large BA/AB efflux ratio (>2). These data indicate that the compounds have low permeability and are likely a substrates of intestinal efflux transporters. Compound 4 was shown to have low permeability.

Example A-4: In vitro MDCK Epithelial Permeability Assay

In order to quantitatively measure the effects of transporter substrate AMPK activators on epithelial permeability in vitro, standard calcium switch protocols from the literature were adapted for use with Madin-Darby Canine Kidney (MDCK) cells grown on Corning Transwell inserts for use with fluorescein isothiocyanate-dextran, average molecular weight 4 kDa (FITC-dextran). FITC-dextran is a large, metabolically inert sugar molecule that is not readily transferrable across healthy epithelial barriers in vitro or in vivo. This compound has been tagged with a fluorophore to easily track its movement.

Briefly, MDCK cells were seeded onto Transwell inserts and grown according to manufacturer instructions until confluent. On the day of the experiment, a baseline reading was taken in standard growth media in which FITC-dextran was spiked into the apical chamber and the percent permeation of FITC-dextran from the apical to the basolateral chamber was measured. The inserts were then washed in low calcium medium (LCM) containing either vehicle or compound to remove residual FITC-dextran and calcium, and FITC-dextran was once again spiked into the apical chamber and the percent permeation in LCM was measured. Values were determined by reading fluorescence intensity on a standard plate reader and calculated by fitting back to 12-point standard curve in either growth media or LCM+ vehicle, respectively. The fold induction of FITC-dextran permeation to the basolateral chamber when each well was transferred from baseline growth media to LCM was then calculated.

Compound 1 reduced the amount of FITC-dextran that permeated from the apical chamber to the basolateral chamber in the LCM condition relative to baseline and showed a reduction of 35% and 33%, respectively, at 10 µM and 0.1 µM relative to the vehicle treated epithelial cell monolayers.

Example A-5: Effects of AMPK Activators on Intestinal .Barrier Function in a Mouse in vivo Acute Dextran Sulfate Sodium (DSS) Colitis Model Compounds were formulated in vehicle (0.25% methyl cellulose, 5% Tween 80, 0.02% sodium dodecyl sulfate (SDS) in Hanks' Buffered Salt Solution with $Ca^{2+}$ and $Mg^{2+}$). Vehicle or compound was administered once daily by oral gavage to C57B1/6 mice. After 3 days of pre-dosing, dextran sulfate sodium (DSS) was simultaneously administered at 3% in drinking water, and appropriate water-only controls were included.

After 7 days of DSS administration, animals treated were switched back to their regular water source and administered a single oral bolus dose of FITC-dextran (FD) four hours prior to necropsy. The animals were sacrificed by cardiac puncture and serum was collected. The concentration of HTC-dextran present in serum was determined by measuring fluorescence intensity on a standard plate reader, and fitting values back to a standard curve.

As shown in Table C, administration of Compound 4 and Compound 31 produced reductions in plasma or serum fluorescence intensity compared to vehicle treatment in animals given DSS. This is indicative of improved intestinal barrier function in these compound-treated animals relative to vehicle-treated controls..

TABLE C

| Compound (dose) | Change in Fluorescence Intensity vs. Vehicle |
|---|---|
| 4 (30 mg/kg QD) | −43% |
| 31 (30 mg/kg QD) | −41% |

Example A-6: Effects of AMPK Activators on Diarrhea in a Mouse in vivo Chemotherapy-induced Intestinal Injury Model Compounds were formulated in vehicle (0.25% methyl cellulose, 5% Tween 80, 0.02% sodium dodecyl sulfate (SDS) in Hanks' Buffered Salt Solution with Ca' and Mg'). On day 1, either saline or a 400 mg/kg dose of 5-fluorouracil (5FU) in saline was administered by intraperitoneal injection to BALB/c mice. Starting on day 2, vehicle or compound was administered twice a day by oral gavage. From days 5 to 6 post-5FU, the animals were scored for diarrhea severity once a day. The diarrhea was scored 0-3 as follows: 0—normal consistency (black and solid), 1—soft (black and a bit lighter/yellow), 2—loosely shaped stool (yellowish and somewhat watery), 3—extreme diarrhea (very watery). Day 5 and day 6 diarrhea scores following administration of the tested compounds were lower than vehicle control mice suggesting robust protection from 5—FU-induced intestinal injury.

Results for exemplary compounds are shown in Table D.

TABLE D

| | Diarrhea Score (% Change vs. Vehicle) | |
|---|---|---|
| Compound (dose) | Day 5 | Day 6 |
| 4 (10 mpk BID) | 0.25 (−72%) | 0.38 (−79%) |
| 4 (3 mpk BID) | 0.75 (−16%) | 1.00 (−44%) |
| 31 (30 mpk BID) | 0.43 (−67%) | 0.63 (−61%) |
| 32 (20 mpk BID) | 0.63 (−43%) | 0.88 (−52%) |
| 40 (30 mpk BID) | 0.38 (−66%) | 0.75 (−59%) |
| 56 (30 mpk BID) | 0.38 (−71%) | 0.25 (−77%) |
| 58 (30 mpk BID) | 0.25 (−81%) | 0.38 (−66%) |
| 60 (30 mpk BID) | 0.38 (−71%) | 0.38 (−66%) |

Example A-7: Effects of AMPK Activators on an Intraperitoneal (IP) Glucose Tolerance Test in Mice Systemic AMPK target engagement in vivo can be assessed by measuring the glucose levels in blood following administration of compounds, whereby AMPK activation in skeletal muscle leads in a decrease in overall blood glucose levels.

Compounds were formulated in vehicle (0.25% methyl cellulose, 5% Tween 80, 0.02% sodium dodecyl sulfate (SDS) in Hanks' Buffered Salt Solution with Ca$^{2+}$ and Mg$^2$). Immediately prior to compound dosing, the tip of the tail was removed with scissors and a drop of blood was collected onto a glucometer strip (Bayer Contour Next) for a −1 hour blood glucose measure. The mice were then immediately administered vehicle or compound at 10 mL/kg PO. Approximately one hour later, mice were tail bled for a 0 min blood glucose reading, and then immediately after were administered D(+) glucose (2 g/kg, made up in saline) at 5 mL/kg IP. Tail bleeds were then performed on all mice at 20 min, 40 min, 60 min, and 90 min post D(+) glucose administration for blood glucose measures. Area under the curves (AUCs) for blood glucose measures were then calculated for each treatment from 0-90 mins. Only the systemic AMPK activator MK-8722 caused a significant change in the AUC vs. vehicle suggesting that Compounds 1, 2, and 4 at the administered doses (30 mpk for all compounds; and up to 100 mpk for Compound 4) do not lead to activation of AMPK in skeletal muscle.

Results for exemplary compounds are shown in Table E.

TABLE E

| Compound (dose) | % Change in Average Total AUC (0-90 min) vs. Vehicle |
|---|---|
| MK-8722 (30 mpk) | −28% |
| 1 (30 mpk) | −7.5% |
| 2 (30 mpk) | +6.6% |
| 4 (30 mpk) | −0.9% |
| 4 (100 mpk) | +2.3% |

What is claimed is:

1. A compound of Formula (III):

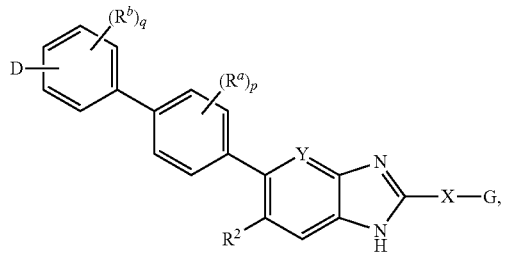

Formula (III)

or a pharmaceutically acceptable salt, solvate, stereoisomer, or prodrug thereof, wherein:

X is —O— or —S—;

Y is N or CH;

G is monocyclic 3- to 6-membered heterocycloalkyl containing 1 oxygen atom, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

or G is bicyclic 8- to 10-membered heterocycloalkyl containing 2 oxygen atoms, which is substituted with 1 or 2 substituents selected from —C(O)OH, —CH$_2$C(O)OH, —P(O)(Me)OH, —P(O)(OH)$_2$, —S(O)$_2$OH, —OH, and —CH$_2$OH;

D is K or —Z—NR$^5$R$^6$;

Z is —(CH$_2$)—, —(CH(CH$_3$))—, —C(=O)—, or —S(=O)$_2$—;

K is —SO—$_2$OH, —S(O)OH, —P(O)(OH)(R$^d$), —P(O)(OH)(OR$^d$), —CH$_2$P(O)(OH)(OR$^d$), —B(OR$^d$)(OH), —NHC(O)H, —N(R$^d$)C(O)NHSO$_2$(R$^d$), —C(O)

$NHSO_2(R^d)$, $-SO_2NHC(O)(R^d)$, $-NHC(O)NH(R^d)$, $-N(R^d)C(=N(R^d))N(R^d)_2$, $-N(R^d)C(=NH)NHC(=NH)NH_2$,

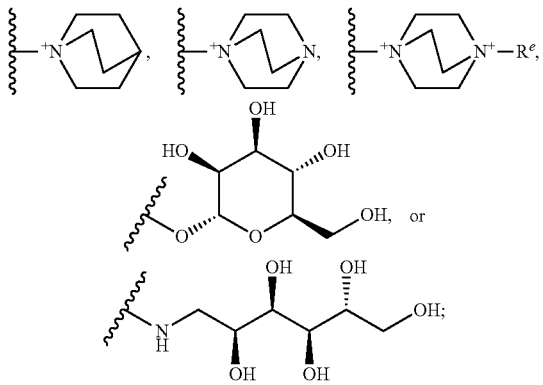

$R^a$ and $R^b$ are each independently halogen, $-CN$, $-OH$, $-OR^{13}$, $-NR^{14}R^{14}$, $-C(O)OR^{14}$, $-C(O)NR^{14}R^{14}$, $C_1-C_6$ alkyl, or $C_1-C_6$ fluoroalkyl;
each $R^d$ is independently hydrogen or $C_{1-6}$ alkyl;
each $R^e$ is independently $C^{1-6}$ alkyl;
each $R^2$ is independently halogen, $-CN$, $C_1-C_4$ alkyl, $C_1-C_4$ fluoroalkyl, or $C_3-C_6$ cycloalkyl;
$R^5$ is $C_6-C_{10}$ alkyl that is substituted by 5 to 9 $-OH$ groups;
or $R^5$ is $C_{1-10}$ alkyl which is substituted by 1-6 groups selected from $-N(R^e)_3^+$ and K; or with 2-6 groups selected from $-CO_2H$, $-OH$, and $-N(R^d)_2$; and is optionally further substituted by 1, 2, or 3 $R^f$ groups;
each $R^f$ is independently halogen, $-CN$, $-OH$, $-OR^{13}$, $-NR^{14}R^{14}$, $-C(O)OR^{14}$, $-C(O)NR^{14}R^{14}$, $NR^{14}C(O)R^{14}$, $-NR^{14}C(O)NR^{14}R^{14}$, $C_1-C_6$ alkyl, $C_3-C_6$ cycloalkyl, or phenyl, wherein the alkyl, cycloalkyl, or phenyl, is unsubstituted or substituted by 1, 2, or 3 halogen or $-OH$ groups;
or $R^5$ is $-[(C(R^d)_2)_s-V]_t-R^9$; wherein each V is independently $-C(R^d)_2O-$, $-C(R^d)_2NR^d-$, $-N(R^d)-C(O)-N(R^d)-$, or $-C(O)N(R^d)-$;
or $R^5$ is $-(C_1-C_6$ alkylene)-aryl, or $-(C_1-C_6$ alkylene)-heteroaryl; wherein the aryl or heteroaryl is substituted by 1-6 groups selected from $-CO_2H$, $-OH$, $-N(R^d)_2$, $-N(R^e)_3^+$, and K; and wherein the alkylene is unsubstituted or substituted by 1, 2, or 3 $R^f$ groups;
$R^6$ is hydrogen or $C_{1-6}$ alkyl;
or $R^5$ and $R^6$ are taken together with the nitrogen to which they are attached to form a 3- to 6-membered N-heterocycloalkyl which is substituted with 1-6 groups selected from $-CH_3$, $-CH_2OH$, $-CH_2NH_2$, $-CH_2CH_2OH$, $-CH_2OCH_2CH_2OH$, $-N(R^e)_3^+$, and K; or with 2-6 groups selected from $-CO_2H$, $-OH$, $-CH_2OH$, $-CH_2NH_2$, $-CH_2CH_2OH$, $-CH_2OCH_2CH_2OH$, and $-N(R^d)_2$;
$R^9$ is hydrogen, $C_{1-8}$ alkyl, phenyl, or naphthyl, wherein the alkyl, phenyl, or naphthyl is unsubstituted or substituted by 1-6 groups selected from $-OH$, $-CO_2H$, $-N(R^e)_2$, $-N(R^e)_3^+$, and K;
each $R^{13}$ is independently $C_1-C_6$ alkyl, $C_2-C_6$ alkenyl, $C_2-C_6$ alkynyl, $C_1-C_6$ fluoroalkyl, $C_3-C_6$ cycloalkyl, 3- to 6-membered heterocycloalkyl, phenyl, or monocyclic heteroaryl;

each $R^{14}$ is independently hydrogen, $C_1-C_6$ alkyl, $C_2-C_6$ alkenyl, $C_2-C_6$ alkynyl, $C_1-C_6$ fluoroalkyl, $C_3-C_6$ cycloalkyl, 3- to 6-membered heterocycloalkyl, phenyl, or monocyclic heteroaryl;
or two $R^{14}$ on the same nitrogen atom are taken together with the nitrogen to which they are attached to form a 3- to 6-membered N-heterocycloalkyl;
p is 0 or 1;
q is 0 or 1;
each s is independently 1-6; and
each t is independently 1-6.

2. The compound of claim 1, or a pharmaceutically acceptable salt, solvate, stereoisomer, or prodrug thereof, wherein:
$R^2$ is $-F$, $-Cl$, or $-CN$;
$R^3$ is $-F$, $-Cl$, $-CN$, $-OH$, $-OCH_3$, $-OCF_3$, methyl, ethyl, n-propyl, i-propyl, n-butyl, i-butyl, sec-butyl, tert-butyl, $-CH_2F$, $-CHF2$, or $-CF_3$; and
$R^b$ is $-F$, $-Cl$, $-CN$, $-OH$, $-OCH_3$, $-OCF_3$, methyl, ethyl, n-propyl, i-propyl, n-butyl, i-butyl, sec-butyl, tert-butyl, $-CH_2F$, $-CHF2$, or $-CF_3$.

3. The compound of claim 1, having the structure of Formula (IV):

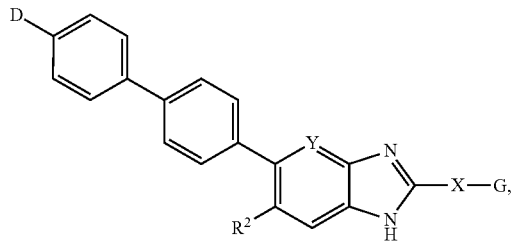

Formula (IV)

or a pharmaceutically acceptable salt, solvate, stereoisomer, or prodrug thereof.

4. The compound of claim 1, or a pharmaceutically acceptable salt, solvate, stereoisomer, or prodrug thereof, wherein:
X is $-O-$.

5. The compound of claim 1, or a pharmaceutically acceptable salt, solvate, stereoisomer, or prodrug thereof, wherein:
G is monocyclic 3- to 6-membered heterocycloalkyl containing 1 oxygen atom, which is substituted with 1 or 2 substituents selected from $-C(O)OH$, $-CH_2C(O)OH$, $-P(O)(Me)OH$, $-P(O)(OH)_2$, $-S(O)_2OH$, $-OH$, and $-CH_2OH$.

6. The compound of claim 1, or a pharmaceutically acceptable salt, solvate, stereoisomer, or prodrug thereof, wherein:
G is bicyclic 8- to 10-membered heterocycloalkyl containing 2 oxygen atoms, which is substituted with 1 or 2 substituents selected from $-C(O)OH$, $-CH_2C(O)OH$, $-P(O)(Me)OH$, $-P(O)(OH)_2$, $-S(O)_2OH$, $-OH$, and $-CH_2OH$.

7. The compound of claim 1, or a pharmaceutically acceptable salt, solvate, stereoisomer, or prodrug thereof, wherein:
D is K; and
K is $-SO_2OH$, $-P(O)(OH)(R^d)$, $-P(O)(OH)(OR^d)$, $-CH_2P(O)(OH)(OR^d)$, $-C(O)NHSO_2(R^d)$, or $-SO_2NHC(O)(R^d)$.

8. The compound of claim 1, or a pharmaceutically acceptable salt, solvate, stereoisomer, or prodrug thereof, wherein:

D is —Z—NR⁵R⁶.

9. The compound of claim 8, or a pharmaceutically acceptable salt, solvate, stereoisomer, or prodrug thereof, wherein:

R⁵ is $C_6$-$C_{10}$ alkyl that is substituted by 5 to 9 —OH groups.

10. The compound of claim 8, or a pharmaceutically acceptable salt, solvate, stereoisomer, or prodrug thereof, wherein:

R⁵ is $C_{1-10}$ alkyl which is substituted by 1-6 groups selected from —N(Rᵉ)₃⁺ and K; or with 2-6 groups selected from —CO₂H, —OH, and —N(Rᵈ)₂; and is optionally further substituted by 1, 2, or 3 Rᶠ groups;

each Rᶠ is independently halogen, —CN, —OH, —OR¹³, —NR¹⁴R¹⁴, —C(O)OR¹⁴, —C(O)NR¹⁴R¹⁴, —NR¹⁴C(O)R¹⁴, —NR¹⁴C(O)NR¹⁴, R¹⁴, $C_1$-$C_6$ alkyl, $C_3$-$C_6$ cycloalkyl, or phenyl, wherein the alkyl, cycloalkyl, or phenyl, is unsubstituted or substituted by 1, 2, or 3 halogen or —OH groups; and K is —SO₂OH, —P(O)(OH)₂, —CH₂P(O)(OH)₂, —P(O)(OH)(Me), —P(O)(OH)(H), or —P(O)(OH)(OMe).

11. The compound of claim 8, or a pharmaceutically acceptable salt, solvate, stereoisomer, or prodrug thereof, wherein:

R⁵ is [(C(Rᵈ)₂)ₛ—V]ₜ—R⁹; wherein each V is independently —C(Rᵈ)₂O—, —C(Rᵈ)₂NRᵈ—, —N(Rᵈ)—C(O)—N(Rᵈ)—, or —C(O)N(Rᵈ)—; each Rᵈ is independently hydrogen or $C_{1-6}$ alkyl;

R⁶ is hydrogen or $C_{1-6}$ alkyl;

R⁹ is hydrogen, $C_{1-8}$ alkyl, phenyl, or naphthyl, wherein the alkyl, phenyl, or naphthyl is unsubstituted or substituted by 1-6 groups selected from —OH, —CO₂H, —N(Rᵉ)₂, —N(Rᵉ)₃⁺, and K; and K is —SO₂OH, —P(O)(OH)₂, —CH₂P(O)(OH)₂, —P(O)(OH)(Me), —P(O)(OH)(H), or —P(O)(OH)(OMe).

12. The compound of claim 8, or a pharmaceutically acceptable salt, solvate, stereoisomer, or prodrug thereof, wherein:

R⁵ and R⁶ are taken together with the nitrogen to which they are attached to form a 4- to 6-membered N-heterocycloalkyl which is substituted with 2-4 groups selected from —OH and —CH₂OH.

13. The compound of claim 1, or a pharmaceutically acceptable salt, solvate, stereoisomer, or prodrug thereof, wherein:

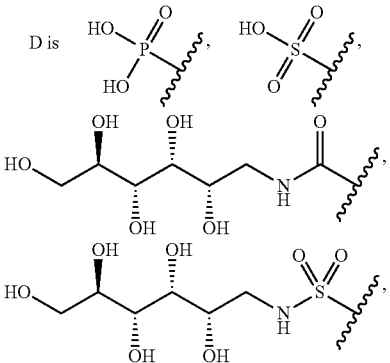

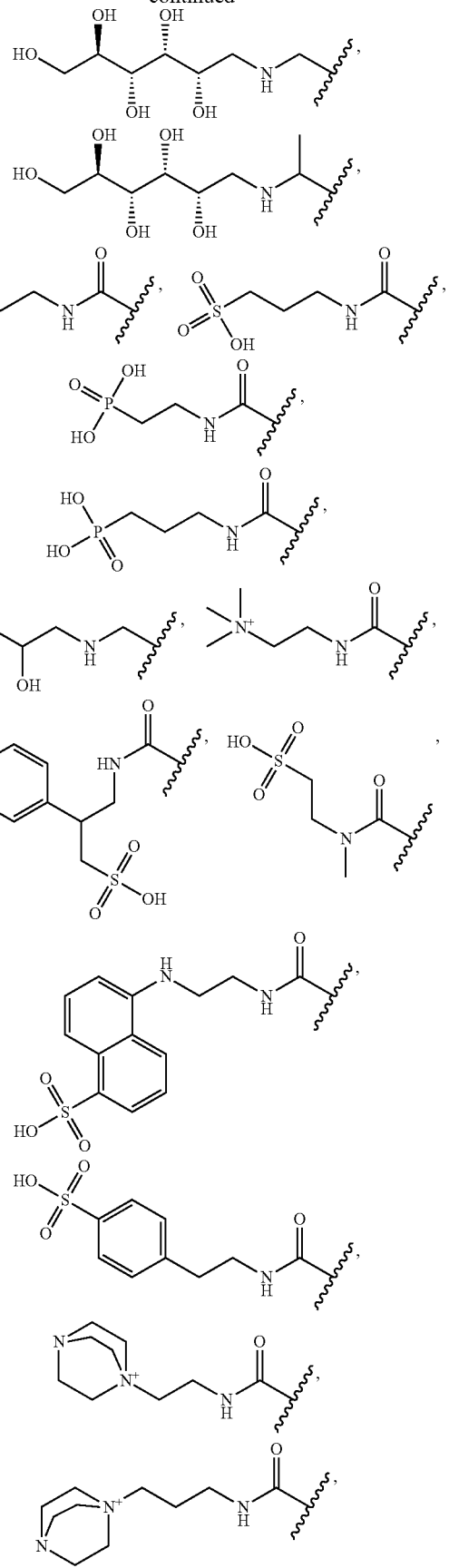

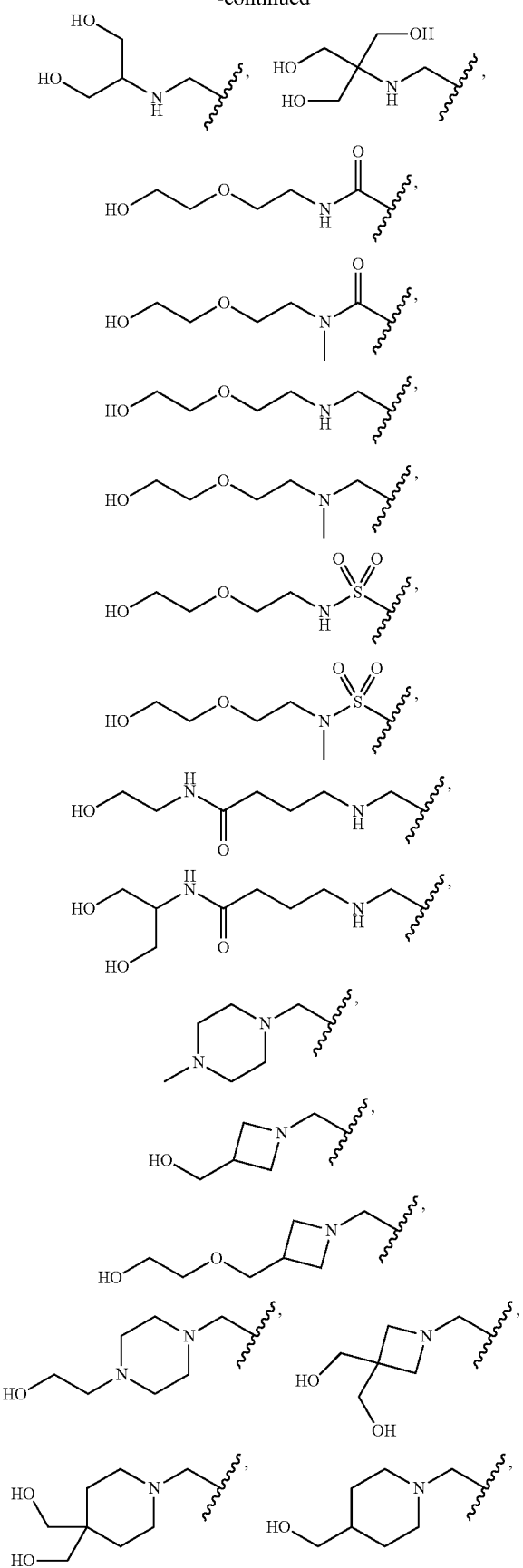

14. A compound selected from:
1: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(2S,3R,4R,5R)-2,3,4,5,6-pentahydroxyhexyl)-[1,1'-biphenyl]-4-carboxamide;
2: (4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)phosphonic acid;
3: 4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(2S,3R,4R,5R)-2,3,4,5,6-pentahydroxyhexyl)-[1,1'-biphenyl]-4-sulfonamide;
4: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)hexane-1,2,3,4,5-pentaol;
5: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethane-1-sulfonic acid;
6: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propane-1-sulfonic acid;
7: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)-2-(4-chlorophenyl)propane-1-sulfonic acid;
8: 2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-methyl-[1,1'-biphenyl]-4-carboxamido)ethane-1-sulfonic acid;
9: 2-(N-(2-amino-2-oxoethyl)-4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethane-1-sulfonic acid;
10: 5-((2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)amino)naphthalene-1-sulfonic acid;
11: 4-(2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)benzenesulfonic acid;
12: (4'-(6-chloro-2-(((3R,5S,6R)-5-hydroxy-6-(hydroxymethyl)tetrahydro-2H-pyran-3-yl)oxy)-1H-imidazo[4,5-b]pyridin-5-yl)-[1,1'-biphenyl]-4-yl)phosphonic acid;
13: (2-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)ethyl)phosphonic acid;
14: (3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-carboxamido)propyl)phosphonic acid;

15: 3-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-N-(1,3-dihydroxy-2-(hydroxymethyl)propan-2-yl)-[1,1'-biphenyl]-4-carboxamido)propane-1-sulfonic acid;

16: (4-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-1-hydroxybutane-1,1-diyl)bis(phosphonic acid);

17: (2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2,3-dihydro-1H-inden-2-yl)phosphonic acid;

18: (S)-2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-3-(4-(phosphonomethyl)phenyl)propanoic acid;

19: N-((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)-N-(phosphonomethyl)glycine;

20: 3-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)pentanedioic acid;

21: 2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-4-(hydroxy(methyl)phosphoryl)butanoic acid;

22: 3-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-hydroxypropanoic acid;

23: ((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)-L-aspartic acid;

24: (2R,3R,4R,5S)-6-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)(methyl)amino)hexane-1,2,3,4,5-pentaol;

25: (2R,3R,4R,5S)-1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)-2-(hydroxymethyl)piperidine-3,4,5-triol;

26: (4-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)butyl)phosphonic acid;

27: ((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)methyl)phosphonic acid;

28: ((4'-(6-chloro-2-(((3R,3aR,6R,6aR)-6-hydroxyhexahydrofuro[3,2-b]furan-3-yl)oxy)-1H-benzo[d]imidazol-5-yl)-N-(phosphonomethyl)-[1,1'-biphenyl]-4-carboxamido)methyl)phosphonic acid;

29: 2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)-N,N,N-trimethylethan-1-aminium;

30: 4'-(6-chloro-2-(((3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1,1'-biphenyl]-4-carboxamide;

31: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-[1,1'-biphenyl]-4-carboxamide;

32: 1-(2-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)ethyl)-1,4-diazabicyclo[2.2.2]octan-1-ium;

33: 1-(3-(4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-carboxamido)propyl)-1,4- diazabicyclo[2.2.2]octan-1-ium;

34: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(3-(1,3-dihydroxypropan-2-yl)ureido)ethyl)-[1,1'-biphenyl]-4-carboxamide;

35: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(3-(2-hydroxyethyl)ureido)ethyl)-[1,1'-biphenyl]-4-carboxamide;

36: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-2-(hydroxymethyl)propane-1,3-diol;

37: 4-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(2-hydroxyethyl)butanamide;

38: 4-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(1,3-dihydroxypropan-2-yl)butanamide;

39: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)(methyl)amino)-N,N,N-trimethylethan-1-aminium;

40: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)propane-1,3-diol;

41: 1-(2-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)ethyl)-3-(1,3-dihydroxy-2-(hydroxymethyl)propan-2-yl)urea;

42: (1R,2S,3R,5R)-3-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-5-(hydroxymethyl)cyclopentane-1,2-diol;

43: (2R,3R)-2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)butane-1,3-diol;

44: 2-(2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)ethyl)guanidine;

45: (4'-(6-chloro-2-(((3S,4R,5R)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid;

46: 2-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)-N-(2-(dimethylamino)ethyl)-2-methylpropanamide;

48: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-carboxamide;

49: (3R,3aR,6R,6aR)-6-(6-chloro-5-(4'-(piperazin-1-ylmethyl)-[1,1'-biphenyl]-4-yl)-1H-benzo[d]imidazol-2-yl)oxy)hexahydrofuro[3,2-b]furan-3-ol;

50: (3R,3aR,6R,6aR)-6-(6-chloro-5-(4'-(3-(2-hydroxyethoxy)methyl)azetidin-1-yl)methyl)-[1,1'-biphenyl]-4-yl)-1H-benzo[d]imidazol-2-yl)oxy)hexahydrofuro[3,2-b]furan-3-ol;

51: (3R,3aR,6R,6aR)-6-(6-chloro-5-(4'-(4-(2-hydroxyethyl)piperazin-1-yl)methyl)-[1,1'-biphenyl]-4-yl)-1H-imidazo[4,5-b]pyridin-2-yl)oxy)hexahydrofuro[3,2-b]furan-3-ol;

52: (1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)azetidine-3,3-diyl)dimethanol;

53: 2-(((4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)amino)-2-(hydroxymethyl)propane-1,3-diol;

54: (1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)methyl)piperidine-4,4-diyl)dimethanol;

55: (3R,3aR,6R,6aR)-6-((6-chloro-5-(4'-(4-(hydroxymethyl)piperidin-1-yl)methyl)-[1,1'-biphenyl]-4-yl)-1H-benzo[d]imidazol-2-yl)oxy)hexahydrofuro[3,2-b]furan-3-ol;

56: (3R,3aR,6R,6aR)-6-(6-chloro-5-(4'-(4-(2-hydroxyethyl)piperazin-1-yl)methyl)-[1,1'-biphenyl]-4-yl)-1H-benzo[d]imidazol-2-yl)oxy)hexahydrofuro[3,2-b]furan-3-ol;

57: (3R,3aR,6R,6aR)-6-((6-chloro-5-(4'-((4-methylpiperazin-1-yl)methyl)-[1,1'-biphenyl]-4-yl)-1H-benzo[d]imidazol-2-yl)oxy)hexahydrofuro[3,2-b]furan-3-ol;

58: (3R,3aR,6R,6aR)-6-((6-chloro-5-(4'-(((2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol;

59: (R)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidin-3-ol;

60: (1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)piperidine-4,4-diyl)dimethanol;

61: (3S,4R)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidine-3,4-diol;

62: (3R,3aR,6R,6aR)-6-((6-chloro-5-(4'4 (2-(2-hydroxyethoxy)ethyl)(methyl)amino)methyl)-[1,1'-biphenyl]-4-yl)-1H-benzo[d]imidazol-2-yl)oxy)hexahydrofuro[3,2-b]furan-3-ol;

63: (3R,3aR,6R,6aR)-6-((6-chloro-5-(4'-((3-(hydroxymethyl)azetidin-1-yl)methyl)-[1,1'-biphenyl]-4-yl)-1H-benzo[d]imidazol-2-yl)oxy)hexahydrofuro[3,2-b]furan-3-ol;

64: (3S,4S)-1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)pyrrolidine-3,4-diol;

65: (2R,3R,4R,5S)-6-(((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)amino)hexane-1,2,3,4,5-pentaol;

66: (1-((4'-(6-chloro-2-(((3R,3aR,6R,6aR)-6-hydroxyhexahydrofuro[3,2-b]furan-3-yl)oxy)-1H-benzo[d]imidazol-5-yl)-[1,1'-biphenyl]-4-yl)methyl)azetidine-3,3-diyl)dimethanol;

67: (3R,3aR,6R,6aR)-6-((5-(4'-((3-(aminomethyl)azetidin-1-yl)methyl)-[1,1'-biphenyl]-4-yl)-6-chloro-1H-benzo[d]imidazol-2-yl)oxy)hexahydrofuro[3,2-b]furan-3-ol;

68: (4'-(6-chloro-2-(((3R,4S,5S)-4-hydroxy-5-(hydroxymethyl)tetrahydrofuran-3-yl)oxy)-1H-imidazo[4,5-b]pyridin-5-yl)-[1,1'-biphenyl]-4-yl)phosphonic acid;

69: 4'-(6-chloro-2-(((3R,3aR,6R,6aR)-6-hydroxyhexahydrofuro [3,2-b]furan-3-yl)oxy)-1H-imidazo[4,5-b]pyridin-5-yl)-[1,1'-biphenyl]-4-sulfonic acid;

70: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-[1,1'-biphenyl]-4-sulfonamide;

71: 4'-(6-chloro-2-(((3R,3aR,6R,6aR)-6-hydroxyhexahydrofuro[3,2-b]furan-3-yl)oxy)-1H-benzo[d]imidazol-5-yl)-N-((2S,3R,4R,5R)-2,3,4,5,6-pentahydroxyhexyl)-[1,1'-biphenyl]-4-sulfonamide;

72: 4'-(6-chloro-2-(((3R,3aR,6R,6aR)-6-hydroxyhexahydrofuro[3,2-b]furan-3-yl)oxy)-1H-benzo[d]imidazol-5-yl)-N-(2-(2-hydroxyethoxy)ethyl)-N-methyl-[1,1'-biphenyl]-4-sulfonamide;

73: (2R,3R,4R,5S)-6-((1-(4'-(6-chloro-2-(((3R,3aR,6R,6aR)-6-hydroxyhexahydrofuro[3,2-b]furan-3-yl)oxy)-1H-imidazo[4,5-b]pyridin-5-yl)-[1,1'-biphenyl]-4-yl)ethyl)amino)hexane-1,2,3,4,5-pentaol;

74: (3R,3aR,6R,6aR)-6-((6-chloro-5-(2'-hydroxy-4'4 (2-(2-hydroxyethoxy)ethyl)amino)methyl)-[1,1'-biphenyl]-4-yl)-1H-benzo[d]imidazol-2-yl)oxy)hexahydrofuro[3,2-b]furan-3-ol; and 75: 4'-(6-chloro-2-(((3R,3aR,6R,6aR)-6-hydroxyhexahydrofuro[3,2-b]furan-3-yl)oxy)-1H-benzo[d]imidazol-5-yl)-2-hydroxy-N-(2-(2-hydroxyethoxy)ethyl)-[1,1'-biphenyl]-4-carboxamide;

or a pharmaceutically acceptable salt, solvate, stereoisomer, or prodrug thereof.

15. A pharmaceutical composition comprising a compound of claim 1, or a pharmaceutically acceptable salt, solvate, stereoisomer, or prodrug thereof, and at least one pharmaceutically acceptable excipient.

16. A method of treating an adenosine 5'-monophosphate-activated protein kinase (AMPK) associated condition or disorder in a subject in need thereof, the method comprising administering to the subject a therapeutically effective amount of a compound of claim 1, or a pharmaceutically acceptable salt, solvate, stereoisomer, or prodrug thereof.

17. The method of claim 16, wherein the condition or disorder is associated with systemic infection and inflammation from having a leaky gut barrier.

18. The method of claim 16, wherein the condition or disorder is metabolic syndrome, obesity, type 2 diabetes, coronary artery disease, fatty liver, nonalcoholic steatohepatitis (NASH), cirrhosis, hepatic encephalopathy, scleroderma, inflammatory bowel disease, Crohn's disease, ulcerative colitis, checkpoint inhibitor-induced colitis, psoriasis, celiac disease, necrotizing enterocolitis, gastrointestinal injury resulting from toxic insults, environmental enteric dysfunction, allergy, graft vs. host disease, irritable bowel syndrome, spontaneous bacterial peritonitis, ischemic colitis, sclerosing cholangitis, Alzheimer's disease, Parkinson's disease, cancer, depression, or a combination thereof.

19. The method of claim 18, wherein the allergy is food allergy, celiac sprue, or childhood allergy, or a combination thereof.

20. A method of treating gastrointestinal injury resulting from toxic insult, the method comprising administering to the subject a therapeutically effective amount of a compound of claim 1, or a pharmaceutically acceptable salt, solvate, stereoisomer, or prodrug thereof.

21. The method of claim 20, wherein the toxic insult is from radiation, chemotherapy, or a combination thereof.

* * * * *